US012344847B2

(12) United States Patent
Argyros et al.

(10) Patent No.: US 12,344,847 B2
(45) Date of Patent: Jul. 1, 2025

(54) CELL-ASSOCIATED HETEROLOGOUS FOOD AND/OR FEED ENZYMES

(71) Applicant: Lallemand Hungary Liquidity Management LLC, Budapest (HU)

(72) Inventors: Aaron Argyros, Lebanon, NH (US); Michelle Oeser, Croydon, NH (US); Erin Wiswall, Danbury, NH (US); Janet Fisher, Enfield, VT (US); Johannes Van Eijk, Longueuil (CA); J. Kevin Kraus, Tenafly, NJ (US); Kevin Wenger, Hanover, NH (US); Brooks Henningsen, Salisbury, NH (US); Ryan Skinner, South Royalton, VT (US)

(73) Assignee: DANSTAR FERMENT AG, Zug (CH)

(*) Notice: Subject to any disclaimer, the term of this patent is extended or adjusted under 35 U.S.C. 154(b) by 1094 days.

(21) Appl. No.: 16/493,245

(22) PCT Filed: Mar. 13, 2018

(86) PCT No.: PCT/IB2018/051670
§ 371 (c)(1),
(2) Date: Sep. 11, 2019

(87) PCT Pub. No.: WO2018/167669
PCT Pub. Date: Sep. 20, 2018

(65) Prior Publication Data
US 2020/0087672 A1    Mar. 19, 2020

Related U.S. Application Data

(60) Provisional application No. 62/470,568, filed on Mar. 13, 2017, provisional application No. 62/625,751, filed on Feb. 2, 2018.

(51) Int. Cl.
*A23K 10/18*      (2016.01)
*A21D 8/04*       (2006.01)
*A23K 20/189*     (2016.01)
*A23L 33/14*      (2016.01)
*C12N 1/18*       (2006.01)
*C12N 9/16*       (2006.01)
*C12N 9/30*       (2006.01)
*C12N 9/34*       (2006.01)
*C12N 15/81*      (2006.01)

(52) U.S. Cl.
CPC ............ *C12N 15/81* (2013.01); *A21D 8/047* (2013.01); *A23K 10/18* (2016.05); *A23K 20/189* (2016.05); *A23L 33/14* (2016.08); *C12N 1/18* (2013.01); *C12N 9/16* (2013.01); *C12N 9/242* (2013.01); *C12N 9/2428* (2013.01); *C12Y 302/01133* (2013.01)

(58) Field of Classification Search
CPC ........ C12N 1/18; C12N 9/2414; C12N 1/063; C12N 9/16; C12N 9/2428; C12N 9/242; C12Y 302/01001; C12Y 302/01133; C12Y 301/03; C12P 7/10; Y02E 50/10; C07K 2319/035; C07K 2319/03; A23K 20/189
USPC ................... 435/69.9, 95, 204, 320.1, 254.2
See application file for complete search history.

(56) References Cited

U.S. PATENT DOCUMENTS 5,108,925 A   4/1992   Enari et al.
6,162,628 A   12/2000  Cherry et al.

FOREIGN PATENT DOCUMENTS

EP    2505655 A2    10/2012
WO    99/43794 A1    9/1999

OTHER PUBLICATIONS

Kisselev L., Structure, 2002, vol. 10: 8-9.*
Kwiatkowski et al., Biochemistry 38:11643-11650, 1999.*
Wristlock et al., Quarterly Reviews of Biophysics 2003, vol. 36 (3): 307-340.*
Davos et al., Proteins: Structure, Function and Genetics, 2000, vol. 41: 98-107.*
Blomqvist et al., "Chromosomal Integration and Expression of Two Bacterial α-Acetolactate Decarboxylase Genes in Brewer's Yeast," *Applied and Environmental Microbiology* 57(10):2796-2803, 1991.
Cejnar et al., "Surface-*engineered Saccharomyces cerevisiae* displaying α-acetolactate decarboxylase from *Acetobacter aceti* ssp *xylinum,*" *Biotechnol Lett* 38:2145-2151, 2016.
Hong et al., "Optimizing promoters and secretory signal sequences for producing ethanol from inulin by recombinant *Saccharomyces cerevisiae* carrying *Kluyveromyces marxianus* inulinase," *Bioprocess Biosyst Eng* 38:263-272, 2015.
Inokuma et al., "Efficient co-displaying and artificial ratio control of α-amylase and glucoamylase on the yeast cell surface by using combinations of different anchoring domains," *Appl Microbiol Biotechnol* 99:1655-1663, 2015.
Li et al., "Engineering a family 27 carbohydrate-binding module into an *Aspergillus usamii* β-mannanase to perfect its enzymatic properties," *Journal of Bioscience and Bioengineering* 123(3):294-299, 2017.
Liao et al., "Amylolytic activity and fermentative ability of *Saccharomyces cerevisiae* strains that express barley α-amylase," *Biochemical Engineering Journal* 53:63-70, 2010.
Lilly et al., "Heterologous expression of a Clostridium minicellulosome in *Saccharomyces cerevisiae,*" *FEMS Yeast Res* 9:1236-1249, 2009.
Mehta et al., "Bacterial and Archaeal α-Amylases: Diversity and Amelioration of the Desirable Characteristics for Industrial Applications," *Frontiers in Microbiology* 7, 2016, 22 pages.

(Continued)

*Primary Examiner* — Robert B Mondesi
*Assistant Examiner* — Mohammad Y Meah
(74) *Attorney, Agent, or Firm* — Seed IP Law Group LLP

(57) ABSTRACT

The present disclosure concerns recombinant yeast host cells expressing cell-associated heterologous food and/or feed enzymes which are expressed during the propagation phase of the recombinant yeast hosts cells. The recombinant yeast host cells can be used in a subsequent production process to make food and/or feed products, for example, baked products.

15 Claims, 27 Drawing Sheets

Specification includes a Sequence Listing.

(56) References Cited

OTHER PUBLICATIONS

Murai et al., "Development of an arming yeast strain for efficient utilization of starch by co-display of sequential amylolytic enzymes on the cell surface," *Appl Microbiol Biotechnol* 51:65-70, 1999.

Murai et al., "Genetic immobilization of cellulose on the cell surface of *Saccharomyces cerevisiae*," *Appl Microbiol Biotechnol* 48:499-503, 1997.

Paciello et al., "Bread making with *Saccharomyces cerevisiae* CEN.PK113-5D expressing lipase A from *Bacillus subtilis*: leavening characterisation and aroma enhancement," *International Journal of Food Science and Technology* 50:2120-2128, 2015.

Pérez-Torrado et al., "Monitoring Stress-Related Genes during the Process of Biomass Propagation of *Saccharomyces cerevisiae* Strains Used for Wine Making," *Applied and Environmental Microbiology* 71(11):6831-6837, 2005.

Praekelt et al., "*MOL1*, a *Saccharomyces cerevisiae* Gene that is Highly Expressed in Early Stationary Phase During Growth on Molasses," *Yeast* 8:699-710, 1992.

Shimizu et al., "Brewing Performance of a Genetically Transformed Yeast with Acetolactate Decarboxylase Activity," *MBAA Technical Quarterly* 26:47-50, 1989.

Ueda et al., "Cell Surface Engineering of Yeast: Construction of Arming Yeast with Biocatalyst," *Journal of Bioscience and Bioengineering* 90(2):125-136, 2000.

van Rooyen et al., "Construction of cellobiose-growing and fermenting *Saccharomyces cerevisiae strains*," *Journal of Biotechnology* 120:284-295, 2005.

Yamano et al., "Brewing performance of a brewer's yeast having α-acetolactate decarboxylase from *Acetobacter aceti* subsp. *xylinum*," Journal of Biotechnology 39:21-26, 1995.

Tao et al., "Technologies for Yeast Surface Display of Enzymes," *Progress in Modern Biomedicine* 10(3):593, Jan. 2010, 13 pages.

Andreu et al., "Development of a new yeast surface display system based on Spi1 as an anchor protein," *Appl Microbiol Biotechnol* 101:287-299, 2017 [Published online Oct. 15, 2016]. (13 pages).

Bankar et al., "Glucose oxidase—An overview," *Biotechnology Advances* 27:489-501, 2009 [Published online Apr. 15, 2009]. (13 pages).

Blazic et al., "Yeast surface display for the expression, purification and characterization of wild-type and B11 mutant glucose oxidases," *Protein Expression and Purification* 89:175-180, 2013 [Published online Apr. 3, 2013]. (6 pages).

Malherbe et al., "Expression of the Aspergillus niger glucose oxidase gene in *Saccharomyces cerevisiae* and its potential applications in wine production," *Appl Microbiol Biotechnol* 61:502-511, 2003 [Published online Feb. 11, 2003]. (10 pages).

\* cited by examiner

| | Control | 10 ppm Gluzyme Mono 10000 BG (100 GOU/kg flour) | 20 ppm Gluzyme Mono 10000 BG (200 GOU/kg flour) | M16780 cell pellet (127 GOU/kg flour) | Control |
|---|---|---|---|---|---|
| Average proof height | 100 | 100 | 100 | 100 | 101 |
| Average oven height | 111 | 114 | 112 | 114 | 111 |
| Oven Spring | 11 | 15 | 12 | 14 | 10 |
| Crumb structure | 2 | 3 | 4 | 3 | 2.5 |

Figure 21

SEQUENCE LISTING

```
<160> NUMBER OF SEQ ID NOS: 108

<210> SEQ ID NO 1
<211> LENGTH: 719
<212> TYPE: PRT
<213> ORGANISM: Geobacillus stearothermophilus

<400> SEQUENCE: 1

Met Lys Lys Lys Thr Leu Ser Leu Phe Val Gly Leu Met Leu Leu Ile
1               5                   10                  15

Gly Leu Leu Phe Ser Gly Ser Leu Pro Tyr Asn Pro Asn Ala Ala Glu
            20                  25                  30

Ala Ser Ser Ser Ala Ser Val Lys Gly Asp Val Ile Tyr Gln Ile Ile
        35                  40                  45

Ile Asp Arg Phe Tyr Asp Gly Asp Thr Thr Asn Asn Asn Pro Ala Lys
    50                  55                  60

Ser Tyr Gly Leu Tyr Asp Pro Thr Lys Ser Lys Trp Lys Met Tyr Trp
65                  70                  75                  80

Gly Gly Asp Leu Glu Gly Val Arg Gln Lys Leu Pro Tyr Leu Lys Gln
                85                  90                  95

Leu Gly Val Thr Thr Ile Trp Leu Ser Pro Val Leu Asp Asn Leu Asp
            100                 105                 110

Thr Leu Ala Gly Thr Asp Asn Thr Gly Tyr His Gly Tyr Trp Thr Arg
        115                 120                 125

Asp Phe Lys Gln Ile Glu Glu His Phe Gly Asn Trp Thr Thr Phe Asp
    130                 135                 140

Thr Leu Val Asn Asp Ala His Gln Asn Gly Ile Lys Val Ile Val Asp
145                 150                 155                 160

Phe Val Pro Asn His Ser Thr Pro Phe Lys Ala Asn Asp Ser Thr Phe
                165                 170                 175

Ala Glu Gly Gly Ala Leu Tyr Asn Asn Gly Thr Tyr Met Gly Asn Tyr
            180                 185                 190

Phe Asp Asp Ala Thr Lys Gly Tyr Phe His His Asn Gly Asp Ile Ser
        195                 200                 205

Asn Trp Asp Asp Arg Tyr Glu Ala Gln Trp Lys Asn Phe Thr Asp Pro
    210                 215                 220

Ala Gly Phe Ser Leu Ala Asp Leu Ser Gln Glu Asn Gly Thr Ile Ala
225                 230                 235                 240

Gln Tyr Leu Thr Asp Ala Ala Val Gln Leu Val Ala His Gly Ala Asp
                245                 250                 255

Gly Leu Arg Ile Asp Ala Val Lys His Phe Asn Ser Gly Phe Ser Lys
            260                 265                 270

Ser Leu Ala Asp Lys Leu Tyr Gln Lys Lys Asp Ile Phe Leu Val Gly
        275                 280                 285
```

```
Glu Trp Tyr Gly Asp Asp Pro Gly Thr Ala Asn His Leu Glu Lys Val
290                 295                 300
Arg Tyr Ala Asn Ser Gly Val Asn Val Leu Asp Phe Asp Leu Asn
305                 310                 315                 320
Thr Val Ile Arg Asn Val Phe Gly Thr Phe Thr Gln Thr Met Tyr Asp
                325                 330                 335
Leu Asn Asn Met Val Asn Gln Thr Gly Asn Glu Tyr Lys Tyr Lys Glu
                340                 345                 350
Asn Leu Ile Thr Phe Ile Asp Asn His Asp Met Ser Arg Phe Leu Ser
                355                 360                 365
Val Asn Ser Asn Lys Ala Asn Leu His Gln Ala Leu Ala Phe Ile Leu
370                 375                 380
Thr Ser Arg Gly Thr Pro Ser Ile Tyr Tyr Gly Thr Glu Gln Tyr Met
385                 390                 395                 400
Ala Gly Gly Asn Asp Pro Tyr Asn Arg Gly Met Met Pro Ala Phe Asp
                405                 410                 415
Thr Thr Thr Thr Ala Phe Lys Glu Val Ser Thr Leu Ala Gly Leu Arg
                420                 425                 430
Arg Asn Asn Ala Ala Ile Gln Tyr Gly Thr Thr Thr Gln Arg Trp Ile
                435                 440                 445
Asn Asn Asp Val Tyr Ile Tyr Glu Arg Lys Phe Phe Asn Asp Val Val
450                 455                 460
Leu Val Ala Ile Asn Arg Asn Thr Gln Ser Ser Tyr Ser Ile Ser Gly
465                 470                 475                 480
Leu Gln Thr Ala Leu Pro Asn Gly Ser Tyr Ala Asp Tyr Leu Ser Gly
                485                 490                 495
Leu Leu Gly Gly Asn Gly Ile Ser Val Ser Asn Gly Ser Val Ala Ser
                500                 505                 510
Phe Thr Leu Ala Pro Gly Ala Val Ser Val Trp Gln Tyr Ser Thr Ser
                515                 520                 525
Ala Ser Ala Pro Gln Ile Gly Ser Val Ala Pro Asn Met Gly Ile Pro
                530                 535                 540
Gly Asn Val Val Thr Ile Asp Gly Lys Gly Phe Gly Thr Thr Gln Gly
545                 550                 555                 560
Thr Val Thr Phe Gly Gly Val Thr Ala Thr Val Lys Ser Trp Thr Ser
                565                 570                 575
Asn Arg Ile Glu Val Tyr Val Pro Asn Met Ala Ala Gly Leu Thr Asp
                580                 585                 590
Val Lys Val Thr Ala Gly Gly Val Ser Ser Asn Leu Tyr Ser Tyr Asn
                595                 600                 605
Ile Leu Ser Gly Thr Gln Thr Ser Val Val Phe Thr Val Lys Ser Ala
                610                 615                 620
Pro Pro Thr Asn Leu Gly Asp Lys Ile Tyr Leu Thr Gly Asn Ile Pro
625                 630                 635                 640
Glu Leu Gly Asn Trp Ser Thr Asp Thr Ser Gly Ala Val Asn Asn Ala
                645                 650                 655
Gln Gly Pro Leu Leu Ala Pro Asn Tyr Pro Asp Trp Phe Tyr Val Phe
                660                 665                 670
Ser Val Pro Ala Gly Lys Thr Ile Gln Phe Lys Phe Ile Lys Arg
                675                 680                 685
Ala Asp Gly Thr Ile Gln Trp Glu Asn Gly Ser Asn His Val Ala Thr
690                 695                 700
```

```
Thr Pro Thr Gly Ala Thr Gly Asn Ile Thr Val Thr Trp Gln Asn
705                 710                 715
```

<210> SEQ ID NO 2
<211> LENGTH: 499
<212> TYPE: PRT
<213> ORGANISM: Aspergillus oryzae

<400> SEQUENCE: 2

```
Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
                20                  25                  30

Tyr Phe Leu Leu Thr Asp Arg Phe Ala Arg Thr Asp Gly Ser Thr Thr
            35                  40                  45

Ala Thr Cys Asn Thr Ala Asp Arg Lys Tyr Cys Gly Gly Thr Trp Gln
        50                  55                  60

Gly Ile Ile Asp Lys Leu Asp Tyr Ile Gln Gly Met Gly Phe Thr Ala
65                  70                  75                  80

Ile Trp Ile Thr Pro Val Thr Ala Gln Leu Pro Gln Thr Thr Ala Tyr
                85                  90                  95

Gly Asp Ala Tyr His Gly Tyr Trp Gln Gln Asp Ile Tyr Ser Leu Asn
            100                 105                 110

Glu Asn Tyr Gly Thr Ala Asp Asp Leu Lys Ala Leu Ser Ser Ala Leu
        115                 120                 125

His Glu Arg Gly Met Tyr Leu Met Val Asp Val Val Ala Asn His Met
130                 135                 140

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Leu Ile Gln Asn Tyr
                165                 170                 175

Glu Asp Gln Thr Gln Val Glu Asp Cys Trp Leu Gly Asp Asn Thr Val
            180                 185                 190

Ser Leu Pro Asp Leu Asp Thr Thr Lys Asp Val Val Lys Asn Glu Trp
        195                 200                 205

Tyr Asp Trp Val Gly Ser Leu Val Ser Asn Tyr Ser Ile Asp Gly Leu
210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Gly Asp
                245                 250                 255

Pro Ala Tyr Thr Cys Pro Tyr Gln Asn Val Met Asp Gly Val Leu Asn
            260                 265                 270

Tyr Pro Ile Tyr Tyr Pro Leu Leu Asn Ala Phe Lys Ser Thr Ser Gly
        275                 280                 285

Ser Met Asp Asp Leu Tyr Asn Met Ile Asn Thr Val Lys Ser Asp Cys
290                 295                 300

Pro Asp Ser Thr Leu Leu Gly Thr Phe Val Glu Asn His Asp Asn Pro
305                 310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
            340                 345                 350
```

```
Glu Gln His Tyr Ala Gly Gly Asn Asp Pro Ala Asn Arg Glu Ala Thr
            355                 360                 365

Trp Leu Ser Gly Tyr Pro Thr Asp Ser Glu Leu Tyr Lys Leu Ile Ala
370                 375                 380

Ser Ala Asn Ala Ile Arg Asn Tyr Ala Ile Ser Lys Asp Thr Gly Phe
385                 390                 395                 400

Val Thr Tyr Lys Asn Trp Pro Ile Tyr Lys Asp Asp Thr Thr Ile Ala
                405                 410                 415

Met Arg Lys Gly Thr Asp Gly Ser Gln Ile Val Thr Ile Leu Ser Asn
            420                 425                 430

Lys Gly Ala Ser Gly Asp Ser Tyr Thr Leu Ser Leu Ser Gly Ala Gly
            435                 440                 445

Tyr Thr Ala Gly Gln Gln Leu Thr Glu Val Ile Gly Cys Thr Thr Val
            450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser

<210> SEQ ID NO 3
<211> LENGTH: 515
<212> TYPE: PRT
<213> ORGANISM: Saccharomycopsis fibuligera

<400> SEQUENCE: 3

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
                20                  25                  30

Ala Tyr Ser Gly Tyr Thr Val Ala Arg Ser Asn Phe Thr Gln Trp Ile
            35                  40                  45

His Glu Gln Pro Ala Val Ser Trp Tyr Tyr Leu Leu Gln Asn Ile Asp
        50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
                100                 105                 110

Phe Ser Asn Thr Thr Leu Ala Lys Val Val Glu Tyr Tyr Ile Ser Asn
            115                 120                 125

Thr Tyr Thr Leu Gln Arg Val Ser Asn Pro Ser Gly Asn Phe Asp Ser
        130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
                180                 185                 190

Asn Gly Lys Leu Leu Leu Ala Gly Gln Asn Gly Ile Pro Tyr Ser Ser
            195                 200                 205

Ala Ser Asp Ile Tyr Trp Lys Ile Ile Lys Pro Asp Leu Gln His Val
        210                 215                 220
```

```
Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
            245                 250                 255

Gly Ile Pro Leu Ser Lys Thr Tyr Asn Asp Pro Gly Phe Thr Ser Trp
        260                 265                 270

Leu Glu Lys Gln Lys Asp Ala Leu Asn Ser Tyr Ile Asn Ser Ser Gly
    275                 280                 285

Phe Val Asn Ser Gly Lys Lys His Ile Val Glu Ser Pro Gln Leu Ser
290                 295                 300

Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
            325                 330                 335

Ser Tyr Val Leu Asn Ser Leu Tyr Tyr Leu Val Asp Asn Lys Asn
        340                 345                 350

Arg Tyr Lys Ile Asn Gly Asn Tyr Lys Ala Gly Ala Ala Val Gly Arg
    355                 360                 365

Tyr Pro Glu Asp Val Tyr Asn Gly Val Gly Thr Ser Glu Gly Asn Pro
370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
            405                 410                 415

Tyr Asp Leu Tyr Asn Ser Phe Ile Ala Asp Leu Ser Lys Ile Asp Ser
                420                 425                 430

Ser Tyr Ala Ser Lys Asp Ser Leu Thr Leu Thr Tyr Gly Ser Asp Asn
    435                 440                 445

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 4
<211> LENGTH: 551
<212> TYPE: PRT
<213> ORGANISM: Pseudomonas saccharophila

<400> SEQUENCE: 4

Met Ser His Ile Leu Arg Ala Ala Val Leu Ala Ala Val Leu Leu Pro
1               5                   10                  15

Phe Pro Ala Leu Ala Asp Gln Ala Gly Lys Ser Pro Ala Gly Val Arg
            20                  25                  30

Tyr His Gly Gly Asp Glu Ile Ile Leu Gln Gly Phe His Trp Asn Val
        35                  40                  45

Val Arg Glu Ala Pro Asn Asp Trp Tyr Asn Ile Leu Arg Gln Gln Ala
    50                  55                  60
```

```
Ser Thr Ile Ala Ala Asp Gly Phe Ser Ala Ile Trp Met Pro Val Pro
 65                  70                  75                  80

Trp Arg Asp Phe Ser Ser Trp Thr Asp Gly Lys Ser Gly Gly Gly
                 85                  90                  95

Glu Gly Tyr Phe Trp His Asp Phe Asn Lys Asn Gly Arg Tyr Gly Ser
                100                 105                 110

Asp Ala Gln Leu Arg Gln Ala Ala Gly Ala Leu Gly Gly Ala Gly Val
            115                 120                 125

Lys Val Leu Tyr Asp Val Val Pro Asn His Met Asn Arg Gly Tyr Pro
        130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Glu Ser Asp Leu Asn Thr Gly His Pro Gln Ile Tyr
                180                 185                 190

Gly Met Phe Arg Asp Glu Leu Ala Asn Leu Arg Ser Gly Tyr Gly Ala
            195                 200                 205

Gly Gly Phe Arg Phe Asp Phe Val Arg Gly Tyr Ala Pro Glu Arg Val
        210                 215                 220

Asp Ser Trp Met Ser Asp Ser Ala Asp Ser Ser Phe Cys Val Gly Glu
225                 230                 235                 240

Leu Trp Lys Gly Pro Ser Glu Tyr Pro Ser Trp Asp Trp Arg Asn Thr
                245                 250                 255

Ala Ser Trp Gln Gln Ile Ile Lys Asp Trp Ser Asp Arg Ala Lys Cys
                260                 265                 270

Pro Val Phe Asp Phe Ala Leu Lys Glu Arg Met Gln Asn Gly Ser Val
            275                 280                 285

Ala Asp Trp Lys His Gly Leu Asn Gly Asn Pro Asp Pro Arg Trp Arg
        290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
        355                 360                 365

Leu Ile Gln Val Arg Arg Thr Ala Gly Val Arg Ala Asp Ser Ala Ile
370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Ala Asn Pro Gly
                405                 410                 415

Gln Val Ala Ser Gly Ser Phe Ser Glu Ala Val Asn Ala Ser Asn Gly
            420                 425                 430

Gln Val Arg Val Trp Arg Ser Gly Ser Gly Asp Gly Gly Asn Asp
        435                 440                 445

Gly Gly Glu Gly Gly Leu Val Asn Val Asn Phe Arg Cys Asp Asn Gly
        450                 455                 460

Val Thr Gln Met Gly Asp Ser Val Tyr Ala Val Gly Asn Val Ser Gln
465                 470                 475                 480
```

Leu Gly Asn Trp Ser Pro Ala Ser Ala Val Arg Leu Thr Asp Thr Ser
                    485                 490                 495

Ser Tyr Pro Thr Trp Lys Gly Ser Ile Ala Leu Pro Asp Gly Gln Asn
                500                 505                 510

Val Glu Trp Lys Cys Leu Ile Arg Asn Glu Ala Asp Ala Thr Leu Val
            515                 520                 525

Arg Gln Trp Gln Ser Gly Gly Asn Asn Gln Val Gln Ala Ala Ala Gly
        530                 535                 540

Ala Ser Thr Ser Gly Ser Phe
545                 550

<210> SEQ ID NO 5
<211> LENGTH: 926
<212> TYPE: PRT
<213> ORGANISM: Bacillus naganoensis

<400> SEQUENCE: 5

Asp Gly Asn Thr Thr Asn Ile Val Val His Tyr Phe Arg Pro Ser Gly
1               5                   10                  15

Asp Tyr Thr Asp Trp Asn Leu Trp Met Trp Pro Glu Asn Gly Asp Gly
                20                  25                  30

Ala Glu Tyr Asp Phe Asn Gln Pro Thr Asp Ser Tyr Gly Glu Val Ala
            35                  40                  45

Ser Val Asp Ile Pro Gly Asn Pro Ser Gln Val Gly Ile Ile Val Arg
        50                  55                  60

Lys Gly Asn Trp Asp Ala Lys Asp Ile Asp Ser Asp Arg Tyr Ile Asp
65                  70                  75                  80

Leu Ser Lys Gly His Glu Ile Trp Leu Val Gln Gly Asn Ser Gln Ile
                85                  90                  95

Phe Tyr Ser Glu Lys Asp Ala Glu Ala Ala Gln Pro Ala Val Ser
                100                 105                 110

Asn Ala Tyr Leu Asp Ala Ser Asn Gln Val Leu Val Lys Leu Ser Gln
            115                 120                 125

Pro Phe Thr Leu Gly Glu Gly Ser Ser Gly Phe Thr Val His Asp Asp
        130                 135                 140

Thr Ala Asn Lys Asp Ile Pro Val Thr Ser Val Ser Asp Ala Asn Gln
145                 150                 155                 160

Val Thr Ala Val Leu Ala Gly Thr Phe Gln His Ile Phe Gly Gly Ser
                165                 170                 175

Asp Trp Ala Pro Asp Asn His Asn Thr Leu Leu Lys Lys Val Asn Ser
            180                 185                 190

Asn Leu Tyr Gln Phe Ser Gly Asn Leu Pro Glu Gly Asn Tyr Gln Tyr
        195                 200                 205

Lys Val Ala Leu Asn Asp Ser Trp Asn Asn Pro Ser Tyr Pro Ser Asp
    210                 215                 220

Asn Ile Asn Leu Thr Val Pro Ala Gly Gly Ala His Val Thr Phe Ser
225                 230                 235                 240

Tyr Ile Pro Ser Thr His Ala Val Tyr Asp Thr Ile Asn Asn Pro Asn
                245                 250                 255

Ala Asp Leu Gln Val Asp Ser Ser Gly Val Lys Thr Asp Leu Val Ala
            260                 265                 270

Val Thr Leu Gly Glu Asn Pro Asp Val Ser His Thr Leu Ser Ile Gln
        275                 280                 285

Thr Glu Asp Tyr Gln Ala Gly Gln Val Ile Pro Arg Lys Val Leu Asp
    290                 295                 300

-continued

Ser Ser Gln Tyr Tyr Tyr Ser Gly Asp Asp Leu Gly Asn Thr Tyr Thr
305                 310                 315                 320

Lys Asn Ala Thr Thr Phe Lys Val Trp Ala Pro Thr Ser Thr Gln Val
            325                 330                 335

Asn Val Leu Leu Tyr Asn Ser Ala Thr Gly Ala Val Thr Lys Thr Val
                340                 345                 350

Pro Met Thr Ala Ser Gly His Gly Val Trp Glu Ala Thr Val Asn Gln
            355                 360                 365

Asp Leu Glu Asn Trp Tyr Tyr Met Tyr Glu Val Thr Gly Gln Gly Ser
        370                 375                 380

Thr Arg Thr Ala Val Asp Pro Tyr Ala Thr Ala Ile Ala Pro Asn Gly
385                 390                 395                 400

Thr Arg Gly Met Ile Val Asp Leu Ala Lys Thr Asp Pro Ala Gly Trp
                405                 410                 415

Glu Ser Asp Lys His Ile Thr Pro Lys Asn Ile Glu Asp Glu Val Ile
            420                 425                 430

Tyr Glu Met Asp Val Arg Asp Phe Ser Ile Asp Ser Asn Ser Gly Met
        435                 440                 445

Lys Asn Lys Gly Lys Tyr Leu Ala Leu Thr Glu Lys Gly Thr Lys Gly
450                 455                 460

Pro Asp Asn Val Lys Thr Gly Val Asp Ser Leu Lys Gln Leu Gly Ile
465                 470                 475                 480

Thr His Val Gln Leu Gln Pro Val Phe Ala Phe Asn Ser Val Asn Glu
            485                 490                 495

Asn Asp Pro Thr Gln Tyr Asn Trp Gly Tyr Asp Pro Arg Asn Tyr Asn
            500                 505                 510

Val Pro Glu Gly Gln Tyr Ala Thr Asn Ala Asn Gly Thr Thr Arg Ile
        515                 520                 525

Lys Glu Phe Lys Glu Met Val Leu Ser Leu His Gln Asp His Ile Gly
530                 535                 540

Val Asn Met Asp Val Val Tyr Asn His Thr Phe Ala Thr Gln Ile Ser
545                 550                 555                 560

Asp Phe Asp Lys Ile Val Pro Glu Tyr Tyr Tyr Arg Thr Asp Asp Ala
            565                 570                 575

Gly Asn Tyr Thr Asn Gly Ser Gly Thr Gly Asn Glu Ile Ala Ala Glu
            580                 585                 590

Arg Pro Met Val Gln Lys Phe Ile Ile Asp Ser Leu Lys Phe Trp Val
        595                 600                 605

Asn Glu Tyr His Val Asp Gly Phe Arg Phe Asp Leu Met Ala Leu Leu
        610                 615                 620

Gly Lys Asp Thr Met Ser Lys Ala Ala Thr Gln Leu His Ala Ile Asp
625                 630                 635                 640

Pro Gly Ile Ala Leu Tyr Gly Glu Pro Trp Thr Gly Gly Thr Ser Ala
                645                 650                 655

Leu Pro Ala Asp Gln Leu Leu Thr Lys Gly Ala Gln Lys Gly Met Gly
            660                 665                 670

Val Ala Val Phe Asn Asp Asn Leu Arg Asn Gly Leu Asp Gly Ser Val
            675                 680                 685

Phe Asp Ser Ser Ala Gln Gly Phe Ala Thr Gly Ala Thr Gly Leu Thr
        690                 695                 700

Asp Ala Ile Lys Asn Gly Val Glu Gly Ser Ile Asn Asp Phe Thr Ala
705                 710                 715                 720

Ser Pro Gly Glu Thr Ile Asn Tyr Val Thr Ser His Asp Asn Tyr Thr
                725                 730                 735

Leu Trp Asp Lys Ile Ala Gln Ser Asn Pro Asn Asp Ser Glu Ala Asp
            740                 745                 750

Arg Ile Lys Met Asp Glu Leu Ala Gln Ala Ile Val Met Thr Ser Gln
        755                 760                 765

Gly Ile Pro Phe Met Gln Gly Glu Glu Met Leu Arg Thr Lys Gly
    770                 775                 780

Gly Asn Asp Asn Ser Tyr Asn Ala Gly Asp Val Val Asn Glu Phe Asp
785                 790                 795                 800

Trp Ser Arg Lys Ala Gln Tyr Pro Asp Val Phe Asn Tyr Tyr Ser Gly
            805                 810                 815

Leu Ile His Leu Arg Leu Asp His Pro Ala Phe Arg Met Thr Thr Ala
        820                 825                 830

Asn Glu Ile Asn Ser His Leu Gln Phe Leu Asn Ser Pro Glu Asn Thr
    835                 840                 845

Val Ala Tyr Glu Leu Ser Asp His Ala Asn Lys Asp Thr Trp Gly Asn
850                 855                 860

Ile Val Val Ile Tyr Asn Pro Asn Lys Thr Ala Glu Thr Ile Asn Leu
865                 870                 875                 880

Pro Ser Gly Lys Trp Glu Ile Asn Ala Thr Ser Gly Lys Val Gly Glu
            885                 890                 895

Ser Thr Leu Gly Gln Ala Glu Gly Ser Val Gln Val Pro Gly Ile Ser
        900                 905                 910

Met Met Ile Leu His Gln Glu Val Ser Pro Ser Asp Gly Lys
    915                 920                 925

<210> SEQ ID NO 6
<211> LENGTH: 829
<212> TYPE: PRT
<213> ORGANISM: Bacillus acidopullulyticus

<400> SEQUENCE: 6

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Thr Ser Asp Asp Leu His
65              70                  75                  80

Ile Asp Leu Thr Lys Gly His Glu Ile Trp Ile Val Gln Gly Asp Pro
            85                  90                  95

Asn Ile Tyr Tyr Asn Leu Ser Asp Ala Gln Ala Ala Thr Pro Lys
        100                 105                 110

Val Ser Asn Ala Tyr Leu Asp Asn Glu Lys Thr Val Leu Ala Lys Leu
    115                 120                 125

Thr Asn Pro Met Thr Leu Ser Asp Gly Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
            165                 170                 175

```
Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
            195                 200                 205

Tyr Tyr Tyr Ser Gly Asn Asp Leu Gly Asn Val Tyr Ser Asn Lys Ala
        210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
                245                 250                 255

Lys Ser Asp Asn Gly Thr Trp Lys Leu Lys Val Pro Gly Asn Leu Lys
                260                 265                 270

Asn Trp Tyr Tyr Leu Tyr Gln Val Thr Val Asn Gly Lys Thr Gln Thr
            275                 280                 285

Ala Val Asp Pro Tyr Val Arg Ala Ile Ser Val Asn Ala Thr Arg Gly
            290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
                340                 345                 350

Gly Lys Tyr Leu Ala Phe Thr Glu His Gly Thr Lys Gly Pro Asp Asn
            355                 360                 365

Val Lys Thr Gly Ile Asp Ser Leu Lys Glu Leu Gly Ile Asn Ala Val
            370                 375                 380

Gln Leu Gln Pro Ile Glu Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
            435                 440                 445

Asp Val Val Tyr Asn His Thr Phe Asn Val Gly Val Ser Asp Phe Asp
450                 455                 460

Lys Ile Val Pro Gln Tyr Tyr Arg Thr Asp Ser Ala Gly Asn Tyr
465                 470                 475                 480

Thr Asn Gly Ser Gly Val Gly Asn Glu Ile Ala Thr Glu Arg Pro Met
            485                 490                 495

Val Gln Lys Phe Val Leu Asp Ser Val Lys Tyr Trp Val Lys Glu Tyr
            500                 505                 510

His Ile Asp Gly Phe Arg Phe Asp Leu Met Ala Leu Leu Gly Lys Asp
            515                 520                 525

Thr Met Ala Lys Ile Ser Lys Glu Leu His Ala Ile Asn Pro Gly Ile
            530                 535                 540

Val Leu Tyr Gly Glu Pro Trp Thr Gly Gly Thr Ser Gly Leu Ser Ser
545                 550                 555                 560

Asp Gln Leu Val Thr Lys Gly Gln Gln Lys Gly Leu Gly Ile Gly Val
                565                 570                 575

Phe Asn Asp Asn Ile Arg Asn Gly Leu Asp Gly Asn Val Phe Asp Lys
            580                 585                 590
```

```
Ser Ala Gln Gly Phe Ala Thr Gly Asp Pro Asn Gln Val Asn Val Ile
            595                 600                 605

Lys Asn Arg Val Met Gly Ser Ile Ser Asp Phe Thr Ser Ala Pro Ser
610                 615                 620

Glu Thr Ile Asn Tyr Val Thr Ser His Asp Asn Met Thr Leu Trp Asp
625                 630                 635                 640

Lys Ile Ser Ala Ser Asn Pro Asn Asp Thr Gln Ala Asp Arg Ile Lys
                645                 650                 655

Met Asp Glu Leu Ala Gln Ala Val Val Phe Thr Ser Gln Gly Val Pro
            660                 665                 670

Phe Met Gln Gly Gly Glu Glu Met Leu Arg Thr Lys Gly Gly Asn Asp
        675                 680                 685

Asn Ser Tyr Asn Ala Gly Asp Ser Val Asn Gln Phe Asp Trp Ser Arg
690                 695                 700

Lys Ala Gln Phe Glu Asn Val Phe Asp Tyr Tyr Ser Trp Leu Ile His
705                 710                 715                 720

Leu Arg Asp Asn His Pro Ala Phe Arg Met Thr Thr Ala Asp Gln Ile
                725                 730                 735

Lys Gln Asn Leu Thr Phe Leu Asp Ser Pro Thr Asn Thr Val Ala Phe
            740                 745                 750

Glu Leu Lys Asn His Ala Asn His Asp Lys Trp Lys Asn Ile Ile Val
        755                 760                 765

Met Tyr Asn Pro Asn Lys Thr Ala Gln Thr Leu Thr Leu Pro Ser Gly
770                 775                 780

Asn Trp Thr Ile Val Gly Leu Gly Asn Gln Val Gly Glu Lys Ser Leu
785                 790                 795                 800

Gly His Val Asn Gly Thr Val Glu Val Pro Ala Leu Ser Thr Ile Ile
                805                 810                 815

Leu His Gln Gly Thr Ser Glu Asp Val Ile Asp Gln Asn
            820                 825

<210> SEQ ID NO 7
<211> LENGTH: 776
<212> TYPE: PRT
<213> ORGANISM: Pseudomonas amyloderamosa

<400> SEQUENCE: 7

Met Lys Cys Pro Lys Ile Leu Ala Ala Leu Leu Gly Cys Ala Val Leu
1               5                   10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
        35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ile Lys Ala Ala Gly Ile
                85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Phe Val Ser
        115                 120                 125

Asp Val Asp Ala Asn Gly Asp Arg Phe Asn Pro Asn Lys Leu Leu Leu
    130                 135                 140
```

```
Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
            165                 170                 175

Ser Gly Ile Tyr Ala Pro Lys Gly Val Val Val Pro Ser Thr Gln
        180                 185                 190

Ser Thr Gly Thr Lys Pro Thr Arg Ala Gln Lys Asp Asp Val Ile Tyr
        195                 200                 205

Glu Val His Val Arg Gly Phe Thr Glu Gln Asp Thr Ser Ile Pro Ala
        210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
            245                 250                 255

Gln Asn Asp Ala Asn Asp Val Val Pro Asn Ser Asp Ala Asn Gln Asn
            260                 265                 270

Tyr Trp Gly Tyr Met Thr Glu Asn Tyr Phe Ser Pro Asp Arg Arg Tyr
        275                 280                 285

Ala Tyr Asn Lys Ala Ala Gly Gly Pro Thr Ala Glu Phe Gln Ala Met
290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
            325                 330                 335

Thr Ala Thr Ile Tyr Ser Trp Arg Gly Leu Asp Asn Ala Thr Tyr Tyr
        340                 345                 350

Glu Leu Thr Ser Gly Asn Gln Tyr Phe Tyr Asp Asn Thr Gly Ile Gly
        355                 360                 365

Ala Asn Phe Asn Thr Tyr Asn Thr Val Ala Gln Asn Leu Ile Val Asp
        370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
            405                 410                 415

Ala Ser Ala Pro Asn Cys Pro Asn Gly Gly Tyr Asn Phe Asp Ala Ala
            420                 425                 430

Asp Ser Asn Val Ala Ile Asn Arg Ile Leu Arg Glu Phe Thr Val Arg
        435                 440                 445

Pro Ala Ala Gly Gly Ser Gly Leu Asp Leu Phe Ala Glu Pro Trp Ala
        450                 455                 460

Ile Gly Gly Asn Ser Tyr Gln Leu Gly Gly Phe Pro Gln Gly Trp Ser
465                 470                 475                 480

Glu Trp Asn Gly Leu Phe Arg Asp Ser Leu Arg Gln Ala Gln Asn Glu
            485                 490                 495

Leu Gly Ser Met Thr Ile Tyr Val Thr Gln Asp Ala Asn Asp Phe Ser
            500                 505                 510

Gly Ser Ser Asn Leu Phe Gln Ser Ser Gly Arg Ser Pro Trp Asn Ser
        515                 520                 525

Ile Asn Phe Ile Asp Val His Asp Gly Met Thr Leu Lys Asp Val Tyr
        530                 535                 540

Ser Cys Asn Gly Ala Asn Asn Ser Gln Ala Trp Pro Tyr Gly Pro Ser
545                 550                 555                 560
```

```
Asp Gly Gly Thr Ser Thr Asn Tyr Ser Trp Asp Gln Gly Met Ser Ala
            565                 570                 575

Gly Thr Gly Ala Ala Val Asp Gln Arg Arg Ala Ala Arg Thr Gly Met
        580                 585                 590

Ala Phe Glu Met Leu Ser Ala Gly Thr Pro Leu Met Gln Gly Gly Asp
        595                 600                 605

Glu Tyr Leu Arg Thr Leu Gln Cys Asn Asn Asn Ala Tyr Asn Leu Asp
        610                 615                 620

Ser Ser Ala Asn Trp Leu Thr Tyr Ser Trp Thr Asp Gln Ser Asn
625                 630                 635                 640

Phe Tyr Thr Phe Ala Gln Arg Leu Ile Ala Phe Arg Lys Ala His Pro
        645                 650                 655

Ala Leu Arg Pro Ser Ser Trp Tyr Ser Gly Ser Gln Leu Thr Trp Tyr
        660                 665                 670

Gln Pro Ser Gly Ala Val Ala Asp Ser Asn Tyr Trp Asn Asn Thr Ser
        675                 680                 685

Asn Tyr Ala Ile Ala Tyr Ala Ile Asn Gly Pro Ser Leu Gly Asp Ser
        690                 695                 700

Asn Ser Ile Tyr Val Ala Tyr Asn Gly Trp Ser Ser Val Thr Phe
705                 710                 715                 720

Thr Leu Pro Ala Pro Pro Ser Gly Thr Gln Trp Tyr Arg Val Thr Asp
        725                 730                 735

Thr Cys Asp Trp Asn Asp Gly Ala Ser Thr Phe Val Ala Pro Gly Ser
        740                 745                 750

Glu Thr Leu Ile Gly Gly Ala Gly Thr Thr Tyr Gly Gln Cys Gly Gln
        755                 760                 765

Ser Leu Leu Leu Leu Ile Ser Lys
770                 775

<210> SEQ ID NO 8
<211> LENGTH: 500
<212> TYPE: PRT
<213> ORGANISM: Thermus thermophilus

<400> SEQUENCE: 8

Met Glu Leu Pro Arg Ala Phe Gly Leu Leu His Pro Thr Ser Leu
1                 5                  10                  15

Pro Gly Pro Tyr Gly Val Gly Val Leu Gly Gln Glu Ala Arg Asp Phe
        20                  25                  30

Leu Arg Phe Leu Lys Glu Ala Gly Gly Arg Tyr Trp Gln Val Leu Pro
        35                  40                  45

Leu Gly Pro Thr Gly Tyr Gly Asp Ser Pro Tyr Gln Ser Phe Ser Ala
    50                  55                  60

Phe Ala Gly Asn Pro Tyr Leu Ile Asp Leu Arg Pro Leu Ala Glu Arg
65                  70                  75                  80

Gly Tyr Val Arg Leu Glu Asp Pro Gly Phe Pro Gln Gly Arg Val Asp
                85                  90                  95

Tyr Gly Leu Leu Tyr Ala Trp Lys Trp Pro Ala Leu Lys Glu Ala Phe
            100                 105                 110

Arg Gly Phe Lys Glu Lys Ala Ser Pro Glu Glu Arg Glu Ala Phe Ala
        115                 120                 125

Ala Phe Arg Glu Arg Glu Ala Trp Trp Leu Glu Asp Tyr Ala Leu Phe
    130                 135                 140

Met Ala Leu Lys Gly Ala His Gly Gly Leu Pro Trp Asn Arg Trp Pro
145                 150                 155                 160
```

```
Leu Pro Leu Arg Lys Arg Glu Lys Ala Leu Arg Glu Ala Lys Ser
            165                 170                 175

Ala Leu Ala Glu Glu Val Ala Phe His Ala Phe Thr Gln Trp Leu Phe
        180                 185                 190

Phe Arg Gln Trp Gly Ala Leu Lys Ala Glu Ala Glu Ala Leu Gly Ile
        195                 200                 205

Arg Ile Ile Gly Asp Met Pro Ile Phe Val Ala Glu Asp Ser Ala Glu
    210                 215                 220

Val Trp Ala His Pro Glu Trp Phe His Leu Asp Glu Gly Arg Pro
225                 230                 235                 240

Thr Val Val Ala Gly Val Pro Pro Asp Tyr Phe Ser Glu Thr Gly Gln
                245                 250                 255

Arg Trp Gly Asn Pro Leu Tyr Arg Trp Asp Val Leu Gly Arg Glu Gly
            260                 265                 270

Phe Ser Phe Trp Ile Arg Arg Leu Glu Lys Ala Leu Glu Leu Phe His
        275                 280                 285

Leu Val Arg Ile Asp His Phe Arg Gly Phe Glu Ala Tyr Trp Glu Ile
    290                 295                 300

Pro Ala Ser Cys Pro Thr Ala Val Glu Gly Arg Trp Val Lys Ala Pro
305                 310                 315                 320

Gly Glu Lys Leu Phe Gln Lys Ile Gln Glu Val Phe Gly Val Pro
                325                 330                 335

Val Leu Ala Glu Asp Leu Gly Val Ile Thr Pro Glu Val Glu Ala Leu
                340                 345                 350

Arg Asp Arg Phe Gly Leu Pro Gly Met Lys Val Leu Gln Phe Ala Phe
            355                 360                 365

Asp Asp Gly Met Glu Asn Pro Phe Leu Pro His Asn Tyr Pro Ala His
    370                 375                 380

Gly Arg Val Val Val Tyr Thr Gly Thr His Asp Asn Asp Thr Thr Leu
385                 390                 395                 400

Gly Trp Tyr Arg Thr Ala Thr Pro His Glu Lys Ala Phe Met Ala Arg
                405                 410                 415

Tyr Leu Ala Asp Trp Gly Ile Thr Phe Arg Glu Glu Glu Val Pro
                420                 425                 430

Trp Ala Leu Met His Leu Gly Met Lys Ser Val Ala Arg Leu Ala Val
        435                 440                 445

Tyr Pro Val Gln Asp Val Leu Ala Leu Gly Ser Glu Ala Arg Met Asn
    450                 455                 460

Tyr Pro Gly Arg Pro Ser Gly Asn Trp Ala Trp Arg Leu Leu Pro Gly
465                 470                 475                 480

Glu Leu Ser Pro Glu His Gly Ala Arg Leu Arg Ala Met Ala Glu Ala
                485                 490                 495

Thr Glu Arg Leu
            500

<210> SEQ ID NO 9
<211> LENGTH: 1641
<212> TYPE: DNA
<213> ORGANISM: Artificial Sequence
<220> FEATURE:
<223> OTHER INFORMATION: Flo1 tether
<220> FEATURE:
<221> NAME/KEY: CDS
<222> LOCATION: (1)..(1641)
```

<400> SEQUENCE: 9

| | | | | | | | | | | | | | | | | |
|---|---|---|---|---|---|---|---|---|---|---|---|---|---|---|---|---|
| aag | gac | aat | agc | tcg | acg | att | gaa | ggt | aga | tac | cca | tac | gac | gtt | cca | 48 |
| Lys | Asp | Asn | Ser | Ser | Thr | Ile | Glu | Gly | Arg | Tyr | Pro | Tyr | Asp | Val | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | tac | gct | ctg | cag | gct | agt | ggt | ggt | ggt | ggt | tct | ggt | ggt | ggt | ggt | 96 |
| Asp | Tyr | Ala | Leu | Gln | Ala | Ser | Gly | Gly | Gly | Gly | Ser | Gly | Gly | Gly | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| tct | ggt | ggt | ggt | ggt | tct | gct | agc | atc | aga | act | cca | acc | agt | gaa | ggt | 144 |
| Ser | Gly | Gly | Gly | Gly | Ser | Ala | Ser | Ile | Arg | Thr | Pro | Thr | Ser | Glu | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| ttg | gtt | aca | acc | acc | act | gaa | cca | tgg | act | ggt | act | ttt | act | tcg | act | 192 |
| Leu | Val | Thr | Thr | Thr | Thr | Glu | Pro | Trp | Thr | Gly | Thr | Phe | Thr | Ser | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| tcc | act | gaa | atg | tct | act | gtc | act | gga | acc | aat | ggc | ttg | cca | act | gat | 240 |
| Ser | Thr | Glu | Met | Ser | Thr | Val | Thr | Gly | Thr | Asn | Gly | Leu | Pro | Thr | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gaa | act | gtc | att | gtt | gtc | aaa | act | cca | act | act | gcc | atc | tca | tcc | agt | 288 |
| Glu | Thr | Val | Ile | Val | Val | Lys | Thr | Pro | Thr | Thr | Ala | Ile | Ser | Ser | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ttg | tca | tca | tca | tct | tca | gga | caa | atc | acc | agc | tct | atc | acg | tct | tcg | 336 |
| Leu | Ser | Ser | Ser | Ser | Ser | Gly | Gln | Ile | Thr | Ser | Ser | Ile | Thr | Ser | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| cgt | cca | att | att | acc | cca | ttc | tat | cct | agc | aat | gga | act | tct | gtg | att | 384 |
| Arg | Pro | Ile | Ile | Thr | Pro | Phe | Tyr | Pro | Ser | Asn | Gly | Thr | Ser | Val | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| tct | tcc | tca | gta | att | tct | tcc | tca | gtc | act | tct | tct | cta | ttc | act | tct | 432 |
| Ser | Ser | Ser | Val | Ile | Ser | Ser | Ser | Val | Thr | Ser | Ser | Leu | Phe | Thr | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| tct | cca | gtc | att | tct | tcc | tca | gtc | att | tct | tct | tct | aca | aca | acc | tcc | 480 |
| Ser | Pro | Val | Ile | Ser | Ser | Ser | Val | Ile | Ser | Ser | Ser | Thr | Thr | Thr | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| act | tct | ata | ttt | tct | gaa | tca | tct | aaa | tca | tcc | gtc | att | cca | acc | agt | 528 |
| Thr | Ser | Ile | Phe | Ser | Glu | Ser | Ser | Lys | Ser | Ser | Val | Ile | Pro | Thr | Ser | |
| | | | 165 | | | | | 170 | | | | | 175 | | | |

| | | | | | | | | | | | | | | | | |
|---|---|---|---|---|---|---|---|---|---|---|---|---|---|---|---|---|
| agt | tcc | acc | tct | ggt | tct | tct | gag | agc | gaa | acg | agt | tca | gct | ggt | tct | 576 |
| Ser | Ser | Thr | Ser | Gly | Ser | Ser | Glu | Ser | Glu | Thr | Ser | Ser | Ala | Gly | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | tct | tct | tcc | tct | ttt | atc | tct | tct | gaa | tca | tca | aaa | tct | cct | aca | 624 |
| Val | Ser | Ser | Ser | Ser | Phe | Ile | Ser | Ser | Glu | Ser | Ser | Lys | Ser | Pro | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| tat | tct | tct | tca | tca | tta | cca | ctt | gtt | acc | agt | gcg | aca | aca | agc | cag | 672 |
| Tyr | Ser | Ser | Ser | Ser | Leu | Pro | Leu | Val | Thr | Ser | Ala | Thr | Thr | Ser | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| gaa | act | gct | tct | tca | tta | cca | cct | gct | acc | act | aca | aaa | acg | agc | gaa | 720 |
| Glu | Thr | Ala | Ser | Ser | Leu | Pro | Pro | Ala | Thr | Thr | Thr | Lys | Thr | Ser | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | acc | act | ttg | gtt | acc | gtg | aca | tcc | tgc | gag | tct | cat | gtg | tgc | act | 768 |
| Gln | Thr | Thr | Leu | Val | Thr | Val | Thr | Ser | Cys | Glu | Ser | His | Val | Cys | Thr | |
| | | | 245 | | | | | 250 | | | | | 255 | | | |

| | | | | | | | | | | | | | | | | |
|---|---|---|---|---|---|---|---|---|---|---|---|---|---|---|---|---|
| gaa | tcc | atc | tcc | cct | gcg | att | gtt | tcc | aca | gct | act | gtt | act | gtt | agc | 816 |
| Glu | Ser | Ile | Ser | Pro | Ala | Ile | Val | Ser | Thr | Ala | Thr | Val | Thr | Val | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| ggc | gtc | aca | aca | gag | tat | acc | aca | tgg | tgc | cct | att | tct | act | aca | gag | 864 |
| Gly | Val | Thr | Thr | Glu | Tyr | Thr | Thr | Trp | Cys | Pro | Ile | Ser | Thr | Thr | Glu | |
| | | | 275 | | | | | 280 | | | | | 285 | | | |

| | | | | | | | | | | | | | | | | |
|---|---|---|---|---|---|---|---|---|---|---|---|---|---|---|---|---|
| aca | aca | aag | caa | acc | aaa | ggg | aca | aca | gag | caa | acc | aca | gaa | aca | aca | 912 |
| Thr | Thr | Lys | Gln | Thr | Lys | Gly | Thr | Thr | Glu | Gln | Thr | Thr | Glu | Thr | Thr | |
| | 290 | | | | | 295 | | | | | 300 | | | | | |

```
aaa caa acc acg gta gtt aca att tct tct tgt gaa tct gac gta tgc    960
Lys Gln Thr Thr Val Val Thr Ile Ser Ser Cys Glu Ser Asp Val Cys
305                 310                 315                 320 tct aag act gct tct cca gcc att gta tct aca agc act gct act att   1008
Ser Lys Thr Ala Ser Pro Ala Ile Val Ser Thr Ser Thr Ala Thr Ile
                325                 330                 335 aac ggc gtt act aca gaa tac aca aca tgg tgt cct att tcc acc aca   1056
Asn Gly Val Thr Thr Glu Tyr Thr Thr Trp Cys Pro Ile Ser Thr Thr
            340                 345                 350 gaa tcg agg caa caa aca acg cta gtt act gtt act tcc tgc gaa tct   1104
Glu Ser Arg Gln Gln Thr Thr Leu Val Thr Val Thr Ser Cys Glu Ser
        355                 360                 365 ggt gtg tgt tcc gaa act gct tca cct gcc att gtt tcg acg gcc acg   1152
Gly Val Cys Ser Glu Thr Ala Ser Pro Ala Ile Val Ser Thr Ala Thr
    370                 375                 380 gct act gtg aat gat gtt gtt acg gtc tat cct aca tgg agg cca cag   1200
Ala Thr Val Asn Asp Val Val Thr Val Tyr Pro Thr Trp Arg Pro Gln
385                 390                 395                 400 act gcg aat gaa gag tct gtc agc tct aaa atg aac agt gct acc ggt   1248
Thr Ala Asn Glu Glu Ser Val Ser Ser Lys Met Asn Ser Ala Thr Gly
                405                 410                 415 gag aca aca acc aat act tta gct gct gaa acg act acc aat act gta   1296
Glu Thr Thr Thr Asn Thr Leu Ala Ala Glu Thr Thr Thr Asn Thr Val
            420                 425                 430 gct gct gag acg att acc aat act gga gct gct gag acg aaa aca gta   1344
Ala Ala Glu Thr Ile Thr Asn Thr Gly Ala Ala Glu Thr Lys Thr Val
        435                 440                 445 gtc acc tct tcg ctt tca aga tct aat cac gct gaa aca cag acg gct   1392
Val Thr Ser Ser Leu Ser Arg Ser Asn His Ala Glu Thr Gln Thr Ala
    450                 455                 460 tcc gcg acc gat gtg att ggt cac agc agt agt gtt gtt tct gta tcc   1440
Ser Ala Thr Asp Val Ile Gly His Ser Ser Ser Val Val Ser Val Ser
465                 470                 475                 480 gaa act ggc aac acc aag agt cta aca agt tcc ggg ttg agt act atg   1488
Glu Thr Gly Asn Thr Lys Ser Leu Thr Ser Ser Gly Leu Ser Thr Met
                485                 490                 495 tcg caa cag cct cgt agc aca cca gca agc agc atg gta gga tat agt   1536
Ser Gln Gln Pro Arg Ser Thr Pro Ala Ser Ser Met Val Gly Tyr Ser
            500                 505                 510 aca gct tct tta gaa att tca acg tat gct ggc agt gcc aac agc tta   1584
Thr Ala Ser Leu Glu Ile Ser Thr Tyr Ala Gly Ser Ala Asn Ser Leu
        515                 520                 525 ctg gcc ggt agt ggt tta agt gtc ttc att gcg tcc tta ttg ctg gca   1632
Leu Ala Gly Ser Gly Leu Ser Val Phe Ile Ala Ser Leu Leu Leu Ala
    530                 535                 540 att att taa                                                       1641
Ile Ile
545
```

<210> SEQ ID NO 10
<211> LENGTH: 546
<212> TYPE: PRT
<213> ORGANISM: Artificial Sequence
<220> FEATURE:
<223> OTHER INFORMATION: Synthetic Construct

<400> SEQUENCE: 10

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Gly Ser Gly Gly Gly Gly
            20                  25                  30
```

-continued

```
Ser Gly Gly Gly Gly Ser Ala Ser Ile Arg Thr Pro Thr Ser Glu Gly
            35              40              45

Leu Val Thr Thr Thr Thr Glu Pro Trp Thr Gly Thr Phe Thr Ser Thr
 50              55              60

Ser Thr Glu Met Ser Thr Val Thr Gly Thr Asn Gly Leu Pro Thr Asp
 65              70              75              80

Glu Thr Val Ile Val Lys Thr Pro Thr Thr Ala Ile Ser Ser Ser
                85              90              95

Leu Ser Ser Ser Ser Ser Gly Gln Ile Thr Ser Ser Ile Thr Ser Ser
            100             105             110

Arg Pro Ile Ile Thr Pro Phe Tyr Pro Ser Asn Gly Thr Ser Val Ile
            115             120             125

Ser Ser Ser Val Ile Ser Ser Ser Val Thr Ser Ser Leu Phe Thr Ser
            130             135             140

Ser Pro Val Ile Ser Ser Ser Val Ile Ser Ser Thr Thr Thr Ser
145             150             155             160

Thr Ser Ile Phe Ser Glu Ser Ser Lys Ser Ser Val Ile Pro Thr Ser
                165             170             175

Ser Ser Thr Ser Gly Ser Ser Glu Ser Glu Thr Ser Ser Ala Gly Ser
            180             185             190

Val Ser Ser Ser Phe Ile Ser Ser Glu Ser Ser Lys Ser Pro Thr
            195             200             205

Tyr Ser Ser Ser Leu Pro Leu Val Thr Ala Thr Thr Ser Gln
            210             215             220

Glu Thr Ala Ser Ser Leu Pro Pro Ala Thr Thr Lys Thr Ser Glu
225             230             235             240

Gln Thr Thr Leu Val Thr Val Thr Ser Cys Glu Ser His Val Cys Thr
                245             250             255

Glu Ser Ile Ser Pro Ala Ile Val Ser Thr Ala Thr Val Thr Val Ser
            260             265             270

Gly Val Thr Thr Glu Tyr Thr Thr Trp Cys Pro Ile Ser Thr Thr Glu
            275             280             285

Thr Thr Lys Gln Thr Lys Gly Thr Thr Glu Gln Thr Thr Glu Thr Thr
            290             295             300

Lys Gln Thr Thr Val Val Thr Ile Ser Ser Cys Glu Ser Asp Val Cys
305             310             315             320

Ser Lys Thr Ala Ser Pro Ala Ile Val Ser Thr Ser Thr Ala Thr Ile
            325             330             335

Asn Gly Val Thr Thr Glu Tyr Thr Thr Trp Cys Pro Ile Ser Thr Thr
            340             345             350

Glu Ser Arg Gln Gln Thr Thr Leu Val Thr Val Thr Ser Cys Glu Ser
            355             360             365

Gly Val Cys Ser Glu Thr Ala Ser Pro Ala Ile Val Ser Thr Ala Thr
            370             375             380

Ala Thr Val Asn Asp Val Val Thr Val Tyr Pro Thr Trp Arg Pro Gln
385             390             395             400

Thr Ala Asn Glu Glu Ser Val Ser Ser Lys Met Asn Ser Ala Thr Gly
            405             410             415

Glu Thr Thr Thr Asn Thr Leu Ala Ala Glu Thr Thr Asn Thr Val
            420             425             430

Ala Ala Glu Thr Ile Thr Asn Thr Gly Ala Ala Glu Thr Lys Thr Val
            435             440             445
```

-continued

```
Val Thr Ser Ser Leu Ser Arg Ser Asn His Ala Glu Thr Gln Thr Ala
    450                 455                 460

Ser Ala Thr Asp Val Ile Gly His Ser Ser Val Val Ser Val Ser
465                 470                 475                 480

Glu Thr Gly Asn Thr Lys Ser Leu Thr Ser Ser Gly Leu Ser Thr Met
                485                 490                 495

Ser Gln Gln Pro Arg Ser Thr Pro Ala Ser Ser Met Val Gly Tyr Ser
            500                 505                 510

Thr Ala Ser Leu Glu Ile Ser Thr Tyr Ala Gly Ser Ala Asn Ser Leu
        515                 520                 525

Leu Ala Gly Ser Gly Leu Ser Val Phe Ile Ala Ser Leu Leu Leu Ala
    530                 535                 540

Ile Ile
545

<210> SEQ ID NO 11
<211> LENGTH: 807
<212> TYPE: DNA
<213> ORGANISM: Artificial Sequence
<220> FEATURE:
<223> OTHER INFORMATION: Sed1 tether
<220> FEATURE:
<221> NAME/KEY: CDS
<222> LOCATION: (1)..(807)

<400> SEQUENCE: 11 aag gac aat agc tcg acg att gaa ggt aga tac cca tac gac gtt cca       48
Lys Asp Asn Ser Ser Thr Ile Glu Gly Arg Tyr Pro Tyr Asp Val Pro
1               5                   10                  15 gac tac gct ctg cag gct agt ggt ggt ggt ggt tct ggt ggt ggt ggt       96
Asp Tyr Ala Leu Gln Ala Ser Gly Gly Gly Gly Ser Gly Gly Gly Gly
            20                  25                  30 tct ggt ggt ggt ggt tct gct agc gct ctt cca act aac ggt act tct      144
Ser Gly Gly Gly Gly Ser Ala Ser Ala Leu Pro Thr Asn Gly Thr Ser
        35                  40                  45 act gaa gct cca act gat act act act gaa gct cca acc acc ggt ctt      192
Thr Glu Ala Pro Thr Asp Thr Thr Thr Glu Ala Pro Thr Thr Gly Leu
    50                  55                  60 cca acc aac ggt acc act tca gct ttc cca cca act aca tct ttg cca      240
Pro Thr Asn Gly Thr Thr Ser Ala Phe Pro Pro Thr Thr Ser Leu Pro
65                  70                  75                  80 cca agc aac act acc acc act cct cct tac aac cca tct act gac tac      288
Pro Ser Asn Thr Thr Thr Thr Pro Pro Tyr Asn Pro Ser Thr Asp Tyr
                85                  90                  95 acc act gac tac act gta gtc act gaa tat act act tac tgt cca gaa      336
Thr Thr Asp Tyr Thr Val Val Thr Glu Tyr Thr Thr Tyr Cys Pro Glu
            100                 105                 110 cca acc act ttc acc aca aac ggt aag act tac acc gtc act gaa cca      384
Pro Thr Thr Phe Thr Thr Asn Gly Lys Thr Tyr Thr Val Thr Glu Pro
        115                 120                 125 acc aca ttg act atc act gac tgt cca tgc acc att gaa aag cca aca      432
Thr Thr Leu Thr Ile Thr Asp Cys Pro Cys Thr Ile Glu Lys Pro Thr
    130                 135                 140 acc aca tca acc acc gaa tac act gta gtc act gag tac act act tac      480
Thr Thr Ser Thr Thr Glu Tyr Thr Val Val Thr Glu Tyr Thr Thr Tyr
145                 150                 155                 160 tgt cca gaa cca acc act ttc acc aca aac ggt aag act tac acc gtc      528
Cys Pro Glu Pro Thr Thr Phe Thr Thr Asn Gly Lys Thr Tyr Thr Val
                165                 170                 175
```

```
act gaa cca acc act ttg act atc act gac tgt cca tgt act att gaa      576
Thr Glu Pro Thr Thr Leu Thr Ile Thr Asp Cys Pro Cys Thr Ile Glu
            180                 185                 190 aag agc gaa gcc cct gag tct tct gtc cca gtt acc gaa tct aag ggc      624
Lys Ser Glu Ala Pro Glu Ser Ser Val Pro Val Thr Glu Ser Lys Gly
        195                 200                 205 act acc acc aaa gaa aca ggt gtt act acc aaa caa acc aca gcc aac      672
Thr Thr Thr Lys Glu Thr Gly Val Thr Thr Lys Gln Thr Thr Ala Asn
    210                 215                 220 cca agt cta acc gtc tcc aca gtc gtc cca gtt tca tcc tct gct tct      720
Pro Ser Leu Thr Val Ser Thr Val Val Pro Val Ser Ser Ser Ala Ser
225                 230                 235                 240 tct cat tcc gtt gtc atc aac agt aac ggt gct aac gtc gtc gtt cca      768
Ser His Ser Val Val Ile Asn Ser Asn Gly Ala Asn Val Val Val Pro
                245                 250                 255 ggt gct tta ggt ttg gct ggt gtt gct atg tta ttc taa                  807
Gly Ala Leu Gly Leu Ala Gly Val Ala Met Leu Phe
            260                 265
```

<210> SEQ ID NO 12
<211> LENGTH: 268
<212> TYPE: PRT
<213> ORGANISM: Artificial Sequence
<220> FEATURE:
<223> OTHER INFORMATION: Synthetic Construct

<400> SEQUENCE: 12

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Gly Ser Ala Ser Ala Leu Pro Thr Asn Gly Thr Ser
        35                  40                  45

Thr Glu Ala Pro Thr Asp Thr Thr Thr Glu Ala Pro Thr Thr Gly Leu
    50                  55                  60

Pro Thr Asn Gly Thr Thr Ser Ala Phe Pro Pro Thr Thr Ser Leu Pro
65                  70                  75                  80

Pro Ser Asn Thr Thr Thr Pro Pro Tyr Asn Pro Ser Thr Asp Tyr
                85                  90                  95

Thr Thr Asp Tyr Thr Val Val Thr Glu Tyr Thr Thr Tyr Cys Pro Glu
                100                 105                 110

Pro Thr Thr Phe Thr Thr Asn Gly Lys Thr Tyr Thr Val Thr Glu Pro
            115                 120                 125

Thr Thr Leu Thr Ile Thr Asp Cys Pro Cys Thr Ile Glu Lys Pro Thr
    130                 135                 140

Thr Thr Ser Thr Thr Glu Tyr Thr Val Val Thr Glu Tyr Thr Thr Tyr
145                 150                 155                 160

Cys Pro Glu Pro Thr Thr Phe Thr Thr Asn Gly Lys Thr Tyr Thr Val
                165                 170                 175

Thr Glu Pro Thr Thr Leu Thr Ile Thr Asp Cys Pro Cys Thr Ile Glu
            180                 185                 190

Lys Ser Glu Ala Pro Glu Ser Ser Val Pro Val Thr Glu Ser Lys Gly
        195                 200                 205

Thr Thr Thr Lys Glu Thr Gly Val Thr Thr Lys Gln Thr Thr Ala Asn
    210                 215                 220

Pro Ser Leu Thr Val Ser Thr Val Val Pro Val Ser Ser Ser Ala Ser
225                 230                 235                 240
```

Ser His Ser Val Val Ile Asn Ser Asn Gly Ala Asn Val Val Pro
            245                 250                 255

Gly Ala Leu Gly Leu Ala Gly Val Ala Met Leu Phe
            260                 265

<210> SEQ ID NO 13
<211> LENGTH: 759
<212> TYPE: DNA
<213> ORGANISM: Artificial Sequence
<220> FEATURE:
<223> OTHER INFORMATION: Tir1 tether
<220> FEATURE:
<221> NAME/KEY: CDS
<222> LOCATION: (1)..(759)

<400> SEQUENCE: 13

| aag gac aat agc tcg acg att gaa ggt aga tac cca tac gac gtt cca | 48 |
|---|---|
| Lys Asp Asn Ser Ser Thr Ile Glu Gly Arg Tyr Pro Tyr Asp Val Pro | |
| 1               5                   10                  15 | |

| gac tac gct ctg cag gct agt ggt ggt ggt ggt tct ggt ggt ggt ggt | 96 |
|---|---|
| Asp Tyr Ala Leu Gln Ala Ser Gly Gly Gly Gly Ser Gly Gly Gly Gly | |
|             20                  25                  30 | |

| tct ggt ggt ggt ggt tct gct agc agc tta gct tct gat tct tcc tct | 144 |
|---|---|
| Ser Gly Gly Gly Gly Ser Ala Ser Ser Leu Ala Ser Asp Ser Ser Ser | |
|         35                  40                  45 | |

| gga ttt tcc tta agc agt atg cca gct ggt gtt ttg gat atc ggt atg | 192 |
|---|---|
| Gly Phe Ser Leu Ser Ser Met Pro Ala Gly Val Leu Asp Ile Gly Met | |
| 50                  55                  60 | |

| gct tta gct tcc gcc act gac gac tcc tac act act ttg tac tct gag | 240 |
|---|---|
| Ala Leu Ala Ser Ala Thr Asp Asp Ser Tyr Thr Thr Leu Tyr Ser Glu | |
| 65                  70                  75                  80 | |

| gtt gac ttt gct ggt gtt agc aag atg ttg acc atg gtt cca tgg tac | 288 |
|---|---|
| Val Asp Phe Ala Gly Val Ser Lys Met Leu Thr Met Val Pro Trp Tyr | |
|                 85                  90                  95 | |

| tcc tct aga ttg gaa cca gct ttg aag tct ttg aat ggt gat gct tct | 336 |
|---|---|
| Ser Ser Arg Leu Glu Pro Ala Leu Lys Ser Leu Asn Gly Asp Ala Ser | |
|             100                 105                 110 | |

| tct tct gct gcc cca agc tct tct gct gcc cca act tct tct gct gcc | 384 |
|---|---|
| Ser Ser Ala Ala Pro Ser Ser Ser Ala Ala Pro Thr Ser Ser Ala Ala | |
|         115                 120                 125 | |

| cca agc tca tct gct gcc cca act tct tct gct gcc tca agc tct tct | 432 |
|---|---|
| Pro Ser Ser Ser Ala Ala Pro Thr Ser Ser Ala Ala Ser Ser Ser Ser | |
|     130                 135                 140 | |

| gaa gct aag tct tct tct gct gcc cca agc tct tct gaa gct aag tct | 480 |
|---|---|
| Glu Ala Lys Ser Ser Ser Ala Ala Pro Ser Ser Ser Glu Ala Lys Ser | |
| 145                 150                 155                 160 | |

| tct tct gct gcc cca agc tct tct gaa gct aag tct tct tct gct gcc | 528 |
|---|---|
| Ser Ser Ala Ala Pro Ser Ser Ser Glu Ala Lys Ser Ser Ser Ala Ala | |
|                 165                 170                 175 | |

| cca agc tct tct gaa gct aag tct tct tct gct gct cca agc tcc act | 576 |
|---|---|
| Pro Ser Ser Ser Glu Ala Lys Ser Ser Ser Ala Ala Pro Ser Ser Thr | |
|             180                 185                 190 | |

| gaa gct aag ata act tct gct gct cca agc tcc act ggt gcc aag acc | 624 |
|---|---|
| Glu Ala Lys Ile Thr Ser Ala Ala Pro Ser Ser Thr Gly Ala Lys Thr | |
|         195                 200                 205 | |

| tct gcc atc tct caa att acc gat ggt caa atc caa gct acc aag gct | 672 |
|---|---|
| Ser Ala Ile Ser Gln Ile Thr Asp Gly Gln Ile Gln Ala Thr Lys Ala | |
|     210                 215                 220 | |

| gtt tct gag caa act gaa aac ggt gct gct aag gcc ttt gtt ggt atg | 720 |
|---|---|
| Val Ser Glu Gln Thr Glu Asn Gly Ala Ala Lys Ala Phe Val Gly Met | |
| 225                 230                 235                 240 | |

```
ggt gct ggt gtt gtc gca gct gcc gct atg ttg tta taa          759
Gly Ala Gly Val Val Ala Ala Ala Ala Met Leu Leu
            245                 250
```

<210> SEQ ID NO 14
<211> LENGTH: 252
<212> TYPE: PRT
<213> ORGANISM: Artificial Sequence
<220> FEATURE:
<223> OTHER INFORMATION: Synthetic Construct

<400> SEQUENCE: 14

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Gly Ser Ala Ser Ser Leu Ala Ser Asp Ser Ser Ser
        35                  40                  45

Gly Phe Ser Leu Ser Ser Met Pro Ala Gly Val Leu Asp Ile Gly Met
    50                  55                  60

Ala Leu Ala Ser Ala Thr Asp Asp Ser Tyr Thr Thr Leu Tyr Ser Glu
65                  70                  75                  80

Val Asp Phe Ala Gly Val Ser Lys Met Leu Thr Met Val Pro Trp Tyr
                85                  90                  95

Ser Ser Arg Leu Glu Pro Ala Leu Lys Ser Leu Asn Gly Asp Ala Ser
            100                 105                 110

Ser Ser Ala Ala Pro Ser Ser Ala Ala Pro Thr Ser Ser Ala Ala
        115                 120                 125

Pro Ser Ser Ser Ala Ala Pro Thr Ser Ser Ala Ala Ser Ser Ser Ser
130                 135                 140

Glu Ala Lys Ser Ser Ser Ala Ala Pro Ser Ser Ser Glu Ala Lys Ser
145                 150                 155                 160

Ser Ser Ala Ala Pro Ser Ser Ser Glu Ala Lys Ser Ser Ser Ala Ala
                165                 170                 175

Pro Ser Ser Ser Glu Ala Lys Ser Ser Ser Ala Ala Pro Ser Ser Thr
            180                 185                 190

Glu Ala Lys Ile Thr Ser Ala Ala Pro Ser Ser Thr Gly Ala Lys Thr
        195                 200                 205

Ser Ala Ile Ser Gln Ile Thr Asp Gly Gln Ile Gln Ala Thr Lys Ala
    210                 215                 220

Val Ser Glu Gln Thr Glu Asn Gly Ala Ala Lys Ala Phe Val Gly Met
225                 230                 235                 240

Gly Ala Gly Val Val Ala Ala Ala Ala Met Leu Leu
                245                 250
```

<210> SEQ ID NO 15
<211> LENGTH: 450
<212> TYPE: DNA
<213> ORGANISM: Artificial Sequence
<220> FEATURE:
<223> OTHER INFORMATION: Cwp2 tether
<220> FEATURE:
<221> NAME/KEY: CDS
<222> LOCATION: (1)..(450)

<400> SEQUENCE: 15

```
aag gac aat agc tcg acg att gaa ggt aga tac cca tac gac gtt cca    48
Lys Asp Asn Ser Ser Thr Ile Glu Gly Arg Tyr Pro Tyr Asp Val Pro
1               5                   10                  15
```

```
gac tac gct ctg cag gct agt ggt ggt ggt ggt tct ggt ggt ggt ggt      96
Asp Tyr Ala Leu Gln Ala Ser Gly Gly Gly Gly Ser Gly Gly Gly Gly
         20                  25                  30 tct ggt ggt ggt ggt tct gct agc gga tcc ggt ggc ggt gga tct gga     144
Ser Gly Gly Gly Gly Ser Ala Ser Gly Ser Gly Gly Gly Gly Ser Gly
     35                  40                  45 gga ggc ggt tct tgg tct cac cca caa ttt gaa aag ggt gga gaa aac     192
Gly Gly Gly Ser Trp Ser His Pro Gln Phe Glu Lys Gly Gly Glu Asn
 50                  55                  60 ttg tac ttt caa ggt ggt gga ggt tct ggc gga ggt ggc tcc ggc         240
Leu Tyr Phe Gln Gly Gly Gly Gly Ser Gly Gly Gly Gly Ser Gly
 65              70                  75                  80 tca gct atc tct caa atc acc gac ggt caa atc caa gcc act acc aca     288
Ser Ala Ile Ser Gln Ile Thr Asp Gly Gln Ile Gln Ala Thr Thr Thr
                 85                  90                  95 gct acc act gaa gct aca act acc gct gct cct tca tct act gtt gaa     336
Ala Thr Thr Glu Ala Thr Thr Thr Ala Ala Pro Ser Ser Thr Val Glu
             100                 105                 110 act gtt tct cca tct tcc acc gaa acc atc tct caa caa acc gaa aac     384
Thr Val Ser Pro Ser Ser Thr Glu Thr Ile Ser Gln Gln Thr Glu Asn
         115                 120                 125 ggt gct gct aag gct gct gtt ggt atg ggt gct ggt gct ttg gct gct     432
Gly Ala Ala Lys Ala Ala Val Gly Met Gly Ala Gly Ala Leu Ala Ala
     130                 135                 140 gct gct atg ttg ttg taa                                             450
Ala Ala Met Leu Leu
145

<210> SEQ ID NO 16
<211> LENGTH: 149
<212> TYPE: PRT
<213> ORGANISM: Artificial Sequence
<220> FEATURE:
<223> OTHER INFORMATION: Synthetic Construct

<400> SEQUENCE: 16

Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Gly Ser Gly Gly Gly Gly
         20                  25                  30

Ser Gly Gly Gly Gly Ser Ala Ser Gly Ser Gly Gly Gly Gly Ser Gly
     35                  40                  45

Gly Gly Gly Ser Trp Ser His Pro Gln Phe Glu Lys Gly Gly Glu Asn
 50                  55                  60

Leu Tyr Phe Gln Gly Gly Gly Gly Ser Gly Gly Gly Gly Ser Gly
 65              70                  75                  80

Ser Ala Ile Ser Gln Ile Thr Asp Gly Gln Ile Gln Ala Thr Thr Thr
                 85                  90                  95

Ala Thr Thr Glu Ala Thr Thr Thr Ala Ala Pro Ser Ser Thr Val Glu
             100                 105                 110

Thr Val Ser Pro Ser Ser Thr Glu Thr Ile Ser Gln Gln Thr Glu Asn
         115                 120                 125

Gly Ala Ala Lys Ala Ala Val Gly Met Gly Ala Gly Ala Leu Ala Ala
     130                 135                 140

Ala Ala Met Leu Leu
145

<210> SEQ ID NO 17
```

<211> LENGTH: 468
<212> TYPE: DNA
<213> ORGANISM: Artificial Sequence
<220> FEATURE:
<223> OTHER INFORMATION: Ccw12 tether
<220> FEATURE:
<221> NAME/KEY: CDS
<222> LOCATION: (1)..(468)

<400> SEQUENCE: 17

```
aag gac aat agc tcg acg att gaa ggt aga tac cca tac gac gtt cca    48
Lys Asp Asn Ser Ser Thr Ile Glu Gly Arg Tyr Pro Tyr Asp Val Pro
1               5                   10                  15 gac tac gct ctg cag gct agt ggt ggt ggt tct ggt ggt ggt ggt       96
Asp Tyr Ala Leu Gln Ala Ser Gly Gly Gly Ser Gly Gly Gly Gly
            20                  25                  30 tct ggt ggt ggt ggt tct gct agc gct gct aac gtt acc act gct act  144
Ser Gly Gly Gly Gly Ser Ala Ser Ala Ala Asn Val Thr Thr Ala Thr
        35                  40                  45 gtc agc caa gaa tct acc act ttg gtc acc atc act tct tgt gaa gac  192
Val Ser Gln Glu Ser Thr Thr Leu Val Thr Ile Thr Ser Cys Glu Asp
50                  55                  60 cac gtc tgt tct gaa act gtc tcc cca gct ttg gtt tcc acc gct acc  240
His Val Cys Ser Glu Thr Val Ser Pro Ala Leu Val Ser Thr Ala Thr
65                  70                  75                  80 gtc acc gtc gat gac gtt atc act caa tac acc acc tgg tgc cca ttg  288
Val Thr Val Asp Asp Val Ile Thr Gln Tyr Thr Thr Trp Cys Pro Leu
                85                  90                  95 acc act gaa gcc cca aag aac ggt act tct act gct gct cca gtt acc  336
Thr Thr Glu Ala Pro Lys Asn Gly Thr Ser Thr Ala Ala Pro Val Thr
            100                 105                 110 tct act gaa gct cca aag aac acc acc tct gct gct cca act cac tct  384
Ser Thr Glu Ala Pro Lys Asn Thr Thr Ser Ala Ala Pro Thr His Ser
        115                 120                 125 gtc acc tct tac act ggt gct gct gct aag gct ttg cca gct gct ggt  432
Val Thr Ser Tyr Thr Gly Ala Ala Ala Lys Ala Leu Pro Ala Ala Gly
130                 135                 140 gct ttg ttg gct ggt gcc gct gct ttg ttg ttg taa                   468
Ala Leu Leu Ala Gly Ala Ala Ala Leu Leu Leu
145                 150                 155
```

<210> SEQ ID NO 18
<211> LENGTH: 155
<212> TYPE: PRT
<213> ORGANISM: Artificial Sequence
<220> FEATURE:
<223> OTHER INFORMATION: Synthetic Construct

<400> SEQUENCE: 18

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Gly Ser Ala Ser Ala Ala Asn Val Thr Thr Ala Thr
        35                  40                  45

Val Ser Gln Glu Ser Thr Thr Leu Val Thr Ile Thr Ser Cys Glu Asp
50                  55                  60

His Val Cys Ser Glu Thr Val Ser Pro Ala Leu Val Ser Thr Ala Thr
65                  70                  75                  80

Val Thr Val Asp Asp Val Ile Thr Gln Tyr Thr Thr Trp Cys Pro Leu
                85                  90                  95
```

```
Thr Thr Glu Ala Pro Lys Asn Gly Thr Ser Thr Ala Ala Pro Val Thr
            100                 105                 110

Ser Thr Glu Ala Pro Lys Asn Thr Thr Ser Ala Ala Pro Thr His Ser
        115                 120                 125

Val Thr Ser Tyr Thr Gly Ala Ala Lys Ala Leu Pro Ala Ala Gly
    130                 135                 140

Ala Leu Leu Ala Gly Ala Ala Leu Leu Leu
145                 150             155

<210> SEQ ID NO 19
<211> LENGTH: 510
<212> TYPE: DNA
<213> ORGANISM: Artificial Sequence
<220> FEATURE:
<223> OTHER INFORMATION: Spi1 tether
<220> FEATURE:
<221> NAME/KEY: CDS
<222> LOCATION: (1)..(510)

<400> SEQUENCE: 19 aag gac aat agc tcg acg att gaa ggt aga tac cca tac gac gtt cca      48
Lys Asp Asn Ser Ser Thr Ile Glu Gly Arg Tyr Pro Tyr Asp Val Pro
1               5                   10                  15 gac tac gct ctg cag gct agt ggt ggt ggt tct ggt ggt ggt ggt          96
Asp Tyr Ala Leu Gln Ala Ser Gly Gly Gly Ser Gly Gly Gly Gly
            20                  25                  30 tct ggt ggt ggt ggt tct gct agc ttg gta tct aat tct agt tcc tct    144
Ser Gly Gly Gly Gly Ser Ala Ser Leu Val Ser Asn Ser Ser Ser Ser
                35                  40                  45 gta atc gtg gta cca tca agc gat gct act att gcc ggt aac gat aca    192
Val Ile Val Val Pro Ser Ser Asp Ala Thr Ile Ala Gly Asn Asp Thr
        50                  55                  60 gcc acg cca gca cca gag cca tca tcc gcc gct cca ata ttc tac aac    240
Ala Thr Pro Ala Pro Glu Pro Ser Ser Ala Ala Pro Ile Phe Tyr Asn
65                  70                  75                  80 tcg act gct act gca aca cag tac gaa gtt gtc agt gaa ttc act act    288
Ser Thr Ala Thr Ala Thr Gln Tyr Glu Val Val Ser Glu Phe Thr Thr
                85                  90                  95 tac tgc cca gaa cca acg act ttc gta acg aat ggc gct aca ttc act    336
Tyr Cys Pro Glu Pro Thr Thr Phe Val Thr Asn Gly Ala Thr Phe Thr
            100                 105                 110 gtt act gcc cca act acg tta aca att acc aac tgt cct tgc act atc    384
Val Thr Ala Pro Thr Thr Leu Thr Ile Thr Asn Cys Pro Cys Thr Ile
        115                 120                 125 gag aag cct act tca gaa aca tcg gtt tct tct aca cat gat gtg gag    432
Glu Lys Pro Thr Ser Glu Thr Ser Val Ser Ser Thr His Asp Val Glu
130                 135                 140 aca aat tct aat gct gct aac gca aga gca atc cca gga gcc cta ggt    480
Thr Asn Ser Asn Ala Ala Asn Ala Arg Ala Ile Pro Gly Ala Leu Gly
145                 150                 155                 160 ttg gct ggt gca gtt atg atg ctt tta tga                            510
Leu Ala Gly Ala Val Met Met Leu Leu
                165

<210> SEQ ID NO 20
<211> LENGTH: 169
<212> TYPE: PRT
<213> ORGANISM: Artificial Sequence
<220> FEATURE:
<223> OTHER INFORMATION: Synthetic Construct
```

<400> SEQUENCE: 20

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Ser Ala Ser Leu Val Ser Asn Ser Ser Ser
        35                  40                  45

Val Ile Val Val Pro Ser Ser Asp Ala Thr Ile Ala Gly Asn Asp Thr
    50                  55                  60

Ala Thr Pro Ala Pro Glu Pro Ser Ser Ala Ala Pro Ile Phe Tyr Asn
65                  70                  75                  80

Ser Thr Ala Thr Ala Thr Gln Tyr Glu Val Val Ser Glu Phe Thr Thr
                85                  90                  95

Tyr Cys Pro Glu Pro Thr Thr Phe Val Thr Asn Gly Ala Thr Phe Thr
                100                 105                 110

Val Thr Ala Pro Thr Thr Leu Thr Ile Thr Asn Cys Pro Cys Thr Ile
            115                 120                 125

Glu Lys Pro Thr Ser Glu Thr Ser Val Ser Ser Thr His Asp Val Glu
            130                 135                 140

Thr Asn Ser Asn Ala Ala Asn Ala Arg Ala Ile Pro Gly Ala Leu Gly
145                 150                 155                 160

Leu Ala Gly Ala Val Met Met Leu Leu
                165
```

<210> SEQ ID NO 21
<211> LENGTH: 1398
<212> TYPE: DNA
<213> ORGANISM: Artificial Sequence
<220> FEATURE:
<223> OTHER INFORMATION: Pst1 tether
<220> FEATURE:
<221> NAME/KEY: CDS
<222> LOCATION: (1)..(1398)

<400> SEQUENCE: 21

```
aag gac aat agc tcg acg att gaa ggt aga tac cca tac gac gtt cca      48
Lys Asp Asn Ser Ser Thr Ile Glu Gly Arg Tyr Pro Tyr Asp Val Pro
1               5                   10                  15 gac tac gct ctg cag gct agt ggt ggt ggt ggt tct ggt ggt ggt ggt      96
Asp Tyr Ala Leu Gln Ala Ser Gly Gly Gly Gly Ser Gly Gly Gly Gly
            20                  25                  30 tct ggt ggt ggt ggt tct gct agc gct act tcc tct tct tcc agc ata    144
Ser Gly Gly Gly Gly Ser Ala Ser Ala Thr Ser Ser Ser Ser Ser Ile
        35                  40                  45 ccc tct tcc tgt acc ata agc tca cat gcc acg gcc aca gct cag agt    192
Pro Ser Ser Cys Thr Ile Ser Ser His Ala Thr Ala Thr Ala Gln Ser
    50                  55                  60 gac tta gat aaa tat agc cgc tgt gat acg tta gtc ggg aac tta act    240
Asp Leu Asp Lys Tyr Ser Arg Cys Asp Thr Leu Val Gly Asn Leu Thr
65                  70                  75                  80 att ggt ggt ggt ttg aag act ggt gct ttg gct aat gtt aaa gaa atc    288
Ile Gly Gly Gly Leu Lys Thr Gly Ala Leu Ala Asn Val Lys Glu Ile
                85                  90                  95 aac ggg tct cta act ata ttt aac gct aca aat cta acc tca ttc gct    336
Asn Gly Ser Leu Thr Ile Phe Asn Ala Thr Asn Leu Thr Ser Phe Ala
                100                 105                 110
```

| | | |
|---|---|---|
| gct gat tcc ttg gag tcc atc aca gat tct ttg aac cta cag agt ttg<br>Ala Asp Ser Leu Glu Ser Ile Thr Asp Ser Leu Asn Leu Gln Ser Leu<br>              115                     120                  125 | 384 | |
| aca atc ttg act tct gct tca ttt ggg tct tta cag agc gtt gat agt<br>Thr Ile Leu Thr Ser Ala Ser Phe Gly Ser Leu Gln Ser Val Asp Ser<br>130                     135                    140 | 432 | |
| ata aaa ctg att act cta ccc gcc atc tcc agt ttt act tca aat atc<br>Ile Lys Leu Ile Thr Leu Pro Ala Ile Ser Ser Phe Thr Ser Asn Ile<br>145                     150                    155                160 | 480 | |
| aaa tct gct aac aac att tat att tcc gac act tcg tta caa tct gtc<br>Lys Ser Ala Asn Asn Ile Tyr Ile Ser Asp Thr Ser Leu Gln Ser Val<br>                   165                    170                175 | 528 | |
| gat gga ttc tca gcc ttg aaa aaa gtt aac gtg ttc aac gtc aat aac<br>Asp Gly Phe Ser Ala Leu Lys Lys Val Asn Val Phe Asn Val Asn Asn<br>              180                    185                    190 | 576 | |
| aat aag aaa tta acc tcg atc aaa tct cca gtt gaa aca gtc agc gat<br>Asn Lys Lys Leu Thr Ser Ile Lys Ser Pro Val Glu Thr Val Ser Asp<br>                   195                    200                205 | 624 | |
| tct tta caa ttt tcg ttc aac ggt aac cag act aaa atc acc ttc gat<br>Ser Leu Gln Phe Ser Phe Asn Gly Asn Gln Thr Lys Ile Thr Phe Asp<br>          210                    215                    220 | 672 | |
| gac ttg gtt tgg gca aac aat atc agt ttg acc gat gtc cac tct gtt<br>Asp Leu Val Trp Ala Asn Asn Ile Ser Leu Thr Asp Val His Ser Val<br>225                     230                    235                240 | 720 | |
| tcc ttc gct aac ttg caa aag att aac tct tca ttg ggt ttc atc aac<br>Ser Phe Ala Asn Leu Gln Lys Ile Asn Ser Ser Leu Gly Phe Ile Asn<br>                   245                    250                255 | 768 | |
| aac tcc atc tca agt ttg aat ttc act aag cta aac acc att ggc caa<br>Asn Ser Ile Ser Ser Leu Asn Phe Thr Lys Leu Asn Thr Ile Gly Gln<br>              260                    265                    270 | 816 | |
| acc ttc agt atc gtt tcc aat gac tac ttg aag aac ttg tcg ttc tct<br>Thr Phe Ser Ile Val Ser Asn Asp Tyr Leu Lys Asn Leu Ser Phe Ser<br>                   275                    280                285 | 864 | |
| aat ttg tca acc ata ggt ggt gct ctt gtc gtt gct aac aac act ggt<br>Asn Leu Ser Thr Ile Gly Gly Ala Leu Val Val Ala Asn Asn Thr Gly<br>          290                    295                    300 | 912 | |
| tta caa aaa att ggt ggt ctc gac aac cta aca acc att ggc ggt act<br>Leu Gln Lys Ile Gly Gly Leu Asp Asn Leu Thr Thr Ile Gly Gly Thr<br>305                     310                    315                320 | 960 | |
| ttg gaa gtt gtt ggt aac ttc acc tcc ttg aac cta gac tct ttg aag<br>Leu Glu Val Val Gly Asn Phe Thr Ser Leu Asn Leu Asp Ser Leu Lys<br>                   325                    330                335 | 1008 | |
| tct gtc aag ggt ggc gca gat gtc gaa tca aag tca agc aat ttc tcc<br>Ser Val Lys Gly Gly Ala Asp Val Glu Ser Lys Ser Ser Asn Phe Ser<br>              340                    345                    350 | 1056 | |
| tgt aat gct ttg aaa gct ttg caa aag aaa ggg ggt atc aag ggt gaa<br>Cys Asn Ala Leu Lys Ala Leu Gln Lys Lys Gly Gly Ile Lys Gly Glu<br>                   355                    360                365 | 1104 | |
| tct ttt gtc tgc aaa aat ggt gca tca tcc aca tct gtt aaa cta tcg<br>Ser Phe Val Cys Lys Asn Gly Ala Ser Ser Thr Ser Val Lys Leu Ser<br>              370                    375                    380 | 1152 | |
| tcc act tcc aaa tct caa tca agc caa act act gcc aag gtt tcc aag<br>Ser Thr Ser Lys Ser Gln Ser Ser Gln Thr Thr Ala Lys Val Ser Lys<br>385                     390                    395                400 | 1200 | |
| tca tct tct aag gcc gag gaa aag aag ttc act tct ggc gat atc aag<br>Ser Ser Ser Lys Ala Glu Glu Lys Lys Phe Thr Ser Gly Asp Ile Lys<br>                   405                    410                415 | 1248 | |

```
gct gct gct tct gcc tct agt gtt tct agt tct ggc gct tcc agc tct   1296
Ala Ala Ala Ser Ala Ser Ser Val Ser Ser Ser Gly Ala Ser Ser Ser
            420                 425                 430 agc tct aag agt tcc aaa ggc aat gcc gct atc atg gca cca att ggc   1344
Ser Ser Lys Ser Ser Lys Gly Asn Ala Ala Ile Met Ala Pro Ile Gly
            435                 440                 445 caa aca acc cct ttg gtc ggt ctt ttg acg gca atc atc atg tct ata   1392
Gln Thr Thr Pro Leu Val Gly Leu Leu Thr Ala Ile Ile Met Ser Ile
            450                 455                 460 atg taa                                                            1398
Met
465

<210> SEQ ID NO 22
<211> LENGTH: 465
<212> TYPE: PRT
<213> ORGANISM: Artificial Sequence
<220> FEATURE:
<223> OTHER INFORMATION: Synthetic Construct

<400> SEQUENCE: 22

Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Ser Ala Ser Ala Thr Ser Ser Ser Ser Ile
            35                  40                  45

Pro Ser Ser Cys Thr Ile Ser Ser His Ala Thr Ala Thr Ala Gln Ser
50                  55                  60

Asp Leu Asp Lys Tyr Ser Arg Cys Asp Thr Leu Val Gly Asn Leu Thr
65                  70                  75                  80

Ile Gly Gly Gly Leu Lys Thr Gly Ala Leu Ala Asn Val Lys Glu Ile
            85                  90                  95

Asn Gly Ser Leu Thr Ile Phe Asn Ala Thr Asn Leu Thr Ser Phe Ala
            100                 105                 110

Ala Asp Ser Leu Glu Ser Ile Thr Asp Ser Leu Asn Leu Gln Ser Leu
            115                 120                 125

Thr Ile Leu Thr Ser Ala Ser Phe Gly Ser Leu Gln Ser Val Asp Ser
            130                 135                 140

Ile Lys Leu Ile Thr Leu Pro Ala Ile Ser Ser Phe Thr Ser Asn Ile
145                 150                 155                 160

Lys Ser Ala Asn Asn Ile Tyr Ile Ser Asp Thr Ser Leu Gln Ser Val
            165                 170                 175

Asp Gly Phe Ser Ala Leu Lys Lys Val Asn Val Phe Asn Val Asn Asn
            180                 185                 190

Asn Lys Lys Leu Thr Ser Ile Lys Ser Pro Val Glu Thr Val Ser Asp
            195                 200                 205

Ser Leu Gln Phe Ser Phe Asn Gly Asn Gln Thr Lys Ile Thr Phe Asp
            210                 215                 220

Asp Leu Val Trp Ala Asn Asn Ile Ser Leu Thr Asp Val His Ser Val
225                 230                 235                 240

Ser Phe Ala Asn Leu Gln Lys Ile Asn Ser Ser Leu Gly Phe Ile Asn
            245                 250                 255

Asn Ser Ile Ser Ser Leu Asn Phe Thr Lys Leu Asn Thr Ile Gly Gln
            260                 265                 270
```

```
Thr Phe Ser Ile Val Ser Asn Asp Tyr Leu Lys Asn Leu Ser Phe Ser
        275                 280                 285
Asn Leu Ser Thr Ile Gly Gly Ala Leu Val Val Ala Asn Asn Thr Gly
    290                 295                 300
Leu Gln Lys Ile Gly Gly Leu Asp Asn Leu Thr Thr Ile Gly Gly Thr
305                 310                 315                 320
Leu Glu Val Val Gly Asn Phe Thr Ser Leu Asn Leu Asp Ser Leu Lys
                325                 330                 335
Ser Val Lys Gly Gly Ala Asp Val Glu Ser Lys Ser Ser Asn Phe Ser
            340                 345                 350
Cys Asn Ala Leu Lys Ala Leu Gln Lys Lys Gly Gly Ile Lys Gly Glu
        355                 360                 365
Ser Phe Val Cys Lys Asn Gly Ala Ser Ser Thr Ser Val Lys Leu Ser
    370                 375                 380
Ser Thr Ser Lys Ser Gln Ser Ser Gln Thr Thr Ala Lys Val Ser Lys
385                 390                 395                 400
Ser Ser Ser Lys Ala Glu Glu Lys Lys Phe Thr Ser Gly Asp Ile Lys
                405                 410                 415
Ala Ala Ala Ser Ala Ser Ser Val Ser Ser Gly Ala Ser Ser Ser
            420                 425                 430
Ser Ser Lys Ser Lys Gly Asn Ala Ala Ile Met Ala Pro Ile Gly
        435                 440                 445
Gln Thr Thr Pro Leu Val Gly Leu Leu Thr Ala Ile Ile Met Ser Ile
    450                 455                 460
Met
465

<210> SEQ ID NO 23
<211> LENGTH: 330
<212> TYPE: DNA
<213> ORGANISM: Artificial Sequence
<220> FEATURE:
<223> OTHER INFORMATION: Aga1/2 tether
<220> FEATURE:
<221> NAME/KEY: CDS
<222> LOCATION: (1)..(330)

<400> SEQUENCE: 23 aag gac aat agc tcg acg att gaa ggt aga tac cca tac gac gtt cca    48
Lys Asp Asn Ser Ser Thr Ile Glu Gly Arg Tyr Pro Tyr Asp Val Pro
1               5                   10                  15 gac tac gct ctg cag gct agt ggt ggt ggt ggt tct ggt ggt ggt ggt    96
Asp Tyr Ala Leu Gln Ala Ser Gly Gly Gly Gly Ser Gly Gly Gly Gly
            20                  25                  30 tct ggt ggt ggt ggt tct gct agc cag gaa ctg aca act ata tgc gag   144
Ser Gly Gly Gly Gly Ser Ala Ser Gln Glu Leu Thr Thr Ile Cys Glu
        35                  40                  45 caa atc ccc tca cca act tta gaa tcg acg ccg tac tct ttg tca acg   192
Gln Ile Pro Ser Pro Thr Leu Glu Ser Thr Pro Tyr Ser Leu Ser Thr
    50                  55                  60 act act att ttg gcc aac ggg aag gca atg caa gga gtt ttt gaa tat   240
Thr Thr Ile Leu Ala Asn Gly Lys Ala Met Gln Gly Val Phe Glu Tyr
65                  70                  75                  80 tac aaa tca gta acg ttt gtc agt aat tgc ggt tct cac ccc tca aca   288
Tyr Lys Ser Val Thr Phe Val Ser Asn Cys Gly Ser His Pro Ser Thr
                85                  90                  95
```

```
act agc aaa ggc agc ccc ata aac aca cag tat gtt ttt taa         330
Thr Ser Lys Gly Ser Pro Ile Asn Thr Gln Tyr Val Phe
            100                 105
```

<210> SEQ ID NO 24
<211> LENGTH: 109
<212> TYPE: PRT
<213> ORGANISM: Artificial Sequence
<220> FEATURE:
<223> OTHER INFORMATION: Synthetic Construct

<400> SEQUENCE: 24

```
Lys Asp Asn Ser Ser Thr Ile Glu Gly Arg Tyr Pro Tyr Asp Val Pro
1               5                   10                  15

Asp Tyr Ala Leu Gln Ala Ser Gly Gly Gly Ser Gly Gly Gly Gly
            20                  25                  30

Ser Gly Gly Gly Gly Ser Ala Ser Gln Glu Leu Thr Thr Ile Cys Glu
            35                  40                  45

Gln Ile Pro Ser Pro Thr Leu Glu Ser Thr Pro Tyr Ser Leu Ser Thr
        50                  55                  60

Thr Thr Ile Leu Ala Asn Gly Lys Ala Met Gln Gly Val Phe Glu Tyr
65                  70                  75                  80

Tyr Lys Ser Val Thr Phe Val Ser Asn Cys Gly Ser His Pro Ser Thr
                85                  90                  95

Thr Ser Lys Gly Ser Pro Ile Asn Thr Gln Tyr Val Phe
            100                 105
```

<210> SEQ ID NO 25
<211> LENGTH: 381
<212> TYPE: DNA
<213> ORGANISM: Artificial Sequence
<220> FEATURE:
<223> OTHER INFORMATION: Aga1/2 tether
<220> FEATURE:
<221> NAME/KEY: CDS
<222> LOCATION: (1)..(381)

<400> SEQUENCE: 25

```
atg cag tta ctt cgc tgt ttt tca ata ttt tct gtt att gct tca gtt    48
Met Gln Leu Leu Arg Cys Phe Ser Ile Phe Ser Val Ile Ala Ser Val
1               5                   10                  15 tta gca cag gag ctg aca act ata tgc gag caa atc ccc tca cca act    96
Leu Ala Gln Glu Leu Thr Thr Ile Cys Glu Gln Ile Pro Ser Pro Thr
            20                  25                  30 tta gaa tcg acg ccg tac tct ttg tca acg act act att ttg gcc aac   144
Leu Glu Ser Thr Pro Tyr Ser Leu Ser Thr Thr Thr Ile Leu Ala Asn
        35                  40                  45 ggg aag gca atg caa gga gtt ttt gaa tat tac aaa tca gta acg ttt   192
Gly Lys Ala Met Gln Gly Val Phe Glu Tyr Tyr Lys Ser Val Thr Phe
    50                  55                  60 gtc agt aat tgc gat tct cac ccc tca aca act agc aaa gac agc ccc   240
Val Ser Asn Cys Asp Ser His Pro Ser Thr Thr Ser Lys Asp Ser Pro
65                  70                  75                  80 ata aac aca cag tat gtt ttt aag gac aat agc tcg acg att gaa ggt   288
Ile Asn Thr Gln Tyr Val Phe Lys Asp Asn Ser Ser Thr Ile Glu Gly
                85                  90                  95 aga tac cca tac gac gtt cca gac tac gct ctg cag gct agt ggt ggt   336
Arg Tyr Pro Tyr Asp Val Pro Asp Tyr Ala Leu Gln Ala Ser Gly Gly
            100                 105                 110
```

```
ggt ggt tct ggt ggt ggt ggt tct ggt ggt ggt ggt tct gct agc      381
Gly Gly Ser Gly Gly Gly Gly Ser Gly Gly Gly Gly Ser Ala Ser
        115                 120                 125
```

<210> SEQ ID NO 26
<211> LENGTH: 127
<212> TYPE: PRT
<213> ORGANISM: Artificial Sequence
<220> FEATURE:
<223> OTHER INFORMATION: Synthetic Construct

<400> SEQUENCE: 26

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Asp Ser His Pro Ser Thr Thr Ser Lys Asp Ser Pro
65                  70                  75                  80

Ile Asn Thr Gln Tyr Val Phe Lys Asp Asn Ser Ser Thr Ile Glu Gly
                85                  90                  95

Arg Tyr Pro Tyr Asp Val Pro Asp Tyr Ala Leu Gln Ala Ser Gly Gly
            100                 105                 110

Gly Gly Ser Gly Gly Gly Gly Ser Gly Gly Gly Gly Ser Ala Ser
        115                 120                 125
```

<210> SEQ ID NO 27
<211> LENGTH: 750
<212> TYPE: DNA
<213> ORGANISM: Artificial Sequence
<220> FEATURE:
<223> OTHER INFORMATION: Promoter of tdh1 gene

<400> SEQUENCE: 27

```
agaaacgaat gtatatgctc atttacactc tatatcacca tatggaggat aagttgggct      60
gagcttctga tccaatttat tctatccatt agttgctgat atgtcccacc agccaacact     120
tgatagtatc tactcgccat tcacttccag cagcgccagt agggttgttg agcttagtaa     180
aaatgtgcgc accacaagcc tacatgactc cacgtcacat gaaaccacac cgtggggcct     240
tgttacgcta ggaataggat atgcgacgaa gacgcttctg cttagtaacc acaccacatt     300 ttcaagggt cgatctgctt gcttccttta ctgtcacgag cggcccataa tcgcgctttt     360
tttttaaaat gcgcgagaca gcaaacagga agctcgggtt tcaaccttcg gagtggtcgc     420
agatctggag actggatcct tacaatacag taaggcaagc caccatctgc ttcttaggtg     480
catgcgacgg tatccacgtg cagaacaaca tagtctgaag aaggggggga ggagcatgtt     540
cattctctgt agcactaaga gcttggtgat aatgaccaaa actggagtct cgaaatcata     600
taaatagaca atatattttc acacaatgtg atttgtagta cagttctact ctctctcttg     660
cataaataag aaattcatca agaacttggt ttgatatttc accaacacac acaaaaaaca     720
gtacttcact aaatttacac acaaaacaaa                                     750
```

<210> SEQ ID NO 28
<211> LENGTH: 750
<212> TYPE: DNA

<213> ORGANISM: Artificial Sequence
<220> FEATURE:
<223> OTHER INFORMATION: Promotoer of hor7 gene

<400> SEQUENCE: 28

```
acctccatga aattttttt tttctttcga ttagcacgca cacacatcac atagactgcg      60
tcataaaaat acactacgga aaaccataa agagcaaagc gatacctact tggaaggaaa     120
aggagcacgc ttgtaagggg gatgggggct aagaagtcat tcactttctt ttcccttcgc    180
ggtccggacc cgggacccct cctctccccg cacaatttct tcctttcata tcttcctttt    240
attcctatcc cgttgaagca accgcactat gactaaatgg tgctggacat ctccatggct    300
gtgacttgtg tgtatctcac agtggtaacg gcaccgtggc tcggaaacgg ttccttcgtg    360
acaattctag aacaggggct acagtctcga taatagaata ataagcgcat ttttgttagc    420
gccgccgcgg cgcccgtttc ccaatagggga ggcgcagttt atcggcggag ctttacttct    480
tcctatttgg gtaagcccct ttctgttttc ggccagtggt tgctgcaggc tgcgccggag    540
aacatagtga taagggatgt aactttcgat gagagaatta gcaagcggaa aaaaaactat    600
ggctagctgg gagttgtttt tcaatcatat aaaagggaga aattgttgct cactatgtga    660
cagtttctgg gacgtcttaa cttttattgc agaggactat caaatcatac agatattgtc    720
aaaaaaaaa aaaagacta ataataaaaa                                       750
```

<210> SEQ ID NO 29
<211> LENGTH: 750
<212> TYPE: DNA
<213> ORGANISM: Artificial Sequence
<220> FEATURE:
<223> OTHER INFORMATION: Promoter of hsp150 gene

<400> SEQUENCE: 29

```
tgtaaaaaca agcaaaaaaa aaccaagaag gaacaaatgc accaaactgt tgatctattc      60
tgcaaaaaaa gtatggtaaa tttttttccat tatcctggcc gctaatccat atggaggtga    120
acttagaact tgcacaagga tgcgatgaat gataggcttt gtgctataat taatgcaggc    180
aggtccgcca tgtccaacac gttgctggcc gcaaaacgag tcaatctcac tgctttgcca    240
cgctcatttc tcccccttc tgcccaatta ggcgaccctc acaatgcaca tacacatttc    300
ccacctctat tggaaggggc cgtaaatggt aattcttggg agttattcat attaagtgat    360
cttactattt cctatttcgg aaattattaa agacaaaaaa gctcatttat ggctttccgt    420
ctgtagtgat aagtcgccaa ctcagcctaa ttttcattt ctttaccaga tcaggaaaac    480
taatagtaca aatgagtttt ttctcaagcg gaacaccaca ttttgagcta aatttagatt    540
ttggtcaaaa taagaaagat cctaaaaaag gaatggttgg tgaaaaattt attagcttga    600
atggtaggaa tcctcgagat ataaaggaa cacttgaagt ctaacgacaa tcaatttcga    660
ttatgtcctt ccttttacct caaagctcaa aaaaacatca ataagaaact catattcctt    720
ttctaaccct agtacaataa taataatata                                     750
```

<210> SEQ ID NO 30
<211> LENGTH: 450
<212> TYPE: DNA
<213> ORGANISM: Artificial Sequence
<220> FEATURE:
<223> OTHER INFORMATION: Promoter of hxt7 gene

<400> SEQUENCE: 30

```
ccagaaaggc aacgcaaaat ttttttcca gggaataaac tttttatgac ccactacttc    60
tcgtaggaac aatttcgggc ccctgcgtgt tcttctgagg ttcatctttt acatttgctt   120
ctgctggata attttcagag gcaacaagga aaaattagat ggcaaaaagt cgtcttcaa    180
ggaaaaatcc ccaccatctt tcgagatccc ctgtaactta ttggcaactg aaagaatgaa   240
aaggaggaaa atacaaaata tactagaact gaaaaaaaaa aagtataaat agagacgata   300
tatgccaata cttcacaatg ttcgaatcta ttcttcattt gcagctattg taaaataata   360
aaacatcaag aacaaacaag ctcaacttgt cttttctaag aacaaagaat aaacacaaaa   420
acaaaaagtt ttttaattt taatcaaaaa                                    450
```

<210> SEQ ID NO 31
<211> LENGTH: 1000
<212> TYPE: DNA
<213> ORGANISM: Artificial Sequence
<220> FEATURE:
<223> OTHER INFORMATION: Promoter of gpm1 gene

<400> SEQUENCE: 31

```
tgtggtagaa ttcaaaagac tatgtgatgc cataggcaag aagggagact ctcactccga    60
gatgggcagc ttgatcgccc aggaattgaa ttgtattgtg gtggagaaag gtcagtcaga   120
taagatattc tcacccgata gtgaaaaaga catgttgacg aacagcgaag agggcagcaa   180
caagagggta ggaggccaag gtgatacttt gacaggagct atatcatgca tgcttgcatt   240
tagtcgtgca atgtatgact ttaagatttg tgagcaggaa gaaaagggag aatcttctaa   300
cgataaaccc ttgaaaaact gggtagacta cgctatgttg agttgctacg caggctgcac   360
aattacacga gaatgctccc gcctaggatt taaggctaag ggacgtgcaa tgcagacgac   420
agatctaaat gaccgtgtcg gtgaagtgtt cgccaaactt tcggttaac acatgcagtg    480
atgcacgcgc gatggtgcta agttacatat atatatatat atatatatat atatatat    540
agccatagtg atgtctaagt aacctttatg gtatatttct taatgtggaa agatactagc   600
gcgcgcaccc acacacaagc ttcgtctttt cttgaagaaa agaggaagct cgctaaatgg   660
gattccactt tccgttccct gccagctgat ggaaaaaggt tagtggaacg atgaagaata   720
aaaagagaga tccactgagg tgaaatttca gctgacagcg agtttcatga tcgtgatgaa   780
caatggtaac gagttgtggc tgttgccagg gagggtggtt ctcaacttttt aatgtatggc   840
caaatcgcta cttgggtttg ttatataaca agaagaaat aatgaactga ttctcttcct   900
ccttcttgtc ctttcttaat tctgttgtaa ttaccttcct ttgtaattttt ttttgtaatt   960
attcttctta ataatccaaa caaacacaca tattacaata                        1000
```

<210> SEQ ID NO 32
<211> LENGTH: 750
<212> TYPE: DNA
<213> ORGANISM: Artificial Sequence
<220> FEATURE:
<223> OTHER INFORMATION: Promoter of pgk1 gene

<400> SEQUENCE: 32

```
acgcacagat attataacat ctgcacaata ggcatttgca agaattactc gtgagtaagg    60
aaagagtgag gaactatcgc atacctgcat ttaaagatgc cgatttgggc gcgaatcctt   120
tattttggct tcaccctcat actattatca gggccagaaa aaggaagtgt ttccctcctt   180
```

| | |
|---|---:|
| cttgaattga tgttacccctc ataaagcacg tggcctctta tcgagaaaga aattaccgtc | 240 |
| gctcgtgatt tgtttgcaaa aagaacaaaa ctgaaaaaac ccagacacgc tcgacttcct | 300 |
| gtcttcctat tgattgcagc ttccaatttc gtcacacaac aaggtcctag cgacggctca | 360 |
| caggttttgt aacaagcaat cgaaggttct ggaatggcgg gaaagggttt agtaccacat | 420 |
| gctatgatgc ccactgtgat ctccagagca agttcgttc gatcgtactg ttactctctc | 480 |
| tctttcaaac agaattgtcc gaatcgtgtg acaacaacag cctgttctca cacactcttt | 540 |
| tcttctaacc aaggggggtgg tttagtttag tagaacctcg tgaaacttac atttacatat | 600 |
| atataaactt gcataaattg gtcaatgcaa gaaatacata tttggtctttt tctaattcgt | 660 |
| agttttcaa gttcttagat gctttctttt tctcttttt acagatcatc aaggaagtaa | 720 |
| ttatctactt tttacaacaa atataaaaca | 750 |

<210> SEQ ID NO 33
<211> LENGTH: 1020
<212> TYPE: DNA
<213> ORGANISM: Artificial Sequence
<220> FEATURE:
<223> OTHER INFORMATION: Promoter of stl1 gene

<400> SEQUENCE: 33

| | |
|---|---:|
| tggtctcgcg tgtgaatcag caatgattct gaaatactcc ttttacaacc tttgcaaaga | 60 |
| taatgtcatt cagtctgata ttcgagcga cctggaagca ctaatccata ttcttcattc | 120 |
| aacttactcc atttttccttg gcaaacaatg ccccacaatc atatacgtca taactataag | 180 |
| ggatatgtct ggaatgcggc caagatagaa ttaaagggct gcagaacacc actactgata | 240 |
| ctcattgcca aggctaggag gcaccatccg tttcatttc tttgaggtaa gccaatcatg | 300 |
| aaatagtata cacatccata acggacgtac ggacgaaata agtgccgttg tcccactatt | 360 |
| ccaccgcatt tggcccattt ggctcacttt gactcaactt gcgtcatttt aactgatatg | 420 |
| aagggtccga ctttgtcctt tttcggccac cgcatacccc acggcgacgc ctccgctacc | 480 |
| tgcatttgag tagcatctcc gtttcgcggg gtattcggcg ctacgtcgcc tgttcgagcg | 540 |
| gctctgttcg ttgcatgaaa ctaaaataag cggaaagtgt ccagccatcc actacgtcag | 600 |
| aaagaaataa tggttgtaca ctgtttctcg gctatatacc gttttggtt ggttaatcct | 660 |
| cgccaggtgc agctattgcg cttggctgct tcgcgatagt agtaatctga aaagtgcag | 720 |
| atcccggtaa gggaaacact tttggttcac ctttgatagg gctttcattg gggcattcgt | 780 |
| aacaaaaagg aagtagatag agaaattgag aaagcttaag tgagatgttt tagcttcaat | 840 |
| tttgtcccct tcaacgctgc ttggccttag agggtcagaa ttgcagttca ggagtagtca | 900 |
| cactcatagt atataaacaa gcccttatt gattttgaat aattattttg tatacgtgtt | 960 |
| ctagcataca agttagaata aataaaaaat agaaaaatag aacatagaaa gttttagacc | 1020 |

<210> SEQ ID NO 34
<211> LENGTH: 500
<212> TYPE: DNA
<213> ORGANISM: Artificial Sequence
<220> FEATURE:
<223> OTHER INFORMATION: Terminator of dit1 gene

<400> SEQUENCE: 34

| | |
|---|---:|
| taaagtaaga gcgctacatt ggtctacctt tttgttctttt tacttaaaca ttagttagtt | 60 |
| cgttttcttt ttctcatttt tttatgtttc ccctcaaaag ttctgatttt ataatatttt | 120 |
| atttcacaca attccaatta acagaggggg aatagattct ttagcttaga aaattagtga | 180 |

```
tcaatatata tttgcctttc ttttcatctt ttcagtgata ttaatggttt cgagacactg    240
caatggccct agttgtctaa gaggatagat gttactgtca aagatgatat tttgaatttc    300
aattgacgta attaatgata ctattaataa tacagagcgt atatgaagta ttgcaaataa    360
catgcacagt tcttttggga tgagaatgag aatgagaggc gaaggcgggc gttcagaaaa    420
gcgttgcgga gtaacaagtg attaaatagc acccaaataa tcttctttga tactaccgat    480
tgcgtgaata gaactcactt                                                500
```

<210> SEQ ID NO 35
<211> LENGTH: 500
<212> TYPE: DNA
<213> ORGANISM: Artificial Sequence
<220> FEATURE:
<223> OTHER INFORMATION: Terminator of idp1 gene

<400> SEQUENCE: 35

```
tcgaatttac gtagcccaat ctaccacttt tttttcatt tttaaagtg ttatacttag      60 ttatgctcta ggataatgaa ctactttttt tttttttac tgttatcata aatatatata    120
ccttattgat gtttgcaacc gtcggttaat tccttatcaa ggttcccaa gttcggatca    180 ttaccatcaa tttccaacat cttcatgagt tcttcttctt cattaccgtg ttttaggggg    240
ctgttcgcac ttctaatagg gctatcacca agctgttcta attcgtccaa agttcagta    300 acacgatctt tatgcttcag ttcgtcataa tctttcaatt cataaatatt tacaatttcg    360
tctacgatat taaattgcct cttgtaggtg cctatctttt ccttatgctc ttcattttca    420
ccgttttctt gaaaccaaac accgaactca ctacgcattt ctttcatagg ctcatataat    480
acttcttttg acgtcatttg                                                500
```

<210> SEQ ID NO 36
<211> LENGTH: 401
<212> TYPE: DNA
<213> ORGANISM: Artificial Sequence
<220> FEATURE:
<223> OTHER INFORMATION: Terminator of gpm1 gene

<400> SEQUENCE: 36

```
gtctgaagaa tgaatgattt gatgatttct ttttccctcc attttttctta ctgaatatat    60 caatgatata gacttgtata gtttattatt tcaaattaag tagctatata tagtcaagat   120
aacgtttgtt tgacacgatt acattattcg tcgacatctt ttttcagcct gtcgtggtag   180
caatttgagg agtattatta attgaatagg ttcattttgc gctcgcataa acagttttcg   240
tcagggacag tatgttggaa tgagtggtaa ttaatggtga catgacatgt tatagcaata   300
accttgatgt ttacatcgta gtttaatgta caccccgcga attcgttcaa gtaggagtgc   360
accaattgca aagggaaaag ctgaatgggc agttcgaata g                       401
```

<210> SEQ ID NO 37
<211> LENGTH: 500
<212> TYPE: DNA
<213> ORGANISM: Artificial Sequence
<220> FEATURE:
<223> OTHER INFORMATION: Terminator of pma1 gene

<400> SEQUENCE: 37

```
tcctgttgaa gtagcattta atcataattt ttgtcacatt ttaatcaact tgattttct     60 ggtttaattt ttctaatttt aattttaatt tttttatcaa tgggaactga tacactaaaa   120
```

```
agaattagga gccaacaaga ataagccgct tatttcctac tagagtttgc ttaaaatttc      180
atctcgaatt gtcattctaa tattttatcc acacacacac cttaaaattt ttagattaaa      240
tggcatcaac tcttagcttc acacacacac acacaccgaa gctggttgtt ttatttgatt      300
tgatataatt ggtttctctg gatggtactt tttctttctt ggttatttcc tattttaaaa      360
tatgaaacgc acacaagtca taattattct aatagagcac aattcacaac acgcacattt      420
caactttaat attttttag aaacacttta tttagtctaa ttcttaattt ttaatatata       480
taatgcacac acactaattt                                                   500

<210> SEQ ID NO 38
<211> LENGTH: 500
<212> TYPE: DNA
<213> ORGANISM: Artificial Sequence
<220> FEATURE:
<223> OTHER INFORMATION: Terminator of tdh3 gene

<400> SEQUENCE: 38
gtgaatttac tttaaatctt gcatttaaat aaatttctt tttatagctt tatgacttag        60
tttcaattta tatactattt taatgacatt ttcgattcat tgattgaaag ctttgtgttt      120
tttcttgatg cggtattgca ttgttcttgt cttttcgcc acatgtaata tctgtaatag       180
atatctgata cattgtggat gctgagtgaa attttagtta ataatggagg cgctcttaat      240
aattttgggg atattggctt tttttttaa agttacaaa tgaattttt ccgccaggat         300 aacgattctg aagttactct tagcgttcct atcggtacag ccatcaaatc atgcctataa     360
atcatgccta tatttgcgtg cagtcagtat catctcacatg aaaaaaactc ccgcaatttc    420
ttatagaata cgttgaaaat taaatgtacg cgccaagata agataacata aatctagatg     480
cagtaatata cacagattcc                                                   500

<210> SEQ ID NO 39
<211> LENGTH: 500
<212> TYPE: DNA
<213> ORGANISM: Artificial Sequence
<220> FEATURE:
<223> OTHER INFORMATION: Terminator of hxt2 gene

<400> SEQUENCE: 39
gagattatac ttaaactagc actgattttt ttaaggctaa tggctactaa tactttaata      60
gatgatcttc atacttttt atttaacgat ttttaatgat gttttatttt gtaccactca      120
tttatctaga tttttttaat actgatcaaa tcttacggac tcgacgttaa aaagttccta     180
catacgtctg gtacttgaaa cgctgcttcg aggtattgac actataagaa tacgatccaa     240
atacttacac cgcatgtaaa aatatgccga caatatgaat acttgttgat gaatgatatt     300
tgattttaat ccggcaattt acctccttta tataatccaa taattgttga taattagtgg     360
ttaggttgca gtactaataa gaattaagac aaatattctt ctactatata aaaggtgcaa     420
acaaaacaca cgccgatcgg ccatactaaa caagaccaac ataataatgg tggaaccatt    480
tactgtattt tcaatgtaac                                                   500

<210> SEQ ID NO 40
<211> LENGTH: 500
<212> TYPE: DNA
<213> ORGANISM: Artificial Sequence
<220> FEATURE:
<223> OTHER INFORMATION: Terminator of ira2 gene
```

<400> SEQUENCE: 40

```
aggtgttaca taaactaatg aaagaaatat caatatctat ctgtaagcat gaatgtacat    60
atctcatgtt agggttttct tatcgctaat ttttcgcaat ttgttacgtg ggttgctttt   120
atacagctac aatttttata tattctatca tgtaatgaat ggctcagtaa attcaagcgc   180
cacatagact aatgtacata ccaatgcatt taattgtaag aatgaaaggg gccattcatc   240
taccgtctta gttgaaagtg tttctgtgaa ttttttcaaa ttccgttttt tccttttttat   300
ataatagcat ggtggcgcga gcatcttcga ctgaagaatg ctcaccttct tgaatggaaa   360
tttttaaaac ctccttggtt aatttcttta agctgggtgt tttaccctta gcatacaact   420
tcctgaatgg gagtgtctt gaagtgtccc tgagtagtga ctttgggtgg gataacatca   480
atgcttcgag atcatgcttt                                              500
```

<210> SEQ ID NO 41
<211> LENGTH: 5
<212> TYPE: PRT
<213> ORGANISM: Artificial Sequence
<220> FEATURE:
<223> OTHER INFORMATION: G4S motif

<400> SEQUENCE: 41

Gly Gly Gly Gly Ser
1               5

<210> SEQ ID NO 42
<211> LENGTH: 457
<212> TYPE: PRT
<213> ORGANISM: Penicillium funiculosum

<400> SEQUENCE: 42

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
                20                  25                  30

Ser Gly Ala Thr Ser Cys Ala Ala Gly Ser Thr Cys Ser Thr Leu Asn
            35                  40                  45

Pro Tyr Tyr Ala Gln Cys Ile Pro Gly Thr Ala Thr Ser Thr Thr Leu
        50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Ala Ala Ala
                85                  90                  95

Ser Gly Asn Pro Phe Ser Gly Tyr Gln Leu Tyr Ala Asn Pro Tyr Tyr
                100                 105                 110

Ser Ser Glu Val His Thr Leu Ala Ile Pro Ser Leu Thr Gly Ser Leu
            115                 120                 125

Ala Ala Ala Ala Thr Lys Ala Ala Glu Ile Pro Ser Phe Val Trp Leu
130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
                180                 185                 190
```

-continued

Gly Glu Tyr Thr Val Ala Asn Asn Gly Val Ala Asn Tyr Lys Ala Tyr
            195                 200                 205

Ile Asp Ser Ile Val Ala Gln Leu Lys Ala Tyr Pro Asp Val His Thr
210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
            245                 250                 255

Asn Tyr Ala Leu Ile Lys Pro His Leu Ala His Val Ala Met Tyr Ile
            260                 265                 270

Asp Ala Gly His Ala Gly Trp Leu Gly Trp Ser Ala Asn Leu Ser Pro
            275                 280                 285

Ala Ala Gln Leu Phe Ala Thr Val Tyr Lys Asn Ala Ser Ala Pro Ala
            290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asp Ala His Phe Ile Met Asp Thr Ser Arg Asn Gly Val Gln Pro
            355                 360                 365

Thr Lys Gln Gln Ala Trp Gly Asp Trp Cys Asn Val Ile Gly Thr Gly
            370                 375                 380

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Gly Ala Leu Gln
            420                 425                 430

Pro Ala Pro Glu Ala Gly Thr Trp Phe Gln Ala Tyr Phe Val Gln Leu
            435                 440                 445

Leu Thr Asn Ala Asn Pro Ala Leu Val
            450                 455

<210> SEQ ID NO 43
<211> LENGTH: 408
<212> TYPE: PRT
<213> ORGANISM: Rasamsonia emersonii

<400> SEQUENCE: 43

Met Val Arg Leu Ser Pro Val Leu Leu Ala Ser Ile Ala Gly Ser Gly
1               5                   10                  15

Leu Pro Leu Ala Gln Ala Ala Gly Leu Asn Thr Ala Ala Lys Ala Ile
            20                  25                  30

Gly Leu Lys Tyr Phe Gly Thr Ala Thr Asp Asn Pro Glu Leu Ser Asp
            35                  40                  45

Thr Ala Tyr Glu Thr Gln Leu Asn Asn Thr Gln Asp Phe Gly Gln Leu
        50                  55                  60

Thr Pro Ala Asn Ser Met Lys Trp Asp Ala Thr Glu Pro Glu Gln Asn
65                  70                  75                  80

Val Phe Thr Phe Ser Ala Gly Asp Gln Ile Ala Asn Leu Ala Lys Ala
                85                  90                  95

Asn Gly Gln Met Leu Arg Cys His Asn Leu Val Trp Tyr Asn Gln Leu
            100                 105                 110

Pro Ser Trp Val Thr Ser Gly Ser Trp Thr Asn Glu Thr Leu Leu Ala
        115                 120                 125

Ala Met Lys Asn His Ile Thr Asn Val Val Thr His Tyr Lys Gly Gln
    130                 135                 140

Cys Tyr Ala Trp Asp Val Val Asn Glu Ala Leu Asn Asp Asp Gly Thr
145                 150                 155                 160

Tyr Arg Ser Asn Val Phe Tyr Gln Tyr Ile Gly Glu Ala Tyr Ile Pro
                165                 170                 175

Ile Ala Phe Ala Thr Ala Ala Ala Asp Pro Asn Ala Lys Leu Tyr
            180                 185                 190

Tyr Asn Asp Tyr Asn Ile Glu Tyr Pro Gly Ala Lys Ala Thr Ala Ala
                195                 200                 205

Gln Asn Leu Val Lys Leu Val Gln Ser Tyr Gly Ala Arg Ile Asp Gly
            210                 215                 220

Val Gly Leu Gln Ser His Phe Ile Val Gly Glu Thr Pro Ser Thr Ser
225                 230                 235                 240

Ser Gln Gln Gln Asn Met Ala Ala Phe Thr Ala Leu Gly Val Glu Val
                245                 250                 255

Ala Ile Thr Glu Leu Asp Ile Arg Met Gln Leu Pro Glu Thr Glu Ala
            260                 265                 270

Leu Leu Thr Gln Gln Ala Thr Asp Tyr Gln Ser Thr Val Gln Ala Cys
            275                 280                 285

Ala Asn Thr Lys Gly Cys Val Gly Ile Thr Val Trp Asp Trp Thr Asp
            290                 295                 300

Lys Tyr Ser Trp Val Pro Ser Thr Phe Ser Gly Tyr Gly Asp Ala Cys
305                 310                 315                 320

Pro Trp Asp Ala Asn Tyr Gln Lys Lys Pro Ala Tyr Glu Gly Ile Leu
                325                 330                 335

Thr Gly Leu Gly Gln Thr Val Thr Ser Thr Thr Tyr Ile Ile Ser Pro
            340                 345                 350

Thr Thr Ser Val Gly Thr Gly Thr Thr Thr Ser Gly Gly Ser Gly
            355                 360                 365

Gly Thr Thr Gly Val Ala Gln His Trp Glu Gln Cys Gly Gly Leu Gly
    370                 375                 380

Trp Thr Gly Pro Thr Val Cys Ala Ser Gly Tyr Thr Cys Thr Val Ile
385                 390                 395                 400

Asn Glu Tyr Tyr Ser Gln Cys Leu
                405

<210> SEQ ID NO 44
<211> LENGTH: 605
<212> TYPE: PRT
<213> ORGANISM: Aspergillus niger

<400> SEQUENCE: 44

Met Gln Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Asp Val Ser Gly Arg Thr Val Asp Tyr Ile Ile Ala Gly
        35                  40                  45

```
Gly Gly Leu Thr Gly Leu Thr Thr Ala Ala Arg Leu Thr Glu Asn Pro
 50                  55                  60

Asn Ile Ser Val Leu Val Ile Glu Ser Gly Ser Tyr Glu Ser Asp Arg
 65                  70                  75                  80

Gly Pro Ile Ile Glu Asp Leu Asn Ala Tyr Gly Asp Ile Phe Gly Ser
                 85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
130                 135                 140

Glu Thr Val Phe Gly Asn Glu Gly Trp Asn Trp Asp Asn Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Val Asn Gly Thr
            180                 185                 190

Val His Ala Gly Pro Arg Asp Thr Gly Asp Tyr Ser Pro Ile Val
            195                 200                 205

Lys Ala Leu Met Ser Ala Val Glu Asp Arg Gly Val Pro Thr Lys Lys
210                 215                 220

Asp Phe Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Gln Tyr Val
                260                 265                 270

Gly Lys Val Leu Leu Ser Gln Asn Gly Thr Thr Pro Arg Ala Val Gly
            275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ala Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ser
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Ala Leu Leu Ile
                405                 410                 415

Gln Tyr Glu Asn Tyr Arg Asp Trp Ile Val Asn His Asn Val Ala Tyr
                420                 425                 430

Ser Glu Leu Phe Leu Asp Thr Ala Gly Val Ala Ser Phe Asp Val Trp
            435                 440                 445

Asp Leu Leu Pro Phe Thr Arg Gly Tyr Val His Ile Leu Asp Lys Asp
450                 455                 460
```

```
Pro Tyr Leu His His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
            485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Thr Glu Tyr
            515                 520                 525

Ile Pro Tyr His Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Val Met Thr Val Phe Tyr Ala Met Ala Leu Lys
            580                 585                 590

Ile Ser Asp Ala Ile Leu Glu Asp Tyr Ala Ser Met Gln
        595                 600                 605

<210> SEQ ID NO 45
<211> LENGTH: 291
<212> TYPE: PRT
<213> ORGANISM: Thermomyces lanuginosus

<400> SEQUENCE: 45

Met Arg Ser Ser Leu Val Leu Phe Phe Leu Ser Ala Trp Thr Ala Leu
1               5                   10                  15

Ala Arg Pro Val Arg Arg Ala Val Pro Gln Asp Leu Leu Asp Gln Phe
                20                  25                  30

Glu Leu Phe Ser Gln Tyr Ser Ala Ala Tyr Cys Ala Ala Asn Asn
        35                  40                  45

His Ala Pro Val Gly Ser Asp Val Thr Cys Ser Glu Asn Val Cys Pro
    50                  55                  60

Glu Val Asp Ala Ala Asp Ala Thr Phe Leu Tyr Ser Phe Glu Asp Ser
65                  70                  75                  80

Gly Leu Gly Asp Val Thr Gly Leu Leu Ala Leu Asp Asn Thr Asn Lys
                85                  90                  95

Leu Ile Val Leu Ser Phe Arg Gly Ser Arg Ser Val Glu Asn Trp Ile
                100                 105                 110

Ala Asn Leu Ala Ala Asp Leu Thr Glu Ile Ser Asp Ile Cys Ser Gly
            115                 120                 125

Cys Glu Gly His Val Gly Phe Val Thr Ser Trp Arg Ser Val Ala Asp
        130                 135                 140

Thr Ile Arg Glu Gln Val Gln Asn Ala Val Asn Glu His Pro Asp Tyr
145                 150                 155                 160

Arg Val Val Phe Thr Gly His Ser Leu Gly Gly Ala Leu Ala Thr Ile
                165                 170                 175

Ala Ala Ala Ala Leu Arg Gly Asn Gly Tyr Asn Ile Asp Val Phe Ser
            180                 185                 190

Tyr Gly Ala Pro Arg Val Gly Asn Arg Ala Phe Ala Glu Phe Leu Thr
            195                 200                 205

Ala Gln Thr Gly Gly Thr Leu Tyr Arg Ile Thr His Thr Asn Asp Ile
        210                 215                 220

Val Pro Arg Leu Pro Pro Arg Asp Trp Gly Tyr Ser His Ser Ser Pro
225                 230                 235                 240
```

```
Glu Tyr Trp Val Thr Ser Gly Asn Asp Val Pro Val Thr Ala Asn Asp
                245                 250                 255

Ile Thr Val Val Glu Gly Ile Asp Ser Thr Asp Gly Asn Asn Gln Gly
                260                 265                 270

Asn Ile Pro Asp Ile Pro Ser His Leu Trp Tyr Phe Gly Pro Ile Ser
                275                 280                 285

Glu Cys Asp
    290

<210> SEQ ID NO 46
<211> LENGTH: 146
<212> TYPE: PRT
<213> ORGANISM: Sus scrofa

<400> SEQUENCE: 46

Met Lys Phe Leu Val Leu Ala Val Leu Leu Thr Val Gly Ala Ala Gln
1               5                   10                  15

Glu Gly Ile Ser Ser Arg Ala Leu Trp Gln Phe Arg Ser Met Ile Lys
                20                  25                  30

Cys Ala Ile Pro Gly Ser His Pro Leu Met Asp Phe Asn Asn Tyr Gly
                35                  40                  45

Cys Tyr Cys Gly Leu Gly Gly Ser Gly Thr Pro Val Asp Glu Leu Asp
            50                  55                  60

Arg Cys Cys Glu Thr His Asp Asn Cys Tyr Arg Asp Ala Lys Asn Leu
65                  70                  75                  80

Asp Ser Cys Lys Phe Leu Val Asp Asn Pro Tyr Thr Glu Ser Tyr Ser
                85                  90                  95

Tyr Ser Cys Ser Asn Thr Glu Ile Thr Cys Asn Ser Lys Asn Asn Ala
                100                 105                 110

Cys Glu Ala Phe Ile Cys Asn Cys Asp Arg Asn Ala Ala Ile Cys Phe
            115                 120                 125

Ser Lys Ala Pro Tyr Asn Lys Glu His Lys Asn Leu Asp Thr Lys Lys
            130                 135                 140

Tyr Cys
145

<210> SEQ ID NO 47
<211> LENGTH: 150
<212> TYPE: PRT
<213> ORGANISM: Streptomyces vialaceoruber

<400> SEQUENCE: 47

Met Arg Thr Thr Thr Arg Thr Arg Thr Thr Leu Ala Ala Val Gly Ala
1               5                   10                  15

Ala Leu Ala Leu Gly Val Ala Ala Pro Pro Gln Ala Pro Ala Pro Ala
                20                  25                  30

Asp Lys Pro Gln Val Leu Ala Ser Phe Thr Gln Thr Ser Ala Ser Ser
                35                  40                  45

Gln Asn Ala Trp Leu Ala Ala Asn Arg Asn Gln Ser Ala Trp Ala Ala
            50                  55                  60

Tyr Glu Phe Asp Trp Ser Thr Asp Leu Cys Ser Gln Ala Pro Asp Asn
65                  70                  75                  80

Pro Phe Gly Phe Pro Phe Asn Thr Ala Cys Ala Arg His Asp Phe Gly
                85                  90                  95

Tyr Arg Asn Tyr Lys Ala Ala Gly Ser Phe Asp Ala Asn Lys Ser Arg
                100                 105                 110
```

```
Ile Asp Ser Ala Phe Tyr Glu Asp Met Lys Arg Val Cys Thr Gly Tyr
        115                 120                 125

Thr Gly Glu Lys Asn Thr Ala Cys Asn Ser Thr Ala Trp Thr Tyr Tyr
        130                 135                 140

Gln Ala Val Lys Ile Leu
145                 150

<210> SEQ ID NO 48
<211> LENGTH: 295
<212> TYPE: PRT
<213> ORGANISM: Aspergillus niger

<400> SEQUENCE: 48

Met Phe Ser Leu Ala Arg Leu Gly Thr Val Ala Gly Leu Phe Leu Leu
1               5                   10                  15

Ala Gln Ala Ala Pro Ala Ser Leu Arg Arg Asp Val Ser Ser Ser Leu
            20                  25                  30

Leu Asn Asn Leu Asp Leu Phe Ala Gln Tyr Ser Ala Ala Ala Tyr Cys
        35                  40                  45

Asp Glu Asn Leu Asn Ser Thr Gly Thr Lys Leu Thr Cys Ser Val Gly
50                  55                  60

Asn Cys Pro Leu Val Glu Ala Ala Ser Thr Gln Ser Leu Asp Glu Phe
65                  70                  75                  80

Asn Glu Ser Ser Ser Tyr Gly Asn Pro Ala Gly Tyr Leu Ala Ala Asp
                85                  90                  95

Glu Thr Asn Lys Leu Leu Val Leu Ser Phe Arg Gly Ser Ala Asp Leu
            100                 105                 110

Ala Asn Trp Val Ala Asn Leu Asn Phe Gly Leu Glu Asp Ala Ser Asp
        115                 120                 125

Leu Cys Ser Gly Cys Glu Val His Ser Gly Phe Trp Lys Ala Trp Ser
    130                 135                 140

Glu Ile Ala Asp Thr Ile Thr Ser Lys Val Glu Ser Ala Leu Ser Asp
145                 150                 155                 160

His Ser Asp Tyr Ser Leu Val Leu Thr Gly His Ser Tyr Gly Ala Ala
                165                 170                 175

Leu Ala Ala Leu Ala Ala Thr Ala Leu Arg Asn Ser Gly His Ser Val
            180                 185                 190

Glu Leu Tyr Asn Tyr Gly Gln Pro Arg Leu Gly Asn Glu Ala Leu Ala
        195                 200                 205

Thr Tyr Ile Thr Asp Gln Asn Lys Gly Gly Asn Tyr Arg Val Thr His
    210                 215                 220

Thr Asn Asp Ile Val Pro Lys Leu Pro Pro Thr Leu Leu Gly Tyr His
225                 230                 235                 240

His Phe Ser Pro Glu Tyr Tyr Ile Ser Ser Ala Asp Glu Ala Thr Val
                245                 250                 255

Thr Thr Thr Asp Val Thr Glu Val Thr Gly Ile Asp Ala Thr Gly Gly
            260                 265                 270

Asn Asp Gly Thr Asp Gly Thr Ser Ile Asp Ala His Arg Trp Tyr Phe
        275                 280                 285

Ile Tyr Ile Ser Glu Cys Ser
    290                 295

<210> SEQ ID NO 49
<211> LENGTH: 515
<212> TYPE: PRT
```

<213> ORGANISM: Artificial Sequence
<220> FEATURE:
<223> OTHER INFORMATION: Mutated glucoamylase

<400> SEQUENCE: 49

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Asn Arg Ser Asn Phe Thr Gln Trp Ile
        35                  40                  45

His Glu Gln Pro Ala Val Ser Trp Tyr Tyr Leu Leu Gln Asn Ile Asp
50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335

Ser Tyr Val Leu Asn Ser Leu Tyr Tyr Leu Leu Val Asp Asn Lys Asn
            340                 345                 350

Arg Tyr Lys Ile Asn Gly Asn Tyr Lys Ala Gly Ala Ala Val Gly Arg
        355                 360                 365

Tyr Pro Glu Asp Val Tyr Asn Gly Val Gly Thr Ser Glu Gly Asn Pro
370                 375                 380
```

```
Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
            405                 410                 415

Tyr Asp Leu Tyr Asn Ser Phe Ile Ala Asp Leu Ser Lys Ile Asp Ser
        420                 425                 430

Ser Tyr Ala Ser Lys Asp Ser Leu Thr Leu Tyr Gly Ser Asp Asn
        435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 50
<211> LENGTH: 652
<212> TYPE: PRT
<213> ORGANISM: Artificial Sequence
<220> FEATURE:
<223> OTHER INFORMATION: Mutated alpha-amylase

<400> SEQUENCE: 50

Met Leu Leu Gln Ala Phe Leu Phe Leu Leu Ala Gly Phe Ala Ala Lys
1               5                   10                  15

Ile Ser Ala Gly Pro Ala Ala Asn Ala Glu Thr Ala Asn Lys Ser
            20                  25                  30

Asn Asn Val Thr Ala Ser Ser Val Lys Asn Gly Thr Ile Leu His Ala
            35                  40                  45

Trp Asn Trp Ser Phe Asn Thr Leu Thr Gln Asn Met Lys Asp Ile Arg
    50                  55                  60

Asp Ala Gly Tyr Ala Ala Ile Gln Thr Ser Pro Ile Asn Gln Val Lys
65                  70                  75                  80

Glu Gly Asn Gln Gly Asp Lys Ser Met Arg Asn Trp Tyr Trp Leu Tyr
                85                  90                  95

Gln Pro Thr Ser Tyr Gln Ile Gly Asn Arg Tyr Leu Gly Thr Glu Gln
            100                 105                 110

Glu Phe Lys Asp Met Cys Ala Ala Glu Lys Tyr Gly Val Lys Val
        115                 120                 125

Ile Val Asp Ala Val Ile Asn His Thr Thr Ser Asp Tyr Gly Ala Ile
130                 135                 140

Ser Asp Glu Ile Lys Arg Ile Pro Asn Trp Thr His Gly Asn Thr Gln
145                 150                 155                 160

Ile Lys Asn Trp Ser Asp Arg Trp Asp Val Thr Gln Asn Ser Leu Leu
                165                 170                 175

Gly Leu Tyr Asp Trp Asn Thr Gln Asn Thr Glu Val Gln Val Tyr Leu
            180                 185                 190

Lys Arg Phe Leu Glu Arg Ala Leu Asn Asp Gly Ala Asp Gly Phe Arg
        195                 200                 205

Tyr Asp Ala Ala Lys His Ile Glu Leu Pro Asp Asp Gly Asn Tyr Gly
    210                 215                 220
```

```
Ser Gln Phe Trp Pro Asn Ile Thr Asn Thr Ser Ala Glu Phe Gln Tyr
225                 230                 235                 240

Gly Glu Ile Leu Gln Asp Ser Ala Ser Arg Asp Thr Ala Tyr Ala Asn
                245                 250                 255

Tyr Met Asn Val Thr Ala Ser Asn Tyr Gly His Ser Ile Arg Ser Ala
            260                 265                 270

Leu Lys Asn Arg Asn Leu Ser Val Ser Asn Ile Ser His Tyr Ala Ser
        275                 280                 285

Asp Val Ser Ala Asp Lys Leu Val Thr Trp Val Glu Ser His Asp Thr
    290                 295                 300

Tyr Ala Asn Asp Asp Glu Glu Ser Thr Trp Met Ser Asp Asp Asp Ile
305                 310                 315                 320

Arg Leu Gly Trp Ala Val Ile Gly Ser Arg Ser Gly Ser Thr Pro Leu
                325                 330                 335

Phe Phe Ser Arg Pro Glu Gly Gly Asn Gly Val Arg Phe Pro Gly
                340                 345                 350

Lys Ser Gln Ile Gly Asp Arg Gly Ser Ala Leu Phe Lys Asp Gln Ala
                355                 360                 365

Ile Thr Ala Val Asn Thr Phe His Asn Val Met Ala Gly Gln Pro Glu
370                 375                 380

Glu Leu Ser Asn Pro Asn Gly Asn Asn Gln Val Phe Met Asn Gln Arg
385                 390                 395                 400

Gly Ser Lys Gly Val Val Leu Ala Asn Ala Gly Ser Ser Ser Val Thr
                405                 410                 415

Ile Asn Thr Ser Ala Lys Leu Pro Asp Gly Arg Tyr Asp Asn Arg Ala
                420                 425                 430

Gly Ala Gly Ser Phe Gln Val Ala Asn Gly Lys Leu Thr Gly Thr Ile
                435                 440                 445

Asn Ala Arg Ser Ala Ala Val Leu Tyr Pro Asp Asp Ile Gly Asn Ala
450                 455                 460

Pro His Val Phe Leu Glu Asn Tyr Gln Thr Gly Ala Val His Ser Phe
465                 470                 475                 480

Asn Asp Gln Leu Thr Val Thr Leu Arg Ala Asn Ala Lys Thr Thr Lys
                485                 490                 495

Ala Val Tyr Gln Ile Asn Asn Gly Gln Gln Thr Ala Phe Lys Asp Gly
                500                 505                 510

Asp Arg Leu Thr Ile Gly Lys Gly Asp Pro Ile Gly Thr Thr Tyr Asn
                515                 520                 525

Ile Lys Leu Thr Gly Thr Asn Gly Glu Gly Ala Ala Arg Thr Gln Glu
                530                 535                 540

Tyr Thr Phe Val Lys Lys Asp Pro Ser Gln Thr Asn Ile Ile Gly Tyr
545                 550                 555                 560

Gln Asn Pro Asp His Trp Gly Gln Val Asn Ala Tyr Ile Tyr Lys His
                565                 570                 575

Asp Gly Gly Arg Ala Ile Glu Leu Thr Gly Ser Trp Pro Gly Lys Ala
                580                 585                 590

Met Thr Lys Asn Ala Asn Gly Met Tyr Thr Leu Thr Leu Pro Glu Asn
                595                 600                 605

Thr Asp Thr Ala Asn Ala Lys Val Ile Phe Asn Asn Gly Ser Ala Gln
                610                 615                 620

Val Pro Gly Gln Asn Gln Pro Gly Phe Asp Tyr Val Gln Asn Gly Leu
625                 630                 635                 640
```

Tyr Asn Asn Ser Gly Leu Asn Gly Tyr Leu Pro His
            645                 650

<210> SEQ ID NO 51
<211> LENGTH: 713
<212> TYPE: PRT
<213> ORGANISM: Artificial Sequence
<220> FEATURE:
<223> OTHER INFORMATION: Mutated maltogenic alpha-amylase

<400> SEQUENCE: 51

Met Leu Leu Gln Ala Phe Leu Phe Leu Leu Ala Gly Phe Ala Ala Lys
1               5                   10                  15

Ile Ser Ala Tyr Asn Pro Asn Ala Ala Glu Ala Ser Ser Ser Ala Ser
            20                  25                  30

Val Lys Gly Asp Val Ile Tyr Gln Ile Ile Asp Arg Phe Tyr Asp
        35                  40                  45

Gly Asp Thr Thr Asn Asn Asn Pro Ala Lys Ser Tyr Gly Leu Tyr Asp
    50                  55                  60

Pro Thr Lys Ser Lys Trp Lys Met Tyr Trp Gly Gly Asp Leu Glu Gly
65                  70                  75                  80

Val Arg Gln Lys Leu Pro Tyr Leu Lys Gln Leu Gly Val Thr Thr Ile
                85                  90                  95

Trp Leu Ser Pro Val Leu Asp Asn Leu Asp Thr Leu Ala Gly Thr Asp
            100                 105                 110

Asn Thr Gly Tyr His Gly Tyr Trp Thr Arg Asp Phe Lys Gln Ile Glu
        115                 120                 125

Glu His Phe Gly Asn Trp Thr Thr Phe Asp Thr Leu Val Asn Asp Ala
130                 135                 140

His Gln Asn Gly Ile Lys Val Ile Val Asp Phe Val Pro Asn His Ser
145                 150                 155                 160

Thr Pro Phe Lys Ala Asn Asp Ser Thr Phe Ala Glu Gly Gly Ala Leu
                165                 170                 175

Tyr Asn Asn Gly Thr Tyr Met Gly Asn Tyr Phe Asp Asp Ala Thr Lys
            180                 185                 190

Gly Tyr Phe His His Asn Gly Asp Ile Ser Asn Trp Asp Asp Arg Tyr
        195                 200                 205

Glu Ala Gln Trp Lys Asn Phe Thr Asp Pro Ala Gly Phe Ser Leu Ala
    210                 215                 220

Asp Leu Ser Gln Glu Asn Gly Thr Ile Ala Gln Tyr Leu Thr Asp Ala
225                 230                 235                 240

Ala Val Gln Leu Val Ala His Gly Ala Asp Gly Leu Arg Ile Asp Ala
                245                 250                 255

Val Lys His Phe Asn Ser Gly Phe Ser Lys Ser Leu Ala Asp Lys Leu
            260                 265                 270

Tyr Gln Lys Lys Asp Ile Phe Leu Val Gly Glu Trp Tyr Gly Asp Asp
        275                 280                 285

Pro Gly Thr Ala Asn His Leu Glu Lys Val Arg Tyr Ala Asn Asn Ser
    290                 295                 300

Gly Val Asn Val Leu Asp Phe Asp Leu Asn Thr Val Ile Arg Asn Val
305                 310                 315                 320

Phe Gly Thr Phe Thr Gln Thr Met Tyr Asp Leu Asn Asn Met Val Asn
                325                 330                 335

Gln Thr Gly Asn Glu Tyr Lys Tyr Lys Glu Asn Leu Ile Thr Phe Ile
            340                 345                 350

Asp Asn His Asp Met Ser Arg Phe Leu Ser Val Asn Ser Asn Lys Ala
        355                 360                 365

Asn Leu His Gln Ala Leu Ala Phe Ile Leu Thr Ser Arg Gly Thr Pro
    370                 375                 380

Ser Ile Tyr Tyr Gly Thr Glu Gln Tyr Met Ala Gly Gly Asn Asp Pro
385                 390                 395                 400

Tyr Asn Arg Gly Met Met Pro Ala Phe Asp Thr Thr Thr Ala Phe
                405                 410                 415

Lys Glu Val Ser Thr Leu Ala Gly Leu Arg Arg Asn Asn Ala Ala Ile
            420                 425                 430

Gln Tyr Gly Thr Thr Thr Gln Arg Trp Ile Asn Asn Asp Val Tyr Ile
        435                 440                 445

Tyr Glu Arg Lys Phe Phe Asn Asp Val Val Leu Val Ala Ile Asn Arg
    450                 455                 460

Asn Thr Gln Ser Ser Tyr Ser Ile Ser Gly Leu Gln Thr Ala Leu Pro
465                 470                 475                 480

Asn Gly Ser Tyr Ala Asp Tyr Leu Ser Gly Leu Leu Gly Gly Asn Gly
                485                 490                 495

Ile Ser Val Ser Asn Gly Ser Val Ala Ser Phe Thr Leu Ala Pro Gly
            500                 505                 510

Ala Val Ser Val Trp Gln Tyr Ser Thr Ser Ala Ser Ala Pro Gln Ile
        515                 520                 525

Gly Ser Val Ala Pro Asn Met Gly Ile Pro Gly Asn Val Val Thr Ile
    530                 535                 540

Asp Gly Lys Gly Phe Gly Thr Thr Gln Gly Thr Val Thr Phe Gly Gly
545                 550                 555                 560

Val Thr Ala Thr Val Lys Ser Trp Thr Ser Asn Arg Ile Glu Val Tyr
                565                 570                 575

Val Pro Asn Met Ala Ala Gly Leu Thr Asp Val Lys Val Thr Ala Gly
            580                 585                 590

Gly Val Ser Ser Asn Leu Tyr Ser Tyr Asn Ile Leu Ser Gly Thr Gln
        595                 600                 605

Thr Ser Val Val Phe Thr Val Lys Ser Ala Pro Pro Thr Asn Leu Gly
    610                 615                 620

Asp Lys Ile Tyr Leu Thr Gly Asn Ile Pro Glu Leu Gly Asn Trp Ser
625                 630                 635                 640

Thr Asp Thr Ser Gly Ala Val Asn Asn Ala Gln Gly Pro Leu Leu Ala
                645                 650                 655

Pro Asn Tyr Pro Asp Trp Phe Tyr Val Phe Ser Val Pro Ala Gly Lys
            660                 665                 670

Thr Ile Gln Phe Lys Phe Phe Ile Lys Arg Ala Asp Gly Thr Ile Gln
        675                 680                 685

Trp Glu Asn Gly Ser Asn His Val Ala Thr Thr Pro Thr Gly Ala Thr
    690                 695                 700

Gly Asn Ile Thr Val Thr Trp Gln Asn
705                 710

<210> SEQ ID NO 52
<211> LENGTH: 19
<212> TYPE: PRT
<213> ORGANISM: Saccharomyces cerevisiae

<400> SEQUENCE: 52

Met Leu Leu Gln Ala Phe Leu Phe Leu Leu Ala Gly Phe Ala Ala Lys
1               5                   10                  15

<210> SEQ ID NO 53
<211> LENGTH: 22
<212> TYPE: PRT
<213> ORGANISM: Artificial Sequence
<220> FEATURE:
<223> OTHER INFORMATION: HA tag

<400> SEQUENCE: 53

Lys Asp Asn Ser Ser Thr Ile Glu Gly Arg Tyr Pro Tyr Asp Val Pro
1               5                   10                  15

Asp Tyr Ala Leu Gln Ala
            20

<210> SEQ ID NO 54
<211> LENGTH: 18
<212> TYPE: PRT
<213> ORGANISM: Artificial Sequence
<220> FEATURE:
<223> OTHER INFORMATION: Modified G4S linker

<400> SEQUENCE: 54

Ser Gly Gly Gly Gly Ser Gly Gly Gly Gly Ser Gly Gly Gly Gly Ser
1               5                   10                  15

Ala Ser

<210> SEQ ID NO 55
<211> LENGTH: 750
<212> TYPE: DNA
<213> ORGANISM: Artificial Sequence
<220> FEATURE:
<223> OTHER INFORMATION: Promoter of trx2 gene

<400> SEQUENCE: 55

```
ataaccacaa tgatcgcaga ccgtcgacat gataatgact tctttaaagt gtgggatatt      60
tactggcttc atatgagttt cacactcttg ggtacacgat ggacaagaag ctctgaatgt     120
ttgcacctcg ttgttaaagt tttcgatgtc ggtggcgtct gacaaaaact gtgggtttgc     180
tgagccaact ttgacagatt cagaaggatt tctttcacgg ttggccaatt gttttaattg     240
ttcttggcga cgttgctcca actggtctct agtaataatg ccaacttgaa cgttttgttc     300
gtcggttctc acgtactggg tatgagacca tttgtgttga ggttcaccgg gtttgtattc     360
gatccaggaa tttcccgcag gatcatccaa aataaatgta atcggaatag tgttgggttc     420
acaattgatg taggatttaa ctttctgtac gaagtcatcg atcttcttgt aaagagcttc     480
gtctatagat tttctcattt cctggtcttg cgacagatcg tcgatcatct cggataacaa     540
accttcaact gtcgtcaatt gacctctctt agcaggaatc tcaatgtcta gctcgacaaa     600
cttacaagtg gcagtttctg acttaataac ttgcctgtta aaatcttcac ggcactccac     660
tttcaaaacg taacgagagc ccttctcttg aatttgagaa gcgggttgga tctcacagtt     720
cttaaaccca cagtgaggac agtcgaatga                                     750
```

<210> SEQ ID NO 56
<211> LENGTH: 750
<212> TYPE: DNA
<213> ORGANISM: Artificial Sequence
<220> FEATURE:
<223> OTHER INFORMATION: Promoter of sti1 gene

<400> SEQUENCE: 56

```
taccacaaag ggtaaaacgt caataaaagc aagcaatgtt attcgtgcca gagaactata    60
tctggcgtac gtcttatata taacacaagc aagggcaaat acgtggttag tggtgtaaaa   120
actgaaggga ttaatttaca tacaactaga tccatctttc tcaaaaatga cttcagtatc   180
gccctcgcca cctgccagtc gatcgggctc aatgtgctcc gacttaccgt cctctttgca   240
gactgagaaa ctggcacata ttataggtct tgatgccgac gatgaagttc tccggcgcgt   300
aaccaagcag ttgagcagat ctaggagaat tgcttgtctg actggggcag gcatttcgtg   360
caacgcgggc attcctgact ttcgctcttc tgatgggctc tacgacctag tgaaaaagga   420
ttgttcacag tattggtcta tcaagtccgg cagggaaatg tttgatattt cgctatttag   480
agatgacttc aaaatatcca tttttgctaa atttatggag aggctctatt caaatgttca   540
attggcaaag ccgactaaga cgcacaagtt cattgcgcat ctaaaagata ggaacaaact   600
gctgcgctgt tacacgcaaa acatcgatgg gctcgaagaa agcataggac ttactttatc   660
aaataggaaa ttaccgctta cctcatttag ttcacattgg aaaaatctgg atgtcgttca   720
gttgcacggc gacctgaaaa ctctttcgtg                                   750
```

<210> SEQ ID NO 57
<211> LENGTH: 750
<212> TYPE: DNA
<213> ORGANISM: Artificial Sequence
<220> FEATURE:
<223> OTHER INFORMATION: Promoter of gdp1 gene

<400> SEQUENCE: 57

```
aaggaaaata tatactcttt cccaggcaag gtgacagcgg tccccgtctc ctccacaaag    60
gcctctcctg gggtttgagc aagtctaagt ttacgtagca taaaaattct cggattgcgt   120
caaataataa aaaagtaac tccacttcta cttctacatc ggaaaaacat tccattcaca   180
tatcgtcttt ggcctatctt gttttgtcct tggtagatca ggtcagtaca aacgcaacac   240
gaaagaacaa aaaagaaga aaacagaag gccaagacag ggtcaatgag actgttgtcc   300
tcctactgtc cctatgtctc tggccgatca cgcgccattg tccctcagaa acaaatcaaa   360
cacccacacc ccgggcaccc aaagtcccca cccacaccac caatacgtaa acggggcgcc   420
ccctgcaggc cctcctgcgc gcggcctccc gccttgcttc tctcccctcc cttttctttt   480
tccagttttc cctattttgt ccctttttcc gcacaacaag tatcagaatg ggttcatcaa   540
atctatccaa cctaattcgc acgtagactg gcttggtatt ggcagtttcg cagttatata   600
tatactacca tgagtgaaac tgttacgtta ccttaaattc tttctcccctt taattttctt   660
ttatcttact ctcctacata agacatcaag aaacaattgt atattgtaca cccccccccc   720
tccacaaaca caaatattga taatataaag                                   750
```

<210> SEQ ID NO 58
<211> LENGTH: 750
<212> TYPE: DNA
<213> ORGANISM: Artificial Sequence
<220> FEATURE:
<223> OTHER INFORMATION: Promoter of cup1 gene

<400> SEQUENCE: 58

```
taaatatatg ctgagattta gcaagaaaaa acaaaatttt gcgagaaact ctgataacaa    60
taatgttaca gattatagtc agtcggcgaa gaacaaaaat gttctcttga aattccccgt   120
```

| | |
|---|---|
| tagtgaactg aacagaatct atttaaaatt taaggagatt tcagatttttt taatggaaag | 180 |
| agaagttgtc caaaggagta taattattga caaggatttg gaatctgata atctgggtat | 240 |
| tactacggca aacttcaacg atttctatga tgcattttat aattagtaag ccgatcccat | 300 |
| taccgacatt tgggcgctat acgtgcatat gttcatgtat gtatctgtat ttaaaacact | 360 |
| tttgtattat ttttcctcat atatgtgtat aggtttatac ggatgattta attattactt | 420 |
| caccacccctt tatttcaggc tgatatctta gccttgttac tagttagaaa aagacattttt | 480 |
| tgctgtcagt cactgtcaag agattctttt gctggcattt cttctagaag caaaaagagc | 540 |
| gatgcgtctt ttccgctgaa ccgttccagc aaaaaagact accaacgcaa tatggattgt | 600 |
| cagaatcata taaagagaa gcaaataact ccttgtcttg tatcaattgc attataatat | 660 |
| cttcttgtta gtgcaatatc atatagaagt catcgaaata gatattaaga aaacaaact | 720 |
| gtacaatcaa tcaatcaatc atcacataaa | 750 |

<210> SEQ ID NO 59
<211> LENGTH: 750
<212> TYPE: DNA
<213> ORGANISM: Artificial Sequence
<220> FEATURE:
<223> OTHER INFORMATION: Promoter of glo1 gene

<400> SEQUENCE: 59

| | |
|---|---|
| tattaatcca aaaagtgaat ctttgacacc cctttctcct atcttgctta gtaccgagtg | 60 |
| atcttttgca taatcaaaac aagtgaagaa ggtcgagttt tgaaccttct ctaatataag | 120 |
| tcgacggtct ttcgtgatgg cgtcaatatt acttagtctt ttgtacttca catataccat | 180 |
| taatggcgtc aatcccttat aattttcctc attaatatct agcttagtca gttgtaaaag | 240 |
| gattggaatg tttgttttca aaacatgcaa caagctattg cccttattat cggtgtggtc | 300 |
| tagatagtca aacaaactgt tgtgctttct ataccaagta tttgcgatat caaatgcggt | 360 |
| cttcaccatt tcttcataat ttggttgatc ataacttcta aagatggaaa ataaaggcgt | 420 |
| ttgtccactg gagtttttttc gtttccaatc aatataatttt ccgatgcttt taagtatatc | 480 |
| catttcatgg gttagataat gagccacggt acgtgcatat ttatctgttt tattgatata | 540 |
| agaaaccagc tcctcttcag tacaattgaa cagcatgatc tttatgagaa cttttcgcggc | 600 |
| ttctaaattt cctgctttta tcgattctat aagcagcgta gaaccatcaa tcgtttcgtc | 660 |
| ctctaaaagg tcttctactg gaaagtcgtt ttcatattca gaaagaatat ctaataagat | 720 |
| gtagtttttta tgatttgtta tacatatgga | 750 |

<210> SEQ ID NO 60
<211> LENGTH: 750
<212> TYPE: DNA
<213> ORGANISM: Artificial Sequence
<220> FEATURE:
<223> OTHER INFORMATION: Promoter of ctt1 gene

<400> SEQUENCE: 60

| | |
|---|---|
| ttaactgcaa agacccgtca cctatgaata agatgactct cttgttgggg tcaatctcct | 60 |
| cagcggcaaa ggcagcacct aaagttgctc ctgttgtaaa accgatagac ccccacaaca | 120 |
| cttgcgagat accgtaggcg tccttaggaa agatagtttg attgataccg aaggcagacg | 180 |
| tgccggtctc ggaaatgata acatcacctt cttgcaagaa cttggacaat tcgttccaca | 240 |
| accactcttg tttcaaggc gtgctagcag atacaccttt gtttgcggga gttttggttg | 300 |
| gtacgggaac gctcttgtag cccttaataa catcgggaat aaccttcagt aagttttgta | 360 |

```
gtgcaaattt catttgtacg ccggggaacg tagcgttctt caccttacg taatcggaat    420 gaaactccac tacattttta gtcttgtagg agtaggaaaa cgaacctgtg ttaaaatcag    480
agagcaaagc accgaccgaa aggatcaaat cagccgactc aacggcctgt ttcacgtctg    540
gtttggacag cgttcccaca taaacaccgc catatctggg atgctgttca tctattgacc    600
ctttacctaa aggtgtcaca aaagctggga attgcgtcaa atcaattaac ttctgggttt    660
cctttttaac gttgtgccta gaagcacagg catccgatag tatgacaggg ttttcgaat    720 tctggatcaa ttctagtacg gtatcaataa                                    750

<210> SEQ ID NO 61
<211> LENGTH: 750
<212> TYPE: DNA
<213> ORGANISM: Artificial Sequence
<220> FEATURE:
<223> OTHER INFORMATION: Promoter of ygp1 gene

<400> SEQUENCE: 61
tctcataatt ggtcagaaga aaggaaatct aggcaattga gttctttggg taaaaaagag     60
tcacaatttt taaggctgcg tagaacgaga ttatcgttag aagatttcca cactgtgaaa    120
gtcattggaa aagggcatt tggtgaagtc agactggttc agaagaaaga caccggaaaa    180
atatatgcaa tgaaactttt attaaaatcc gaaatgtaca aaaaggacca attagcacac    240
gtcaaggctg aaagggatgt tctggctgga agtgattctc catgggtggt ttcgctatat    300
tactcattcc aagatgctca atacttatat ttaatcatgg aatttttgcc cggtggtgat    360
ttgatgacca tgctaatcag gtggcaacta tttacagagg atgttactag atttacatg    420 gctgagtgta ttttggccat cgaaaccatt cataaattag gattcattca cagagatatt    480
aaaccagata atattttgat cgatattaga ggtcatataa aattatctga tttcgggttg    540
tctacggggt tccataaaac tcacgactca aactactata aaaagctttt gcaacaagat    600
gaggcaacta atggtatttc caagccaggt acttacaatg caaatacaac cgatactgca    660 aataaaggc aaacaatggt tgtggattct attagtctaa caatgtcaaa caggcaacaa    720
attcagacat ggagaaaatc acgtcgttta                                    750

<210> SEQ ID NO 62
<211> LENGTH: 750
<212> TYPE: DNA
<213> ORGANISM: Artificial Sequence
<220> FEATURE:
<223> OTHER INFORMATION: Promoter of gsy2 gene

<400> SEQUENCE: 62
tattatagct cttgataaca atgaaatttc aacaattatt cactcaaccc tcaagtgtat     60
atcgccaaga tcctaatcac ccctctctgg tggccttccc tcattgtttt tacacagaac    120
aagaatccat aaaatcaaga tattgggaac aattcattgt cttaggaaca gttttttata    180
atttagtttc attagcctat tgtaacttct tgttttttttt tttattttgg ctggcaaaac    240
aagaagtata aagaagttac cactgctata acgtatatct taaatcaagt gggcaattct    300
tcgaataaac ttagaggcgc tgaagaaaga accgctcaat tagttcgatc atacaaaata    360
cagatattgc gctgtgtatt atcattacag aaagtgtgat ataaacaatg ctgtgttgta    420
ttcggtcttt tttttccgcc tgcagattgt cgttttgtt tttttttctc gtgtagctgc    480
agttatcatc gttttgcatg tctgttctgt cggtgaagcc gatctcatgg cacttcgctt    540
```

```
tgataccgta aagaatcttc ttcattaata cggcactgca aggcgatatc tatctctggg    600
gttaggactg ataaataggt acttatcagt tatcactaga gacgaactgt ttacgttttg    660
aagctcgaca gcaggggttc ttaacgggcg tcggcctaga cctcaccttg cgagaaattt    720
ttagttcata tccaggggat ggtgaatggt                                     750

<210> SEQ ID NO 63
<211> LENGTH: 750
<212> TYPE: DNA
<213> ORGANISM: Artificial Sequence
<220> FEATURE:
<223> OTHER INFORMATION: Promoter of hsp12 gene

<400> SEQUENCE: 63
gcttgtccac aatcaccatg gggttatatt gcattatttt tttatcttcg ttatcattcc     60
atactgtggc ttcattccag tatttatga gtttgctgaa ggattcgggg gtaatagtgc    120
ccacggtggt caaaaccttt agcgtctcag tgacctgttc caaatccccc tcttccattc    180
gccttatata aaatccatcg ggtaagctca ttattttatg ttgatatcca gcttccgttc    240
gtcaactatt ctctcgagct cagttttggg ttttggcatg taaacaatgc cttcgcttgt    300
attacgcaaa aaaaaaaaaa ataaataaaa aaaaaaaaa aaaataagg tataaatcgt     360 tggttctttt atgcacaatt atttaactat agttatctat ttacgtaaag cttctatttt    420
ttccttatct acaagaaatt gcatgaagtt taattttttt tgtcaccttt gatcttcctg    480
aatgtgttgg taatgaaatt ttctagtctc ttcaaagtgt tgtcgtcatc cttttttgcg    540
tgtttttcct cttcttgttt ttgtttcttc agtatctctt cattaatggc tgtacccgcg    600
gctgtgcccg gttgcatggt tttcttggcc atgtcatcgt tggtgacatc tgccagtgcc    660
tcccacaagc attttctgc cagcgattgc ggtttcttaa caacgatctt gtactggact    720
ttcatatcac cgcgaatggt tgatgtttta                                     750

<210> SEQ ID NO 64
<211> LENGTH: 750
<212> TYPE: DNA
<213> ORGANISM: Artificial Sequence
<220> FEATURE:
<223> OTHER INFORMATION: Promoter of mol1/thi4 genes

<400> SEQUENCE: 64
tcgttgaaag ttctagattt gggtacggaa gcagccatgt aaatggtctt cctttgtaat     60
aatatcgtca ctggagtttt taaattagag tacggattca agttaacgaa aaatttctgt    120
tggtatctga tagcaatttg tcgacaaggt ggagagtttt tgaagttttt ttttgtaaca    180
gttatgttac actatttacc agagaaacac caagacagga gccctcagaa gctttcgtgt    240
tgtcagaaca taaatatctt ctatatgttt tattctttta tattaatcaa tatttatgt     300 taaatcatat tattattcgt taatgcttaa cttgccctat ttcaaaatcg aagggtagt    360 atggtgacaa gcggtgtttt tggtgtatgt ttactgctaa gagtataccg tcctgtttac    420
ttttttacct tttgttccgt tattgatttt tcgcagcaag gttgaagctt ccatatttga    480
aaatgaaatt aagaagtaga gatgaaaaac agcgacgaaa ttactttta tagcttcttt    540 cccttctgac tccgttttat aaacagggga tctttaaggg cttacaaaat aaatataaac    600
actaacacat atatattatt cgacctacag ttttgcgac caatgaagtt tacctatttt    660
gagatggtgc ttacgtagtt tgcttaaggt caaggcggga ttaagcttgc gctttctcta    720
aataatatca tatgttacag acagggataa                                     750
```

```
<210> SEQ ID NO 65
<211> LENGTH: 695
<212> TYPE: PRT
<213> ORGANISM: Geobacillus stearothermophilus

<400> SEQUENCE: 65

Met Tyr Asn Pro Asn Ala Ala Glu Ala Ser Ser Ala Ser Val Lys
1               5                   10                  15

Gly Asp Val Ile Tyr Gln Ile Ile Asp Arg Phe Tyr Asp Gly Asp
                20                  25                  30

Thr Thr Asn Asn Asn Pro Ala Lys Ser Tyr Gly Leu Tyr Asp Pro Thr
            35                  40                  45

Lys Ser Lys Trp Lys Met Tyr Trp Gly Gly Asp Leu Glu Gly Val Arg
50                  55                  60

Gln Lys Leu Pro Tyr Leu Lys Gln Leu Gly Val Thr Thr Ile Trp Leu
65                  70                  75                  80

Ser Pro Val Leu Asp Asn Leu Asp Thr Leu Ala Gly Thr Asp Asn Thr
                85                  90                  95

Gly Tyr His Gly Tyr Trp Thr Arg Asp Phe Lys Gln Ile Glu Glu His
            100                 105                 110

Phe Gly Asn Trp Thr Thr Phe Asp Thr Leu Val Asn Asp Ala His Gln
            115                 120                 125

Asn Gly Ile Lys Val Ile Val Asp Phe Val Pro Asn His Ser Thr Pro
        130                 135                 140

Phe Lys Ala Asn Asp Ser Thr Phe Ala Glu Gly Gly Ala Leu Tyr Asn
145                 150                 155                 160

Asn Gly Thr Tyr Met Gly Asn Tyr Phe Asp Asp Ala Thr Lys Gly Tyr
                165                 170                 175

Phe His His Asn Gly Asp Ile Ser Asn Trp Asp Asp Arg Tyr Glu Ala
            180                 185                 190

Gln Trp Lys Asn Phe Thr Asp Pro Ala Gly Phe Ser Leu Ala Asp Leu
        195                 200                 205

Ser Gln Glu Asn Gly Thr Ile Ala Gln Tyr Leu Thr Asp Ala Ala Val
210                 215                 220

Gln Leu Val Ala His Gly Ala Asp Gly Leu Arg Ile Asp Ala Val Lys
225                 230                 235                 240

His Phe Asn Ser Gly Phe Ser Lys Ser Leu Ala Asp Lys Leu Tyr Gln
                245                 250                 255

Lys Lys Asp Ile Phe Leu Val Gly Glu Trp Tyr Gly Asp Asp Pro Gly
            260                 265                 270

Thr Ala Asn His Leu Glu Lys Val Arg Tyr Ala Asn Asn Ser Gly Val
        275                 280                 285

Asn Val Leu Asp Phe Asp Leu Asn Thr Val Ile Arg Asn Val Phe Gly
290                 295                 300

Thr Phe Thr Gln Thr Met Tyr Asp Leu Asn Asn Met Val Asn Gln Thr
305                 310                 315                 320

Gly Asn Glu Tyr Lys Tyr Lys Glu Asn Leu Ile Thr Phe Ile Asp Asn
                325                 330                 335

His Asp Met Ser Arg Phe Leu Ser Val Asn Ser Asn Lys Ala Asn Leu
            340                 345                 350

His Gln Ala Leu Ala Phe Ile Leu Thr Ser Arg Gly Thr Pro Ser Ile
        355                 360                 365
```

-continued

Tyr Tyr Gly Thr Glu Gln Tyr Met Ala Gly Gly Asn Asp Pro Tyr Asn
            370                 375                 380

Arg Gly Met Met Pro Ala Phe Asp Thr Thr Thr Ala Phe Lys Glu
385                 390                 395                 400

Val Ser Thr Leu Ala Gly Leu Arg Arg Asn Asn Ala Ala Ile Gln Tyr
                405                 410                 415

Gly Thr Thr Thr Gln Arg Trp Ile Asn Asn Asp Val Tyr Ile Tyr Glu
            420                 425                 430

Arg Lys Phe Phe Asn Asp Val Val Leu Val Ala Ile Asn Arg Asn Thr
            435                 440                 445

Gln Ser Ser Tyr Ser Ile Ser Gly Leu Gln Thr Ala Leu Pro Asn Gly
            450                 455                 460

Ser Tyr Ala Asp Tyr Leu Ser Gly Leu Leu Gly Gly Asn Gly Ile Ser
465                 470                 475                 480

Val Ser Asn Gly Ser Val Ala Ser Phe Thr Leu Ala Pro Gly Ala Val
                485                 490                 495

Ser Val Trp Gln Tyr Ser Thr Ser Ala Ser Ala Pro Gln Ile Gly Ser
                500                 505                 510

Val Ala Pro Asn Met Gly Ile Pro Gly Asn Val Val Thr Ile Asp Gly
            515                 520                 525

Lys Gly Phe Gly Thr Thr Gln Gly Thr Val Thr Phe Gly Gly Val Thr
530                 535                 540

Ala Thr Val Lys Ser Trp Thr Ser Asn Arg Ile Glu Val Tyr Val Pro
545                 550                 555                 560

Asn Met Ala Ala Gly Leu Thr Asp Val Lys Val Thr Ala Gly Gly Val
                565                 570                 575

Ser Ser Asn Leu Tyr Ser Tyr Asn Ile Leu Ser Gly Thr Gln Thr Ser
            580                 585                 590

Val Val Phe Thr Val Lys Ser Ala Pro Pro Thr Asn Leu Gly Asp Lys
            595                 600                 605

Ile Tyr Leu Thr Gly Asn Ile Pro Glu Leu Gly Asn Trp Ser Thr Asp
610                 615                 620

Thr Ser Gly Ala Val Asn Asn Ala Gln Gly Pro Leu Leu Ala Pro Asn
625                 630                 635                 640

Tyr Pro Asp Trp Phe Tyr Val Phe Ser Val Pro Ala Gly Lys Thr Ile
                645                 650                 655

Gln Phe Lys Phe Phe Ile Lys Arg Ala Asp Gly Thr Ile Gln Trp Glu
            660                 665                 670

Asn Gly Ser Asn His Val Ala Thr Thr Pro Thr Gly Ala Thr Gly Asn
            675                 680                 685

Ile Thr Val Thr Trp Gln Asn
690                 695

<210> SEQ ID NO 66
<211> LENGTH: 411
<212> TYPE: PRT
<213> ORGANISM: Citrobacter braakii

<400> SEQUENCE: 66

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
             35                  40                  45

Pro Arg Gly Gly Glu Leu Val Ser Glu Leu Gly Gln Tyr Gln Arg Leu
 50                  55                  60

Trp Phe Thr Ser Lys Gly Leu Leu Asn Asn Gln Thr Cys Pro Ser Pro
 65                  70                  75                  80

Gly Gln Val Ala Val Ile Ala Asp Thr Asp Gln Arg Thr Arg Lys Thr
                 85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
             115                 120                 125

Lys Met Gly Lys Cys Ser Phe Asn Thr Leu Lys Val Lys Asn Ala Ile
             130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
                180                 185                 190

Leu Pro Ser Glu Phe Lys Val Thr Pro Asp Asn Val Ser Leu Pro Gly
            195                 200                 205

Ala Trp Ser Leu Ser Ser Thr Leu Thr Glu Ile Phe Leu Leu Gln Glu
            210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
            290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 67
<211> LENGTH: 410
<212> TYPE: PRT
<213> ORGANISM: Escherichia coli

<400> SEQUENCE: 67

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

<210> SEQ ID NO 68
<211> LENGTH: 19
<212> TYPE: PRT
<213> ORGANISM: Saccharomyces cerevisiae

<400> SEQUENCE: 68

```
Met Leu Leu Gln Ala Phe Leu Phe Leu Ala Gly Phe Ala Ala Lys
1               5                   10                  15

Ile Ser Ala
```

<210> SEQ ID NO 69
<211> LENGTH: 18
<212> TYPE: PRT
<213> ORGANISM: Saccharomyces cerevisiae

<400> SEQUENCE: 69

```
Met Gln Leu Leu Arg Cys Phe Ser Ile Phe Ser Val Ile Ala Ser Val
1               5                   10                  15

Leu Ala
```

<210> SEQ ID NO 70
<211> LENGTH: 500
<212> TYPE: DNA
<213> ORGANISM: Saccharomyces cerevisiae

<400> SEQUENCE: 70

```
tagcgtgtta cgcacccaaa cttttttatga aagtctttgt ttataatgat gaggtttata      60
aatatatagt ggagcaaaga ttaatcacta aatcaagaag cagtaccagt attttttta      120
tatcaagtag tgataatgga aatagcccaa atttggcttc cgtcggcaca tagcacgttt     180
gagagacatt atcaccatca agcatcgagc cgcccaaacc taactgtata agtttttttca    240
cgttttttgat ttttccttgc acacttcgat attactctca cgataaaagg gccgaagaga    300
atattttttct tgaacatcca gaattttaat tcggagaaat ttcacaagcc gccgatttaa    360
gggtcctgtg ttcttaataa tcagcctctc tcaaagcagg taagaggcag tctttctttt    420
aacaatagga gacattcgaa ctaaaacatc agccccaaaa atgcgcttga aggtcattag     480
gatttggatt tcttcctcat                                                 500
```

<210> SEQ ID NO 71
<211> LENGTH: 460
<212> TYPE: PRT
<213> ORGANISM: Pyrococcus furiosus

<400> SEQUENCE: 71

```
Met Asn Ile Lys Lys Leu Thr Pro Leu Leu Thr Leu Leu Phe Phe
1               5                   10                  15

Ile Val Leu Ala Ser Pro Val Ser Ala Ala Lys Tyr Leu Glu Leu Glu
                20                  25                  30

Glu Gly Gly Val Ile Met Gln Ala Phe Tyr Trp Asp Val Pro Gly Gly
            35                  40                  45

Gly Ile Trp Trp Asp His Ile Arg Ser Lys Ile Pro Glu Trp Tyr Glu
        50                  55                  60

Ala Gly Ile Ser Ala Ile Trp Leu Pro Pro Pro Ser Lys Gly Met Ser
65                  70                  75                  80

Gly Gly Tyr Ser Met Gly Tyr Asp Pro Tyr Asp Tyr Phe Asp Leu Gly
                85                  90                  95
```

```
Glu Tyr Tyr Gln Lys Gly Thr Val Glu Thr Arg Phe Gly Ser Lys Glu
            100                 105                 110

Glu Leu Val Arg Leu Ile Gln Thr Ala His Ala Tyr Gly Ile Lys Val
        115                 120                 125

Ile Ala Asp Val Val Ile Asn His Arg Ala Gly Gly Asp Leu Glu Trp
130                 135                 140

Asn Pro Phe Val Gly Asp Tyr Thr Trp Thr Asp Phe Ser Lys Val Ala
145                 150                 155                 160

Ser Gly Lys Tyr Thr Ala Asn Tyr Leu Asp Phe His Pro Asn Glu Leu
                165                 170                 175

His Cys Cys Asp Glu Gly Thr Phe Gly Gly Phe Pro Asp Ile Cys His
            180                 185                 190

His Lys Glu Trp Asp Gln Tyr Trp Leu Trp Lys Ser Asn Glu Ser Tyr
        195                 200                 205

Ala Ala Tyr Leu Arg Ser Ile Gly Phe Asp Gly Trp Arg Phe Asp Tyr
210                 215                 220

Val Lys Gly Tyr Gly Ala Trp Val Val Arg Asp Trp Leu Asn Trp Trp
225                 230                 235                 240

Gly Gly Trp Ala Val Gly Glu Tyr Trp Asp Thr Asn Val Asp Ala Leu
                245                 250                 255

Leu Ser Trp Ala Tyr Glu Ser Gly Ala Lys Val Phe Asp Phe Pro Leu
            260                 265                 270

Tyr Tyr Lys Met Asp Glu Ala Phe Asp Asn Asn Ile Pro Ala Leu
        275                 280                 285

Val Tyr Ala Leu Gln Asn Gly Gln Thr Val Val Ser Arg Asp Pro Phe
290                 295                 300

Lys Ala Val Thr Phe Val Ala Asn His Asp Thr Asp Ile Ile Trp Asn
305                 310                 315                 320

Lys Tyr Pro Ala Tyr Ala Phe Ile Leu Thr Tyr Glu Gly Gln Pro Val
                325                 330                 335

Ile Phe Tyr Arg Asp Phe Glu Glu Trp Leu Asn Lys Asp Lys Leu Ile
            340                 345                 350

Asn Leu Ile Trp Ile His Asp His Leu Ala Gly Gly Ser Thr Thr Ile
        355                 360                 365

Val Tyr Tyr Asp Asn Asp Glu Leu Ile Phe Val Arg Asn Gly Asp Ser
370                 375                 380

Arg Arg Pro Gly Leu Ile Thr Tyr Ile Asn Leu Ser Pro Asn Trp Val
385                 390                 395                 400

Gly Arg Trp Val Tyr Val Pro Lys Phe Ala Gly Ala Cys Ile His Glu
                405                 410                 415

Tyr Thr Gly Asn Leu Gly Gly Trp Val Asp Lys Arg Val Asp Ser Ser
            420                 425                 430

Gly Trp Val Tyr Leu Glu Ala Pro Pro His Asp Pro Ala Asn Gly Tyr
        435                 440                 445

Tyr Gly Tyr Ser Val Trp Ser Tyr Cys Gly Val Gly
450                 455                 460

<210> SEQ ID NO 72
<211> LENGTH: 457
<212> TYPE: PRT
<213> ORGANISM: Thermococcus hydrothermalis

<400> SEQUENCE: 72

Met Ala Arg Lys Val Leu Val Ala Leu Leu Val Phe Leu Val Val Leu
1               5                   10                  15
```

```
Ser Val Ser Ala Val Pro Ala Lys Ala Glu Thr Leu Glu Asn Gly Gly
            20                  25                  30

Val Ile Met Gln Ala Phe Tyr Trp Asp Val Pro Gly Gly Ile Trp
        35                  40                  45

Trp Asp Thr Ile Ala Gln Lys Ile Pro Asp Trp Ala Ser Ala Gly Ile
 50                  55                  60

Ser Ala Ile Trp Ile Pro Pro Ala Ser Lys Gly Met Ser Gly Gly Tyr
 65                  70                  75                  80

Ser Met Gly Tyr Asp Pro Tyr Asp Phe Phe Asp Leu Gly Tyr Tyr
                85                  90                  95

Gln Lys Gly Ser Val Glu Thr Arg Phe Gly Ser Lys Glu Glu Leu Val
            100                 105                 110

Asn Met Ile Asn Thr Ala His Ala His Asn Met Lys Val Ile Ala Asp
            115                 120                 125

Ile Val Ile Asn His Arg Ala Gly Gly Asp Leu Glu Trp Asn Pro Phe
130                 135                 140

Thr Asn Ser Tyr Thr Trp Thr Asp Phe Ser Lys Val Ala Ser Gly Lys
145                 150                 155                 160

Tyr Thr Ala Asn Tyr Leu Asp Phe His Pro Asn Glu Leu His Ala Gly
                165                 170                 175

Asp Ser Gly Thr Phe Gly Gly Tyr Pro Asp Ile Cys His Asp Lys Ser
            180                 185                 190

Trp Asp Gln His Trp Leu Trp Ala Ser Asn Glu Ser Tyr Ala Ala Tyr
            195                 200                 205

Leu Arg Ser Ile Gly Ile Asp Ala Trp Arg Phe Asp Tyr Val Lys Gly
            210                 215                 220

Tyr Ala Pro Trp Val Val Lys Asn Trp Leu Asn Arg Trp Gly Gly Trp
225                 230                 235                 240

Ala Val Gly Glu Tyr Trp Asp Thr Asn Val Asp Ala Leu Leu Ser Trp
                245                 250                 255

Ala Tyr Asp Ser Gly Ala Lys Val Phe Asp Phe Pro Leu Tyr Tyr Lys
            260                 265                 270

Met Asp Glu Ala Phe Asp Asn Asn Ile Pro Ala Leu Val Asp Ala
            275                 280                 285

Leu Lys Asn Gly Gly Thr Val Val Ser Arg Asp Pro Phe Lys Ala Val
290                 295                 300

Thr Phe Val Ala Asn His Asp Thr Asn Ile Ile Trp Asn Lys Tyr Pro
305                 310                 315                 320

Ala Tyr Ala Phe Ile Leu Thr Tyr Glu Gly Gln Pro Ala Ile Phe Tyr
                325                 330                 335

Arg Asp Tyr Glu Glu Trp Leu Asn Lys Asp Arg Leu Arg Asn Leu Ile
            340                 345                 350

Trp Ile His Asp His Leu Ala Gly Gly Ser Thr Asp Ile Ile Tyr Tyr
            355                 360                 365

Asp Ser Asp Glu Leu Ile Phe Val Arg Asn Gly Tyr Gly Asp Lys Pro
    370                 375                 380

Gly Leu Ile Thr Tyr Ile Asn Leu Gly Ser Ser Lys Ala Gly Arg Trp
385                 390                 395                 400

Val Tyr Val Pro Lys Phe Ala Gly Ser Cys Ile His Glu Tyr Thr Gly
                405                 410                 415

Asn Leu Gly Gly Trp Ile Asp Lys Trp Val Asp Ser Ser Gly Arg Val
            420                 425                 430
```

```
Tyr Leu Glu Ala Pro Ala His Asp Pro Ala Asn Gly Gln Tyr Gly Tyr
            435                 440                 445

Ser Val Trp Ser Tyr Cys Gly Val Gly
    450                 455
```

<210> SEQ ID NO 73
<211> LENGTH: 390
<212> TYPE: DNA
<213> ORGANISM: Artificial Sequence
<220> FEATURE:
<223> OTHER INFORMATION: SPI1 tethering moiety
<220> FEATURE:
<221> NAME/KEY: CDS
<222> LOCATION: (1)..(390)

<400> SEQUENCE: 73

```
ttg gta tct aat tct agt tcc tct gta atc gtg gta cca tca agc gat         48
Leu Val Ser Asn Ser Ser Ser Ser Val Ile Val Val Pro Ser Ser Asp
1               5                   10                  15 gct act att gcc ggt aac gat aca gcc acg cca gca cca gag cca tca         96
Ala Thr Ile Ala Gly Asn Asp Thr Ala Thr Pro Ala Pro Glu Pro Ser
            20                  25                  30 tcc gcc gct cca ata ttc tac aac tcg act gct act gca aca cag tac        144
Ser Ala Ala Pro Ile Phe Tyr Asn Ser Thr Ala Thr Ala Thr Gln Tyr
        35                  40                  45 gaa gtt gtc agt gaa ttc act act tac tgc cca gaa cca acg act ttc        192
Glu Val Val Ser Glu Phe Thr Thr Tyr Cys Pro Glu Pro Thr Thr Phe
    50                  55                  60 gta acg aat ggc gct aca ttc act gtt act gcc cca act acg tta aca        240
Val Thr Asn Gly Ala Thr Phe Thr Val Thr Ala Pro Thr Thr Leu Thr
65                  70                  75                  80 att acc aac tgt cct tgc act atc gag aag cct act tca gaa aca tcg        288
Ile Thr Asn Cys Pro Cys Thr Ile Glu Lys Pro Thr Ser Glu Thr Ser
                85                  90                  95 gtt tct tct aca cat gat gtg gag aca aat tct aat gct gct aac gca        336
Val Ser Ser Thr His Asp Val Glu Thr Asn Ser Asn Ala Ala Asn Ala
            100                 105                 110 aga gca atc cca gga gcc cta ggt ttg gct ggt gca gtt atg atg ctt        384
Arg Ala Ile Pro Gly Ala Leu Gly Leu Ala Gly Ala Val Met Met Leu
        115                 120                 125 tta tga                                                                 390
Leu
```

<210> SEQ ID NO 74
<211> LENGTH: 129
<212> TYPE: PRT
<213> ORGANISM: Artificial Sequence
<220> FEATURE:
<223> OTHER INFORMATION: Synthetic Construct

<400> SEQUENCE: 74

```
Leu Val Ser Asn Ser Ser Ser Ser Val Ile Val Val Pro Ser Ser Asp
1               5                   10                  15

Ala Thr Ile Ala Gly Asn Asp Thr Ala Thr Pro Ala Pro Glu Pro Ser
            20                  25                  30

Ser Ala Ala Pro Ile Phe Tyr Asn Ser Thr Ala Thr Ala Thr Gln Tyr
        35                  40                  45

Glu Val Val Ser Glu Phe Thr Thr Tyr Cys Pro Glu Pro Thr Thr Phe
    50                  55                  60

Val Thr Asn Gly Ala Thr Phe Thr Val Thr Ala Pro Thr Thr Leu Thr
65                  70                  75                  80
```

Ile Thr Asn Cys Pro Cys Thr Ile Glu Lys Pro Thr Ser Glu Thr Ser
            85                  90                  95

Val Ser Ser Thr His Asp Val Glu Thr Asn Ser Asn Ala Ala Asn Ala
            100                 105                 110

Arg Ala Ile Pro Gly Ala Leu Gly Leu Ala Gly Ala Val Met Met Leu
        115                 120                 125

Leu

<210> SEQ ID NO 75
<211> LENGTH: 66
<212> TYPE: DNA
<213> ORGANISM: Artificial Sequence
<220> FEATURE:
<223> OTHER INFORMATION: 21aa-truncation of the SPI1 tethering moiety
<220> FEATURE:
<221> NAME/KEY: CDS
<222> LOCATION: (1)..(66)

<400> SEQUENCE: 75 gct gct aac gca aga gca atc cca gga gcc cta ggt ttg gct ggt gca    48
Ala Ala Asn Ala Arg Ala Ile Pro Gly Ala Leu Gly Leu Ala Gly Ala
1               5                   10                  15 gtt atg atg ctt tta tga                                            66
Val Met Met Leu Leu
            20

<210> SEQ ID NO 76
<211> LENGTH: 21
<212> TYPE: PRT
<213> ORGANISM: Artificial Sequence
<220> FEATURE:
<223> OTHER INFORMATION: Synthetic Construct

<400> SEQUENCE: 76

Ala Ala Asn Ala Arg Ala Ile Pro Gly Ala Leu Gly Leu Ala Gly Ala
1               5                   10                  15

Val Met Met Leu Leu
            20

<210> SEQ ID NO 77
<211> LENGTH: 156
<212> TYPE: DNA
<213> ORGANISM: Artificial Sequence
<220> FEATURE:
<223> OTHER INFORMATION: 51aa-truncation of the SPI1 tethering moiety
<220> FEATURE:
<221> NAME/KEY: CDS
<222> LOCATION: (1)..(156)

<400> SEQUENCE: 77 tta aca att acc aac tgt cct tgc act atc gag aag cct act tca gaa    48
Leu Thr Ile Thr Asn Cys Pro Cys Thr Ile Glu Lys Pro Thr Ser Glu
1               5                   10                  15 aca tcg gtt tct tct aca cat gat gtg gag aca aat tct aat gct gct    96
Thr Ser Val Ser Ser Thr His Asp Val Glu Thr Asn Ser Asn Ala Ala
            20                  25                  30 aac gca aga gca atc cca gga gcc cta ggt ttg gct ggt gca gtt atg   144
Asn Ala Arg Ala Ile Pro Gly Ala Leu Gly Leu Ala Gly Ala Val Met
        35                  40                  45 atg ctt tta tga                                                   156
Met Leu Leu
    50

<210> SEQ ID NO 78

```
<211> LENGTH: 51
<212> TYPE: PRT
<213> ORGANISM: Artificial Sequence
<220> FEATURE:
<223> OTHER INFORMATION: Synthetic Construct

<400> SEQUENCE: 78

Leu Thr Ile Thr Asn Cys Pro Cys Thr Ile Glu Lys Pro Thr Ser Glu
1               5                   10                  15

Thr Ser Val Ser Ser Thr His Asp Val Glu Thr Asn Ser Asn Ala Ala
            20                  25                  30

Asn Ala Arg Ala Ile Pro Gly Ala Leu Gly Leu Ala Gly Ala Val Met
        35                  40                  45

Met Leu Leu
    50

<210> SEQ ID NO 79
<211> LENGTH: 246
<212> TYPE: DNA
<213> ORGANISM: Artificial Sequence
<220> FEATURE:
<223> OTHER INFORMATION: 81aa-truncation of the SPI1 tethering moiety
<220> FEATURE:
<221> NAME/KEY: CDS
<222> LOCATION: (1)..(246)

<400> SEQUENCE: 79 gaa gtt gtc agt gaa ttc act act tac tgc cca gaa cca acg act ttc      48
Glu Val Val Ser Glu Phe Thr Thr Tyr Cys Pro Glu Pro Thr Thr Phe
1               5                   10                  15 gta acg aat ggc gct aca ttc act gtt act gcc cca act acg tta aca      96
Val Thr Asn Gly Ala Thr Phe Thr Val Thr Ala Pro Thr Thr Leu Thr
            20                  25                  30 att acc aac tgt cct tgc act atc gag aag cct act tca gaa aca tcg     144
Ile Thr Asn Cys Pro Cys Thr Ile Glu Lys Pro Thr Ser Glu Thr Ser
        35                  40                  45 gtt tct tct aca cat gat gtg gag aca aat tct aat gct gct aac gca     192
Val Ser Ser Thr His Asp Val Glu Thr Asn Ser Asn Ala Ala Asn Ala
    50                  55                  60 aga gca atc cca gga gcc cta ggt ttg gct ggt gca gtt atg atg ctt     240
Arg Ala Ile Pro Gly Ala Leu Gly Leu Ala Gly Ala Val Met Met Leu
65                  70                  75                  80 tta tga                                                              246
Leu

<210> SEQ ID NO 80
<211> LENGTH: 81
<212> TYPE: PRT
<213> ORGANISM: Artificial Sequence
<220> FEATURE:
<223> OTHER INFORMATION: Synthetic Construct

<400> SEQUENCE: 80

Glu Val Val Ser Glu Phe Thr Thr Tyr Cys Pro Glu Pro Thr Thr Phe
1               5                   10                  15

Val Thr Asn Gly Ala Thr Phe Thr Val Thr Ala Pro Thr Thr Leu Thr
            20                  25                  30

Ile Thr Asn Cys Pro Cys Thr Ile Glu Lys Pro Thr Ser Glu Thr Ser
        35                  40                  45

Val Ser Ser Thr His Asp Val Glu Thr Asn Ser Asn Ala Ala Asn Ala
    50                  55                  60
```

```
Arg Ala Ile Pro Gly Ala Leu Gly Leu Ala Gly Ala Val Met Met Leu
 65                  70                  75                  80

Leu

<210> SEQ ID NO 81
<211> LENGTH: 336
<212> TYPE: DNA
<213> ORGANISM: Artificial Sequence
<220> FEATURE:
<223> OTHER INFORMATION: 111aa-truncation of the SPI1 tethering moiety
<220> FEATURE:
<221> NAME/KEY: CDS
<222> LOCATION: (1)..(336)

<400> SEQUENCE: 81 att gcc ggt aac gat aca gcc acg cca gca cca gag cca tca tcc gcc      48
Ile Ala Gly Asn Asp Thr Ala Thr Pro Ala Pro Glu Pro Ser Ser Ala
  1               5                  10                  15 gct cca ata ttc tac aac tcg act gct act gca aca cag tac gaa gtt      96
Ala Pro Ile Phe Tyr Asn Ser Thr Ala Thr Ala Thr Gln Tyr Glu Val
             20                  25                  30 gtc agt gaa ttc act act tac tgc cca gaa cca acg act ttc gta acg     144
Val Ser Glu Phe Thr Thr Tyr Cys Pro Glu Pro Thr Thr Phe Val Thr
         35                  40                  45 aat ggc gct aca ttc act gtt act gcc cca act acg tta aca att acc     192
Asn Gly Ala Thr Phe Thr Val Thr Ala Pro Thr Thr Leu Thr Ile Thr
     50                  55                  60 aac tgt cct tgc act atc gag aag cct act tca gaa aca tcg gtt tct     240
Asn Cys Pro Cys Thr Ile Glu Lys Pro Thr Ser Glu Thr Ser Val Ser
 65                  70                  75                  80 tct aca cat gat gtg gag aca aat tct aat gct gct aac gca aga gca     288
Ser Thr His Asp Val Glu Thr Asn Ser Asn Ala Ala Asn Ala Arg Ala
                 85                  90                  95 atc cca gga gcc cta ggt ttg gct ggt gca gtt atg atg ctt tta tga     336
Ile Pro Gly Ala Leu Gly Leu Ala Gly Ala Val Met Met Leu Leu
            100                 105                 110

<210> SEQ ID NO 82
<211> LENGTH: 111
<212> TYPE: PRT
<213> ORGANISM: Artificial Sequence
<220> FEATURE:
<223> OTHER INFORMATION: Synthetic Construct

<400> SEQUENCE: 82

Ile Ala Gly Asn Asp Thr Ala Thr Pro Ala Pro Glu Pro Ser Ser Ala
  1               5                  10                  15

Ala Pro Ile Phe Tyr Asn Ser Thr Ala Thr Ala Thr Gln Tyr Glu Val
             20                  25                  30

Val Ser Glu Phe Thr Thr Tyr Cys Pro Glu Pro Thr Thr Phe Val Thr
         35                  40                  45

Asn Gly Ala Thr Phe Thr Val Thr Ala Pro Thr Thr Leu Thr Ile Thr
     50                  55                  60

Asn Cys Pro Cys Thr Ile Glu Lys Pro Thr Ser Glu Thr Ser Val Ser
 65                  70                  75                  80

Ser Thr His Asp Val Glu Thr Asn Ser Asn Ala Ala Asn Ala Arg Ala
                 85                  90                  95

Ile Pro Gly Ala Leu Gly Leu Ala Gly Ala Val Met Met Leu Leu
            100                 105                 110
```

-continued

```
<210> SEQ ID NO 83
<211> LENGTH: 339
<212> TYPE: DNA
<213> ORGANISM: Artificial Sequence
<220> FEATURE:
<223> OTHER INFORMATION: CCW12 tethering moiety
<220> FEATURE:
<221> NAME/KEY: CDS
<222> LOCATION: (1)..(339)

<400> SEQUENCE: 83 gtt acc act gct act gtc agc caa gaa tct acc act ttg gtc acc atc      48
Val Thr Thr Ala Thr Val Ser Gln Glu Ser Thr Thr Leu Val Thr Ile
 1               5                  10                  15 act tct tgt gaa gac cac gtc tgt tct gaa act gtc tcc cca gct ttg      96
Thr Ser Cys Glu Asp His Val Cys Ser Glu Thr Val Ser Pro Ala Leu
            20                  25                  30 gtt tcc acc gct acc gtc acc gtc gat gac gtt atc act caa tac acc     144
Val Ser Thr Ala Thr Val Thr Val Asp Asp Val Ile Thr Gln Tyr Thr
        35                  40                  45 acc tgg tgc cca ttg acc act gaa gcc cca aag aac ggt act tct act     192
Thr Trp Cys Pro Leu Thr Thr Glu Ala Pro Lys Asn Gly Thr Ser Thr
    50                  55                  60 gct gct cca gtt acc tct act gaa gct cca aag aac acc acc tct gct     240
Ala Ala Pro Val Thr Ser Thr Glu Ala Pro Lys Asn Thr Thr Ser Ala
65                  70                  75                  80 gct cca act cac tct gtc acc tct tac act ggt gct gct gct aag gct     288
Ala Pro Thr His Ser Val Thr Ser Tyr Thr Gly Ala Ala Ala Lys Ala
                85                  90                  95 ttg cca gct gct ggt gct ttg ttg gct ggt gcc gct gct ttg ttg ttg     336
Leu Pro Ala Ala Gly Ala Leu Leu Ala Gly Ala Ala Ala Leu Leu Leu
            100                 105                 110 taa                                                                  339

<210> SEQ ID NO 84
<211> LENGTH: 112
<212> TYPE: PRT
<213> ORGANISM: Artificial Sequence
<220> FEATURE:
<223> OTHER INFORMATION: Synthetic Construct

<400> SEQUENCE: 84

Val Thr Thr Ala Thr Val Ser Gln Glu Ser Thr Thr Leu Val Thr Ile
 1               5                  10                  15

Thr Ser Cys Glu Asp His Val Cys Ser Glu Thr Val Ser Pro Ala Leu
            20                  25                  30

Val Ser Thr Ala Thr Val Thr Val Asp Asp Val Ile Thr Gln Tyr Thr
        35                  40                  45

Thr Trp Cys Pro Leu Thr Thr Glu Ala Pro Lys Asn Gly Thr Ser Thr
    50                  55                  60

Ala Ala Pro Val Thr Ser Thr Glu Ala Pro Lys Asn Thr Thr Ser Ala
65                  70                  75                  80

Ala Pro Thr His Ser Val Thr Ser Tyr Thr Gly Ala Ala Ala Lys Ala
                85                  90                  95

Leu Pro Ala Ala Gly Ala Leu Leu Ala Gly Ala Ala Ala Leu Leu Leu
            100                 105                 110

<210> SEQ ID NO 85
<211> LENGTH: 75
<212> TYPE: DNA
<213> ORGANISM: Artificial Sequence
<220> FEATURE:
```

```
<223> OTHER INFORMATION: 24aa-truncation of the CCW12 tethering moiety
<220> FEATURE:
<221> NAME/KEY: CDS
<222> LOCATION: (1)..(75)

<400> SEQUENCE: 85 tac act ggt gct gct gct aag gct ttg cca gct gct ggt gct ttg         48
Tyr Thr Gly Ala Ala Ala Lys Ala Leu Pro Ala Ala Gly Ala Leu
1               5                   10                  15 gct ggt gcc gct gct ttg ttg ttg taa                                 75
Ala Gly Ala Ala Ala Leu Leu Leu
            20

<210> SEQ ID NO 86
<211> LENGTH: 24
<212> TYPE: PRT
<213> ORGANISM: Artificial Sequence
<220> FEATURE:
<223> OTHER INFORMATION: Synthetic Construct

<400> SEQUENCE: 86

Tyr Thr Gly Ala Ala Ala Lys Ala Leu Pro Ala Ala Gly Ala Leu Leu
1               5                   10                  15

Ala Gly Ala Ala Ala Leu Leu Leu
            20

<210> SEQ ID NO 87
<211> LENGTH: 150
<212> TYPE: DNA
<213> ORGANISM: Artificial Sequence
<220> FEATURE:
<223> OTHER INFORMATION: 49aa-truncation of the CCW12 tethering moiety
<220> FEATURE:
<221> NAME/KEY: CDS
<222> LOCATION: (1)..(150)

<400> SEQUENCE: 87 act gct gct cca gtt acc tct act gaa gct cca aag aac acc acc tct    48
Thr Ala Ala Pro Val Thr Ser Thr Glu Ala Pro Lys Asn Thr Thr Ser
1               5                   10                  15 gct gct cca act cac tct gtc acc tct tac act ggt gct gct gct aag    96
Ala Ala Pro Thr His Ser Val Thr Ser Tyr Thr Gly Ala Ala Ala Lys
            20                  25                  30 gct ttg cca gct gct ggt gct ttg ttg gct ggt gcc gct gct ttg ttg   144
Ala Leu Pro Ala Ala Gly Ala Leu Leu Ala Gly Ala Ala Ala Leu Leu
        35                  40                  45 ttg taa                                                           150
Leu

<210> SEQ ID NO 88
<211> LENGTH: 49
<212> TYPE: PRT
<213> ORGANISM: Artificial Sequence
<220> FEATURE:
<223> OTHER INFORMATION: Synthetic Construct

<400> SEQUENCE: 88

Thr Ala Ala Pro Val Thr Ser Thr Glu Ala Pro Lys Asn Thr Thr Ser
1               5                   10                  15

Ala Ala Pro Thr His Ser Val Thr Ser Tyr Thr Gly Ala Ala Ala Lys
            20                  25                  30

Ala Leu Pro Ala Ala Gly Ala Leu Leu Ala Gly Ala Ala Ala Leu Leu
        35                  40                  45

Leu
```

<210> SEQ ID NO 89
<211> LENGTH: 225
<212> TYPE: DNA
<213> ORGANISM: Artificial Sequence
<220> FEATURE:
<223> OTHER INFORMATION: 74aa-truncation of the CCW12 tethering moiety
<220> FEATURE:
<221> NAME/KEY: CDS
<222> LOCATION: (1)..(225)

<400> SEQUENCE: 89

```
acc gtc gat gac gtt atc act caa tac acc acc tgg tgc cca ttg acc      48
Thr Val Asp Asp Val Ile Thr Gln Tyr Thr Thr Trp Cys Pro Leu Thr
1               5                  10                  15 act gaa gcc cca aag aac ggt act tct act gct gct cca gtt acc tct      96
Thr Glu Ala Pro Lys Asn Gly Thr Ser Thr Ala Ala Pro Val Thr Ser
            20                  25                  30 act gaa gct cca aag aac acc acc tct gct gct cca act cac tct gtc     144
Thr Glu Ala Pro Lys Asn Thr Thr Ser Ala Ala Pro Thr His Ser Val
        35                  40                  45 acc tct tac act ggt gct gct gct aag gct ttg cca gct gct ggt gct     192
Thr Ser Tyr Thr Gly Ala Ala Ala Lys Ala Leu Pro Ala Ala Gly Ala
    50                  55                  60 ttg ttg gct ggt gcc gct gct ttg ttg ttg taa                         225
Leu Leu Ala Gly Ala Ala Ala Leu Leu Leu
65                  70
```

<210> SEQ ID NO 90
<211> LENGTH: 74
<212> TYPE: PRT
<213> ORGANISM: Artificial Sequence
<220> FEATURE:
<223> OTHER INFORMATION: Synthetic Construct

<400> SEQUENCE: 90

```
Thr Val Asp Asp Val Ile Thr Gln Tyr Thr Thr Trp Cys Pro Leu Thr
1               5                  10                  15

Thr Glu Ala Pro Lys Asn Gly Thr Ser Thr Ala Ala Pro Val Thr Ser
            20                  25                  30

Thr Glu Ala Pro Lys Asn Thr Thr Ser Ala Ala Pro Thr His Ser Val
        35                  40                  45

Thr Ser Tyr Thr Gly Ala Ala Ala Lys Ala Leu Pro Ala Ala Gly Ala
    50                  55                  60

Leu Leu Ala Gly Ala Ala Ala Leu Leu Leu
65                  70
```

<210> SEQ ID NO 91
<211> LENGTH: 300
<212> TYPE: DNA
<213> ORGANISM: Artificial Sequence
<220> FEATURE:
<223> OTHER INFORMATION: 99aa-truncation of the CCW12 tethering moiety
<220> FEATURE:
<221> NAME/KEY: CDS
<222> LOCATION: (1)..(300)

<400> SEQUENCE: 91

```
gtc acc atc act tct tgt gaa gac cac gtc tgt tct gaa act gtc tcc      48
Val Thr Ile Thr Ser Cys Glu Asp His Val Cys Ser Glu Thr Val Ser
1               5                  10                  15 cca gct ttg gtt tcc acc gct acc gtc acc gtc gat gac gtt atc act      96
Pro Ala Leu Val Ser Thr Ala Thr Val Thr Val Asp Asp Val Ile Thr
            20                  25                  30
```

```
caa tac acc acc tgg tgc cca ttg acc act gaa gcc cca aag aac ggt      144
Gln Tyr Thr Thr Trp Cys Pro Leu Thr Thr Glu Ala Pro Lys Asn Gly
         35                  40                  45 act tct act gct gct cca gtt acc tct act gaa gct cca aag aac acc      192
Thr Ser Thr Ala Ala Pro Val Thr Ser Thr Glu Ala Pro Lys Asn Thr
 50                  55                  60 acc tct gct gct cca act cac tct gtc acc tct tac act ggt gct gct      240
Thr Ser Ala Ala Pro Thr His Ser Val Thr Ser Tyr Thr Gly Ala Ala
 65                  70                  75                  80 gct aag gct ttg cca gct gct ggt gct ttg ttg gct ggt gcc gct gct      288
Ala Lys Ala Leu Pro Ala Ala Gly Ala Leu Leu Ala Gly Ala Ala Ala
                 85                  90                  95 ttg ttg ttg taa                                                      300
Leu Leu Leu
```

<210> SEQ ID NO 92
<211> LENGTH: 99
<212> TYPE: PRT
<213> ORGANISM: Artificial Sequence
<220> FEATURE:
<223> OTHER INFORMATION: Synthetic Construct

<400> SEQUENCE: 92

```
Val Thr Ile Thr Ser Cys Glu Asp His Val Cys Ser Glu Thr Val Ser
 1               5                  10                  15

Pro Ala Leu Val Ser Thr Ala Thr Val Thr Val Asp Asp Val Ile Thr
                 20                  25                  30

Gln Tyr Thr Thr Trp Cys Pro Leu Thr Thr Glu Ala Pro Lys Asn Gly
         35                  40                  45

Thr Ser Thr Ala Ala Pro Val Thr Ser Thr Glu Ala Pro Lys Asn Thr
 50                  55                  60

Thr Ser Ala Ala Pro Thr His Ser Val Thr Ser Tyr Thr Gly Ala Ala
 65                  70                  75                  80

Ala Lys Ala Leu Pro Ala Ala Gly Ala Leu Leu Ala Gly Ala Ala Ala
                 85                  90                  95

Leu Leu Leu
```

<210> SEQ ID NO 93
<211> LENGTH: 15
<212> TYPE: PRT
<213> ORGANISM: Artificial Sequence
<220> FEATURE:
<223> OTHER INFORMATION: Linker 1

<400> SEQUENCE: 93

```
Gly Gly Gly Gly Ser Gly Gly Gly Ser Gly Gly Gly Gly Ser
 1               5                  10                  15
```

<210> SEQ ID NO 94
<211> LENGTH: 8
<212> TYPE: PRT
<213> ORGANISM: Artificial Sequence
<220> FEATURE:
<223> OTHER INFORMATION: Linker 2

<400> SEQUENCE: 94

```
Gly Gly Gly Gly Gly Gly Gly Gly
 1               5
```

<210> SEQ ID NO 95
<211> LENGTH: 40

```
<212> TYPE: PRT
<213> ORGANISM: Artificial Sequence
<220> FEATURE:
<223> OTHER INFORMATION: Linker 3

<400> SEQUENCE: 95

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 96
<211> LENGTH: 12
<212> TYPE: PRT
<213> ORGANISM: Artificial Sequence
<220> FEATURE:
<223> OTHER INFORMATION: Linker 4

<400> SEQUENCE: 96

Gly Ser Ala Gly Ser Ala Ala Gly Ser Gly Glu Phe
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Linker 5

<400> SEQUENCE: 97

Glu Ala Ala Lys Glu Ala Ala Lys Glu Ala Ala Lys
1               5                   10

<210> SEQ ID NO 98
<211> LENGTH: 20
<212> TYPE: PRT
<213> ORGANISM: Artificial Sequence
<220> FEATURE:
<223> OTHER INFORMATION: Linker 6

<400> SEQUENCE: 98

Ala Pro Ala Pro Ala Pro Ala Pro Ala Pro Ala Pro Ala Pro Ala Pro
1               5                   10                  15

Ala Pro Ala Pro
            20

<210> SEQ ID NO 99
<211> LENGTH: 46
<212> TYPE: PRT
<213> ORGANISM: Artificial Sequence
<220> FEATURE:
<223> OTHER INFORMATION: Linker 7

<400> SEQUENCE: 99

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 100
```

```
<211> LENGTH: 4
<212> TYPE: PRT
<213> ORGANISM: Artificial Sequence
<220> FEATURE:
<223> OTHER INFORMATION: EA2K motif

<400> SEQUENCE: 100

Glu Ala Ala Lys
1

<210> SEQ ID NO 101
<211> LENGTH: 5
<212> TYPE: PRT
<213> ORGANISM: Artificial Sequence
<220> FEATURE:
<223> OTHER INFORMATION: EA3K motif

<400> SEQUENCE: 101

Glu Ala Ala Ala Lys
1               5

<210> SEQ ID NO 102
<211> LENGTH: 1752
<212> TYPE: DNA
<213> ORGANISM: Aspergillus niger

<400> SEQUENCE: 102
tccaatggta ttgaggcttc cttgttgact gatccaaaag atgtttctgg tagaaccgtc      60
gattacatta ttgctggtgg tggtttgact ggtttaacta ctgctgctag attgactgaa     120
aacccaaaca tctccgtttt ggttatcgaa tctggttcct acgaatctga tagaggtcca     180
attatcgaag atttgaacgc ctacggtgat atctttggtt cttctgttga tcatgcttac     240
gaaaccgttg aattggctac caacaatcaa actgccttga ttagatctgg taacggttta     300
ggtggttcta ctttggttaa tggtggtact tggactagac cacataaggc tcaagttgat     360
tcttgggaaa ctgttttttgg taacgaaggt tggaattggg ataatgttgc tgcttattca     420
ttgcaagctg aaagggctag agcaccaaat gctaaacaaa ttgctgctgg tcattacttc     480
aatgcctctt gtcatggtgt taacggtact gttcatgctg gtccaagaga tactggtgat     540
gattattctc caatcgttaa ggcttttgatg tccgctgttg aagatagagg tgttccaact     600
aagaaagatt tcggttgtgg tgatccacat ggtgtttcta tgtttccaaa taccttgcac     660
gaagatcaag ttagatctga tgctgcaaga gaatggttgt tgccaaatta tcaaagacca     720
aacttgcagg tcttgactgg tcaatatgtt ggtaaggttt tgttgtccca aaacggtact     780
actccaagag ctgttggtgt tgaatttggt actcataagg gtaacaccca taacgtttac     840
gccaaacatg aagttttgtt agctgctggt tctgctgttt ctccaactat tttggaatac     900
tccggtatcg gtatgaagtc cattttggaa ccattgggta ttgataccgt tgttgatttg     960
ccagttggtt tgaacttaca agatcaaact accgctaccg tcagatctag aattacttct    1020
gctggtgctg gtcaaggtca agctgcttgg tttgctactt taacgaaaac tttcggtgac    1080
tactctgaaa aggcccatga attattgaac accaaattgg aacaatgggc tgaagaggct    1140
gttgctagag gtggttttca taacactact gccttgttga tccagtacga aaattacaga    1200
gattggatcg ttaaccacaa cgttgcttac tctgagttgt ttttggatac tgctggtgtt    1260
gcttcttttg atgtatggga tttgttgcca ttcaccagag gttacgttca cattttggat    1320
aaggatccat acttgcatca tttcgcttac gaccacacaat acttttgaa cgaattggac    1380 ttgttgggtc aagccgctgc tactcaattg gctagaaaca tttctaattc cggtgctatg    1440
```

-continued

```
caaacctatt tcgctggtga aactattcca ggtgataact tggcttatga tgctgatttg   1500
tctgcttgga ctgagtacat tccataccat ttcagaccaa attaccacgg tgttggtact   1560
tgttctatga tgccaaaaga aatgggtggt gttgttgata atgcagctag agtttacggt   1620
gttcaaggtt tgagagttat cgatggttct attccaccaa ctcaaatgtc ctctcatgtt   1680
atgactgttt tctacgctat ggccttgaag atttccgatg caattttgga agattacgcc   1740
tccatgcaat aa                                                       1752
```

<210> SEQ ID NO 103
<211> LENGTH: 583
<212> TYPE: PRT
<213> ORGANISM: Aspergillus niger

<400> SEQUENCE: 103

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300
```

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
            325                 330                 335

Arg Ile Thr Ser Ala Gly Ala Gly Gln Gly Gln Ala Ala Trp Phe Ala
        340                 345                 350

Thr Phe Asn Glu Thr Phe Gly Asp Tyr Ser Glu Lys Ala His Glu Leu
    355                 360                 365

Leu Asn Thr Lys Leu Glu Gln Trp Ala Glu Glu Ala Val Ala Arg Gly
370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
            405                 410                 415

Thr Ala Gly Val Ala Ser Phe Asp Val Trp Asp Leu Leu Pro Phe Thr
        420                 425                 430

Arg Gly Tyr Val His Ile Leu Asp Lys Asp Pro Tyr Leu His His Phe
    435                 440                 445

Ala Tyr Asp Pro Gln Tyr Phe Leu Asn Glu Leu Asp Leu Leu Gly Gln
450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
        500                 505                 510

Pro Asn Tyr His Gly Val Gly Thr Cys Ser Met Met Pro Lys Glu Met
    515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575

Glu Asp Tyr Ala Ser Met Gln
        580

<210> SEQ ID NO 104
<211> LENGTH: 1437
<212> TYPE: DNA
<213> ORGANISM: Aspergillus oryzae

<400> SEQUENCE: 104
gctactccag ctgattggag atcacaatct atctactttt tgttgaccga cagattcgct      60
agaactgatg gttctactac tgctacttgt aataccgctg atagaaagta ttgtggtggt     120
acttggcaag gtatcatcga taagttggat tacattcaag gtatgggttt caccgctatt     180
tggattactc cagttactgc tcaattgcca caaactactg cttatggtga tgcttatcat     240
ggttattggc aacaggatat ctactccttg aacgaaaatt acggtactgc cgatgatttg     300
aaggctttgt catctgcttt acatgaacgt ggtatgtact tgatggttga tgttgttgct     360
aaccacatgg ttatgatgg tgctggttct tctgttgatt actctgtttt taagcccttc     420
agctcccaag attactttca tccattctgc ttgatccaaa actacgaaga tcaaactcaa     480

```
gtcgaagatt gctggttggg tgataatact gtttctttgc cagatttgga taccaccaag      540
gatgttgtta agaacgaatg gtatgattgg gtcggttctt tggtttccaa ctactctatt      600
gatggtttga gaatcgatac cgtcaagcac gttcaaaaag attttggcc aggttacaac       660
aaagctgctg gtgtttactg tattggtgaa gttttagatg gtgatccagc ttacacttgt      720
ccataccaaa atgttatgga tggcgttttg aactacccaa tctactaccc attattgaac     780
gctttcaagt ctacctctgg ttctatggat gacttgtaca acatgatcaa caccgttaag     840
tctgattgtc cagattctac tttgttgggt actttcgttg aaaaccacga taatccaaga    900
ttcgcttctt acaccaacga tattgctttg gctaaaaacg ttgccgcctt cattattttg    960
aacgatggta ttccaattat ctacgccggt caagaacaac attatgctgg tggtaatgat   1020
ccagcaaata gagaagctac ttggttgtct ggttatccaa ctgattccga gttgtacaaa   1080
ttgattgctt ccgctaacgc cattagaaac tacgctattt ctaaggatac tggcttcgtt   1140
acttacaaga attggcctat ctacaaggat gataccacta ttgctatgag aaagggtaca   1200
gatggttctc aaatcgttac catcttgtct aacaaaggtg cttctggtga ttcctacact   1260
ttgtctttgt ctggtgcagg ttatactgct ggtcaacaat tgactgaagt tattggttgt   1320
actaccgtta ccgttggttc tgatggtaat gttcctgttc caatggctgg tggtttgcca   1380
agagtcttgt atccaacaga aaaattggcc ggttccaaga tctgttcttc ttcttga      1437
```

<210> SEQ ID NO 105
<211> LENGTH: 478
<212> TYPE: PRT
<213> ORGANISM: Aspergillus oryzae

<400> SEQUENCE: 105

```
Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Arg Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Leu Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205
```

Lys His Val Gln Lys Asp Phe Trp Pro Gly Tyr Asn Lys Ala Ala Gly
        210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
        290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445

Gly Asn Val Pro Val Pro Met Ala Gly Gly Leu Pro Arg Val Leu Tyr
        450                 455                 460

Pro Thr Glu Lys Leu Ala Gly Ser Lys Ile Cys Ser Ser Ser
465                 470                 475

<210> SEQ ID NO 106
<211> LENGTH: 63
<212> TYPE: DNA
<213> ORGANISM: Artificial Sequence
<220> FEATURE:
<223> OTHER INFORMATION: Signal peptide from fungal amylase from
      Aspergillus oryzae

<400> SEQUENCE: 106
atgatggttg cttggtggtc tttgttcttg tacggtttac aagttgctgc tccagctttg      60
gct                                                                   63

<210> SEQ ID NO 107
<211> LENGTH: 21
<212> TYPE: PRT
<213> ORGANISM: Artificial Sequence
<220> FEATURE:
<223> OTHER INFORMATION: Signal peptide from fungal amylase from
      Aspergillus oryzae

<400> SEQUENCE: 107

Met Met Val Ala Trp Trp Ser Leu Phe Leu Tyr Gly Leu Gln Val Ala
1               5                   10                  15

Ala Pro Ala Leu Ala
            20

<210> SEQ ID NO 108
<211> LENGTH: 687
<212> TYPE: PRT
<213> ORGANISM: Geobacillus stearothermophilus

<400> SEQUENCE: 108

Met Ser Ser Ser Ala Ser Val Lys Gly Asp Val Ile Tyr Gln Ile Ile
1               5                   10                  15

Ile Asp Arg Phe Tyr Asp Gly Asp Thr Thr Asn Asn Asn Pro Ala Lys
            20                  25                  30

Ser Tyr Gly Leu Tyr Asp Pro Thr Lys Ser Lys Trp Lys Met Tyr Trp
        35                  40                  45

Gly Gly Asp Leu Glu Gly Val Arg Gln Lys Leu Pro Tyr Leu Lys Gln
    50                  55                  60

Leu Gly Val Thr Thr Ile Trp Leu Ser Pro Val Leu Asp Asn Leu Asp
65                  70                  75                  80

Thr Leu Ala Gly Thr Asp Asn Thr Gly Tyr His Gly Tyr Trp Thr Arg
                85                  90                  95

Asp Phe Lys Gln Ile Glu Glu His Phe Gly Asn Trp Thr Thr Phe Asp
            100                 105                 110

Thr Leu Val Asn Asp Ala His Gln Asn Gly Ile Lys Val Ile Val Asp
        115                 120                 125

Phe Val Pro Asn His Ser Thr Pro Phe Lys Ala Asn Asp Ser Thr Phe
    130                 135                 140

Ala Glu Gly Gly Ala Leu Tyr Asn Asn Gly Thr Tyr Met Gly Asn Tyr
145                 150                 155                 160

Phe Asp Asp Ala Thr Lys Gly Tyr Phe His His Asn Gly Asp Ile Ser
                165                 170                 175

Asn Trp Asp Asp Arg Tyr Glu Ala Gln Trp Lys Asn Phe Thr Asp Pro
            180                 185                 190

Ala Gly Phe Ser Leu Ala Asp Leu Ser Gln Glu Asn Gly Thr Ile Ala
        195                 200                 205

Gln Tyr Leu Thr Asp Ala Ala Val Gln Leu Val Ala His Gly Ala Asp
    210                 215                 220

Gly Leu Arg Ile Asp Ala Val Lys His Phe Asn Ser Gly Phe Ser Lys
225                 230                 235                 240

Ser Leu Ala Asp Lys Leu Tyr Gln Lys Lys Asp Ile Phe Leu Val Gly
                245                 250                 255

Glu Trp Tyr Gly Asp Asp Pro Gly Thr Ala Asn His Leu Glu Lys Val
            260                 265                 270

Arg Tyr Ala Asn Asn Ser Gly Val Asn Val Leu Asp Phe Asp Leu Asn
        275                 280                 285

Thr Val Ile Arg Asn Val Phe Gly Thr Phe Thr Gln Thr Met Tyr Asp
    290                 295                 300

Leu Asn Asn Met Val Asn Gln Thr Gly Asn Glu Tyr Lys Tyr Lys Glu
305                 310                 315                 320

Asn Leu Ile Thr Phe Ile Asp Asn His Asp Met Ser Arg Phe Leu Ser
                325                 330                 335

Val Asn Ser Asn Lys Ala Asn Leu His Gln Ala Leu Ala Phe Ile Leu
            340                 345                 350

-continued

```
Thr Ser Arg Gly Thr Pro Ser Ile Tyr Tyr Gly Thr Glu Gln Tyr Met
        355                 360                 365

Ala Gly Gly Asn Asp Pro Tyr Asn Arg Gly Met Met Pro Ala Phe Asp
        370                 375                 380

Thr Thr Thr Thr Ala Phe Lys Glu Val Ser Thr Leu Ala Gly Leu Arg
385                 390                 395                 400

Arg Asn Asn Ala Ala Ile Gln Tyr Gly Thr Thr Thr Gln Arg Trp Ile
                405                 410                 415

Asn Asn Asp Val Tyr Ile Tyr Glu Arg Lys Phe Phe Asn Asp Val Val
                420                 425                 430

Leu Val Ala Ile Asn Arg Asn Thr Gln Ser Ser Tyr Ser Ile Ser Gly
        435                 440                 445

Leu Gln Thr Ala Leu Pro Asn Gly Ser Tyr Ala Asp Tyr Leu Ser Gly
        450                 455                 460

Leu Leu Gly Gly Asn Gly Ile Ser Val Ser Asn Gly Ser Val Ala Ser
465                 470                 475                 480

Phe Thr Leu Ala Pro Gly Ala Val Ser Val Trp Gln Tyr Ser Thr Ser
                485                 490                 495

Ala Ser Ala Pro Gln Ile Gly Ser Val Ala Pro Asn Met Gly Ile Pro
            500                 505                 510

Gly Asn Val Val Thr Ile Asp Gly Lys Gly Phe Gly Thr Thr Gln Gly
            515                 520                 525

Thr Val Thr Phe Gly Gly Val Thr Ala Thr Val Lys Ser Trp Thr Ser
        530                 535                 540

Asn Arg Ile Glu Val Tyr Val Pro Asn Met Ala Ala Gly Leu Thr Asp
545                 550                 555                 560

Val Lys Val Thr Ala Gly Gly Val Ser Ser Asn Leu Tyr Ser Tyr Asn
                565                 570                 575

Ile Leu Ser Gly Thr Gln Thr Ser Val Val Phe Thr Val Lys Ser Ala
            580                 585                 590

Pro Pro Thr Asn Leu Gly Asp Lys Ile Tyr Leu Thr Gly Asn Ile Pro
        595                 600                 605

Glu Leu Gly Asn Trp Ser Thr Asp Thr Ser Gly Ala Val Asn Asn Ala
        610                 615                 620

Gln Gly Pro Leu Leu Ala Pro Asn Tyr Pro Asp Trp Phe Tyr Val Phe
625                 630                 635                 640

Ser Val Pro Ala Gly Lys Thr Ile Gln Phe Lys Phe Ile Lys Arg
                645                 650                 655

Ala Asp Gly Thr Ile Gln Trp Glu Asn Gly Ser Asn His Val Ala Thr
            660                 665                 670

Thr Pro Thr Gly Ala Thr Gly Asn Ile Thr Val Thr Trp Gln Asn
            675                 680                 685
```

CELL-ASSOCIATED HETEROLOGOUS FOOD AND/OR FEED ENZYMES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_407USPC_SEQUENCE_LISTING.txt. The text file is 225 KB, was created on Sep. 6, 2019, and is being submitted electronically via EFS-Web.

TECHNOLOGICAL FIELD

The present disclosure relates to a recombinant yeast host cell expressing cell-associated enzymes and acting as a source of enzyme activity in the production of food and/or feed, including those for the production of baked products.

BACKGROUND

Commercial yeast and commercial enzymes are commonly used to produce food and feed such as, for example, bread and other yeast-leavened baked products. Commercial enzymes are also used without yeast for making food and feed, for example in chemically leavened and unleavened baked products such as cakes and flatbreads. Baker's yeasts are produced from strains of *Saccharomyces cerevisiae* by fed-batch propagation and supplied in fresh or dried form. Food and feed enzymes (such as baking, brewery and feed enzymes) are produced from various plants, bacteria and fungi, often enhanced by genetic modification. The bacterial and fungal enzymes are usually expressed and excreted from the production organism during sterile batch fermentation, separated, purified, concentrated, dried and supplied as granulated powders.

Baking enzymes can be added to the flour, dough, or batter that is used to prepare the baked products. They act on carbohydrates, proteins and lipids during mixing, proofing and baking to facilitate processing and improve the appearance, texture and keeping quality of the finished product. For example, maltogenic alpha-amylase (MAA) is added to the dough or batter during the production of breads, cakes, and other baked products. It acts on the amylopectin part of wheat starch in the oven to inhibit starch retrogradation in the finished product and slow the rate of firming.

Food and feed enzymes in general, and baking enzymes in particular, are a significant part of the cost of producing baked products. As such, there is an incentive to lower the utilization or render obsolete the use of exogenous purified food and feed enzymes such as baking enzymes in the process for making same.

BRIEF SUMMARY

The present disclosure provides recombinant yeast host cells which have been genetically engineered to express one or more cell-associated heterologous food and/or feed enzyme as well as process for using them or products derived from them to make food and/or feed products.

According to a first aspect, the present disclosure provides a recombinant yeast host cell having an heterologous nucleic acid molecule encoding a cell-associated heterologous food and/or feed enzyme. The heterologous nucleic acid molecule is operatively associated with an heterologous promoter allowing the expression of the heterologous nucleic acid molecule during propagation. In an embodiment, the heterologous nucleic acid molecule allows the intracellular expression of the heterologous food and/or feed enzyme. In another embodiment, the heterologous nucleic acid molecule allows the expression of a membrane-associated heterologous food and/or feed enzyme. For example, the heterologous nucleic acid molecule can allow the expression of a tethered heterologous food and/or feed enzyme. In an embodiment, the tethered heterologous food and/or feed enzyme is a chimeric protein of formula (I):

$$(NH_2)FFE\text{-}L\text{-}TT(COOH) \qquad (I)$$

wherein FFE is the food and/or feed enzyme; L is present or absent and is an amino acid linker; TT is an amino acid tethering moiety for associating the food and/or feed enzyme to a cell wall of the recombinant yeast host cell; and "-" is an amide linkage. In the chimeric protein of formula (I), $(NH_2)$ indicates the location of the amino terminus of the chimeric protein and (COOH) indicates the location of the carboxyl terminus of the chimeric protein.

In another embodiment, the heterologous food and/or feed enzyme is a chimeric protein of formula (II):

$$(NH_2)TT\text{-}L\text{-}FFE(COOH) \qquad (II)$$

wherein FFE is the food and/or feed enzyme; L is present or absent and is an amino acid linker; TT is an amino acid tethering moiety for associating the food and/or feed enzyme to a cell wall of the recombinant yeast host cell; and "-" is an amide linkage. In the chimeric protein of formula (II), $(NH_2)$ indicates the location of the amino terminus of the chimeric protein and (COOH) indicates the location of the carboxyl terminus of the chimeric protein. In an embodiment, the heterologous nucleic acid molecule encodes the heterologous food enzyme, such as, for example, an alpha-acetolactate decarboxylase, an aminopeptidase, an amylase, a maltogenic amylase, an asparaginase, a bromelain, a carboxypeptidase, a catalase, a cellulase, a chymosin, a cyprosin, a ficin, a glucoamylase, a glucanase, a glucose oxidase, a glucose isomerase, an hemicellulase, an hexose oxidase, an inulinase, an invertase, a lactase, a lipase, a lipoxidase, a lysozyme, a mannanase, a milk coagulating enzyme, a pancreatin, a papain, a pectinase, a pentosanase, a pepsin, a phospholipase, a peroxidase, a protease, a pullulanase, a rennet, a transglutaminase, a trypsin, a urease and/or a xylanase. In still another embodiment, the heterologous food enzyme is an heterologous baking enzyme, such as, for example, an amylolytic enzyme, a cellulase, an hemicellulases, an oxidase, an asparaginase or a lipase. In yet another embodiment, the heterologous food and/or feed enzyme is an amylolytic enzyme, such as, for example, a maltogenic alpha-amylase, a glucoamylase, an alpha-amylase or a fungal amylase. In still another embodiment, the heterologous food and/or feed enzyme is an oxidase such as, for example, a glucose oxidase. In another embodiment, the heterologous nucleic acid molecule encodes the heterologous feed enzyme, such as, for example, a phytase, a beta-glucanase, a xylanase, an alpha-galactosidase, a protease, an amylase, a lipase, a mannanase, a cellulase, an hemicellulase and/or a pectinase. In still yet another embodiment, the heterologous feed enzyme is the phytase. In yet another embodiment of the chimeric protein, L is present and can comprise, for example, one or more $G_4S$ (SEQ ID NO: 41) motifs and/or one or more $EA_2K$ (SEQ ID NO: 100) or $EA_3K$ (SEQ ID NO: 101) motifs. In a further embodiment, TT comprises a transmembrane domain, a variant or a fragment thereof. For example, TT can be from a FLO1 protein. For example, TT can have the amino acid sequence of SEQ ID NO: 14, be a variant of the amino acid sequence of SEQ ID NO: 14 or be a fragment of the amino acid sequence SEQ ID NO: 14. In another embodiment, TT can be modified by a post-translation mechanism to have a glycosylphosphatidylinositol (GPI) anchor. For example, TT can be from a SED1 protein, a TIR1 protein, a CWP2 protein, a CCW12 protein, a SPI1 protein, a PST1 protein or a combination of a AGA1 and a AGA2 protein. In a specific embodiment, TT is from the SPI1 protein and can have, for example, the amino acid sequence of SEQ ID NO: 74, can be a variant of the amino acid sequence of SEQ ID NO: 74 or can be a fragment of the amino acid sequence SEQ ID NO: 74. In a further embodiment, TT can be a fragment of the SPI protein an can have the amino acid sequence of SEQ ID NO: 76, 78, 80 or 82; be a variant of the amino acid sequence of SEQ ID NO: 76, 78, 80 or 82 or be a fragment of the amino acid sequence of SEQ ID NO: 76, 78, 80 or 82. In another specific embodiment, TT is from the CCW12 protein and can have, for example, the amino acid sequence of SEQ ID NO: 84, can be a variant of the amino acid sequence of SEQ ID NO: 84 or can be a fragment of the amino acid sequence of SEQ ID NO: 84. In yet a further embodiment, TT can be a fragment of the CCW12 protein and can have the amino acid sequence of SEQ ID NO: 86, 88, 90 or 92; be a variant of the amino acid sequence of SEQ ID NO: 86, 88, 90 or 92 or be a fragment of the amino acid sequence of SEQ ID NO: 86, 88, 90 or 92. In another embodiment, TT is from the combination of the AGA1 protein and the AGA2 protein and can have, for example, the amino acid sequence of SEQ ID NO: 24, is a variant of the amino acid sequence of SEQ ID NO: 24, is a fragment of the amino acid sequence of SEQ ID NO: 24, has the amino acid sequence of SEQ ID NO: 26, is a variant of the amino acid sequence of SEQ ID NO: 26 or is a fragment of the amino acid sequence of SEQ ID NO: 26. In a further embodiment, the promoter is a native or an heterologous promoter. For example, the heterologous promoter can comprise the promoter the tdh1 gene, the hor7 gene, the hsp150 gene, the hxt7 gene, the gpm1 gene, the pgk1 gene and/or the stl1 gene. The heterologous promoter can comprise, for example, the promoter from the tdh1 gene and/or from the hor7 gene. In some embodiments, the heterologous nucleic acid molecule is operatively associated with a terminator which can be, for example, a native or an heterologous terminator. In some embodiments, the heterologous terminator comprises a terminator from the dit1 gene, the adh3 gene, the idp1 gene, the gpm1 gene, the pma1 gene, the tdh3 gene, the hxt2 gene and/or the ira2 gene. The heterologous terminator can comprise, for example, the terminator from the dit1 gene, from the adh3 gene and/or from the idp1 gene. In an embodiment, the membrane-associated heterologous polypeptide has an heterologous signal peptide, such as, for example, the heterologous signal peptide is from an invertase protein, an AGA2 protein or a fungal amylase. In an embodiment, the heterologous signal peptide is from the invertase protein and can have the amino acid sequence of SEQ ID NO: 68, is a variant of the amino acid sequence of SEQ ID NO: 68 or is a fragment of the amino acid sequence of SEQ ID NO: 68. In still another embodiment, the heterologous signal peptide is from the AGA2 protein and can have the amino acid sequence of SEQ ID NO: 69, is a variant of the amino acid sequence of SEQ ID NO: 69 or is a fragment of the amino acid sequence of SEQ ID NO: 69. In still another embodiment, the heterologous signal peptide is from the fungal amylase and can have the amino acid sequence of SEQ ID NO: 107, is a variant of the amino acid sequence of SEQ ID NO: 107 or is a fragment of the amino acid sequence of SEQ ID NO: 107. In some embodiments, the recombinant yeast host cell can be from the genus Saccharomyces sp. In some further embodiments, the recombinant yeast host cell can be from the species Saccharomyces cerevisiae.

According to a second aspect, the present disclosure provides an additive comprising the food and/or feed enzyme described herein. The additive can comprise or consist essentially of a yeast composition having the recombinant yeast host cell as described herein. In an embodiment, the yeast composition can be provided in a live or inactivated form. The additive can comprise or consist essentially of a yeast product obtained from the recombinant yeast host cell described herein. In an embodiment, the yeast product can be a substantially purified food and/or feed enzyme, a yeast extract or a yeast fraction. The additive can be used as a food additive and/or a feed additive. In an embodiment, the food additive can be a dough conditioner.

According to a fourth aspect, the present disclosure provides a process for making a food or a feed product. The process comprising including the recombinant yeast host cell described herein or the additive described herein in the food or the feed product. In an embodiment, the process further comprises fermenting the food or the feed product in the presence of the recombinant yeast host cells and/or the additive. In another embodiment, the process further comprises baking the food or the feed product to provide a baked product. In such embodiment, the process can be used for extending the shelf-life of the baked product and/or for improving the organoleptic properties of the baked product. In yet another embodiment, the baked product is a bread. In an embodiment, the process can be used to make a food product. In still another embodiment, the process can be used to make a feed product.

BRIEF DESCRIPTION OF THE DRAWINGS

Having thus generally described the nature of the invention, reference will now be made to the accompanying drawings, showing by way of illustration, a preferred embodiment thereof, and in which:

In FIG. 1A, results are shown as the maltogenic amylase activity (provided as MANU/mL) in function of type of yeast tested (from left to right, M10474, T2986, T2987, T2988, T2989, T2990, T2991, T2944; strains are described in Table 1). In FIG. 1B, results are shown as the maltogenic amylase activity (provided as MANU/mL) in function of type and lot of yeast tested (from left to right, M10474, M13819, M13822; strains are described in Table 1).

(FIG. 7A) Absorbance at 700 nm was compared to a standard curve of known phosphate concentrations to express activity in FTUs. The absorbance was measured in the supernatant (grey bars) and the cells (diagonal bars) in different strains (M12548, T2633, T2634, T2635, T2636, T2637 and T2638). (FIG. 7B) FTU were compared between the different strains. The left vertical axis shows supernatant activity and the FTU for each strains is provided as the grey bars. The right axis shows cell-associated FTU activity and is provided as for each strains (M12548, T2633, T2634, T2635, T2636, T2637 and T2638). The values for the parent strain and the Pst1 tether cell associated activity were outside the range of the standard curve and therefore below the detection limit.

FIG. 21 shows the evaluation of cell-associated glucose oxidase activity from a cell pellet of strain M16780 using a bake test. Results are shown for control loaves (prepared in the absence of an additive), for loaves prepared with 10 ppm or 20 ppm Gluzyme Mono® or for loaves prepared with a dosed the cell pellet of strain M16780.

DETAILED DESCRIPTION

Figure 1A:
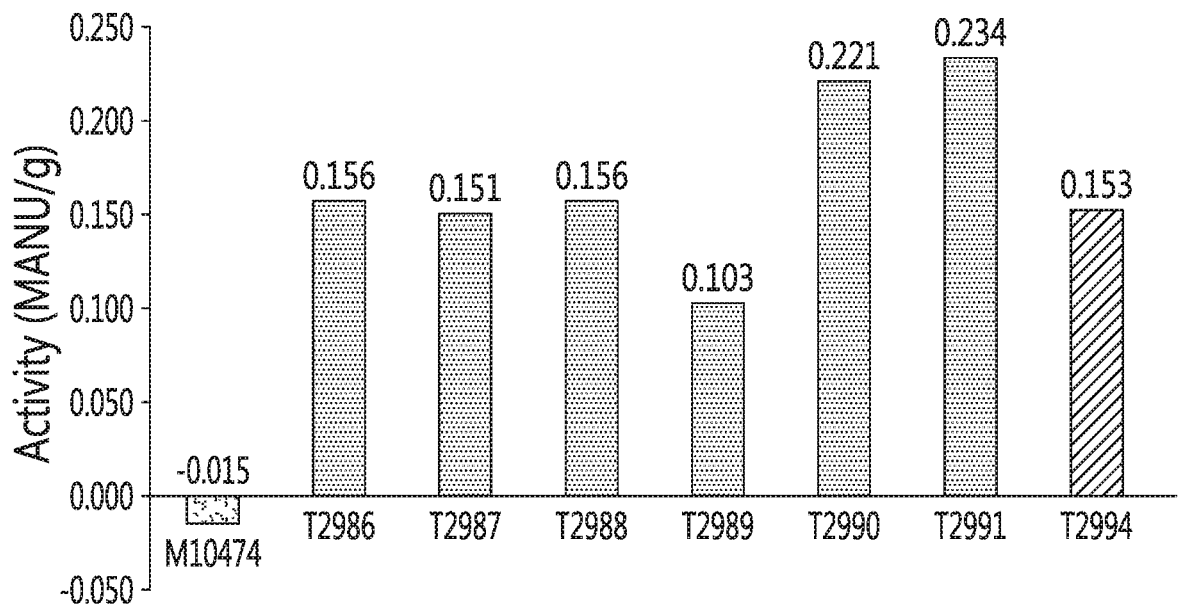
FIGS. 1A and 1B provide the maltogenic amylase (MAA) enzyme activity measured in (FIG. 1A) yeast cell pellets or (FIG. 1B) cream yeast samples of wild-type (M10474) or recombinant yeast host cells.

The present disclosure provides recombinant yeast host cells expressing a cell-associated heterologous food and/or feed enzyme during their propagation phase. As used in the context of the present disclosure, the expression "propagation phase" refers to an expansion phase of a commercial process in which the yeasts are propagated under aerobic conditions to maximize the conversion of a substrate into biomass. In some instances, the propagated biomass can be used in a following fermenting step (usually under anaerobic conditions) to maximize the production of one or more desired metabolite and/or make a fermented food or fee product. The recombinant yeast host cells of the present disclosure are advantageous because they provide a lower cost source of enzyme activity than the purified products that are traditionally used. Such recombinant yeast host cells can be advantageously used in various food and/or feed products, such as, for example, baked products, even though the proofing time and conditions do not provide an opportunity for the yeast to produce the enzymes in situ. Such recombinant yeast host cells can also be used in other baked products, fermented foods, non-fermented foods and animal feed. The recombinant yeast host cells can advantageously be easily measured, dosed and formulated.

Recombinant Yeast Host Cells

The recombinant yeast host cells of the present disclosure are intended to be used for making products for human (food) and/or animal (feed) consumption. As used in the context of the present disclosure, the expression "food and/or feed enzyme" refers to a protein having enzymatic activity and capable of being used in a process for making a food product or a feed product. In some embodiments, the "food and/or feed enzyme" refers to enzymes having applications in transforming starchy (e.g., starch-containing biomass). Food and feed enzymes include, without limitation, baking enzymes, brewing enzymes, distilling enzymes, winemaking enzymes, juice enzymes, starch processing enzymes and feed enzymes. The recombinant yeast host cells of the present disclosure can optionally be used in a fermentation process. In an embodiment, the fermentation process can be a relatively long one and the recombinant yeast host cells can be used, for example, in making distilling products, wine and beer. In another embodiment, the fermentation process can be a relatively short one and the recombinant yeast host cells can be used, for example, in making yeast-leavened bakery products. The recombinant yeast host cells of the present disclosure can also be used in a process which does not include a fermentation step. For example, the recombinant yeast host cell can be used for making food and beverages (e.g., non-yeast-leavened (chemically-leavened) bakery products, dairy products, yeast extracts, juices, fat and oils as well as starch), or feed.

In an embodiment, the recombinant yeast host cells of the present disclosure do express at least one food and/or feed enzyme prior to the introduction of heterologous nucleic acid molecules of the present disclosure and are genetically modified to express a further (a different or the same) cell-associated enzyme. In another embodiment, the recombinant yeast host cells of the present disclosure cannot be used in consolidated bioprocessing for making, for example, biofuels such as bioethanol.

The recombinant yeast host cells of the present disclosure can be provided in an active form (e.g., liquid (such as, for example, a cream yeast), compressed, or fluid-bed dried yeast), in a semi-active form (e.g., liquid, compressed, or fluid-bed dried), in an inactive form (e.g., drum-or spray-dried) as well as a mixture therefore. For example, the recombinant yeast host cells can be a combination of active and semi-active or inactive forms to provide the ratio and dose of the enzyme required for making the food or feed product.

The present disclosure concerns recombinant yeast host cells that have been genetically engineered. The genetic modification(s) is (are) aimed at increasing the expression of a specific targeted gene (which is considered heterologous to the yeast host cell) and can be made in one or multiple (e.g., 1, 2, 3, 4, 5, 6, 7, 8 or more) genetic locations. In the context of the present disclosure, when recombinant yeast cell is qualified as being "genetically engineered", it is understood to mean that it has been manipulated to add at least one or more heterologous or exogenous nucleic acid residue. In some embodiments, the one or more nucleic acid residues that are added can be derived from an heterologous cell or the recombinant host cell itself. In the latter scenario, the nucleic acid residue(s) is (are) added at one or more genomic location which is different than the native genomic location. The genetic manipulations did not occur in nature and are the results of in vitro manipulations of the yeast.

When expressed in a recombinant yeast host cells, the heterologous enzymes described herein are encoded on one or more heterologous nucleic acid molecules. The term "heterologous" when used in reference to a nucleic acid molecule (such as a promoter, a terminator or a coding sequence) or a protein (such as an enzyme) refers to a nucleic acid molecule or a protein that is not natively found in the recombinant host cell. "Heterologous" also includes a native coding region/promoter/terminator, or portion thereof, that was removed from the source organism and subsequently reintroduced into the source organism in a form that is different from the corresponding native gene, e.g., not in its natural location in the organism's genome. The heterologous nucleic acid molecule is purposively introduced into the recombinant host cell. For example, a heterologous element could be derived from a different strain of host cell, or from an organism of a different taxonomic group (e.g., different kingdom, phylum, class, order, family genus, or species, or any subgroup within one of these classifications).

The heterologous nucleic acid molecule present in the recombinant host cell can be integrated in the host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies (e.g., 2, 3, 4, 5, 6, 7, 8 or even more copies) in the yeast host cell's genome. Alternatively, the heterologous nucleic acid molecule can be independently replicating from the yeast's genome. In such embodiment, the nucleic acid molecule can be stable and self-replicating.

In the context of the present disclosure, the recombinant host cell is a yeast and in some embodiments the yeast can be used in the production of food and/or feed. Suitable yeast host cells can be, for example, from the genus *Saccharomyces, Kluyveromyces*, Arxula, Debaryomyces, *Candida, Pichia, Phaffia, Schizosaccharomyces, Hansenula, Kloeckera, Schwanniomyces*, Torula or *Yarrowia*. Suitable yeast species can include, for example, *S. cerevisiae, S. bulderi, S. barnetti, S. exiguus, S. uvarum, S. diastaticus, C. utilis, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis*, Arxula adeninivorans, Debaryomyces *hansenii, Debaryomyces polymorphus, Schizosaccharomyces pombe* and *Schwanniomyces occidentalis*. In one particular embodiment, the yeast is *Saccharomyces cerevisiae*. In some embodiment, the host cell can be an oleaginous yeast cell. For example, the oleaginous yeast host cell can be from the genus Blakeslea, *Candida, Cryptococcus*, Cunninghamella, Lipomyces, *Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus Thraustochytrium or Schizochytrium). In an embodiment, the recombinant yeast host cell is from the genus *Saccharomyces* and, in some embodiments, from the species *Saccharomyces cerevisiae*.

The recombinant yeast host cells of the present disclosure include an heterologous nucleic acid molecule intended to allow the expression of (e.g., encode) one or more heterologous food and/or feed enzymes. In an embodiment, the heterologous enzyme is a food enzyme which can be, without limitation, alpha-acetolactate decarboxylase, aminopeptidase, amylase, maltogenic alpha-amylase, asparaginase, bromelain, carboxypeptidase, catalase, cellulase, chymosin (including chymosin A and B), cyprosin, ficin, glucoamylase (also known as amyloglucosidase or maltase), glucanase, glucose oxidase, glucose isomerase, hemicellulase, hexose oxidase, inulinase, invertase, lactase, lipase, lipoxidase, lysozyme, mannanase, milk coagulating enzyme, pancreatin, papain, pectinase, pentosanase, pepsin, phospholipase, peroxidase, protease, pullulanase, rennet (including bovine rennet), transglutaminase, trypsin, urease and/or xylanase. In an embodiment, the heterologous food and/or feed enzyme is a baking enzyme. As used in the context of the present disclosure, the expression "baking enzyme" refers to a protein having enzymatic activity and capable of being used in a process for making a baked product. In an embodiment, the heterologous nucleic acid molecule of the yeast host cells of the present encodes at least one heterologous baking enzyme. Baking enzymes, include, without limitation, amylolytic enzymes (including, for example, maltogenic alpha-amylases, glucoamylases, alpha-amylases and fungal amylases), cellulases/hemicellulases, oxidases (including, for example, glucose oxidases), asparaginases, and lipases. In another embodiment, the heterologous enzyme is a feed enzyme which can be, without limitation, a phytase, β-glucanase, xylanase, alpha-galactosidase, protease, amylase, lipase, mannanase, cellulase and/or hemicellulasespectinase.

As used herein, the expression "amylolytic enzyme" refers to a class of enzymes capable of hydrolyzing starch or hydrolyzed starch. In baking applications, amylolytic enzymes can participate in releasing of fermentable sugars, increasing bread volume, decreasing fermentation time, reducing staling and/or improving flavor. Amylolytic enzymes include, but are not limited to alpha-amylases (EC 3.2.1.1, sometimes referred to fungal alpha-amylases as well as bacterial alpha-amylases, see below), maltogenic amylase (EC 3.2.1.133), glucoamylase (EC 3.2.1.3), glucan 1,4-alpha-maltotetraohydrolase (EC 3.2.1.60), pullulanase (EC 3.2.1.41), iso-amylase (EC 3.2.1.68), and amylomaltase (EC 2.4.1.25). Fungal alpha-amylases can be used, for example, in the production of baked products (for example, yeast-leavened, chemically-leavened or unleavened products), juices and fermented beverages (like beers). Bacterial α-amylases can be used, for example, in the production of baked products (for example, yeast-leavened, chemically-leavened or unleavened products), fermented beverages (including beers, distilled beverages and the like) as well as in the processing of starch. Maltogenic alpha-amylases can be used, for example, in the production of baked products (for example, yeast-leavened, chemically-leavened or unleavened products). In an embodiment, the one or more amylolytic enzymes can be an α-amylase from *Aspergillus oryzae* (and have, for example, the amino acid sequence of SEQ ID NO: 2 or 105, a variant thereof or a fragment thereof), a maltogenic α-amylase from *Geobacillus stearothermophilus* (and have, for example, the amino acid sequence of SEQ ID NO: 1, 51, 65 or 108, a variant thereof or a fragment thereof), a glucoamylase from Saccharomycopsis fibuligera (and have, for example, the amino acid sequence of SEQ ID NO: 3, a variant thereof or a fragment thereof), a glucan 1,4-alpha-maltotetraohydrolase from *Pseudomonas saccharophila* (and have, for example, the amino acid sequence of SEQ ID NO: 4, a variant thereof or a fragment thereof), a pullulanase from *Bacillus naganoensis* (and have, for example, the amino acid sequence of SEQ ID NO: 5, a variant thereof or a fragment thereof), a pullulanase from *Bacillus* acidopullulyticus (and have, for example, the amino acid sequence of SEQ ID NO: 6, a variant thereof or a fragment thereof), an iso-amylase from *Pseudomonas* amyloderamosa (and have, for example, the amino acid sequence of SEQ ID NO: 7, a variant thereof or a fragment thereof), and/or amylomaltase from *Thermus thermophilus* (and have, for example, the amino acid sequence of SEQ ID NO: 8, a variant thereof or a fragment thereof).

As used herein, the expression "cellulase/hemi-cellulase" refers to a class of enzymes capable of hydrolyzing cellulose, hemi-cellulose, or pentosans. In baking applications, cellulases and hemi-cellulases can participate in establishing the gluten network, providing a soluble dietary fiber, modulating dough viscosity and/or modulating dough rheology. Cellulases/hemi-cellulases include, but are not limited to a cellulase (E.C. 3.2.1.4) and an endoB (1,4) D-xylanase (E.C. 3.2.1.8). In an embodiment, the one or more cellulase/hemi-cellulase can be a cellulase from *Penicillium funiculosum* (and have, for example, the amino acid sequence of SEQ ID NO: 42, a variant thereof or a fragment thereof) and/or an endoB (1,4) D-xylanase from Rasamsonia *emersonii* (and have, for example, the amino acid sequence of SEQ ID NO: 43, a variant thereof or a fragment thereof).

As used herein, the expression "oxidase" refers to a class of enzymes capable of catalyzing an oxidation-reduction reaction. The oxidase can be an oxidoreddutase such as an hexose oxidase (including a glucose oxidase). Oxidases can be used in the production of baked products (such as, for examples, yeast-leavened products including bread). In some embodiments, oxidases (such as glucose oxidases) can improve dough machinability. In baking applications, oxidases can participate in controlling of Maillard reactions and/or establishing crumb structure. In an embodiment, the one or more oxidases can be a glucose oxidase from *Aspergillus niger* (and have, for example, the amino acid sequence of SEQ ID NO: 44 or 103, a variant thereof or a fragment thereof).

As used herein, the expression "asparaginase" refers to a class of enzymes capable of catalyzing the conversion of asparagine into aspartic acid and ammonium. Asparaginase can be used in the production of snacks, cereals (including breakfast cereals) as well as baked products (for example, yeast-leavened (including bread), chemically-leavened or unleavened products).

As used herein, the expression "lipase" refers to a class of enzymes capable of hydrolyzing lipids. In baking applications, lipases can participate in increasing bread volume, increasing dough stability, providing anti-staling and/or facilitating emulsifier formations. Lipases can be used, for example, in the production of baked products (such as yeast-leavened (including bread) and chemically-leavened products). In an embodiment, the one or more lipase can be a triacylglycerol lipase from *Thermomyces* lanuginosis (and have, for example, the amino acid sequence of SEQ ID NO: 45, a variant thereof or a fragment thereof), a phospholipase A2 from *Sus scrofa* (and have, for example, the amino acid sequence of SEQ ID NO: 46, a variant thereof or a fragment thereof), a phospholipase A2 from *Streptomyces* vialaceoruber (and have, for example, the amino acid sequence of SEQ ID NO: 47, a variant thereof or a fragment thereof) and/or a phospholipase A2 from *Aspergillus* oryzea (and have, for example, the amino acid sequence of SEQ ID NO: 48, a variant thereof or a fragment thereof).

In an embodiment, the recombinant yeast host cell of the present disclosure includes (and in an embodiment expresses) a nucleic acid molecule coding for a maltogenic amylase. As used in the present disclosure, the term "maltogenic amylase" refers to a polypeptide capable of hydrolyzing starch or hydrolyzed starch into maltose. Maltogenic amylases include, but are not limited to fungal alpha-amylases (derived, for example, from *Aspergillus* sp. (e.g., *A. Niger*, *A. kawachi*, and *A. oryzae*); *Trichoderma* sp. (e.g., *T. reesie*), Rhisopus sp., *Mucor* sp., and *Penicillium* sp.), acid stable fungal amylase (derive, for example, from *Aspergillus niger*), beta-amylases (derived, for example, from plant (wheat, barley, rye, shorgum, soy, sweet potato, rice) and microorganisms (*Bacillus cereus, Bacillus polymixa, Bacillus megaterium, Arabidopsis thaliana*), maltogenic amylases (E.C.3.2.1.133) (derived, for example, from microorganisms such as *Bacillus subtilis, Geobacillus stearothermophilus, Bacillus thermoalkalophilus, Lactobacillus gasseri, Thermus* sp.). In a specific embodiment, the recombinant yeast host cells of the present disclosure include an heterologous nucleic acid molecule coding for the heterologous maltogenic amylase derived from *Geobacillus stearothermophilus* and having, for example, the amino acid sequence of SEQ ID NO: 1, 51, 65 or 108, a variant thereof or a fragment thereof.

As used herein, the expression "phosphatase" refers to a food/feed enzyme capable, in the presence of water, of catalyzing the cleavage of a phosphoric acid monoester into a phosphate ion and an alcohol. An embodiment of a phosphatase is a phytase, a protein having enzymatic activity and capable of catalyzing the hydrolysis of phytic acid (myo-inositol hexakisphosphate) into inorganic phosphorus. There are four distinct classes of phytase: histidine acid phosphatases (HAPS), beta-propeller phytases, purple acid phosphatases and protein tyrosine phosphatase-like phytases (PTP-like phytases). Phytic acid has six phosphate groups that may be released by phytases at different rates and in different order. Phytases hydrolyze phosphates from phytic acid in a stepwise manner, yielding products that again become substrates for further hydrolysis. Phytases have been grouped based on the first phosphate position of phytic acid that is hydrolyzed: are 3-phytase (EC 3.1.3.8), 4-phytase (EC 3.1.3.26) and 5-phytase (EC 3.1.3.72). In an embodiment, the phytase is derived from a bacterial species, such as, for example, a *Citrobacter* sp. or an *Escherichia* sp.

In a specific embodiment, the heterologous phytase is derived from a *Citrobacter* sp., such as for example *Citrobacter braakii* and can have, for example, the amino acid sequence of SEQ ID NO: 66, a variant thereof or a fragment thereof. In another embodiment, the heterologous phytase is derived from an *Escherichia* sp., such as, for example, *Escherichia coli* and can have, for example, the amino acid sequence of SEQ ID NO: 67, a variant thereof or a fragment thereof.

The heterologous food and/or feed enzyme can be a variant of a known/native food and/or feed enzyme. For example, in embodiments in which the heterologous food and/or feed enzyme is an heterologous baking enzyme, the heterologous baking enzyme can be a variant of a known/native baking enzyme, for example a variant of the heterologous baking enzyme having the amino acid sequence of SEQ ID NO: 1, 2, 3, 4, 5, 6, 7, 8, 42, 43, 44, 45, 46, 47, 48, 51, 65, 66, 67, 103, 105 or 108. A variant comprises at least one amino acid difference when compared to the amino acid sequence of the native food and/or feed enzyme. As used herein, a variant refers to alterations in the amino acid sequence that do not adversely affect the biological functions of the food and/or feed enzyme. A substitution, insertion or deletion is said to adversely affect the protein when the altered sequence prevents or disrupts a biological function associated with the food and/or feed enzyme. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the food and/or feed enzyme. The food and/or feed enzyme variants have at least 50%, 55%, 60%, 65%, 70%, 75%, 80%, 85%, 90%, 95%, 96%, 97%, 98% or 99% identity to the food and/or feed enzymes described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous food and/or feed enzymes described herein (including the food and/or feed enzymes described herein) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the food and/or feed enzyme can be a conservative variant or an allelic variant.

The heterologous food and/or feed enzyme can be a fragment of a known/native food and/or feed enzymes. In embodiments in which the heterologous food and/or feed enzyme is an heterologous baking enzyme, the heterologous baking enzyme can be a fragment of a known/native baking enzyme or fragment of a variant of a known/native baking enzyme (such as, for example, a fragment of the baking enzyme having the amino acid sequence of SEQ ID NO: 1, 2, 3, 4, 5, 6, 7, 8, 42, 43, 44, 45, 46, 47, 48, 51, 65, 66, 67, 103, 105 or 108 or a variant thereof). In an embodiment, a fragment corresponds to the known/native food and/or feed enzyme to which the signal peptide sequence has been removed. Food and/or feed enzyme "fragments" (including baking enzyme "fragments") have at least at least 100, 200, 300, 400, 500, 600, 700 or more consecutive amino acids of the food and/or feed enzyme. A fragment comprises at least one less amino acid residue when compared to the amino acid sequence of the known/native food and/or feed enzyme and still possess the enzymatic activity of the full-length food and/or feed enzyme. In an embodiment, the fragment corresponds to the amino acid sequence of the enzyme lacking the signal peptide. In some embodiments, fragments of the food and/or feed enzymes can be employed for producing the corresponding full-length food and/or feed enzymes by peptide synthesis. Therefore, the fragments can be employed as intermediates for producing the full-length proteins.

In the recombinant yeast host cell of the present disclosure, the heterologous food and/or feed enzyme (including the baking enzyme) is "cell-associated" to the recombinant yeast host cell because it is designed to be expressed and remain physically associated with the recombinant yeast host cells. In an embodiment, the food and/or feed enzyme can be expressed inside the recombinant yeast host cell (intracellularly). In such embodiment, the heterologous food and/or feed enzyme does not need to be associated to the recombinant yeast host cell's wall. When the food and/or feed enzyme is intended to be expressed intracellularly, its signal peptide sequence, if present in the native sequence, can be deleted to allow intracellular expression.

In another embodiment, the heterologous food and/feed enzyme can be secreted, but if it is, it must remain physically associated with the recombinant yeast host cell. In an embodiment, at least one portion (usually at least one terminus) of the heterologous food and/or feed enzyme is bound, covalently, non-covalently and/or electrostatically for example, to the cell wall (and in some embodiments to the cytoplasmic membrane). For example, the heterologous food and/or feed enzyme can be modified to bear one or more transmembrane domains, to have one or more lipid modifications (myristoylation, palmitoylation, farnesylation and/or prenylation), to interact with one or more membrane-associated protein and/or to interactions with the cellular lipid rafts. While the heterologous food and/or feed enzyme may not be directly bound to the cell membrane or cell wall (e.g., such as when binding occurs via a tethering moiety), the protein is nonetheless considered a "cell-associated" heterologous food and/or feed enzyme according to the present disclosure.

In some embodiments, the heterologous food and/or feed enzyme can be expressed to be located at and associated to the cell wall of the recombinant yeast host cell. In some embodiments, the heterologous food and/or feed enzyme is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The heterologous food and/or enzyme can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wall/cytoplasmic membrane of the recombinant yeast host cell" refers to the ability of the heterologous food and/or feed enzyme to physically integrate (in a covalent or non-covalent fashion), at least in part, in the cell wall (and in some embodiments in the cytoplasmic membrane) of the recombinant yeast host cell. The physical integration can be attributed to the presence of, for example, a transmembrane domain on the heterologous food and/or feed enzyme, a domain capable of interacting with a cytoplasmic membrane protein on the heterologous food and/or feed enzyme, a post-translational modification made to the heterologous enzyme food and/or feed enzyme (e.g., lipidation), etc.

Some heterologous food and/or feed enzymes (including baking enzymes) have the intrinsic ability to locate at and associate to the cell wall of a recombinant yeast host cell (e.g., being cell-associated). One example of a food and/or feed enzyme having the intrinsic ability of being cell-associated is shown in FIG. 1A moiety (e.g., strain T2994 column in FIG. 1A). In this figure, results are presented for the maltogenic alpha-amylase of *Geobacillus stearothermophilus* expressed in *S. cerevisiae* in the absence of a tethering moiety and clearly show that this enzyme is intrinsically "cell-associated" and exhibits enzymatic activity (e.g., maltogenic alpha-amylase activity).

However, in some circumstances, it may be warranted to increase or provide cell association to some food and/or feed enzymes because they exhibit insufficient intrinsic cell association or simply lack intrinsic cell association. In such embodiment, it is possible to provide the heterologous food and/or feed enzyme as a chimeric construct by combining it with a tethering amino acid moiety which will provide or increase attachment to the cell wall of the recombinant yeast host cell. In such embodiment, the chimeric food and/or feed enzyme will be considered "tethered". It is preferred that the amino acid tethering moiety of the chimeric protein be neutral with respect to the biological (enzymatic) activity of the heterologous food and/or feed enzyme, e.g., does not interfere with the biological (enzymatic) activity of the heterologous food and/or feed enzyme. In some embodiments, the association of the amino acid tethering moiety with the heterologous food and/or feed enzyme can increase the biological (enzymatic) activity of the heterologous food and/or feed enzyme (when compared to the non-tethered, non-chimeric form).

In an embodiment, a tethering moiety can be used to be expressed with the heterologous food and/or feed enzyme to locate the enzyme to the wall of the recombinant yeast host cell. Various tethering amino acid moieties are known art and can be used in the chimeric proteins of the present disclosure.

The tethering moiety can be a transmembrane domain found on another protein and allow the chimeric protein to have a transmembrane domain. In such embodiment, the tethering moiety can be derived from the FLO1 protein (having, for example, the amino acid sequence of SEQ ID NO: 10, a variant thereof or a fragment thereof or being encoded by the nucleic acid sequence of SEQ ID NO: 9).

In still another example, the amino acid tethering moiety can be modified post-translation to include a glycosylphosphatidylinositol (GPI) anchor and allow the chimeric protein to have a GPI anchor. GPI anchors are glycolipids attached to the terminus of a protein (and in some embodiments, to the carboxyl terminus of a protein) which allows the anchoring of the protein to the cytoplasmic membrane of the cell membrane. Tethering amino acid moieties capable of providing a GPI anchor include, but are not limited to those associated with/derived from a SED1 protein (having, for example, the amino acid sequence of SEQ ID NO: 12, a variant thereof or a fragment thereof or being encoded by the nucleic acid sequence of SEQ ID NO: 11), a TIR1 protein (having, for example, the amino acid sequence of SEQ ID NO: 14, a variant thereof or a fragment thereof or being encoded by the nucleic acid sequence of SEQ ID NO: 13), a CWP2 protein (having, for example, the amino acid sequence of SEQ ID NO: 16, a variant thereof or a fragment thereof or being encoded by the nucleic acid sequence of SEQ ID NO: 15), a CCW12 protein (having, for example, the amino acid sequence of SEQ ID NO: 18 or 84, a variant thereof or a fragment thereof or being encoded by the nucleic acid sequence of SEQ ID NO: 17), a SPI1 protein (having, for example, the amino acid sequence of SEQ ID NO: 20 or 74, a variant thereof or a fragment thereof or being encoded by the nucleic acid sequence of SEQ ID NO: 19), a PST1 protein (having, for example, the amino acid sequence of SEQ ID NO: 22, a variant thereof or a fragment thereof or being encoded by the nucleic acid sequence of SEQ ID NO: 21) or a combination of a AGA1 and a AGA2 protein (having, for example, the amino acid sequence of SEQ ID NO: 24, a variant thereof or a fragment thereof or being encoded by the nucleic acid sequence of SEQ ID NO: 23 or having, for example, the amino acid sequence of SEQ ID NO: 26, a variant thereof or a fragment thereof or being encoded by the nucleic acid sequence of SEQ ID NO: 25). In an embodiment, the tethering moiety provides a GPI anchor and, in still a further embodiment, the tethering moiety is derived from the SPI1 protein (having, for example, the amino acid sequence of SEQ ID NO: 20 or 74, a variant thereof or a fragment thereof or being encoded by the nucleic acid sequence of SEQ ID NO: 19) or the CCW12 protein (having, for example, the amino acid sequence of SEQ ID NO: 18 or 84, a variant thereof or a fragment thereof or being encoded by the nucleic acid sequence of SEQ ID NO: 17).

In an embodiment, the tethering moiety is a fragment of the SPI1 protein that retained its ability to localize to the cell's membrane. The fragment of the SPI1 protein comprises less than 129 amino acid consecutive residues of the amino acid sequence of SEQ ID NO: 74. For example, the tethering moiety fragment from the SPI1 protein can comprise at least 10, 20, 21, 30, 40, 50, 51, 60, 70, 80, 81, 90, 100, 110, 111 or 120 consecutive amino acid residues from the amino acid sequence of SEQ ID NO: 74. In yet another embodiment, the tethering moiety fragment from the SPI1 protein can comprise or consist essentially of the amino acid sequence set forth in any one of SEQ ID NOs: 76, 78, 80 or 82.

In another embodiment, the tethering moiety is a fragment of a CCW12 protein that retained its ability to localize to the cell's membrane. The fragment of the CCW12 protein comprises less than 112 amino acid consecutive residues of the amino acid sequence of SEQ ID NO: 84. For example, the tethering moiety fragment from the CCW12 protein can comprise at least 10, 20, 24, 30, 40, 49, 50, 60, 70, 74, 80, 90, 99, 100 or 110 consecutive amino acid residues from the amino acid sequence of SEQ ID NO: 84. In yet another embodiment, the tethering moiety fragment from the CCW12 protein can comprise or consist essentially of the amino acid sequence set forth in any one of SEQ ID NOs: 86, 88, 90 or 92.

The tethering amino acid moiety can be a variant of a known/native tethering amino acid moiety, for example a variant of the tethering amino acid moiety having the amino acid sequence of SEQ ID NOs: 10, 12, 14, 16, 18, 20, 22, 24, 26, 74, 76, 78, 80, 84, 82, 86, 88, 90 or 92. A variant comprises at least one amino acid difference when compared to the amino acid sequence of the native tethering amino acid moiety. As used herein, a variant refers to alterations in the amino acid sequence that do not adversely affect the biological functions of the tethering amino acid moiety (e.g., the location on the external face and the anchorage of the heterologous food and/or feed enzyme in the cytoplasmic membrane). A substitution, insertion or deletion is said to adversely affect the protein when the altered sequence prevents or disrupts a biological function associated with the tethering amino acid moiety (e.g., the location on the external face and the anchorage of the heterologous food and/or feed enzyme in the cytoplasmic membrane). For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the tethering amino acid moiety. The tethering amino acid moiety variants have at least 50%, 55%, 60%, 65%, 70%, 75%, 80%, 85%, 90%, 95%, 96%, 97%, 98% or 99% identity to the tethering amino acid moieties described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant tethering amino acid moieties described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the tethering amino acid moiety can be a conservative variant or an allelic variant.

The tethering amino acid moiety can be a fragment of a known/native tethering amino acid moiety or fragment of a variant of a known/native tethering amino acid moiety (such as, for example, a fragment of the tethering amino acid moiety having the amino acid sequence of SEQ ID NO: 10, 12, 14, 16, 18, 20, 22, 24, 26, 74, 76, 78, 80, 82, 84, 86, 88, 90 or 92 or a variant thereof). Tethering amino acid moiety "fragments" have at least at least 10, 20, 30, 40, 50, 60, 70, 80, 90, 100 or more consecutive amino acids of the tethering amino acid moiety. A fragment comprises at least one less amino acid residue when compared to the amino acid sequence of the known/native tethering amino acid moiety and still possess the biological activity of the full-length tethering amino acid moiety (e.g., the location to the cell wall).

In embodiments in which an amino acid tethering moiety is desirable, the heterologous food and/or feed enzyme can be provided as a chimeric protein expressed by the recombinant yeast host cell and having one of the following formulae (provided from the amino ($NH_2$) to the carboxyl (COOH) orientation):

FFE-L-TT     (I) or

TT-L-FFE     (II)

In both of these formulae, the residue "FFE" refers to the heterologous food and/or feed enzyme moiety, the residue "L" refers to the presence of an optional linker while the residue "TT" refers to an amino acid tethering moiety. In the chimeric proteins of formula (I), the amino terminus of the amino acid tether is located (directly or indirectly) at the carboxyl (COOH or C) terminus of the heterologous food and/or feed enzyme moiety. In the chimeric proteins of formula (II), the carboxy terminus of the amino acid tether is located (directly or indirectly) at the amino ($NH_2$ or N) terminus of the heterologous food and/or feed enzyme moiety.

In yet another embodiment, in the chimeric proteins of formula (I) and (II), the food and/or feed enzyme can be a baking enzyme. In such embodiments, the chimeric protein can have having one of the following formulae (provided from the amino ($NH_2$) to the carboxyl (COOH) orientation):

BE-L-TT     (Ia) or

TT-L-BE     (IIa)

In both of these formulae, the residue "BE" refers to the heterologous baking enzyme moiety, the residue "L" refers to the presence of an optional linker while the residue "TT" refers to an amino acid tethering moiety. In the chimeric proteins of formula (Ia), the amino acid tether is located (directly or indirectly) at the carboxyl (COOH or C) terminus of the heterologous baking enzyme moiety. In the chimeric proteins of formula (IIa), the amino acid tether is located (directly or indirectly) at the amino ($NH_2$ or N) terminus of the heterologous food and/or feed enzyme moiety.

When the amino acid linker (L) is absent, the tethering amino acid moiety is directly associated with the heterologous food and/or feed enzyme (or with the heterologous baking enzyme). In the chimeras of formulae (I) and (Ia), this means that the carboxyl terminus of the heterologous food and/or feed enzyme moiety (or the carboxyl terminus of the heterologous baking enzyme moiety) is directly associated (with an amide linkage) to the amino terminus of the tethering amino acid moiety. In the chimeras of formulae (II) and (IIa), this means that the carboxyl terminus of the tethering amino acid moiety is directly associated (with an amide linkage) to the amino terminus of the heterologous food and/or feed enzyme (or of the heterologous baking enzyme).

In some embodiments, the presence of an amino acid linker (L) is desirable either to provide, for example, some flexibility between the heterologous food and/or feed enzyme moiety and the tethering amino acid moiety or to facilitate the construction of the heterologous nucleic acid molecule. As used in the present disclosure, the "amino acid linker" or "L" refer to a stretch of one or more amino acids separating the heterologous enzyme moiety FFE or BE and the amino acid tethering moiety TT (e.g., indirectly linking the heterologous food and/or feed enzyme to the amino acid tethering moiety TT). It is preferred that the amino acid linker be neutral, e.g., does not interfere with the biological (enzymatic) activity of the heterologous food and/or feed enzyme nor with the biological (cell-association) activity of the amino acid tethering moiety. In some embodiments, the amino acid linker L can increase the biological activity of the heterologous food and/or feed enzyme moiety and/or of the amino acid tethering moiety.

In instances in which the linker (L) is present in the chimeras of formulae (I) and (Ia), its amino end is associated (with an amide linkage) to the carboxyl end of the heterologous food and/or feed enzyme moiety and its carboxyl end is associated (with an amide linkage) to the amino end of the amino acid tethering moiety. In instances in which the linker (L) is present in the chimeras of formulae (II) and (IIa), its amino end is associated (with an amide linkage) to the carboxyl end of the amino acid tethering moiety and its carboxyl end is associated (with an amide linkage) to the amino end of the heterologous food and/or feed enzyme moiety.

Various amino acid linkers exist and include, without limitations, $(G)_n$, $(GS)_n$; $(GGS)_n$; $(GGGS)_n$; $(GGGGS)_n$; $(GGSG)_n$; $(GSAT)_n$, wherein n=is an integer between 1 to 8 (or more). In an embodiment, the amino acid linker L is $(GGGGS)_n$ (also referred to as $G_4S$) and, in still further embodiments, the amino acid linker L comprises more than one $G_4S$ (SEQ ID NO: 41) motifs. For example, the amino acid linker L can be $(G_4S)$ 3 and have the amino acid sequence of SEQ ID NO: 93. In another example, the amino acid linker L can be (G); and have the amino acid sequence of SEQ ID NO: 94. In still another example, the amino acid linker L can be $(G_4S)$ 8 and have the amino acid sequence of SEQ ID NO: 95.

The amino acid linker can also be, in some embodiments, GSAGSAAGSGEF (SEQ ID NO: 96). Additional amino acid linkers exist and include, without limitations, (EAAK), and $(EAAAK)_n$, wherein n=is an integer between 1 to 8 (or more). In some embodiments, the one or more $(EAAK)_n$/(EAAAK), motifs can be separated by one or more additional amino acid residues. In an embodiment, the amino acid linker comprises one or more $EA_2K$ (SEQ ID NO: 100) or $EA_3K$ (SEQ ID NO: 101) motifs. In an embodiment, the amino acid linker can be (EAAK) 3 and has the amino acid sequence of SEQ ID NO: 97. In another embodiment, the amino acid linker can be $(A(EAAAK)_4ALEA(EAAAK)_4A)$ and has the amino acid sequence of SEQ ID NO: 99.

Further amino acid linkers include those having one or more $(AP)_n$ motifs wherein n=is an integer between 1 to 10 (or more). In an embodiment, the linker is $(AP)_{10}$ and has the amino acid of SEQ ID NO: 98.

In some embodiments, the linker also includes one or more HA tag (SEQ ID NO: 53).

Tools for Making the Recombinant Yeast Host Cell

In order to make the recombinant yeast host cells, heterologous nucleic acid molecules (also referred to as expression cassettes) are made in vitro and introduced into the yeast host cell in order to allow the recombinant expression of the heterologous food and/or feed enzyme.

The heterologous nucleic acid molecules of the present disclosure comprise a coding region for the heterologous polypeptide, e.g., the heterologous food and/or feed enzyme or a chimeric protein comprising same. A DNA or RNA "coding region" is a DNA or RNA molecule (preferably a DNA molecule) which is transcribed and/or translated into an heterologous food and/or feed enzyme in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The heterologous nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

In some embodiments, the heterologous nucleic acid molecules of the present disclosure include a promoter as well as a coding sequence for an heterologous food and/or feed enzyme (including chimeric proteins comprising same). The heterologous nucleic acid sequence can also include a terminator. In the heterologous nucleic acid molecules of the present disclosure, the promoter and the terminator (when present) are operatively linked to the nucleic acid coding sequence of the heterologous food and/or feed enzyme (including chimeric proteins comprising same), e.g., they control the expression and the termination of expression of the nucleic acid sequence of the heterologous food and/or feed enzyme (including chimeric proteins comprising same). The heterologous nucleic acid molecules of the present disclosure can also include a nucleic acid coding for a signal peptide, e.g., a short peptide sequence for exporting the heterologous food and/or feed enzyme outside the host cell. When present, the nucleic acid sequence coding for the signal peptide is directly located upstream and is in frame with the nucleic acid sequence coding for the heterologous food and/or feed enzyme (including chimeric proteins comprising same).

In the heterologous nucleic acid molecule described herein, the promoter and the nucleic acid molecule coding for the heterologous food and/or feed enzyme (including chimeric proteins comprising same) are operatively linked to one another. In the context of the present disclosure, the expressions "operatively linked" or "operatively associated" refers to fact that the promoter is physically associated to the nucleotide acid molecule coding for the heterologous polypeptide in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the heterologous protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous protein. The promoters can be located, in view of the nucleic acid molecule coding for the heterologous protein, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". Promoters which cause a gene to be expressed during the propagation phase of a yeast cell are herein referred to as "propagation promoters". Propagation promoters include both constitutive and inducible promoters, such as, for example, glucose-regulated, molasses-regulated, stress-response promoters (including osmotic stress response promoters) and aerobic-regulated promoters. In the context of the present disclosure, it is important that the selected promoter allows the expression of the heterologous nucleic acid molecule during the propagation phase of the recombinant yeast host cell in order to allow a sufficient amount of cell-associated heterologous food and/or feed enzymes to be expressed. It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be native or heterologous to the nucleic acid molecule encoding the heterologous polypeptide. The promoter can be heterologous or derived from a strain being from the same genus or species as the recombinant host cell. In an embodiment, the promoter is derived from the same genus or species of the yeast host cell and the heterologous polypeptide is derived from a different genus than the host cell. The promoter can be a single promoter or a combination of different promoters.

In the present disclosure, promoters allowing or favoring the expression of the heterologous proteins during the propagation phase of the recombinant yeast host cells are preferred. Yeasts that are facultative anaerobes, are capable of respiratory reproduction under aerobic conditions and fermentative reproduction under anaerobic conditions. In many commercial applications, yeast are propagated under aerobic conditions to maximize the conversion of a substrate to biomass. Optionally, the biomass can be used in a subsequent fermentation under anaerobic conditions to produce a desired metabolite. In the context of the present disclosure, it is important that the promoter or combination of promoters present in the heterologous nucleic acid is/are capable of allowing the expression of the heterologous food and/or feed enzyme or its corresponding chimera during the propagation phase of the recombinant yeast host cell. This will allow the accumulation of the heterologous food and/or feed enzyme associated with the recombinant yeast host cell prior to fermentation (if any). In some embodiments, the promoter allows the expression of the heterologous food and/or feed enzyme or its corresponding chimera during propagation, but not during fermentation (if any) of the recombinant yeast host cell.

The promoters can be native or heterologous to the heterologous gene encoding the heterologous protein. The promoters that can be included in the heterologous nucleic acid molecule can be constitutive or inducible promoters (such as those described in Perez-Torrado et al., 2005). Inducible promoters include, but are not limited to glucose-regulated promoters (e.g., the promoter of the hxt7 gene (referred to as hxt7p) and having the nucleic acid sequence of SEQ ID NO: 30, a functional variant or a functional fragment thereof; the promoter of the ctt1 gene (referred to as ctt1p) and having the nucleic acid sequence of SEQ ID NO: 60, a functional variant or a functional fragment thereof; the promoter of the glo1 gene (referred to as glo1p) and having the nucleic acid sequence of SEQ ID NO: 59, a functional variant or a functional fragment thereof; the promoter of the ygp1 gene (referred to as ygp1p) and having the nucleic acid sequence of SEQ ID NO: 61, a functional variant or a functional fragment thereof; the promoter of the gsy2 gene (referred to as gsy2p) and having the nucleic acid sequence of SEQ ID NO: 53, a functional variant or a functional fragment thereof), molasses-regulated promoters (e.g., the promoter of the mol1 gene (referred to as mol1p) described in Praekelt et al., 1992 or having the nucleic acid sequence of SEQ ID NO: 64, a functional variant or a functional fragment thereof), heat shock-regulated promoters (e.g., the promoter of the glo1 gene (referred to as glo1p) and having the nucleic acid sequence of SEQ ID NO: 59, a functional variant or a functional fragment thereof; the promoter of the sti1 gene (referred to as sti1p) and having the nucleic acid sequence of SEQ ID NO: 56, a functional variant or a functional fragment thereof; the promoter of the ygp1 gene (referred to as ygp1p) and having the nucleic acid sequence of SEQ ID NO: 61, a functional variant or a functional fragment thereof; the promoter of the gsy2 gene (referred to as gsy2p) and having the nucleic acid sequence of SEQ ID NO: 53, a functional variant or a functional fragment thereof), oxidative stress response promoters (e.g., the promoter of the cup1 gene (referred to as cup1p) and having the nucleic acid sequence of SEQ ID NO: 58, a functional variant or a functional fragment thereof; the promoter of the ctt1 gene (referred to as ctt1p) and having the nucleic acid sequence of SEQ ID NO: 60, a functional variant or a functional fragment thereof; the promoter of the trx2 gene (referred to as trx2p) and having the nucleic acid sequence of SEQ ID NO: 55, a functional variant or a functional fragment thereof; the promoter of the gpd1 gene (referred to as gpd1p) and having the nucleic acid sequence of SEQ ID NO: 57, a functional variant or a functional fragment thereof; the promoter of the hsp12 gene (referred to as hsp12p) and having the nucleic acid sequence of SEQ ID NO: 63, a functional variant or a functional fragment thereof), osmotic stress response promoters (e.g., the promoter of the ctt1 gene (referred to as ctt1p) and having the nucleic acid sequence of SEQ ID NO: 60, a functional variant or a functional fragment thereof; the promoter of the glo1 gene (referred to as glo1p) and having the nucleic acid sequence of SEQ ID NO: 59, a functional variant or a functional fragment thereof; the promoter of the gpd1 gene (referred to as gpd1p) and having the nucleic acid sequence of SEQ ID NO: 57, a functional variant or a functional fragment thereof; the promoter of the ygp1 gene (referred to as ygp1p) and having the nucleic acid sequence of SEQ ID NO: 61, a functional variant or a functional fragment thereof) and nitrogen-regulated promoters (e.g., the promoter of the ygp1 gene (referred to as ygp1p) and having the nucleic acid sequence of SEQ ID NO: 61, a functional variant or a functional fragment thereof).

Promoters that can be included in the heterologous nucleic acid molecule of the present disclosure include, without limitation, the promoter of the tdh1 gene (referred to as tdh1p and having, for example, the nucleic acid sequence of SEQ ID NO: 27, a functional variant or a functional fragment thereof), of the hor7 gene (referred to as hor7p and having, for example, the nucleic acid sequence of SEQ ID NO: 28, a functional variant or a functional fragment thereof), of the hsp150 gene (referred to as hsp150p and having, for example, the nucleic acid sequence of SEQ ID NO: 29, a functional variant or a functional fragment thereof), of the hxt7 gene (referred to as hxt7p and having, for example, the nucleic acid sequence of SEQ ID NO: 30, a functional variant or a functional fragment thereof), of the gpm1 gene (referred to as gpm1p and having, for example, the nucleic acid sequence of SEQ ID NO: 31, a functional variant or a functional fragment thereof), of the pgk1 gene (referred to as pgk1p and having, for example, the nucleic acid sequence of SEQ ID NO: 32, a functional variant or a functional fragment thereof) and/or of the stl1 gene (referred to as stl1p and having, for example, the nucleic acid sequence of SEQ ID NO: 33, a functional variant or a functional fragment thereof). In an embodiment, the promoter is or comprises the tdh1p and/or the hor7p. In still another embodiment, the promoter comprises or consists essentially of the tdh1p and the hor7p. In a further embodiment, the promoter is the thd1p.

One or more promoters can be used to allow the expression of each heterologous polypeptides in the recombinant yeast host cell. In the context of the present disclosure, the expression "functional fragment of a promoter" when used in combination to a promoter refers to a shorter nucleic acid sequence than the native promoter which retain the ability to control the expression of the nucleic acid sequence encoding the heterologous food and/or feed enzyme or its chimera during the propagation phase of the recombinant yeast host cells. Usually, functional fragments are either 5' and/or 3' truncation of one or more nucleic acid residue from the native promoter nucleic acid sequence.

In some embodiments, the nucleic acid molecules include a one or a combination of terminator sequence(s) to end the translation of the heterologous food and/or feed enzyme (or of the chimeric protein comprising same). The terminator can be native or heterologous to the nucleic acid sequence encoding the heterologous food and/or feed enzyme or its corresponding chimera. In some embodiments, one or more terminators can be used. In some embodiments, the terminator comprises the terminator from is from the dit1 gene (referred to as dit1t and can have, for example, the nucleic acid sequence of SEQ ID NO: 34, a functional variant or a functional fragment thereof), from the idp1 gene (referred to as idp1t and can have, for example, the nucleic acid sequence of SEQ ID NO: 35, a functional variant or a functional fragment thereof), from the gpm1 gene (referred to as gpm1t and can have, for example, the nucleic acid sequence of SEQ ID NO: 36, a functional variant or a functional fragment thereof), from the pma1 gene (referred to as pma1t and can have, for example, the nucleic acid sequence of SEQ ID NO: 37, a functional variant or a functional fragment thereof), from the tdh3 gene (referred to as tdh3t and can have, for example, the nucleic acid sequence of SEQ ID NO: 38, a functional variant or a functional fragment thereof), from the hxt2 gene (referred to as hxt2t and can have, for example, the nucleic acid sequence of SEQ ID NO: 39, a functional variant or a functional fragment thereof), from the adh3 gene (referred to as adh3t and can have, for example, the nucleic acid sequence of SEQ ID NO: 70, a functional variant or a functional fragment thereof) and/or from the ira2 gene (referred to as ira2t and can have, for example, the nucleic acid sequence of SEQ ID NO: 40, a functional variant or a functional fragment thereof). In an embodiment, the terminator is derived from the dit1 gene (and can have, for example, the nucleic acid sequence of SEQ ID NO: 34, a functional variant or a functional fragment thereof). In another embodiment, the terminator comprises or is derived from the adh3 gene (and can have, for example, the nucleic acid sequence of SEQ ID NO: 70, a functional variant or a functional fragment thereof). In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the heterologous protein or its corresponding chimera. In the context of the present disclosure, the expression "functional fragment of a terminator" refers to a shorter nucleic acid sequence than the native terminator which retain the ability to end the expression of the nucleic acid sequence coding for the heterologous protein or its corresponding chimera.

In some embodiments, the heterologous nucleic acid molecules include a coding sequence for one or a combination of signal peptide sequence(s) allowing the export of the heterologous protein (or of the chimeric protein comprising same) outside the yeast host cell's wall. The signal peptide sequence can simply be added to the nucleic acid molecule (usually in frame with the sequence encoding the heterologous food and/or feed enzyme) or replace the signal peptide sequence already present in the heterologous food and/or feed enzyme. The signal peptide sequence can be native or heterologous to the nucleic acid sequence encoding the heterologous food and/or feed enzyme or its corresponding chimera. In some embodiments, one or more signal sequences can be used. In some embodiments, the signal sequence is from the gene encoding the invertase protein (and can have, for example, the amino acid sequence of SEQ ID NO: 68, a variant thereof or a fragment thereof), the AGA2 protein (and can have, for example, the amino acid sequence of SEQ ID NO: 69, a variant thereof or a fragment thereof) or the fungal amylase protein (and can have, for example, the amino acid sequence of SEQ ID NO: 107, a variant thereof or a fragment thereof). In the context of the present disclosure, the expression "functional variant of a signal sequence" refers to a nucleic acid sequence that has been substituted in at least one nucleic acid position when compared to the native signal sequence which retain the ability to direct the expression of the heterologous food and/or feed enzyme or its corresponding chimera outside the cell. In the context of the present disclosure, the expression "functional fragment of a signal sequence" refers to a shorter nucleic acid sequence than the native signal sequence which retain the ability to direct the expression of the heterologous food and/or feed enzyme or its corresponding chimera outside the cell.

In some embodiments in which it is desirable to express the heterologous food and/or feed enzyme inside the recombinant yeast host cell (intracellularly), the heterologous nucleic acid molecule can exclude the portion coding for the signal peptide sequence which is found in the native gene encoding the food and/or feed enzyme.

The heterologous nucleic acid molecule encoding the heterologous food and/or feed enzyme, chimera, variant or fragment thereof can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the heterologous food and/or enzymes, chimeras, variants or fragments thereof. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded food and/or feed enzymes, chimeras, variants or fragments.

In some embodiments, the heterologous nucleic acid molecules which can be introduced into the recombinant host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules can be introduced in the yeast host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The present disclosure also provides nucleic acid molecules that are hybridizable to the complement nucleic acid molecules encoding the heterologous polypeptides as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA: RNA, DNA: RNA, DNA: DNA. For hybrids of greater than 100 nucleotides in length, equations for calculating Tm have been derived. For hybridizations with shorter nucleic acids, i.e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

Processes for Propagating and Formulating the Recombinant Yeast Host Cell

The present disclosure allows for making a yeast composition comprising the recombinant yeast host cell of the present disclosure. In some embodiments, the yeast composition can be used to reduce or waive the requirement of supplementing a food or feed-making process with exogenous (and purified/isolated) enzymes.

The process for making the yeast composition broadly comprises two steps: a first step of propagating the recombinant yeast host cell and a second step of formulating the yeast composition. As used in the context of the present disclosure, a "yeast composition" is a composition comprising the recombinant yeast host cell of the present disclosure which has been propagated. The yeast composition can be used, for example, in a following fermentation (to provide the heterologous enzyme in situ during fermentation) or to make a food/feed product. In an embodiment, the recombinant yeast host cell is provided in an active or in a semi-active form in the yeast composition. For example, an embodiment of the yeast composition is a cream yeast made from the recombinant yeast host cell of the present disclosure.

The propagation step can be a continuous culture, a batch culture or a fed-batch culture. In the propagation step, the recombinant yeast host cell is placed in a culture medium which can, in some embodiments, allow for rapid growth. For example, the culture medium can comprise a carbon source (such as, for example, molasses, sucrose, glucose, dextrose syrup, ethanol and/or corn steep liquor), a nitrogen source (such as, for example, ammonia) and a phosphorous source (such as, for example, phosphoric acid). The propagation step can be subdivided into two steps, an initial seeding step and a further large-scale propagation step. During the propagation step, it is possible to monitor and adjust the temperature (usually at about 32° C. when the recombinant yeast host cell is from the species *Saccharomyces cerevisiae*), the pH and the aeration conditions to favor or optimize the division of the recombinant yeast host cell. For example, when fed-batch propagation conditions are employed, using high aeration and incremental carbohydrate addition can optimize the yield of the biomass of the yeast composition.

In the formulating step, the mixture obtained after propagation (comprising the propagated recombinant yeast host cell(s)) can be modified. One of the advantages of the recombinant yeast host cells of the present disclosure is that the heterologous food/feed enzyme activity is associated with the recombinant yeast host cell that therefore concentrating the biomass after propagation will also increase the amount/activity of the heterologous food/feed enzyme. In an embodiment for providing a yeast composition, at least one component of the mixture obtained after propagation is removed from the culture medium to provide the yeast composition. This component can be, without limitation, water, amino acids, peptides and proteins, nucleic acid residues and nucleic acid molecules, cellular debris, fermentation products, etc. In an embodiment, the formulating step comprises substantially isolating the propagated yeast recombinant host cells (e.g., the biomass) from the components of the culture medium. As used in the context of the present disclosure, the expression "substantially isolating" refers to the removal of the majority of the components of the culture medium from the propagated recombinant yeast host cells. In order to provide the yeast composition, the propagated recombinant yeast host cells can be centrifuged (and the resulting cellular pellet comprising the propagated recombinant yeast host cells can optionally be washed), filtered and/or dried (optionally using a vacuum-drying technique). The isolated recombinant yeast host cells can then be formulated in a yeast composition. The formulation step can, in some embodiments, preserve the viability (at least in part) of the recombinant yeast host cells. As such, the yeast composition can be provided in an active or a semi-active form. The yeast composition can be provided in a liquid, semi-solid or dry form. In an embodiment, the yeast composition can be provided in the form of a cream yeast.

The yeast composition can further be modified into a yeast product. As used in the context of the present disclosure, a yeast product is a product obtained from the propagated recombinant yeast host cell which comprises the heterologous food and/or feed enzyme. The yeast product can be, for example, a yeast lysate (e.g., an autolysate), a yeast extract, a yeast fraction (e.g., yeast cell walls) and/or the heterologous food and/or feed enzyme in a substantially isolated form. As used in the context of the present disclosure, the expression "substantially isolating/purifying the heterologous food and/or feed enzymes from the lysed recombinant yeast host cells" refers to the removal of the majority of the components of the lysed recombinant yeast host cells from the heterologous food and/or feed enzymes and providing same in an isolated/purified form.

The yeast composition as well as the yeast product can be provided as a food additive. As used in the present disclosure, the expression "food additive" refers to a product used in human nutrition for purposes of improving the quality of food or to improve the production process. In such embodiment, the yeast composition can also include, without limitation, a carrier (such as for example, salt or a wheat grit), a stabilizing agent and/or an oil. In a specific embodiment, the yeast composition can be provided as a live yeast composition (such as, for example, a yeast cream) suitable for downstream food preparation, as an inactivated yeast composition, as a yeast fraction and/or as a purified food enzyme. In another specific embodiment, the yeast composition can be provided as a dried preparation (spray-dried for example) suitable for downstream food preparation.

The yeast composition can be provided as a feed additive. As used in the present disclosure, the expression "feed additive" refers to a product used in animal nutrition for purposes of improving the quality of feed, the quality of food from animal origin and/or to improve the animals' performance and health (e.g., providing enhanced digestibility of the feed materials). In such embodiment, the yeast composition can also include, without limitation, a carrier (such as for example, salt or a wheat grit), a stabilizing agent and/or an oil. In a specific embodiment, the yeast composition can be provided as a live yeast composition (such as, for example, a yeast cream) suitable for downstream feed preparation, as an inactivated yeast composition, as a yeast fraction and/or as a purified feed enzyme. In another specific embodiment, the yeast composition can be provided as a dried preparation (spray-dried for example) suitable for downstream feed preparation. In an embodiment, the feed additive is added to the animal's diet to supplement it.

Processes for Making Food and Feed Products

The recombinant yeast host cell of the present disclosure have been designed to be used in the preparation of products for human (food) or animal (feed) consumption. The present disclosure thus provides a process comprising including the recombinant yeast host cell of the present disclosure in the food or feed product. In some embodiments, it may be advantageous to provide the recombinant yeast host cell of the present disclosure as a food additive or as a feed additive. In some embodiments, the process can also include fermenting the product and/or baking the food or feed product. In instances in which the process includes a fermentation step, the fermentation can be conducted (totally or in part) in the presence of or by the recombinant yeast host cell described herein. The process of the present disclosure can be used to extend the shelf-life of the food or feed products. The enzymatic activity (associated with the heterologous food and/or feed enzyme as well as chimeric proteins comprising same) of the recombinant yeast cells can be dosed prior to use and adjusted depending on the type of activity warranted.

In an embodiment, the food and feed products are baked products. In such embodiment, a recombinant yeast host cell expressing the cell-associated baking enzyme is preferably used. Baked products such as yeast-leavened baked products can be fermented by the recombinant yeast host cell described herein. Yeast-leavened baked products include, without limitation, bread, pastries (including croissants), rolls, pita, tortillas, bagels and pie or pizza crusts and the like. When used during the process for making yeast-leavened products, the recombinant yeast host cells can be the sole fermenting organism that is added to the fermentable substrate. In other instances, the recombinant yeast host cells can be admixed with non-recombinant (e.g., wild-type) yeasts up to provide the adequate dose of heterologous baking enzyme activity. For example, the recombinant yeast host cell (which can be a recombinant *Saccharomyces cerevisiae* yeast host cell) can be combined in any ratio with a wild-type yeast host cell (which can be a wild-type non-recombinant *Saccharomyces cerevisiae*). In an embodiment, the ratio between recombinant: wild-type is between 1:100 and 100:1.

Amylolytic enzymes are of particular interest in the production of yeast-leavened baked products because they favor the hydrolysis of starch (either in a raw or hydrolyzed form) and therefore provide an energy source to the fermenting yeasts to accelerate the fermentation process, increase $CO_2$ production, increase ethanol production and/or improve the organoleptic properties of the fermented product. Maltogenic amylases are, in particular, very useful in the process for making bread because they are known to extend the shelf-life by maintaining the softness and the resilience of baked bread.

In another embodiment, the baked products are not fermented by the recombinant yeast host cell described herein and are instead chemically leavened or unleavened. Chemically leavened and unleavened baked products include, without limitation, cakes and flatbreads.

In the process described herein, the recombinant yeast host cells of the present disclosure can be provided in an active form (e.g., liquid, compressed, or fluid-bed dried yeast), in a semi-active form (e.g., liquid, compressed, or fluid-bed dried), in an inactive form (e.g., drum- or spray-dried) as well as a mixture therefore. For example, the recombinant yeast host cells can be a combination of active and semi-active or inactive forms to provide the ratio and dose of the baking enzyme required for making baked products.

The present invention will be more readily understood by referring to the following examples which are given to illustrate the invention rather than to limit its scope.

Example I—Material and Methods

TABLE 1

Description of the yeast strains used in the examples. These strains were constructed with expression cassettes, integrated into the FCY1 locus on each chromosome, the number of copies is provided in the table. The original strain background used for each strain is also provided in the table. Each integrated cassette included a copy of an heterologous enzyme, one or more promoter and one or more terminator. In some instances, the signal peptide of the heterologous enzyme has been replaced by another signal peptide as indicated in the table. When the heterologous enzyme is expressed in a tethered form, the geometry in of the tether is provided (see definition of formula I and II above) and the linker as well as the tether are provided. N.A. = not applicable.

| Name | Heterologous enzyme expressed | Original strain background | Copies of heterologous enzyme integrated per chromosome | Promoter | Terminator | Type of expression | Signal peptide[1] | Linker[2] | Tether[3] |
|---|---|---|---|---|---|---|---|---|---|
| M2390 (*Saccharomyces cerevisiae*) | None | N.A. | N.A. | N.A. | N.A. | N.A. | N.A. | N.A. | N.A. |
| M8498 | Glucoamylase (SEQ ID NO: 29) | M10474 | 1 | TEF2p | SED1t | Free secreted | Invertase | None | None |
| M10074 | Alpha-amylase (SEQ ID NO: 50) | M10474 | 1 | TEF2p | SED1t | Free secreted | Invertase | None | None |
| M10474 (*Saccharomyces cerevisiae*) | None | N.A. | N.A. | N.A. | N.A. | N.A. | N.A. | N.A. | N.A. |
| M11312 | Phytase (SEQ ID NO: 67) | M2390 | 1 | TEF2p | ADH3t | Free secreted | Invertase | N.A. | N.A. |
| M12550 (*Saccharomyces cerevisiae*) | None | N.A. | N.A. | N.A. | N.A. | N.A. | N.A. | N.A. | N.A. |
| M12548 (*Saccharomyces boulardii*) | None | N.A. | N.A. | N.A. | N.A. | N.A. | N.A. | N.A. | N.A. |
| M12795 | Phytase (SEQ ID NO: 67) | M12550 | 1 | TEF2p | ADH3t | Tethered - Formula (II) | Aga2 | $(G_4S)_2$ | Aga1/2 (Aga2 on N-terminus of enzyme) |
| M12938 | Phytase (SEQ ID NO: 67) | M12550 | 1 | TEF2p | ADH3t | Tethered - Formula (II) | Aga2 | $(G_4S)_2$ | Aga1/2 |
| M12962 (*Saccharomyces cerevisiae* var *diastaticus*) | None | N.A. | N.A. | N.A. | N.A. | N.A. | N.A. | N.A. | N.A. |
| M13819 | Maltogenic alpha-amylase (SEQ ID NO: 51) | M10474 | 2 | TDH1p/HOR7p | DIT1t/DP1t | Tethered - Formula (I) | Invertase | HA/G$_4$S | Spi1 |
| M13822 | Maltogenic alpha-amylase (SEQ ID NO: 51) | M10474 | 2 | TDH1p/HOR7p | DIT1t/IDP1t | Free secreted | Invertase | None | None |
| M13979 | Maltogenic alpha amylase (SEQ ID NO: 51) | M10474 | 4 | TDH1p/HOR7p | DIT1t/IDP1t | Tethered - formula (I) | Invertase | $(G_4S)_2$ | Spi1 |
| M14244 | Glucoamylase (SEQ ID NO: 29) | M10474 | 1 | TEF2p | SED1t | Tethered - formula (I) | Invertase | HA/G$_4$S | Sed1 |
| M14253 | Alpha-amylase (SEQ ID NO: 50) | M10474 | 1 | TEF2p | SED1t | Tethered - Formula (I) | Invertase | HA/G$_4$S linker | Sed1 |
| M14254 | Alpha-amylase (SEQ ID NO: 50) | M10474 | 1 | TEF2p | SED1t | Tethered - Formula (I) | Invertase | None | Sed1 |
| M14851 | Maltogenic alpha amylase (SEQ ID NO: 65) | M10474 | 2 | TDH1p/HOR7p | DIT1t/IDP1t | Intracellular | N.A. | N.A. | N.A. |
| M15215 | Alpha-amylase (SEQ ID NO: 72) | M2390 | 1 | TEF2p | ADH3t | Tethered - Formula (I) | Invertase | HA/$(G_4S)_3$ | SEQ ID NO: 84 |

TABLE 1-continued

Description of the yeast strains used in the examples. These strains were constructed with expression cassettes, integrated into the FCY1 locus on each chromosome, the number of copies is provided in the table. The original strain background used for each strain is also provided in the table. Each integrated cassette included a copy of an heterologous enzyme, one or more promoter and one or more terminator. In some instances, the signal peptide of the heterologous enzyme has been replaced by another signal peptide as indicated in the table. When the heterologous enzyme is expressed in a tethered form, the geometry in of the tether is provided (see definition of formula I and II above) and the linker as well as the tether are provided. N.A. = not applicable.

| Name | Heterologous enzyme expressed | Original strain background | Copies of heterologous enzyme integrated per chromosome | Promoter | Terminator | Type of expression | Signal peptide[1] | Linker[2] | Tether[3] |
|---|---|---|---|---|---|---|---|---|---|
| M15222 | Alpha-amylase (SEQ ID NO: 71) | M2390 | 1 | TEF2p | ADH3t | Tethered - Formula (I) | Invertase | HA/$(G_4S)_3$ | SEQ ID NO: 74 |
| M15532 | Maltogenic alpha amylase (SEQ ID NO: 108) | M10474 | 2 | TDH1p/HOR7p | DIT1t/IDP1t | Intracellular | N.A. | N.A. | N.A. |
| M15771 | Alpha-amylase (SEQ ID NO: 71) | M2390 | 1 | TEF2p | ADH3t | Tethered - Formula (I) | Invertase | HA/$(G_4S)_3$ | SEQ ID NO: 78 |
| M15772 | Alpha-amylase (SEQ ID NO: 71) | M2390 | 1 | TEF2p | ADH3t | Tethered - Formula (I) | Invertase | HA/$(G_4S)_3$ | SEQ ID NO: 82 |
| M15773 | Alpha-amylase (SEQ ID NO: 72) | M2390 | 1 | TEF2p | ADH3t | Tethered - Formula (I) | Invertase | HA/$(G_4S)_3$ | SEQ ID NO: 86 |
| M15774 | Alpha-amylase (SEQ ID NO: 71) | M2390 | 1 | TEF2p | ADH3t | Tethered - Formula (I) | Invertase | HA/$(G_4S)_3$ | SEQ ID NO: 76 |
| M15775 | Alpha-amylase (SEQ ID NO: 72) | M2390 | 1 | TEF2p | ADH3t | Tethered - Formula (I) | Invertase | HA/$(G_4S)_3$ | SEQ ID NO: 92 |
| M15776 | Alpha-amylase (SEQ ID NO: 72) | M2390 | 1 | TEF2p | ADH3t | Tethered - Formula (I) | Invertase | HA/$(G_4S)_3$ | SEQ ID NO: 88 |
| M15777 | Alpha-amylase (SEQ ID NO: 71) | M2390 | 1 | TEF2p | ADH3t | Tethered - Formula (I) | Invertase | HA/$(G_4S)_3$ | SEQ ID NO: 80 |
| M15778 | Alpha-amylase (SEQ ID NO: 71) | M2390 | 1 | TEF2p | ADH3t | Tethered - Formula (I) | Invertase | SEQ ID NO: 94 | SEQ ID NO: 74 |
| M15779 | Alpha-amylase (SEQ ID NO: 71) | M2390 | 1 | TEF2p | ADH3t | Tethered - Formula (I) | Invertase | SEQ ID NO: 95 | SEQ ID NO: 74 |
| M15780 | Alpha-amylase (SEQ ID NO: 71) | M2390 | 1 | TEF2p | ADH3t | Tethered - Formula (I) | Invertase | SEQ ID NO: 97 | SEQ ID NO: 74 |
| M15781 | Alpha-amylase (SEQ ID NO: 72) | M2390 | 1 | TEF2p | ADH3t | Tethered - Formula (I) | Invertase | SEQ ID NO: 98 | SEQ ID NO: 84 |
| M15782 | Alpha-amylase (SEQ ID NO: 72) | M2390 | 1 | TEF2p | ADH3t | Tethered - Formula (I) | Invertase | SEQ ID NO: 95 | SEQ ID NO: 84 |
| M15784 | Alpha-amylase (SEQ ID NO: 71) | M2390 | 1 | TEF2p | ADH3t | Tethered - Formula (I) | Invertase | SEQ ID NO: 93 | SEQ ID NO: 84 |
| M15783 | Alpha-amylase (SEQ ID NO: 71) | M2390 | 1 | TEF2p | ADH3t | Tethered - Formula (I) | Invertase | SEQ ID NO: 99 | SEQ ID NO: 74 |
| M15785 | Alpha-amylase (SEQ ID NO: 72) | M2390 | 1 | TEF2p | ADH3t | Tethered - Formula (I) | Invertase | SEQ ID NO: 93 | SEQ ID NO: 84 |
| M15786 | Alpha-amylase (SEQ ID NO: 72) | M2390 | 1 | TEF2p | ADH3t | Tethered - Formula (I) | Invertase | SEQ ID NO: 94 | SEQ ID NO: 84 |
| M15787 | Alpha-amylase (SEQ ID NO: 71) | M2390 | 1 | TEF2p | ADH3t | Tethered - Formula (I) | Invertase | SEQ ID NO: 96 | SEQ ID NO: 74 |
| M15788 | Alpha-amylase (SEQ ID NO: 71) | M2390 | 1 | TEF2p | ADH3t | Tethered - Formula (I) | Invertase | SEQ ID NO: 98 | SEQ ID NO: 74 |
| M16221 | Alpha-amylase (SEQ ID NO: 72) | M2390 | 1 | TEF2p | ADH3t | Tethered - Formula (I) | Invertase | SEQ ID NO: 97 | SEQ ID NO: 84 |

TABLE 1-continued

Description of the yeast strains used in the examples. These strains were constructed with expression cassettes, integrated into the FCY1 locus on each chromosome, the number of copies is provided in the table. The original strain background used for each strain is also provided in the table. Each integrated cassette included a copy of an heterologous enzyme, one or more promoter and one or more terminator. In some instances, the signal peptide of the heterologous enzyme has been replaced by another signal peptide as indicated in the table. When the heterologous enzyme is expressed in a tethered form, the geometry in of the tether is provided (see definition of formula I and II above) and the linker as well as the tether are provided. N.A. = not applicable.

| Name | Heterologous enzyme expressed | Original strain background | Copies of heterologous enzyme integrated per chromosome | Promoter | Terminator | Type of expression | Signal peptide[1] | Linker[2] | Tether[3] |
|---|---|---|---|---|---|---|---|---|---|
| M16222 | Alpha-amylase (SEQ ID NO: 72) | M2390 | 1 | TEF2p | ADH3t | Tethered - Formula (I) | Invertase | SEQ ID NO: 99 | SEQ ID NO: 84 |
| M16251 | Alpha-amylase (SEQ ID NO: 72) | M2390 | 1 | TEF2p | ADH3t | Tethered - Formula (I) | Invertase | HA/$(G_4S)_3$ | SEQ ID NO: 90 |
| M16252 | Alpha-amylase (SEQ ID NO: 72) | M2390 | 1 | TEF2p | ADH3t | Tethered - Formula (I) | Invertase | SEQ ID NO: 96 | SEQ ID NO: 84 |
| M16273 | Glucose oxidase (SEQ ID NO: 103) | M10474 | 2 | TDH1p/HOR7p | DIT1t/IDP1t | Intracellular | N.A. | N.A. | N.A. |
| M16540 | Fungal amylase (SEQ ID NO: 105) | M10474 | 2 | TDH1p/HOR7p | DIT1t/IDP1t | Free secreted | Fungal amylase | N.A. | N.A. |
| M16772 | Fungal amylase (SEQ ID NO: 105) | M10474 | 2 | TDH1p/HOR7p | DIT1t/IDP1t | Free secreted | Invertase | N.A. | N.A. |
| M16780 | Glucose oxidase (SEQ ID NO: 103) | M10474 | 2 | TDH1p/HOR7p | DIT1t/IDP1t | Free secreted | Invertase | N.A. | N.A. |
| T2633 | Phytase (SEQ ID NO: 66) | M12548 | 1 | TEF2p | ADH3t | Free secreted | Invertase | N.A. | N.A. |
| T2634 | Phytase (SEQ ID NO: 66) | M12548 | 1 | TEF2p | ADH3t | Tethered - Formula (I) | Invertase | $(G_4S)_2$ | Sed1 |
| T2635 | Phytase (SEQ ID NO: 66) | M12548 | 1 | TEF2p | ADH3t | Tethered - Formula (I) | Invertase | $(G_4S)_2$ | Tir1 |
| T2636 | Phytase (SEQ ID NO: 66) | M12548 | 1 | TEF2p | ADH3t | Tethered - Formula (I) | Invertase | $(G_4S)_2$ | Cwp2 |
| T2637 | Phytase (SEQ ID NO: 66) | M12548 | 1 | TEF2p | ADH3t | Tethered - Formula (I) | Invertase | $(G_4S)_2$ | Spi1 |
| T2638 | Phytase (SEQ ID NO: 66) | M12548 | 1 | TEF2p | ADH3t | Tethered - Formula (I) | Invertase | $(G_4S)_2$ | Pst1 |
| T2705 | Phytase (SEQ ID NO: 67) | M2390 | 1 | TEF2p | ADH3t | Tethered - Formula (II) | Aga2 | $(G_4S)_2$ | Aga1/2 |
| T2706 | Phytase (SEQ ID NO: 67) | M2390 | 1 | TEF2p | ADH3t | Tethered - Formula (I) | Invertase | $(G_4S)_2$ | Aga1/2 |
| T2816 | Phytase (SEQ ID NO: 67) | M12550 | 1 | TEF2p | ADH3t | Tethered - Formula (I) | Invertase | $(G_4S)_2$ | Sed1 |
| T2986 | Maltogenic alpha-amylase (SEQ ID NO: 51) | M10474 | 2 | TDH1p/HOR7p | DIT1t/IDP1t | Tethered - Formula (I) | Invertase | HA/$(G_4S)_2$ | Flo1 |
| T2987 | Maltogenic alpha-amylase (SEQ ID NO: 51) | M10474 | 2 | TDH1p/HOR7p | DIT1t/IDP1t | Tethered - Formula (I) | Invertase | HA/$(G_4S)_2$ | Sed1 |
| T2988 | Maltogenic alpha-amylase (SEQ ID NO: 51) | M10474 | 2 | TDH1p/HOR7p | DIT1t/IDP1t | Tethered - Formula (I) | Invertase | HA/$(G_4S)_2$ | Tir1 |

TABLE 1-continued

Description of the yeast strains used in the examples. These strains were constructed with expression cassettes, integrated into the FCY1 locus on each chromosome, the number of copies is provided in the table. The original strain background used for each strain is also provided in the table. Each integrated cassette included a copy of an heterologous enzyme, one or more promoter and one or more terminator. In some instances, the signal peptide of the heterologous enzyme has been replaced by another signal peptide as indicated in the table. When the heterologous enzyme is expressed in a tethered form, the geometry in of the tether is provided (see definition of formula I and II above) and the linker as well as the tether are provided. N.A. = not applicable.

| Name | Heterologous enzyme expressed | Original strain background | Copies of heterologous enzyme integrated per chromosome | Promoter | Terminator | Type of expression | Signal peptide[1] | Linker[2] | Tether[3] |
|---|---|---|---|---|---|---|---|---|---|
| T2989 | Maltogenic alpha-amylase (SEQ ID NO: 51) | M10474 | 2 | TDH1p/HOR7p | DIT1t/IDP1t | Tethered - Formula (I) | Invertase | HA-$(G_4S)_2$ | Cwp2 |
| T2990 | Maltogenic alpha-amylase (SEQ ID NO: 51) | M10474 | 2 | TDH1p/HOR7p | DIT1t/IDP1t | Tethered - Formula (I) | Invertase | HA/$(G_4S)_2$ | Ccw1 |
| T2991 | Maltogenic alpha-amylase (SEQ ID NO: 51) | M10474 | 2 | TDH1p/HOR7p | DIT1t/IDP1t | Tethered - Formula (I) | Invertase | HA/$(G_4S)_2$ | Spi1 |
| T2994 | Maltogenic alpha-amylase (SEQ ID NO: 51) | M10474 | 2 | TDH1p/HOR7p | DIT1t/IDP1t | Free secreted | Invertase | None | None |
| T3892 | Maltogenic alpha amylase (SEQ ID NO: 65) | M10474 | 2 | TDH1p/HOR7p | DIT1t/IDP1t | Intracellular | N.A. | N.A. | N.A. |
| T4328 | Maltogenic alpha amylase (SEQ ID NO: 51) | M10474 | 2 | TDH1p/HOR7p | DIT1t/IDP1t | Tethered | Invertase | $(G_4S)_2$ | Spi1 |
| T4329 | Maltogenic alpha amylase (SEQ ID NO: 51) | M10474 | 2 | TDH1p/HOR7p | DIT1t/IDP1t | Free secreted | Invertase | N.A. | N.A. |
| T4330 | Maltogenic alpha amylase (SEQ ID NO: 65) | M10474 | 2 | TDH1p/HOR7p | DIT1t/IDP1t | Intracellular | N.A. | N.A. | N.A. |
| T4336 | Maltogenic alpha amylase (SEQ ID NO: 51) | M12962 | 2 | TDH1p/HOR7p | DIT1t/IDP1t | Tethered - Formula (I) | Invertase | $(G_4S)_2$ | Spi1 |
| T4337 | Maltogenic alpha amylase (SEQ ID NO: 51) | M12962 | 2 | TDH1p/HOR7p | DIT1t/IDP1t | Free secreted | Invertase | N.A. | N.A. |
| T4338 | Maltogenic alpha amylase (SEQ ID NO: 65) | M12962 | 2 | TDH1p/HOR7p | DIT1t/IDP1t | Intracellular | N.A. | N.A. | N.A. |

[1]Invertase = SEQ ID NO: 52, Aga2 = SEQ ID NO: 69, fungal amylase = SEQ ID NO: 107
[2]HA = SEQ ID NO: 53: $(G_4S)_2$ = SEQ ID NO : 54
[3]Flo1 tether is a transmembrane domain located at the C-terminus = SEQ ID NO: 10; Sed1 tether is a GPI anchor located at the C-terminus = SEQ ID NO: 12; Tir1 tether is a mannoprotein GPI fragment located at the C-terminus = SEQ ID NO: 14; Cwp2 tether is a mannoprotein GPI fragment located at the C-terminus = SEQ ID NO: 16; Ccw12 tether is a mannoprotein GPI fragment located at the C- terminus = SEQ ID NO: 16; Spi1 tether is a GPI anchor located at the C-terminus = SEQ ID NO: 20; Pst1 tether is a GPI anchor = SEQ ID NO: 22; Aga1/2 tether, Aga2 disulfide bond to Aga1; Aga1 has GPI anchor, the enzyme is fused to Aga2 at the C-terminus = SEQ ID NO: 24: Aga1/2 tether, Aga2 disulfide bond to Aga1; Aga1 has GPI anchor, the enzyme is fused to Aga2 at the N-terminus = SEQ ID NO: 26.

Cell growth. Cells were grown overnight in 5 mL YPD (10 g/L yeast extract, 20 g/L bacteriological peptone, 40 g/L glucose). One (1) mL of whole culture as harvested and cells were pelleted by centrifugation. Cell-free supernatant was removed and saved for later analysis. Cell pellet was washed once and resuspended in deionized water.

Seed fed-batch fermentation. A molasses mixture was prepared (85% beet molasses, 15% cane molasses), diluted and its pH is adjust to pH 5.2 with sulfuric acid. The pure culture inoculum was diluted in sterile water and added to the molasses mixture with zinc sulfate, magnesium sulfate, biotin, thiamine, calcium pantothenate and phosphoric acid. The yeasts were propagated at 32° C., at pH 4.5, for 24 hours. The resulting propagated yeast were centrifuged and the propagation broth was washed using a laboratory Alfa Laval separator to reach approximately 20% yeast solids. The yeasts solids were treated with sulfuric acid and pH was adjusted afterwards with sodium hydroxide to provide the cream yeast.

Commercial fed-batch fermentation. A molasses mixture was prepared (85% beet molasses, 15% cane molasses), diluted and its pH is adjust to pH 5.2 with sulfuric acid. The cream yeast from the seed fed-batch was diluted in sterile water and added to the molasses mixture with zinc sulfate, magnesium sulfate, biotin, thiamine, calcium pantothenate. The resulting propagated yeast were centrifuged and the propagation broth was washed using a laboratory Alfa Laval separator to reach approximately 20% yeast solids.

Cream yeast and inactivated cream yeast. After the fermentation, the harvested fermentation broth was centrifuged and washed using a laboratory scale GEA separator to prepare yeast cream with a final dry weight close to 20%. To make the inactivated cream yeast, about 600 g of cream yeast was heated on a temperature controlled stirring/hot plate until 75° C. was reached. The cream was kept for 15 minutes at 75° C. and then removed from heat source.

Spray drying. Spray dried samples were prepared by drying at 150° C. with a mini spray dryer (Buchi B-290). Feeding rate was kept to maintain outlet temperature around 80-85° C.

Bead-milling/making bead-milled homogenate. Cream yeast was disrupted (with typical disruption efficiency of >95% of cells) by bead milling under the following bead mill conditions. Cream yeast (~20% solids) was bead-milled with a Dyno KDL with 0.6 L chamber volume at 4° C., using 0.5-0.75 mm glass beads filling the chamber to 80% with 1.6 g/mL packing capacity and a 64 mm diameter agitator with peripheral speed of 10 m/s. The cream yeast flow rate was 6 kg/L/h.

Preparation of instant dried yeast (IDY). After the commercial fermentations targeting for the production of IDY samples, the harvested broth was centrifuged and washed using a laboratory scale GEA separator to prepare yeast cream with a final dry weight close to 20%. The cream was then filtered in a vacuum filtration system to make cake yeast. To remove additional water, the yeast cake was further pressed to achieve a dry weight of about 35% before extrusion. The pressed cake was then extruded after well mixed with span for 5 minutes. The span addition rate was 1% on yeast dry matter basis. After extrusion, the yeast was dried in a lab-scale fluidized-bed dryer (Aeromatic AG). The drying temperature was set and controlled at 35-40° C. The drying lasted about 20-25 minutes to achieve a solids content of more than 94%. In term of the fermentation recipes, the significant difference for the IDY fermentation recipe is that it has a 2 hrs maturation period towards end of the fermentation, in which ammonia (N) is stopped and fermentation temperature is increased to 35° C.

Fermenter autolysis. At least 3 L (minimum working volume) of cream at 20% solids was transferred into a 20 L fermenter (BIOENGINEERING). Autolysis was performed at 55° C. and pH 5.5 (automated pH control with 2N sulfuric acid) with a gentle agitation at 70 rpm. Autolysate (~20% dry weight) was harvested after a 24 hours incubation and separated as described below.

Lab scale autolysis. This autolysis is similar to the fermenter autolysis described above, but was performed at a smaller scale and with slightly different parameters. The cream yeast (20% solids) was submitted to autolysis and the pH was adjusted to pH 7. The mixture was incubated in 50 ml conical tubes in a 55° C. water bath for 48 hours.

Separation of autolysate without washing. After fermenter autolysis, the total autolysate was separated at 11,000 RCF for 10 minutes in 1 L bottles in a Sorvall Lynx 6000 centrifuge to obtain a soluble fraction (11-13% dry weight, yeast extract) and insoluble fraction (yeast cell wall). Dry weight and enzyme activity were measured for the total autolysate, yeast extract and cell wall fractions for dry weight and MANU balances.

Separation of autolysate with washing. Separations were performed by centrifuging fermenter autolysate in 50 ml conical tubes for 10 minutes at 3,000 RCF. Two additional washes were performed by adding water equal to the weight of supernatant obtained from the centrifuge step. YE (yeast extract) separation yield is calculated as the recovery of solids from separation only (WF=0) and of separation plus one or two washes (WF=1 or 2, respectively), relative to the starting solids in the autolysate. YE MANU recovery is calculated as the activity (in Phadebas MANU) from separation only (WF=0) and of separation plus one or two washes (WF=1 or 2), relative to starting total Phadebas MANU in the autolysate.

Ultrafiltration. Fermenter autolysate was separated by centrifuging in 1 L bottles at 11,000 RCF and the yeast extract fraction was further concentrated by ultrafiltration with a 10 kDa molecular weight cutoff PES membrane (Millipore, Biomax-10). The retentate fraction is retained by the membrane and permeate fraction passes through the membrane.

Maltogenic amylase assay. One Maltogenic Amylase Novo Unit, MANU, is the amount of enzyme which under standard conditions will cleave one micromol maltotriose per minute. Prior to assaying for enzymatic activity, cream yeast samples were inactivated by incubation at 60° C. for 10 minutes in MANU assay buffer (0.1 M citric acid, pH 5.0). Samples were then mixed with 20 mg/ml maltotriose substrate and incubated at 37° C. for 30 minutes. Reactions were stopped by addition of an equal volume of 1 N sodium hydroxide stop reagent. Glucose hydrolyzed by maltogenic amylase activity was measured after a 15-minute room temperature incubation with glucose (HK) assay reagent (Sigma G3293). Absorbance was read at 340 nm in a spectrophotometer. Unknown samples were compared to a dose curve of Novamyl® with known enzyme activity. This method was applied to generate the results of FIG. 1 only.

Phadebas MANU enzyme activity assay. Phadebas tablets contain a water insoluble starch substrate and a blue dye, bound to the dye with crosslinks. The substrate is hydrolyzed by maltogenic amylase, releasing blue dye which is soluble. After terminating the reaction and centrifuging, the absorbance of the solution was measured spectrophotometrically and is considered a proxy for enzyme activity. For each sample, one Phadebas tablet was added to 4.9 mL of citrate-phosphate buffer (70 mM disodium hydrogen phosphate, 30 mM citric acid, pH 5.5), incubated in a 60° C. water bath for 5 minutes. Then, 0.1 mL of standard or sample, diluted in citrate-phosphate buffer, was added to the tablet and buffer solution and incubated for 15 minutes in the 60° C. water bath. The reaction was terminated by adding 1 ml of 0.5 M sodium hydroxide solution and mixing. The tubes were centrifuged to remove solids and absorbance of the substrate was measured at 620 nm with a spectrophotometer. Samples (dry or liquid) are compared to a dose curve of Novamyl® with known activity. This methods was applied to generate all of the MANU results, except for FIG. 1.

Glucose oxidase assay. Cells were grown in batch in yeast extract peptone media plus 2% glucose at 30° C. for 24 hours. To obtain the disrupted washed cell supernatant, the cells were dead-beaten with glass beads 2×1 min in assay buffer, with one minute rest between. The supernatant was separated from the whole lysate by centrifugation. Whole culture, supernatant, disrupted washed cell supernatant (which reflects the intracellular cell-associated activity), washed cells or a positive control of Gluzyme® (2.40 GODU/mL corresponding to 10 000BG) were measured with the K-GLOX™ kit (Megazyme): samples in assay buffer (100 mM potassium phosphate, pH 7, containing 0.5 mg/mL BSA and 0.02% (w/v) sodium azide) were mixed with 90 mg/mL glucose and POD mixture and incubated at room temperature for 20 minutes. Absorbance was measured with a spectrophotometer at 510 nm.

Figure 5:
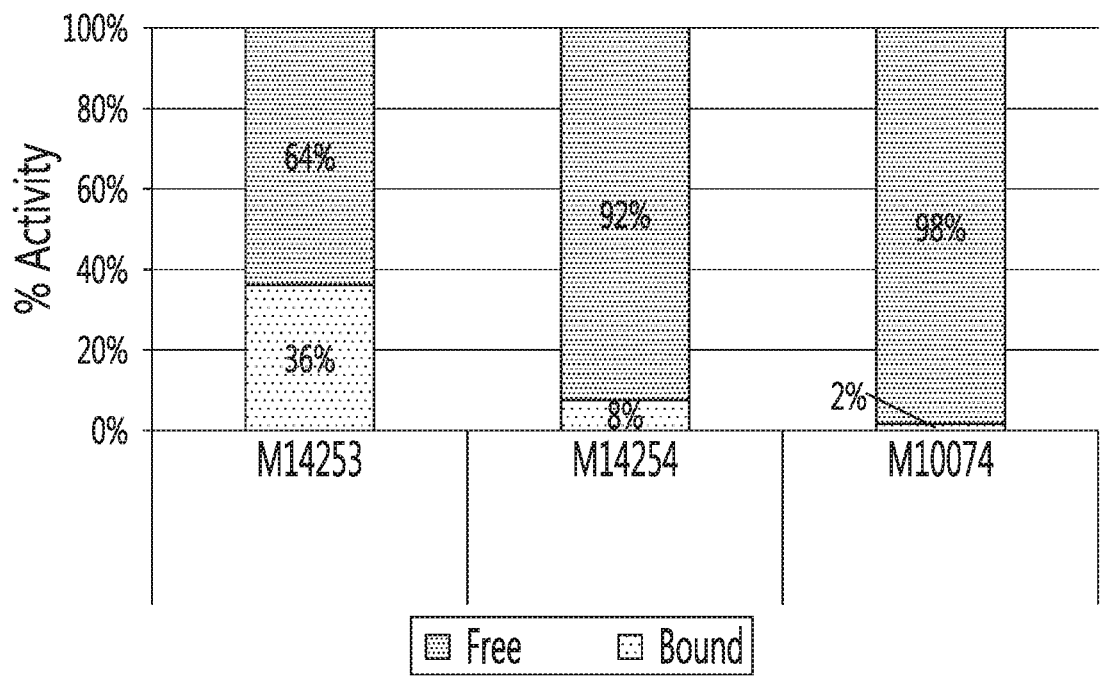
FIG. 5 provides alpha-amylase enzyme activity measured in pellets ("bound", light gray) and supernatant ("free", dark gray) of cultured recombinant yeast host cells expressing an heterologous alpha-amylase in the presence of a Sed1 tether and a linker (strain M14253), in the presence of a Sed1 tether but no linker (M14254) and in the absence of a Sed1 tether (strain M10074). Results are shown as percentage of alpha-amylase activity in function of strain used.
Figure 6:
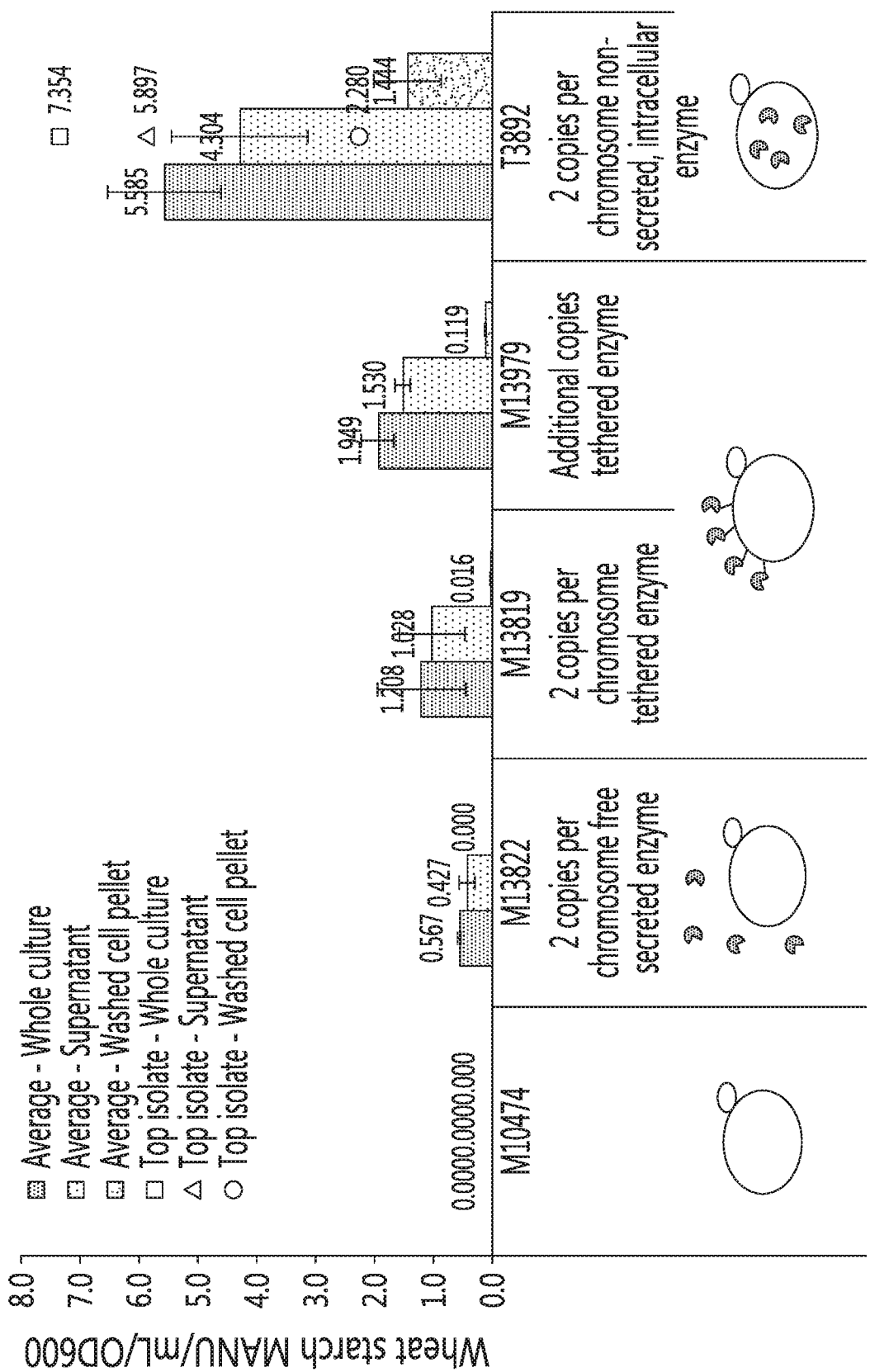
FIG. 6 provides wheat starch activity of various strains expressing a maltogenic amylase. Results are shown as wheat starch MANU per mL (measured at OD 600 nm) for the whole culture (left bars), supernatant (middle bars) and washed pellet (right bars) of the M10474, M13822, M13819, M13879 and T3892 strains (strains are described in Table 1). Data for "M" strains are the average of duplicate cultures. Data for T3892 include the average activity across cultures of eight transformations isolates and the activity of the top performing isolate (□=top isolate, whole culture; Δ=top isolate, supernatant; o=top isolate, washed cell pellet). Graphics below indicate the predicted enzyme localization phenotype of each engineering strategy.

Alpha-amylase assay (FIG. 5). Alpha-amylase activity was measured by adding 25 µL washed cells or cell free supernatant to 25 µL 5 mM p-Nitrophenyl α-D-hexaoside in 50 mM sodium acetate pH 5. The reaction was incubated at 35° C. for 2 hours and terminated by the addition of 50 µL 1M sodium bicarbonate. Cells were pelleted, 50 µL of the assay mixture was transferred to a microtiter plate and absorbance at 405 nm was measured. Activity of the cell fraction was represented as a percentage of the total activity ("bound"+ "free").

Alpha-amylase assay (FIGS. 13 to 16). The strains were initially grown in 600 UL of YPD40 at 35° C. for 48 h in 96-well plates on a shaker at 900 rpm. Alpha-amylase activity was determined by adding 25 µL of washed cells or cell-free supernatant to 100 µL of 1% raw starch with 50 mM sodium acetate buffer (pH 5.2). The assay was treated for 30 min at 85° C. using an Eppendorf Gradient Cycler. The reducing sugars were measured using the Dinitrosalicylic Acid Reagent Solution (DNS) method, using a 2:1 DNS:starch assay ratio and boiled at 100° C. for 5 min. The absorbance was measured at 540 nm.

Fungal amylase activity. Cells were grown in batch in yeast extract peptone media plus 2% glucose at 30° C. for 24 hours. Whole culture, supernatant, and either disrupted cell supernatant or washed cells were resuspended in assay buffer (70 mM disodium hydrogen phosphate, 30 mM citric acid, pH 5.5) were mixed with 1% gelatinized wheat starch in assay buffer and incubated at 30° C. for 1 hour. 3,5-Dinitrosalicylic acid (DNS) was added to react with reducing ends and boiled at 99° C. for 5 minutes. Absorbance was measured with a spectrophotometer at 540 nm.

Wheat starch activity assay. Cells were grown in batch in yeast extract peptone media plus 4% glucose at 35° C. for 48 hours. Whole culture, supernatant and washed cells resuspended in assay buffer (50 mM sodium acetate, pH 5) were mixed with 1% wheat starch in assay buffer and incubated at 60° C. for 5 minutes. Then, 3,5-dinitrosalicylic acid was added to react with reducing ends and boiled at 99° C. for 5 minutes. Absorbance was measured with a spectrophotometer at 540 nm.

Phytase activity assay. A 2-fold serial dilution of 1 M potassium phosphate monobasic was prepared as a standard for calculating FTUs. 190 µl of 5 mM sodium phytate solution pH 5.5 was added to each well of a 96 well PCR plate. Standards or supernatants of overnight cultures of yeast in yeast extract peptone media with 4% glucose were combined with 5 mM sodium phytate solution pH 5.5 and were incubated at 37° C. for 30 min. Cell associated samples were measured again following 2 hours of incubation. Equal volumes of reaction and color change solution (4 parts reagent A to 1 part reagent B, where reagent A is 12 mM ammonium heptamolybdate-HCl in water and reagent B is 2.7% ferrous sulfate in water) were combined and incubated for 10 minutes at room temperature before pelleting at 3500 rpm for 3 minutes. Absorbance of each sample or standard was read at 700 nm in a spectrophotometer Bake test with Novamyl® as a control. Bread was made with the M1074 strain in the presence and absence of externally added doses of the Novamyl® maltogenic amylase product (as indicated in the figures) and was compared to bread made with strains expressing a cell-associated MAA (in the absence of Novamyl®). For bread made with cream yeast expressing MAA, doses of cream yeast were normalized to 1 000 MANU based on the enzyme activity shown in FIG. 1B and supplemented with wild-type C strain cream yeast for sufficient gassing power. Briefly, 1 000 g of white flour, 600 g of water, 35 g of cream yeasts (dosed at 30% solids), 70 g of dextrose, 30 g of canola oil, 20 g of salt, 0.06 g of ascorbic acid, 0.625 g of Novamyl® (when present) and 3.75 g of sodium stearoyl lactylate were combined ingredients in a bowl mixer, mixed for 1 minute at low speed, and mixed for 10 minutes at high speed. Three 400 g dough pieces were formed and proofed for 7 minutes. The dough was then rolled to form loaves, placed in bread pans and proofed at 44° C. until they reached a height of 100 mm. The bread loaves were baked at 225° C. for 17 minutes. Crumb hardness (an indicator of staling), resilience and bread volume were measured after baking.

Texture analysis. Analyzing crumb texture was done 5, 8 and 13 days after bread baking. The loafs were cut with an electric knife, using a 2.5 cm gauge. Two slices in the middle of the loaf were analyzed. The evaluation of the crumb hardness and resilience was done with the TA-XT Plus Texture™ Analyzer. The TA-3 probe was used to compress the crumb to a distance of 10 mm (40% compression). Five measurements per slice were made on two slices for a total of 10 measurements. A macro was used for the calculations of the % resilience.

Bake test with Gluzyme® as a control. White pan bread was made without or with addition of commercial (Gluzyme Mono® 10000 BG, dosed at 100 or 200 GOU/kg flour) or yeast cell-associated glucose oxidase (dosed at 127 GOU/kg flour). 1 000 g of white flour, 600 g of water, 40 g of block yeast (~ 30% solids), 70 g of dextrose, 30 g of vegetable oil, 20 g of salt, and 0.06 g of ascorbic acid were combined in a bowl mixer, mixed for 1 minute at low speed, and mixed for 9 minutes at high speed. Three 400 g dough pieces were formed and placed in bread pans and proofed at 44° C. until they reached a height of 100 mm. The bread loaves were baked at 225° C. for 17 minutes. Strain M16780 was grown in batch in yeast extract peptone media plus 4% glucose at 32° C. for 24 hours. The cell pellet was obtained by centrifuging whole YPD culture and removing the supernatant. The pellet was assayed as described in the glucose oxidase method description, and a volume equivalent to 127 GOU/kg flour was dosed into dough. Three dough pieces each were proofed to 100 mm height and baked, followed by measurement of oven height. Oven spring (oven height minus proof height) was measured and crumb structure (higher score=finer crumb) was evaluated by visual inspection.

Example II—Expression of Cell-Associated Maltogenic Alpha-Amylases

Figure 1B:
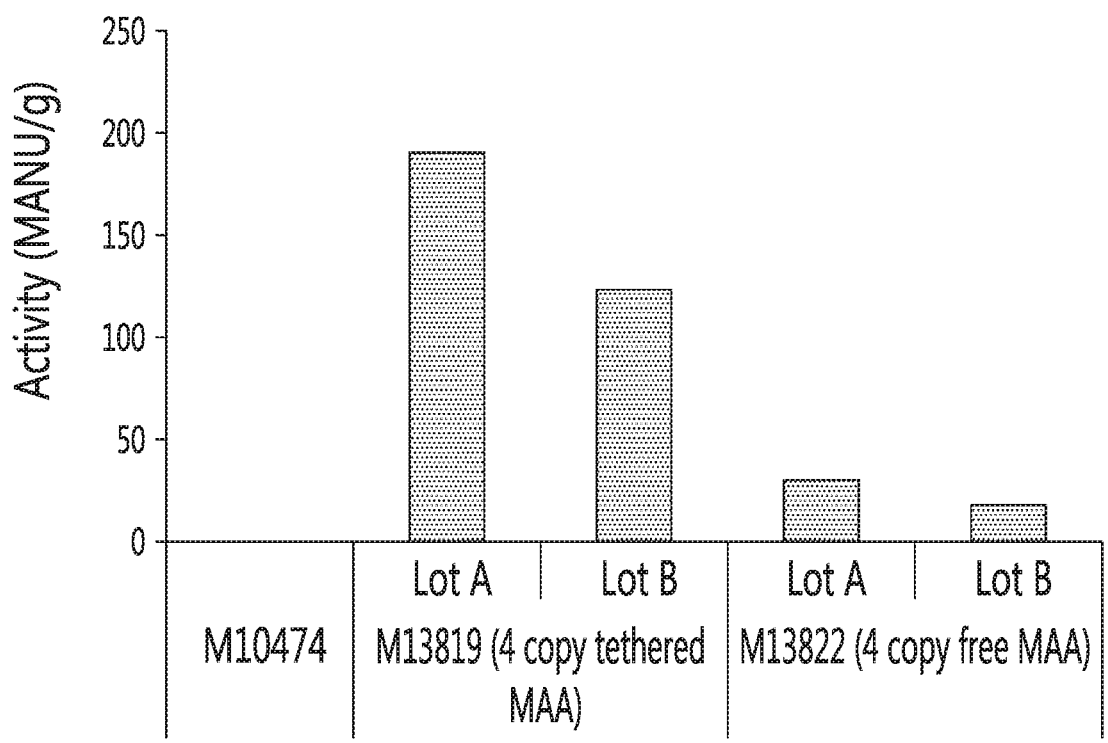

The expression of heterologous MAA, especially in the presence of a tether, provided the recombinant yeasts with maltogenic amylase activity both in the cell pellet (FIG. 1A) and, at a larger scale, in the cream yeasts (FIG. 1B). In comparison, the corresponding wild-type strain failed to exhibit any maltogenic amylase activities (FIGS. 1A and 1B). Results shown in FIGS. 1A and 1B were obtained by expressing the heterologous MAA from the promoters of the tdh1 and hor7 genes. Similar results were obtained with a combination of only one promoter (from the hor7 gene; data not shown).

Figure 2A:
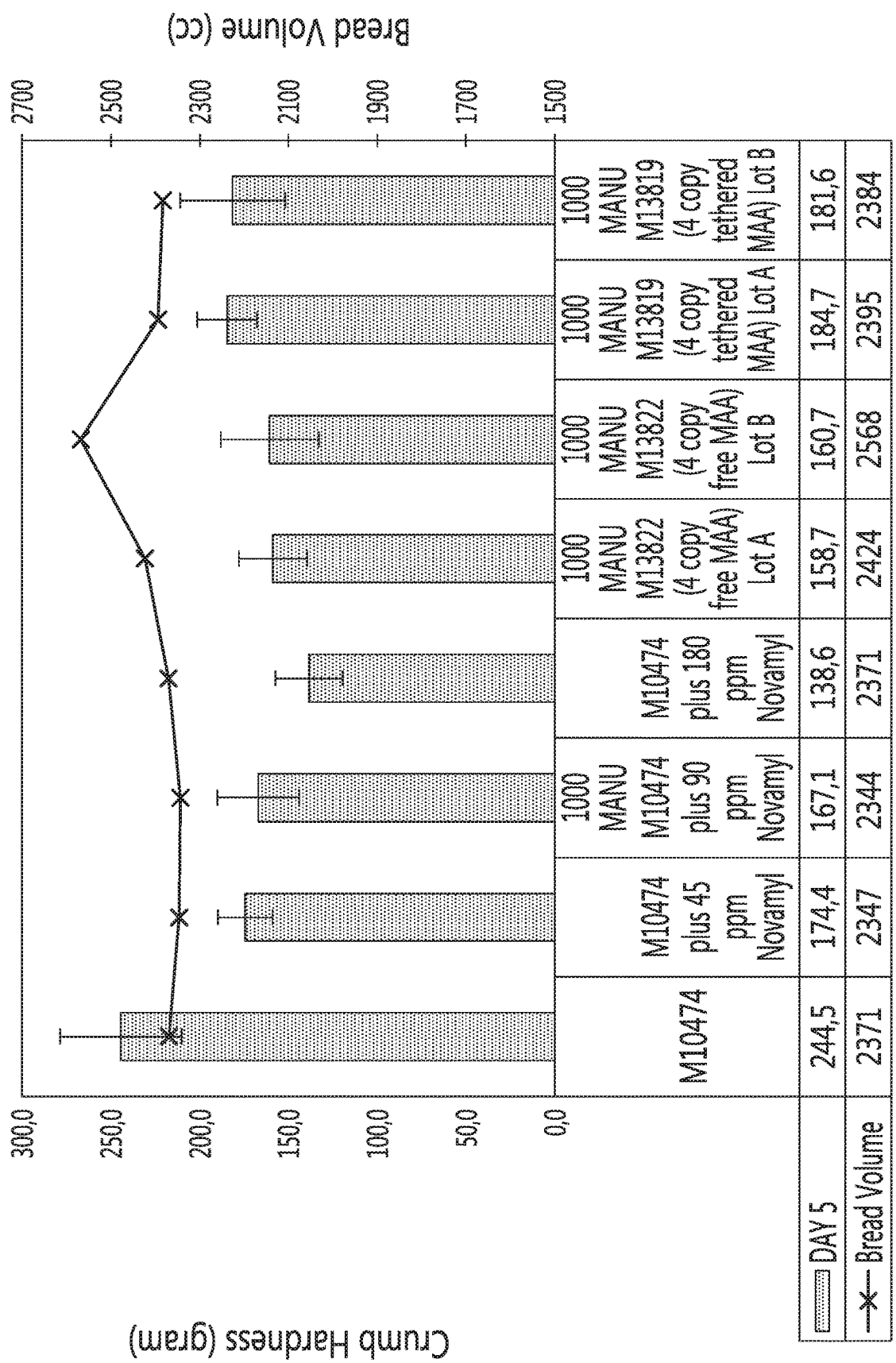
FIGS. 2A to 2C provide crumb hardness (as measured in grams, left axis, shown in the bars) and bread volume (as measured in centimeter cubes, right axis, as shown in the —X— labelled line) in function of bread made with (from left to right) the wild-type strain (M10474) with no enzyme supplementation, wild-type strain supplemented with 45 ppm Novamyl®, wild-type strain supplemented with 90 ppm Novamyl®, wild-type strain supplemented with 180 ppm Novamyl®, M13822 strain (lot A), M13822 strain (lot B), M13819 (lot A) and M13819 (lot B) (strains are described in Table 1). Results are shown 5 (FIG. 2A), 8 (FIG. 2B) and 11 (FIG. 2C) days after baking.
Figure 2B:
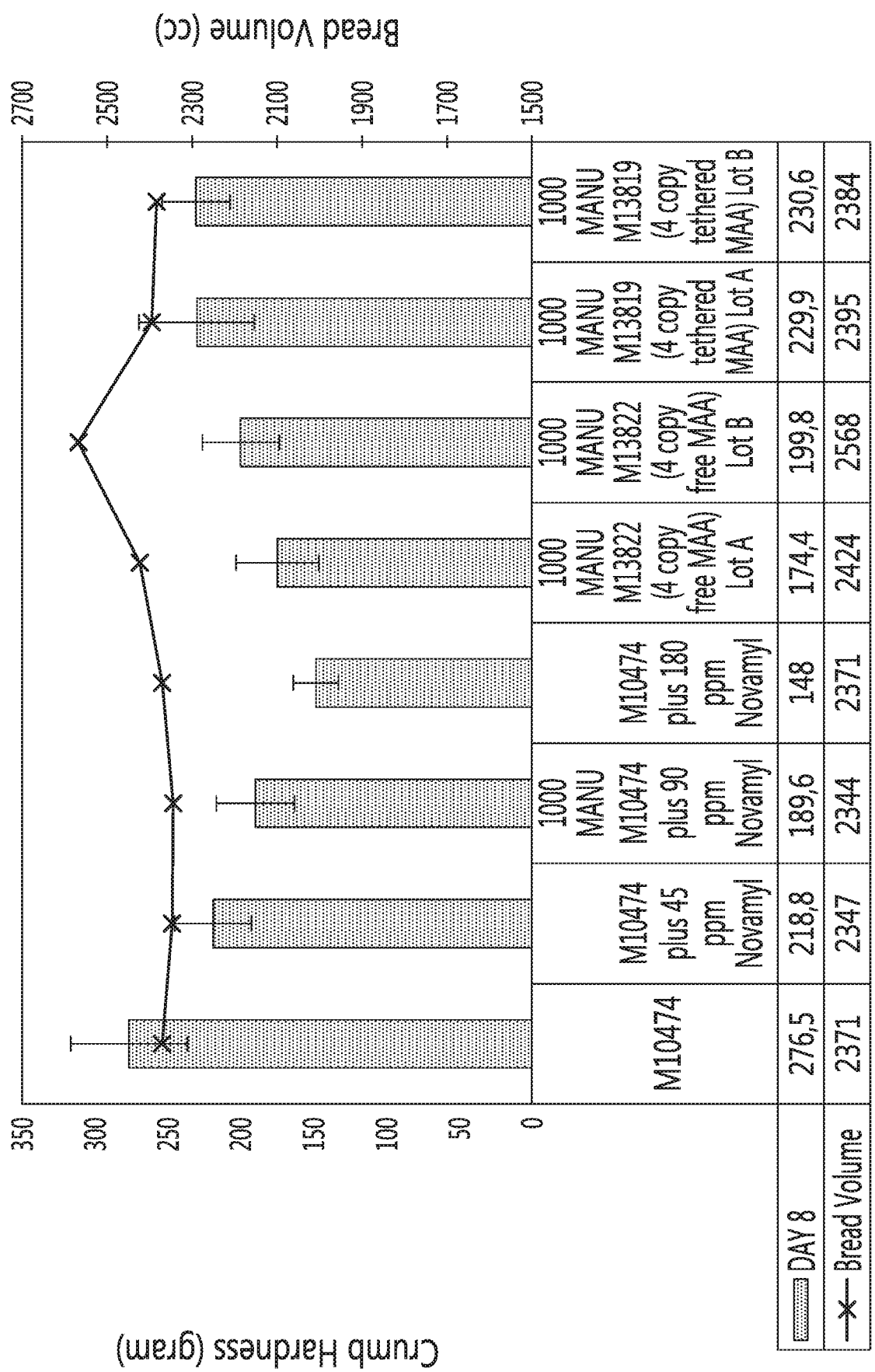
Figure 2C:
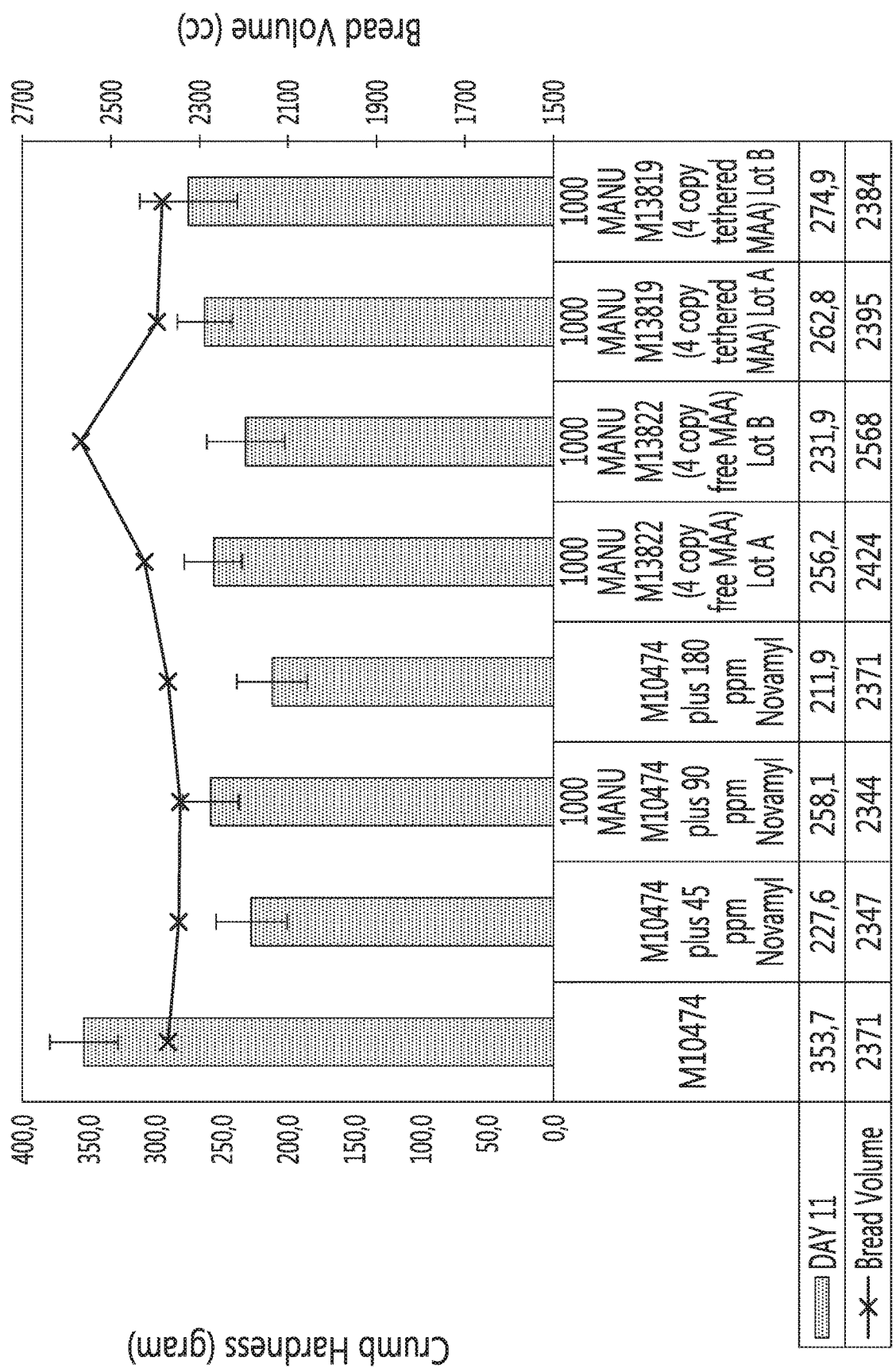

In order to determine the effect(s) of using yeasts expressing heterologous MAA in bread making, different loaf of breads were made with wild-type yeasts (supplemented or not with Novamyl®) or with recombinant yeasts expressing the heterologous MAA. In bread making, quality is associated with softness so the ability to prevent crumb hardness is sought. As shown in FIGS. 2A to 2C, the use of recombinant yeasts expressing the heterologous MAA for making bread reduced crumb hardness, when compared to the bread made with wild-type strain only that is not supplemented with Novamyl®. The use of recombinant yeasts expressing the heterologous MAA provided bread loafs having a similar crumb hardness to those being made with the wild-type yeast supplemented with Novamyl®.

As also shown in FIGS. 2A to 2C, the use of yeasts expressing the heterologous MAA maintained or even increased bread volume, when compared to the wild-type yeasts supplemented or not with Novamyl®.

Figure 3A:
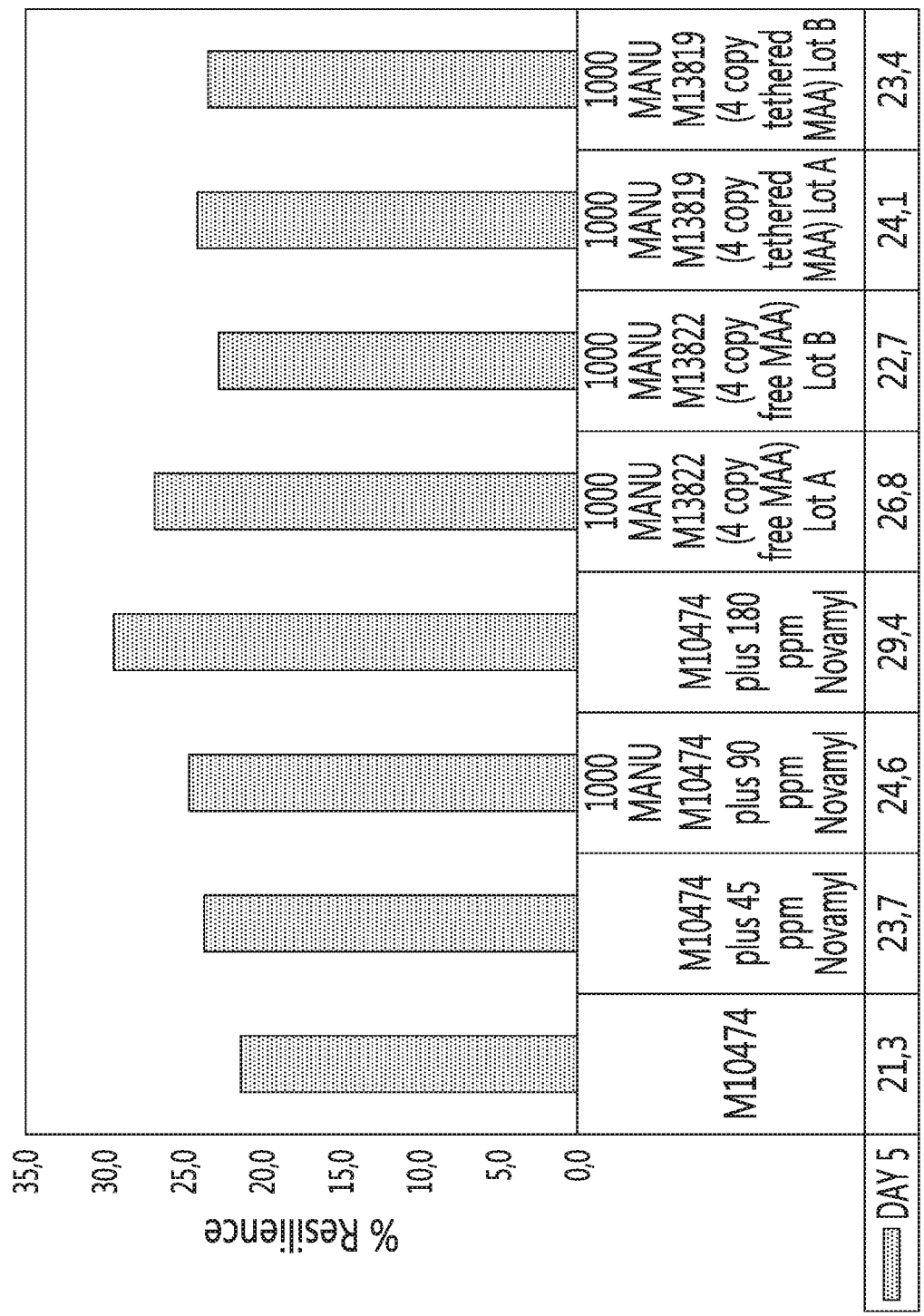
FIGS. 3A to 3C provide percent resilience in function of bread made with (from left to right) the wild-type strain (M10474) with no enzyme supplementation, wild-type strain supplemented with 45 ppm Novamyl®, wild-type strain supplemented with 90 ppm Novamyl®, wild-type strain supplemented with 180 ppm Novamyl®, M13822 strain (lot A), M13822 strain (lot B), M13819 (lot A) and M13819 (lot B). Results are shown 5 (FIG. 3A), 8 (FIG. 3B) and 11 (FIG. 3C) days after baking.
Figure 3B:
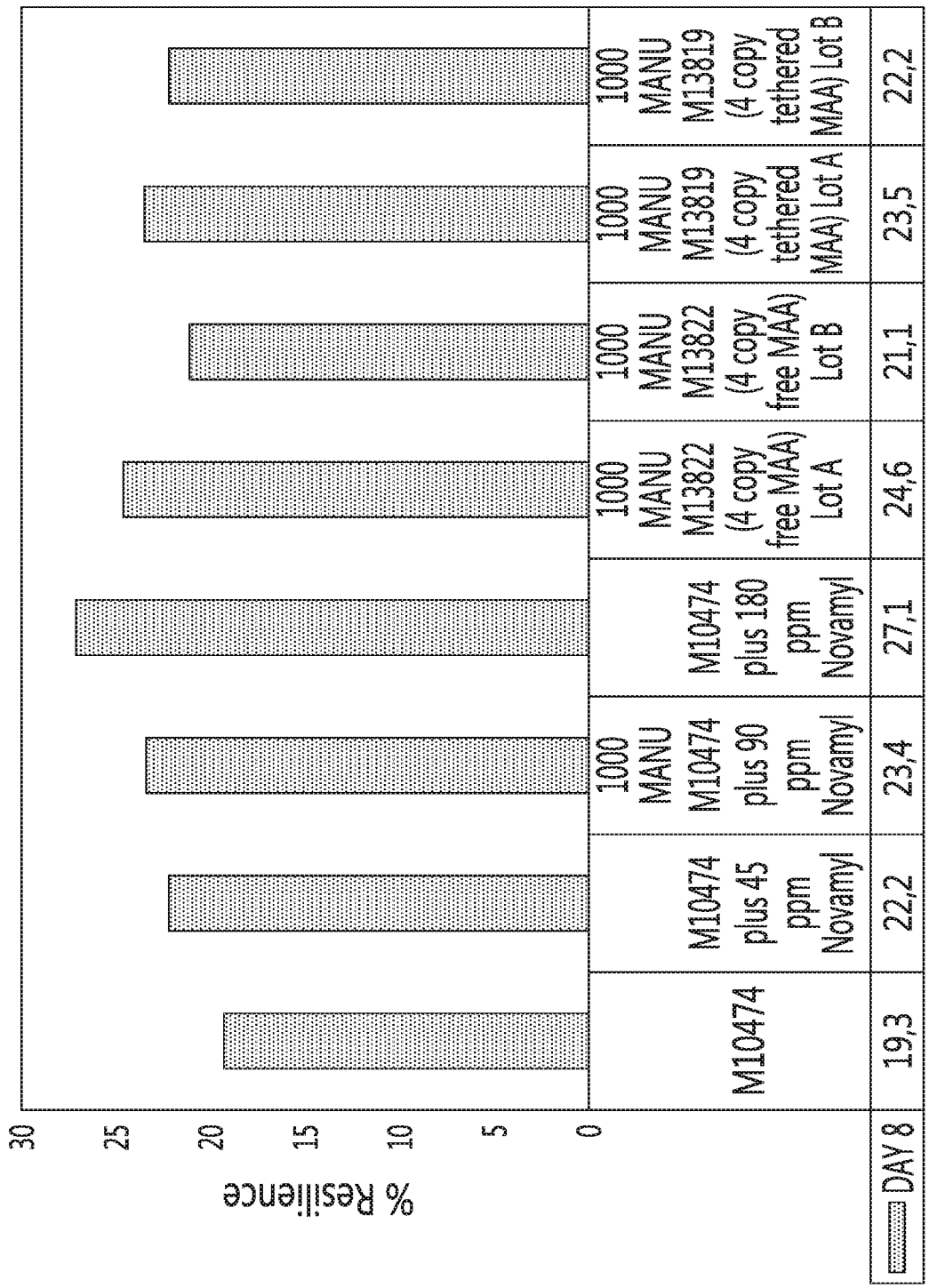
Figure 3C:
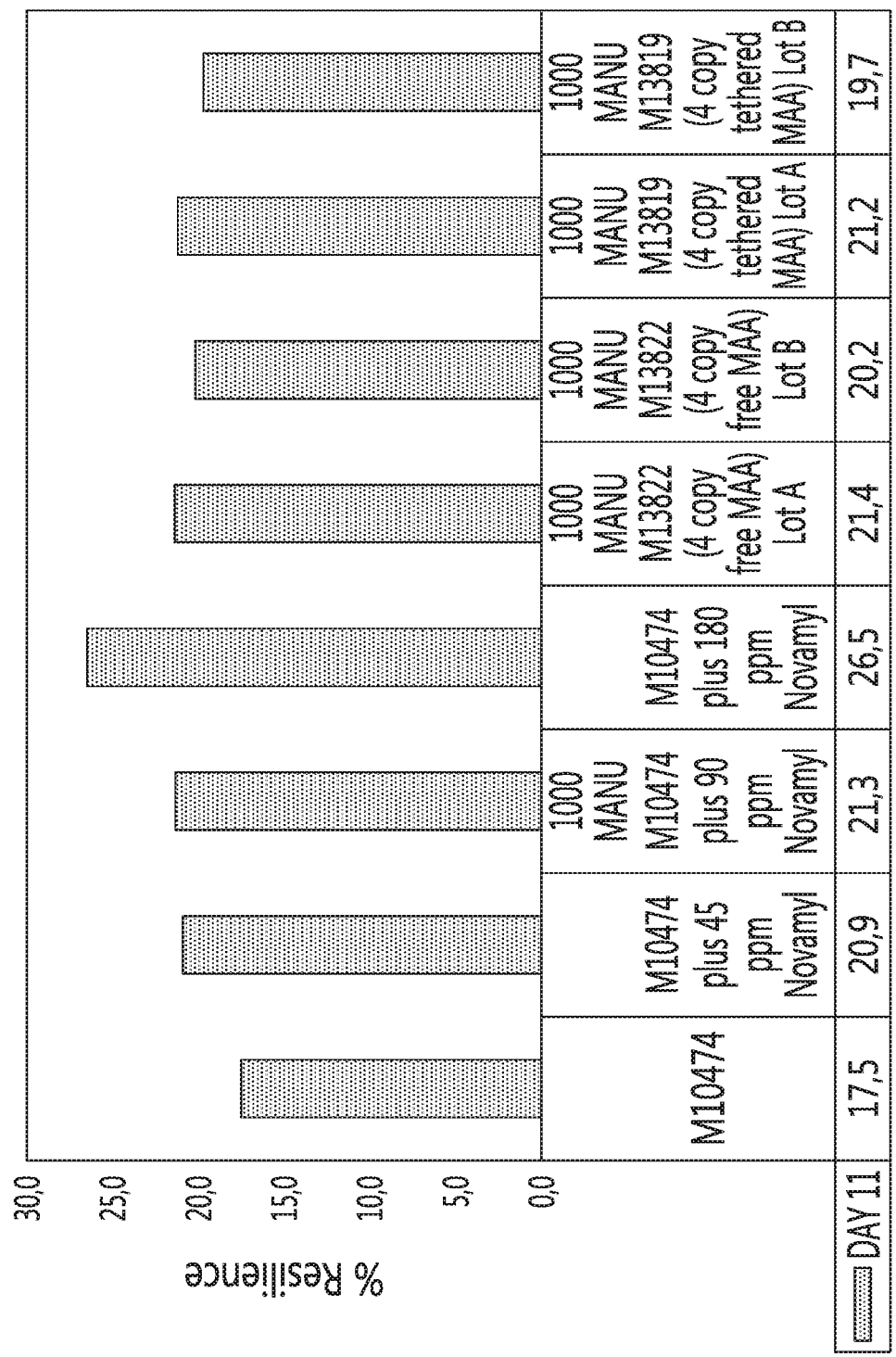

Bread quality can also be assessed by measuring percent resilience, whereas an increase in percent resilience is desirable. As shown in FIGS. 3A to 3C, the use of yeasts expressing the heterologous MAA even increased percent resilience, when compared to the wild-type yeasts which were not supplemented with Novamyl®.

A strain expressing and intracellular G. stearothermophilus MAA (M14851) was propagated (aerobic fed batch on molasses) and MANU activity was determined. As shown in Table 2, in the untreated total broth, between 25.6 and 39.3 MANU activity was detected. After washing and concentrating the cream, between 132 and 288 MANU activity was detected.

TABLE 2

Concentrating yeast biomass concentrates cell-associated maltogenic amylase. Enzyme activity was determined in Phadebas enzyme assays with comparison to a dose curve of Novamyl standards with known maltogenic amylase units (MANU).

| M14851 propagation | Phadebas MANU/ml | |
|---|---|---|
| | Total broth (~6% solids) | Washed and concentrated cream(19-20% solids) |
| I200617 | 25.6 | 112.2 |
| I210617 | 35.6 | 232.0 |
| I220617 | 39.3 | 287.6 |

Another strain expressing a tethered G. stearothermophilus MAA (M13879) was propagated (aerobic fed batch on molasses) and MANU activity was determined in various yeast preparations. The results are shown Table 3. Cream yeast activity data on 1 day after commercial propagation is the most representative measure of the cream in its original form. All other data were obtained on 8 days after the commercial propagation.

TABLE 3

Phadebas MANU activity per gram dry weight of various preparations of M13979. Enzyme activity was determined in Phadebas enzyme assays with comparison to a dose curve of the enzyme Novamyl ® standards with known maltogenic amylase units (MANU).

| | Phadebas MANU equivalent/gram dry weight | |
|---|---|---|
| M13979 sample | 1 day after propagation | 8 days after propagation |
| Cream | 1087 | 3157 |
| Bead-milled homogenate | | 8698 |
| Cream, spray dried | | 1121 |
| Inactivated cream, spray dried | | 2039 |
| Bead-milled homogenate, spray dried | | 6721 |

MANU and wheat starch activity were determined in different preparations of a yeast strain expressing intracellularly the maltogenic alpha amylase from G. stearothermophilus (M15532) and propagated (aerobic fed batch on molasses). The results are provided in Tables 4 to 8 showing the effects of the different preparations on the level of enzymatic activity observed.

TABLE 4

Phadebas and wheat starch enzyme assays to measure maltogenic amylase activity on various M15532 preparations. Enzyme activity was determined in Phadebas enzyme assays with comparison to a dose curve of the enzyme Novamyl ® standards with known maltogenic amylase units (MANU).

| M15532 propagation | Sample | Form | Phadebas MANU/g dry weight | Wheat starch MANU/g dry weight |
|---|---|---|---|---|
| High protein recipe I060917 | Untreated cream | Liquid | 287 | 574 |
| | Bake lab autolyzed cream (pH 7, 48 h, 55° C.) (liquid) | Liquid | 17826 | 15328 |
| Mix of 4 propagations (I280817, B300817, B310817, B300817) | Untreated cream | Liquid | 96 | |
| | Bake lab autolyzed cream (pH 7, 48 h, 55° C.) (liquid) | Liquid | 23614 | 12920 |
| | Bead-milled homogenate (liquid) | Liquid | 15916 | 12903 |
| | Bead-milled homogenate (spray dried) | Dry | 10607 | 7764 |

TABLE 5

Activity results in cream, lab-scale autolyzed cream (incubated 48 h at 55° C., pH 7) and rehydrated instant dry yeast (IDY) samples. Enzyme activity was determined in Phadebas enzyme assays with comparison to a dose curve of the enzyme Novamyl ® standards with known maltogenic amylase units (MANU).

| M15532 Sample | % solids | Phadebas MANU/ml of sample | Phadebas MANU/g DCW |
|---|---|---|---|
| Cream | 17.9 | 58 | 325 |
| Cream after 48 h, 55° C., pH 7 | 17.9 | 3572 | 19955 |
| 37° C. rehydrated IDY | 15.9 | 545 | 3438 |
| Cold shocked IDY | 15.4 | 454 | 2958 |

TABLE 6

Dry weight and enzyme activity balances in autolysate, yeast extract, ultrafiltration retentate and yeast cell wall preparations before and after drying of different preparations of the yeast strain M15532. Enzyme activity was determined in Phadebas enzyme assays with comparison to a dose curve of the enzyme Novamyl ® standards with known maltogenic amylase units (MANU).

| SAMPLE | BEFORE DRYING dw % | BEFORE DRYING MAA MANU/gdw | AFTER DRYING dw NRC10NOV % | AFTER DRYING NRC10NOV MANU/gdw | AFTER DRYING BAKE LAB MANU/gdw AV | AFTER DRYING BAKE LAB % RD | AFTER DRYING NRC24NOV MANU/gdw AV | AFTER DRYING NRC24NOV % CV | dwt BALANCE | MANU BALANCE PROCESS + DRYING BAKE LAB | MANU BALANCE PROCESS + DRYING NRC24NOV |
|---|---|---|---|---|---|---|---|---|---|---|---|
| AUTOLYSATE | 18.0 | 8983 | 91.3 | 13568 | 14812 | 6% | 16864 | 17% | 100 | 100 | 100 |
| YE | 11.6 | 14422 | 93.7 | 23067 | 27566 | 5% | 24028 | 14% | 47 | 87 | 66 |
| 10 kDa RETENTATE | 15.1 | 83332 | 93.7 | 25984 | 80817 | 5% | 75552 | 15% | 18 | 98 | 80 |
| CW | 37.0 | 883 | 94.1 | 700 | 3757 | 4% | 3421 | 4% | 53 | 14 | 13 |

TABLE 7

Results of separation of yeast extract from total autolysate and enzyme recovery with and without washing of yeast strain M15532. YE (yeast extract) separation yield is the recovery of solids from separation only (WF = 0) and of separation plus one or two washes (WF = 1 or 2, respectively), relative to the starting solids in the autolysate. YE MANU recovery is the activity (in Phadebas MANU) from separation only (WF = 0) and of separation plus one or two washes (WF = 1 or 2), relative to starting total Phadebas MANU in the autolysate. Enzyme activity was determined in Phadebas enzyme assays with comparison to a dose curve of the enzyme Novamyl ® standards with known maltogenic amylase units (MANU).

| WASH FACTOR (WF) | YE SEPARATION YIELD (%) | YE MANU RECOVERY (%) | % DW in YE |
|---|---|---|---|
| 0 | 36 | 58 | 12.3 |
| 1 | 50 | 71 | 8.3 |
| 2 | 54 | 75 | 6.0 |

TABLE 8

Results of ultrafiltration of yeast extract of M15532 with a 10 kDa molecular weight cutoff. YE is yeast extract, obtained by centrifuging fermenter autolysate in 1 liter bottles for 10 minutes at 11,000 RCF, to mimic separation at industrial scale. Retentate is the sample retained by ultrafiltration and permeate is the sample not retained. Phadebas MANU/ml was determined for each samples and MANU/g DW (dry weight) was calculated based on the dry weight per sample. Enzyme activity was determined in Phadebas enzyme assays with comparison to a dose curve of the enzyme Novamyl ® standards with known maltogenic amylase units (MANU).

| Sample | Concentration factor | % DW in sample | MANU/mL | MANU/g DW | MANU balance (%) | DW balance (%) |
|---|---|---|---|---|---|---|
| YE | 1.0 | 11.6 | 1672 | 14422 | 100 | 100 |
| 10 kDa RETENTATE | 3.5 | 15.5 | 12583 | 83332 | 222 | 38 |

TABLE 8-continued

Results of ultrafiltration of yeast extract of M15532 with a 10 kDa molecular weight cutoff. YE is yeast extract, obtained by centrifuging fermenter autolysate in 1 liter bottles for 10 minutes at 11,000 RCF, to mimic separation at industrial scale. Retentate is the sample retained by ultrafiltration and permeate is the sample not retained. Phadebas MANU/ml was determined for each samples and MANU/g DW (dry weight) was calculated based on the dry weight per sample. Enzyme activity was determined in Phadebas enzyme assays with comparison to a dose curve of the enzyme Novamyl ® standards with known maltogenic amylase units (MANU).

| Sample | Concentration factor | % DW in sample | MANU/mL | MANU/g DW | MANU balance (%) | DW balance (%) |
|---|---|---|---|---|---|---|
| 10 kDa PERMEATE | | 10.9 | 22 | 203 | 1 | 67 |

Figure 11A:
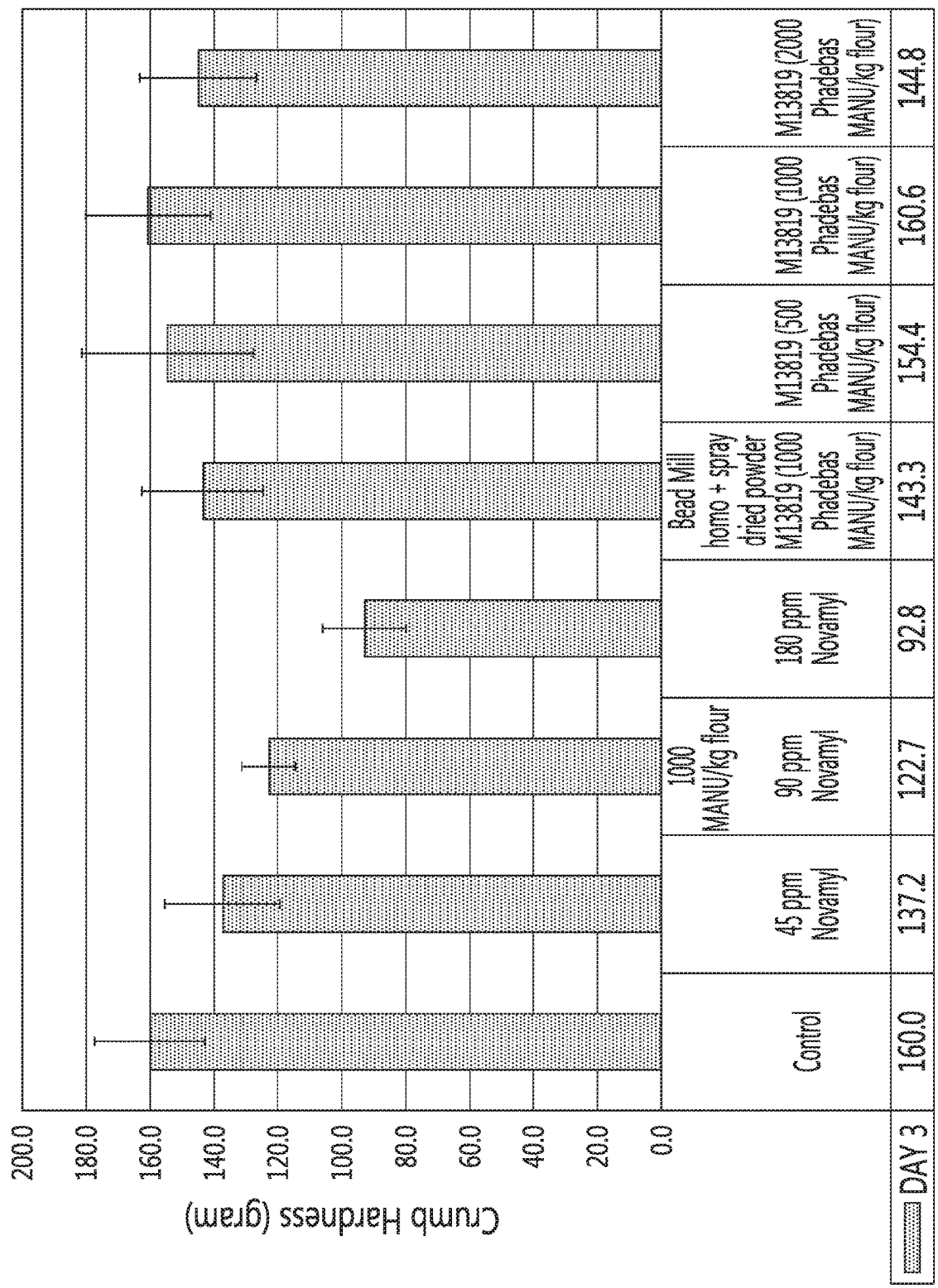
FIG. 11A to 11C provide the crumb hardness (as measured in grams, left axis, results shown in the bars) of breads made with different dough conditioners at days 3 (FIG. 11A), 7 (FIG. 11B) and 11 (FIG. 11C) after baking. Controls were made with (labelled "Novamyl") or without (labelled "Control") externally added the Novamyl® maltogenic amylase product as indicated below the histogram. The control breads were compared to breads made with M13979 spray-dried homogenate (identified as "homo+spray" in the figures) or cream dosed to a specific Phadebas enzyme activity as indicated below the histogram. All breads used wild-type yeast for gassing power.
Figure 11B:
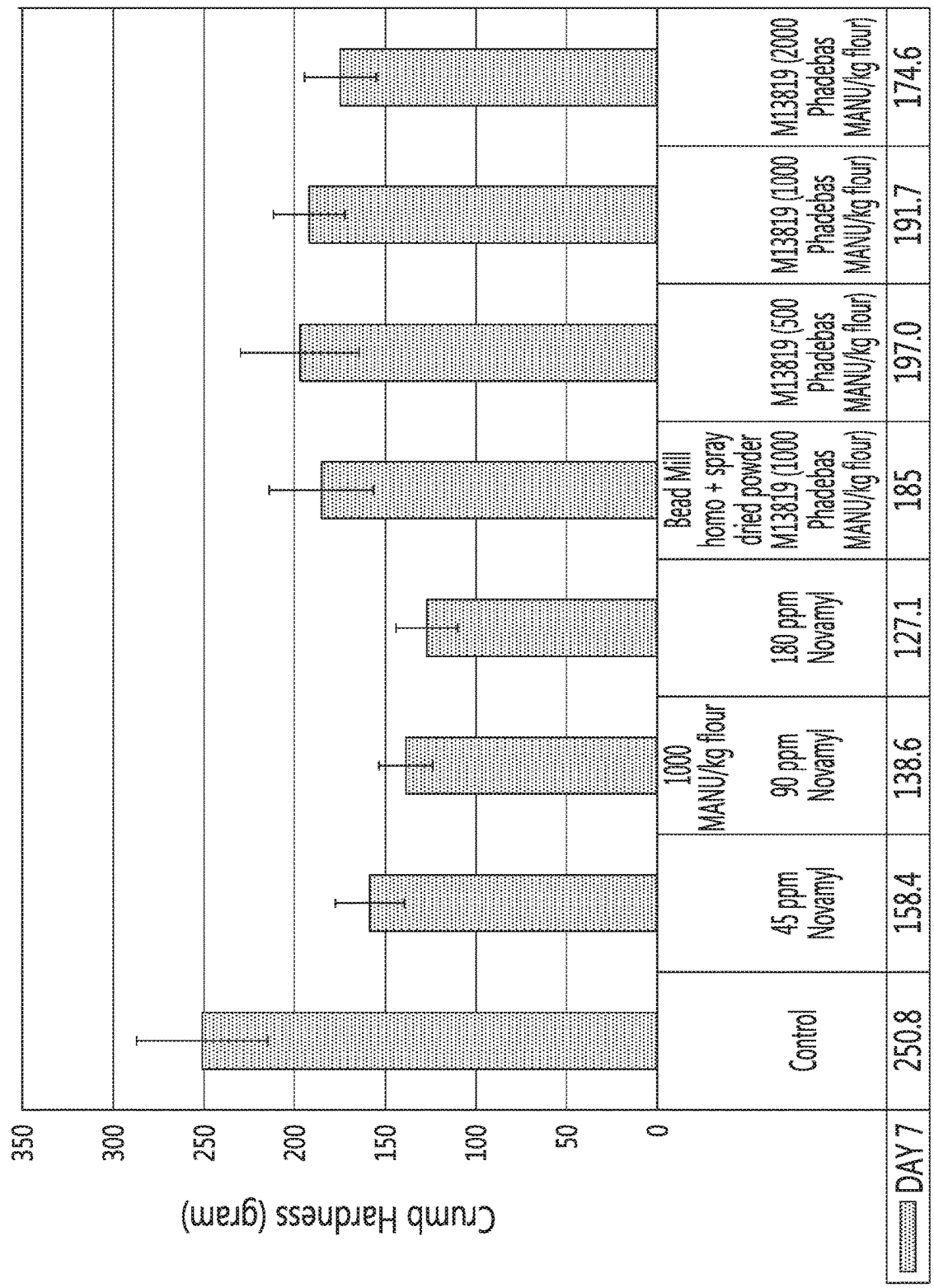
Figure 11C:
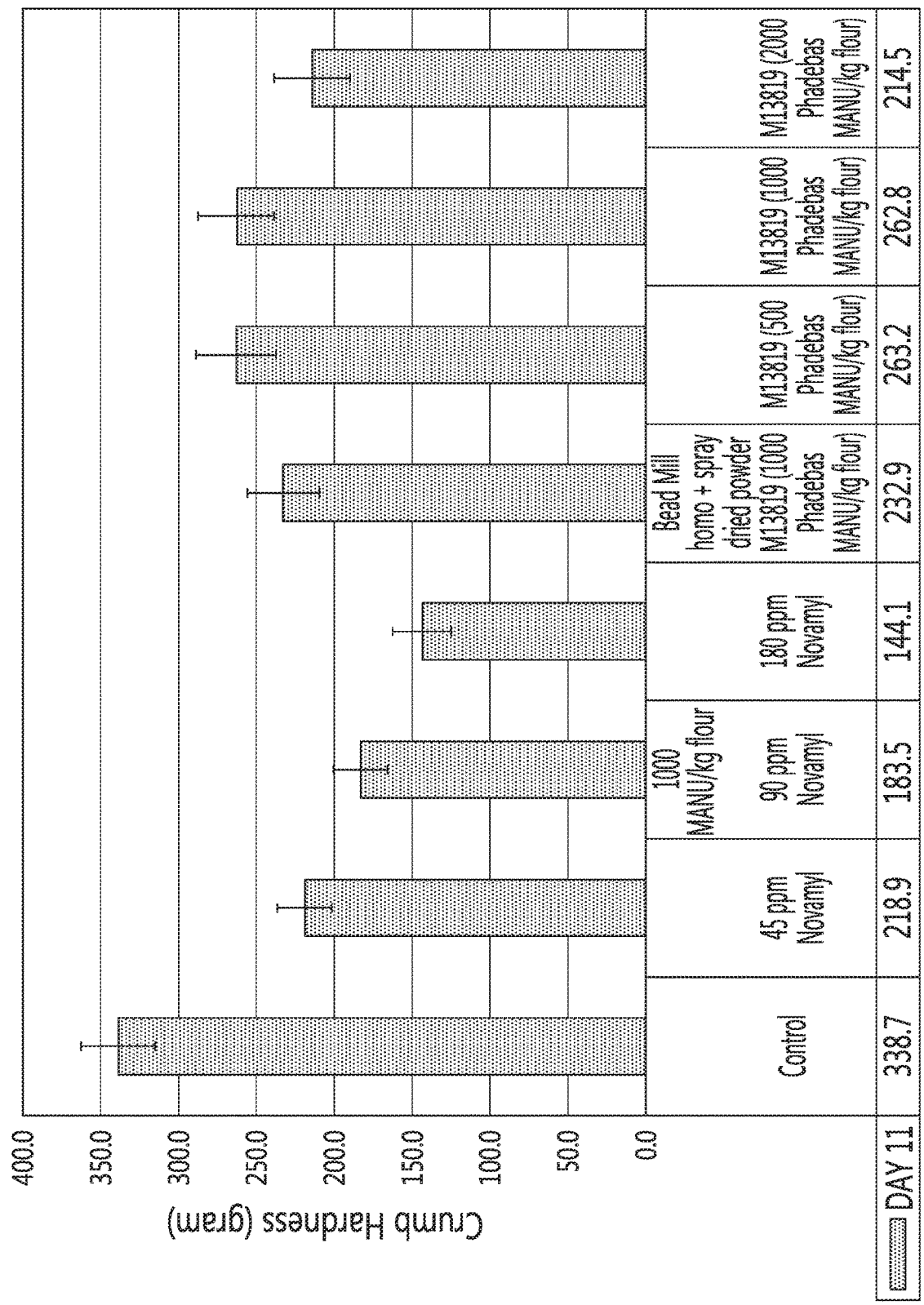
Figure 12A:
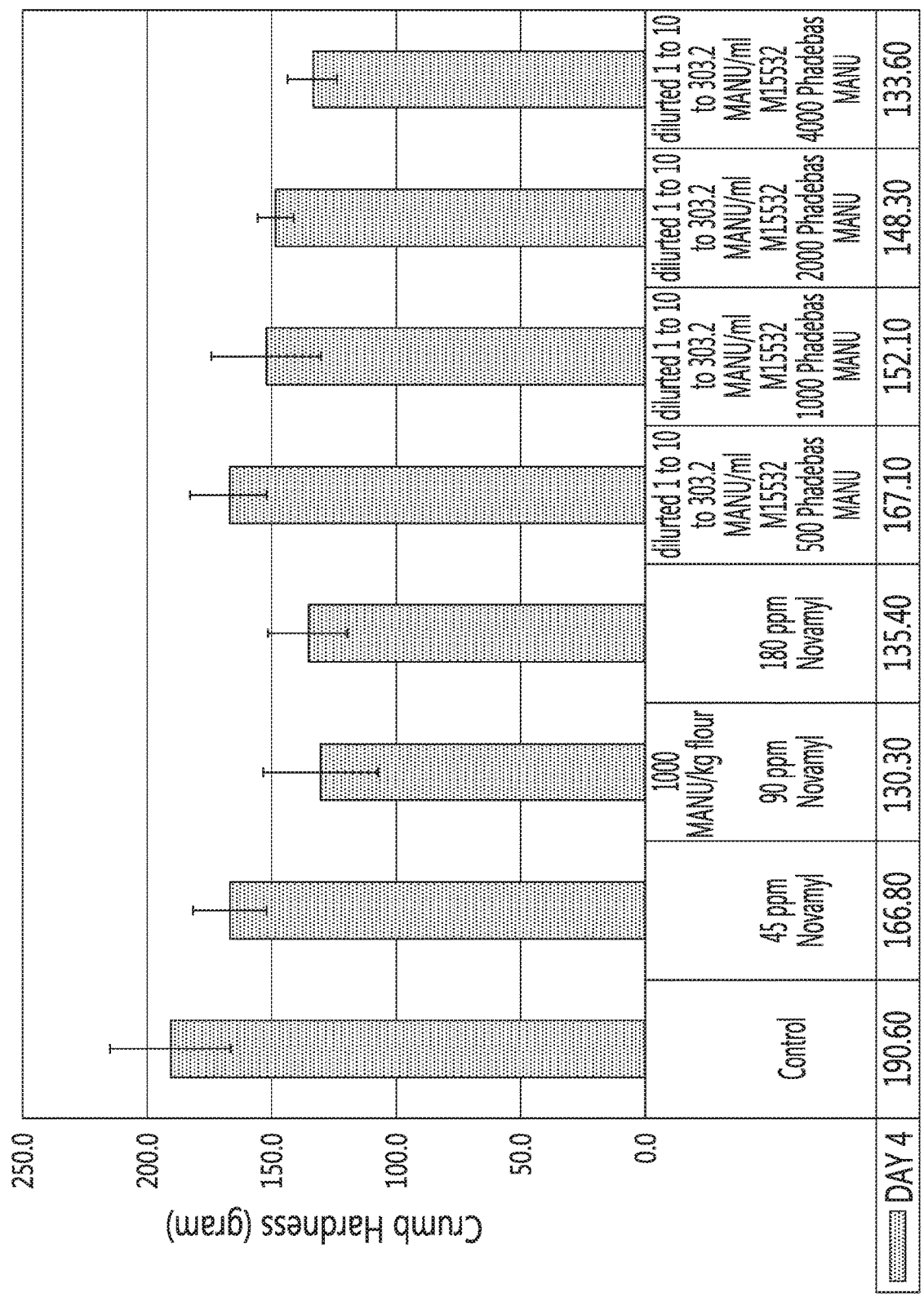
FIGS. 12A to 12F provide the crumb hardness (FIG. 12A-C, as measured in grams) and resilience (FIG. 12D-F, as measured in percentage) of breads made with different dough conditioners at days 4 (FIG. 12A and FIG. 12D), 7 (FIG. 12B and FIG. 12E) and 10 (FIG. 12C and FIG. 12F) after baking. Controls were made with (labelled "Novamyl") or without (labelled "Control") externally added the Novamyl® maltogenic amylase product as indicated below the histogram. The control breads were compared to breads made with M15532 yeast cream that was homogenized to release the intracellular and dosed to a specific Phadebas enzyme assay activity as indicated below the histogram. All breads used wild-type yeast for gassing power.
Figure 12B:
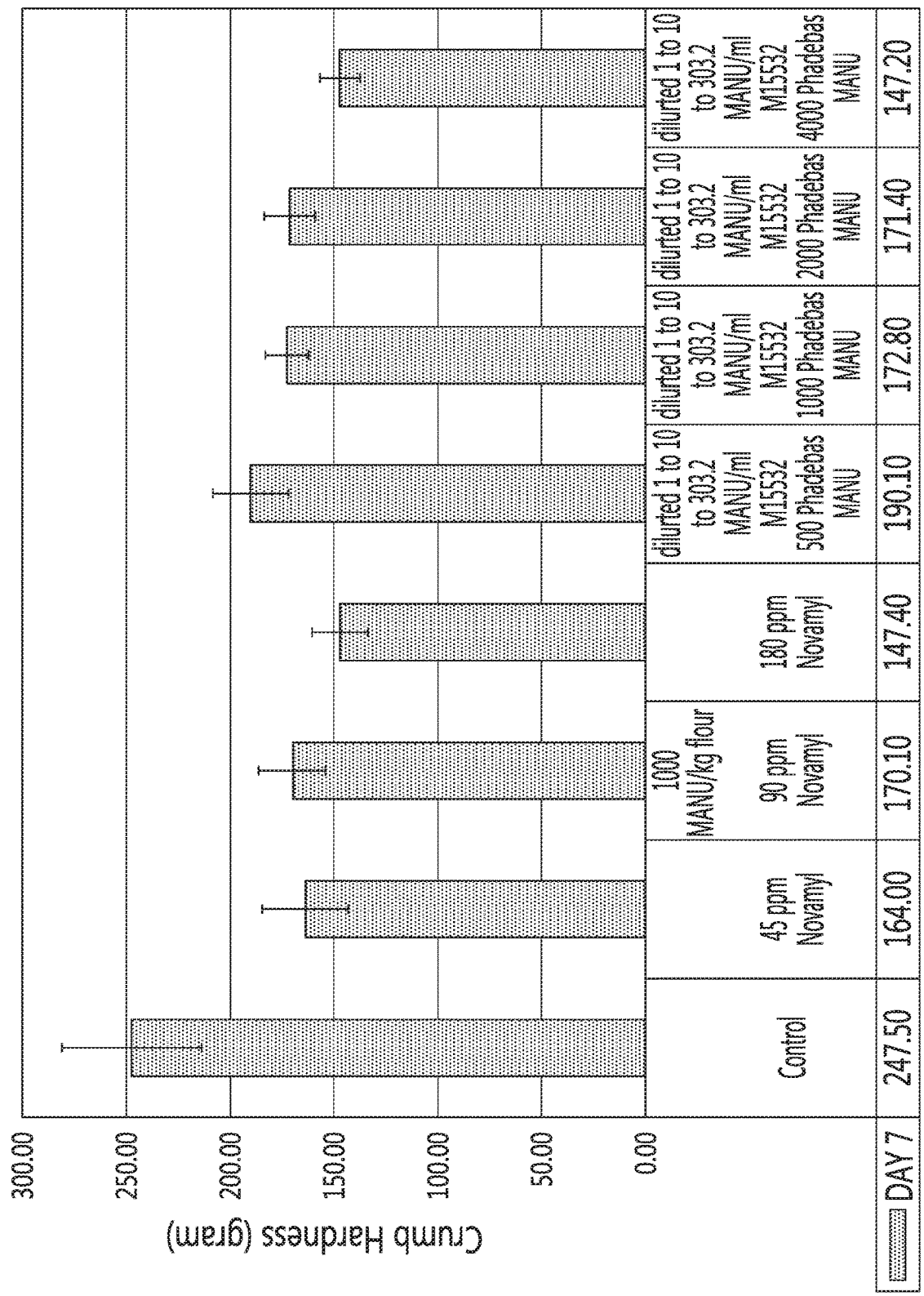
Figure 12C:
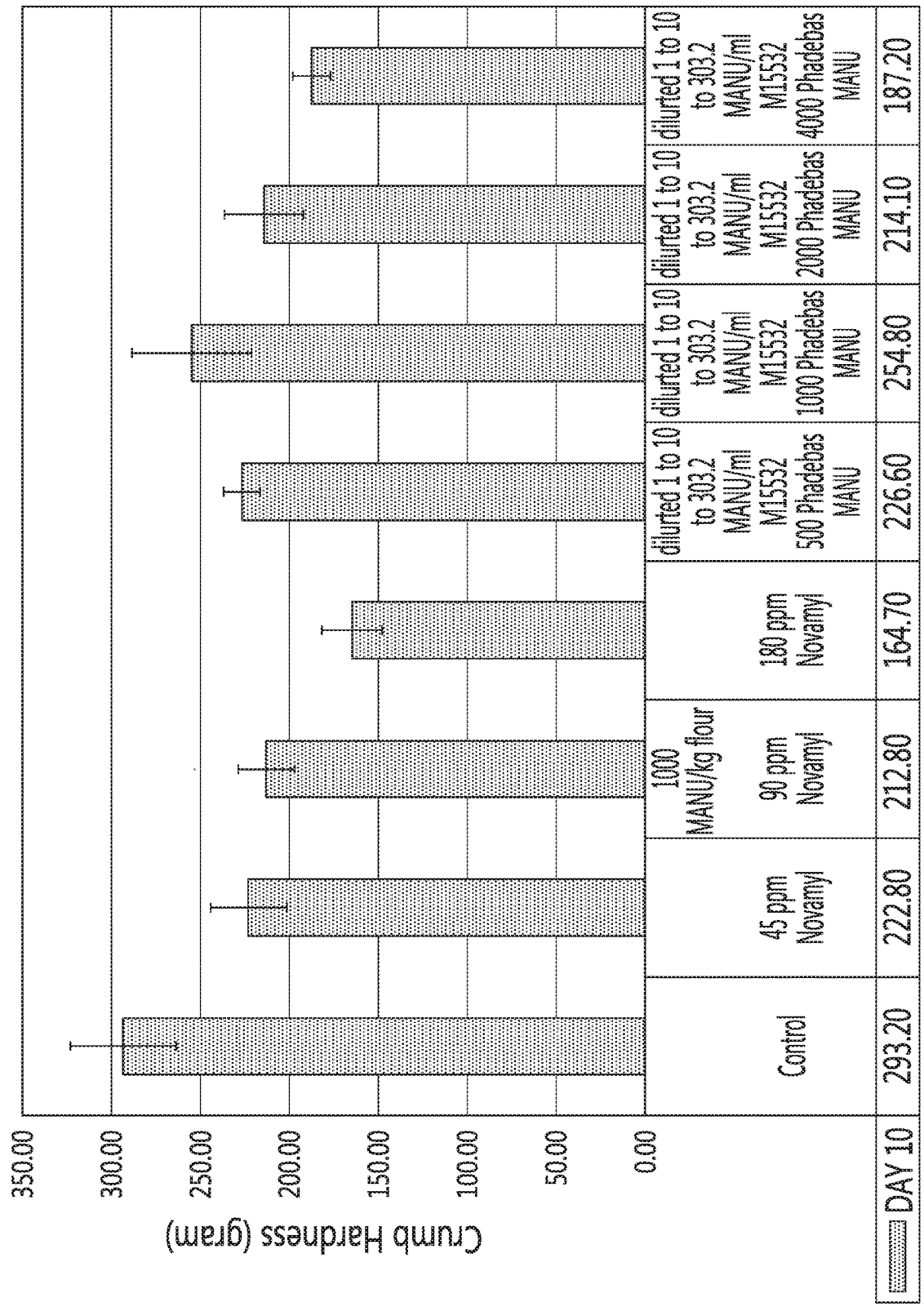
Figure 12D:
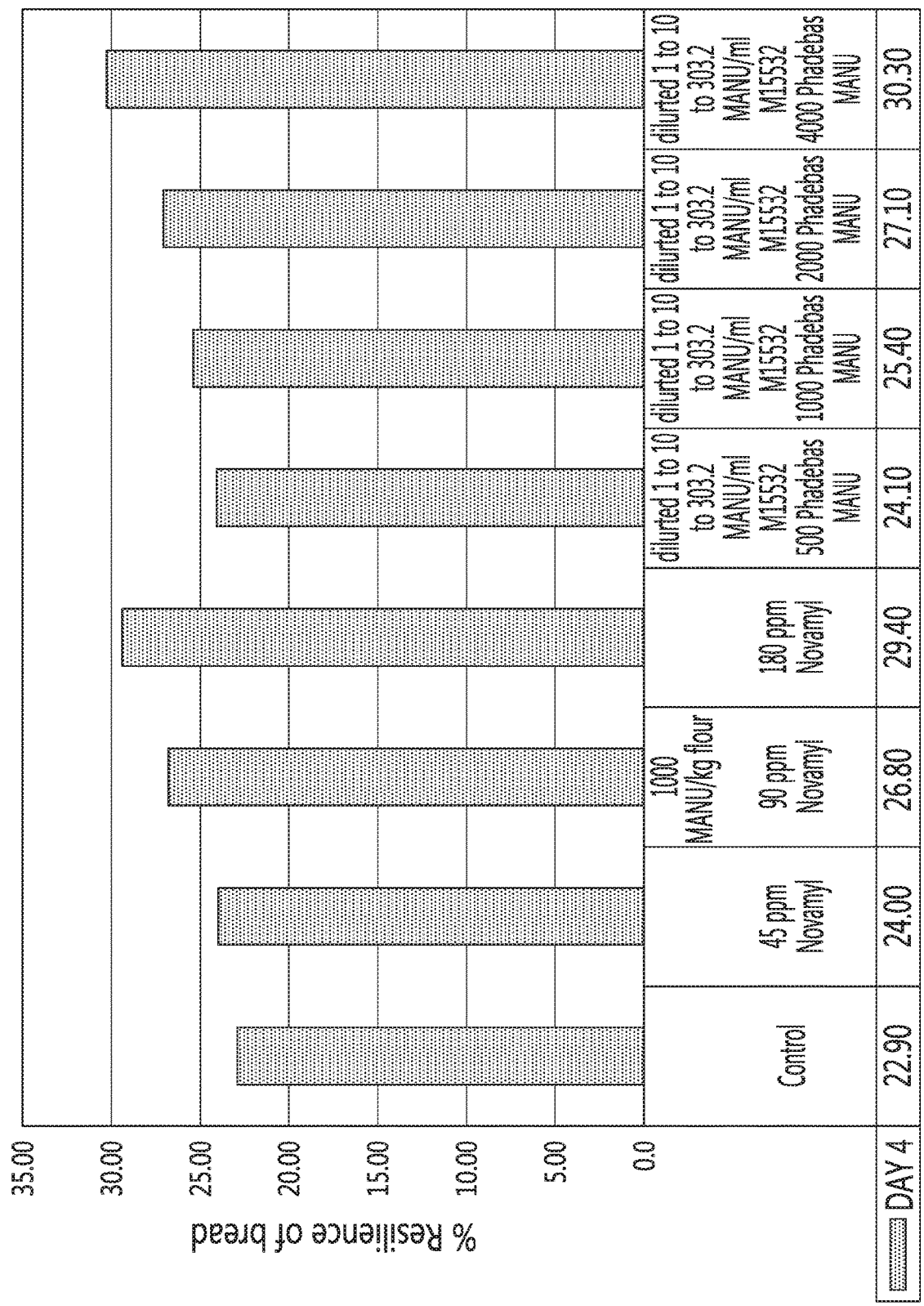
Figure 12E:
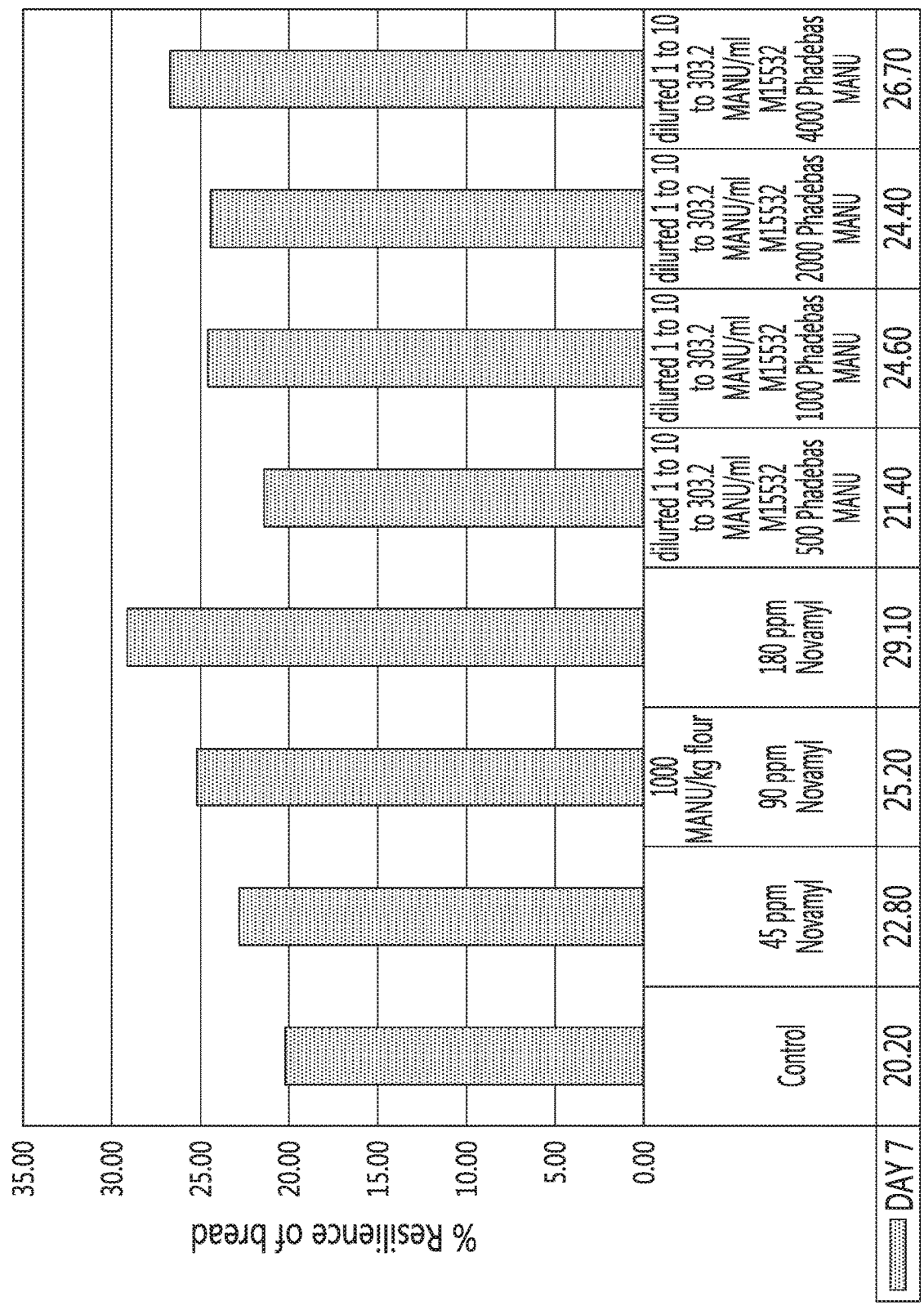
Figure 12F:
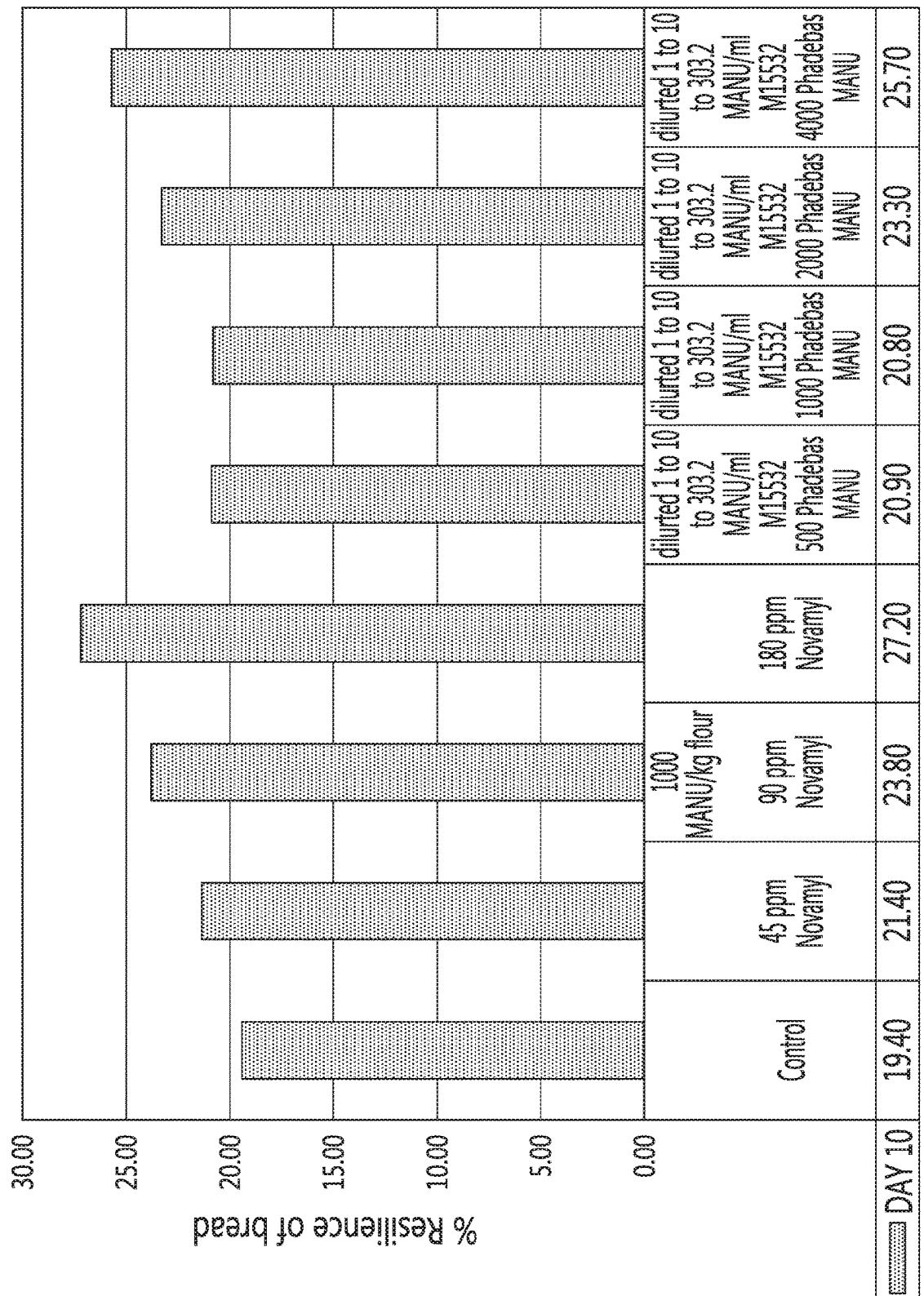

Different preparations (e.g., cream and spray-dried) yeast strains M13979 (expressing a tethered MAA) and M15531 (expressing an intracellular MAA) have been used to make bread loafs. The use of yeasts strains M13979 and M15531, when compared to control breads made in the absence of a dough conditioner, reduces the bread's crumb hardness (FIGS. 11 and 12A) while maintaining its volume (FIG. 11) and increasing its resilience (FIG. 12B).

Figure 8:
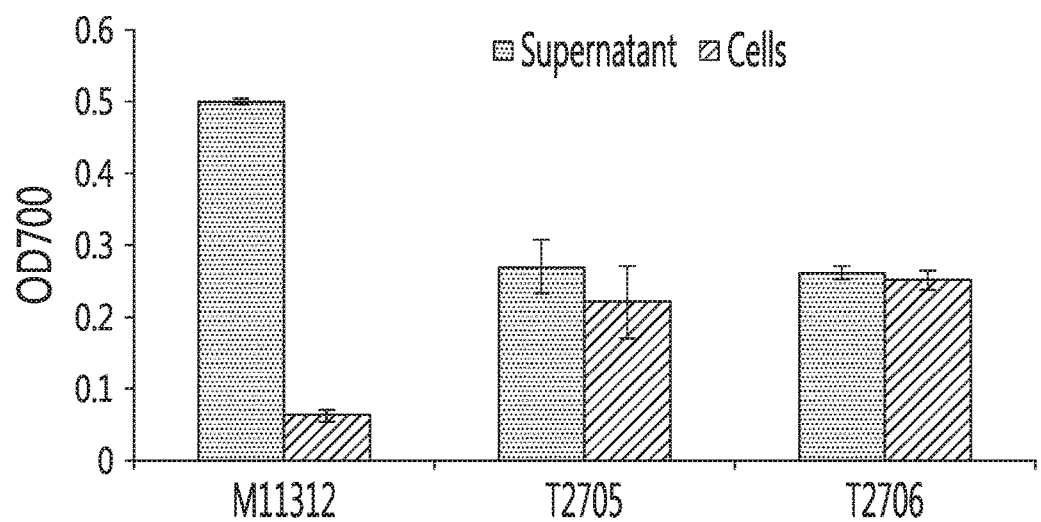
FIG. 8 provides the phytase activity in culture supernatant (grey bars) or associated with cells (diagonally hatched bars) for strains expressing *Escherichia coli* phytase fused with either an N- or C-terminal tether. Supernatant was incubated with 5 mM sodium phytate solution pH 5.5 for 30 minutes and cells were incubated in the same solution for 2 hours. Results are shown as the optical density at 700 nm in function of each strain (M11312, T2705 and T2706).
Figure 10:
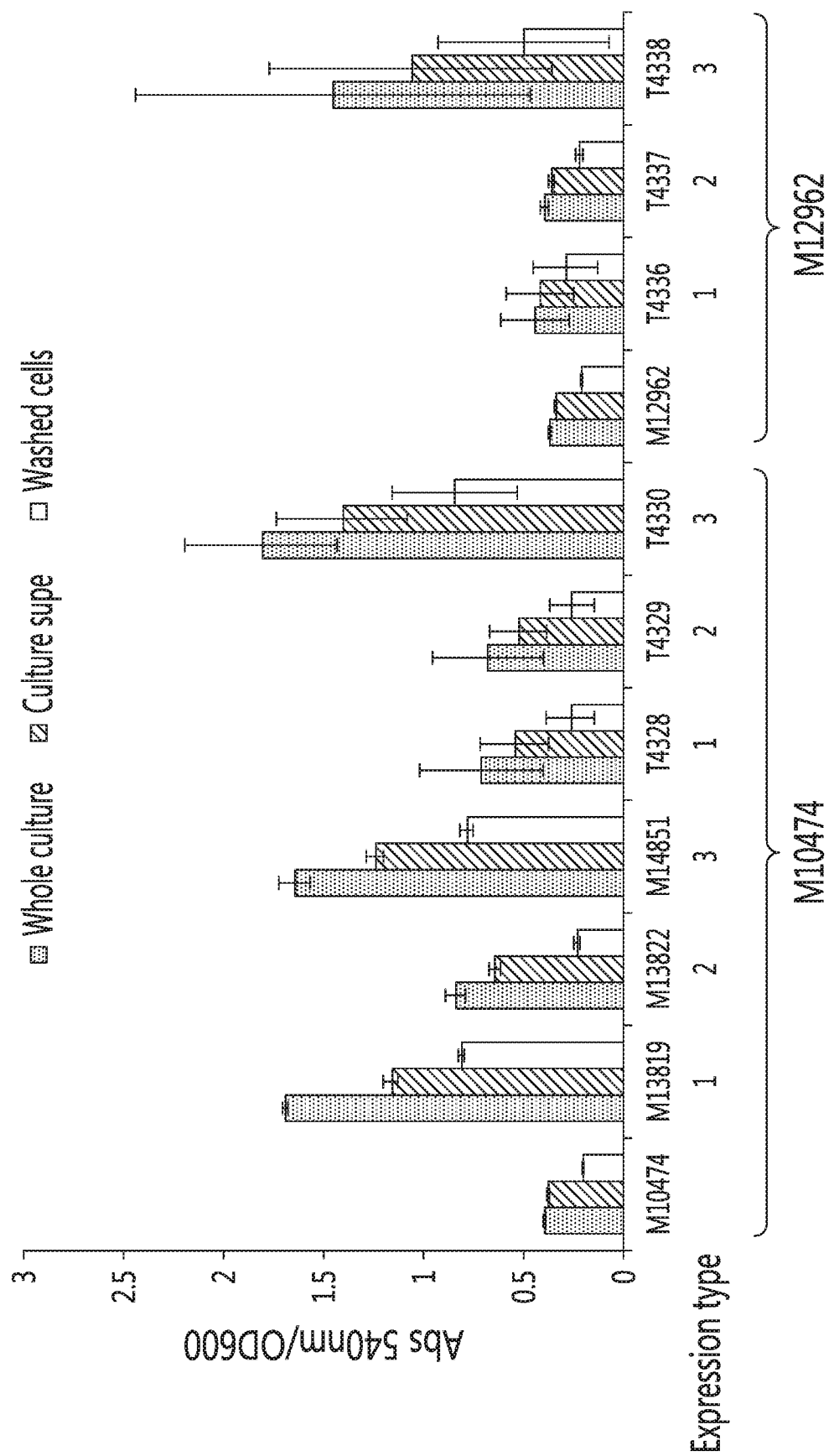
FIG. 10 provides the wheat starch activity of strains expressing maltogenic amylase. Results are provided as the ratio of absorbance at 450 nm/optical density at 600 nm for the whole culture (left bars), the supernatant (middle bars) and washed cells (left bars) for the different strains (M10474, M13819, M13822, M14851, T4328, T4329, T4330, M12962, T4336, T4337 and T4338). Data for "M" strains are the average of duplicate cultures. Data for "T" strains include the average activity across cultures of seven transformations isolates. Expression type 1 refers to the presence of an invertase signal peptide and a Spi1 tether to generate a tethered enzyme. Expression type 2 refers to the presence of an invertase signal peptide and the absence of a tether to generate a secreted enzyme. Expression type 3 refers to the absence of a signal peptide and the absence of a tether to generate an intracellular enzyme.

The wheat starch activity normalized to cell density was determined in the whole culture, the culture supernatant and the washed cells of various yeast strains expressing the maltogenic alpha amylase from G. stearothermophilus expressed in a secreted form, in a tethered form or expressed intracellularly as explained in the legend of FIG. 10. The results are shown in FIG. 8 and indicated that the highest activities are observed when the MAA is expressed intracellularly.

Figure 4:
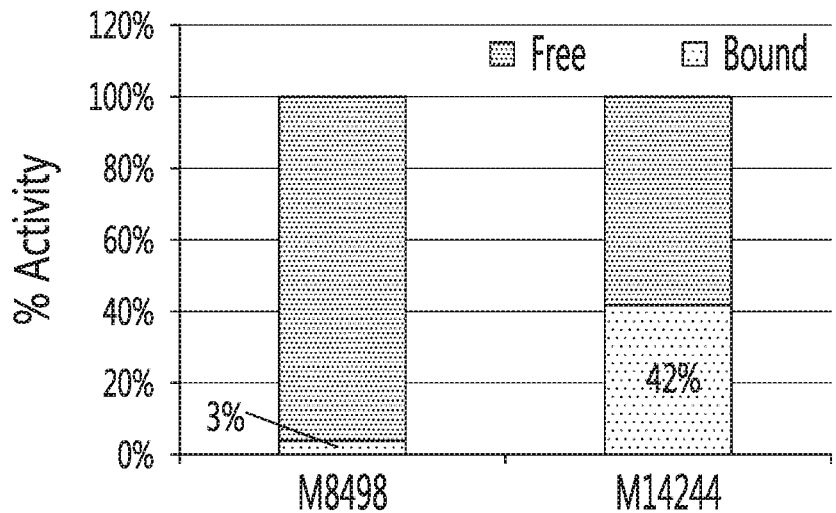
FIG. 4 provides the glucoamylase enzyme activity measured in pellets ("bound", light gray) and supernatant ("free", dark gray) of cultured recombinant yeast host cells expressing an heterologous glucoamylase in the absence (strain M8498) and in the presence (strain M14244) of a Sed1 tether. Results are shown as percentage of glucoamylase activity in function of strain used.

Example III—Expression of Heterologous Alpha-Amylases, Glucoamylases, Phytases, Glucose Oxidases and Fungal Amylases An heterologous glucoamylase (GA) was expressed in S. cerevisiae from the promoter of the tef2 gene. When GA was expressed as a tethered enzyme, activity associated with cellular pellet is increased (FIG. 4).

An heterologous alpha-amylase (AA) from the promoter of the tef2 gene. When the AA was expressed as a tethered enzyme, activity associated with pellet is increased, especially in the presence of a linker (FIG. 5).

Figure 7A:
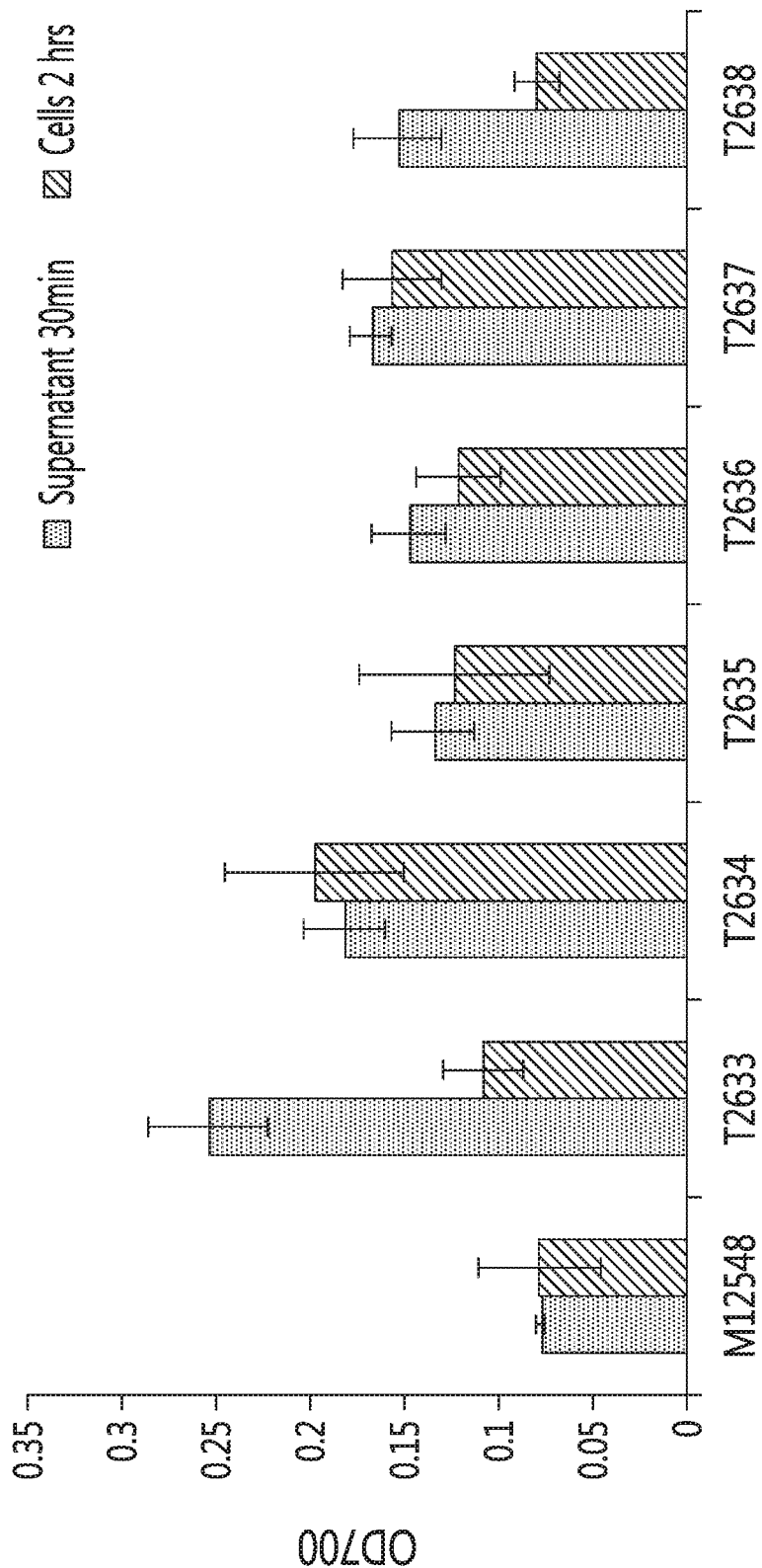
FIGS. 7A and 7B provide the phytase activity in culture supernatant (gray bars) or associated with cells (diagonally hatched bars in FIG. 7A or u in FIG. 7B) for strains expressing free or tethered *Citrobacter braakii* phytase. Supernatant was incubated with 5 mM sodium phytate solution pH 5.5 for 30 minutes and cells were incubated in the same solution for 2 hours.
Figure 7B:
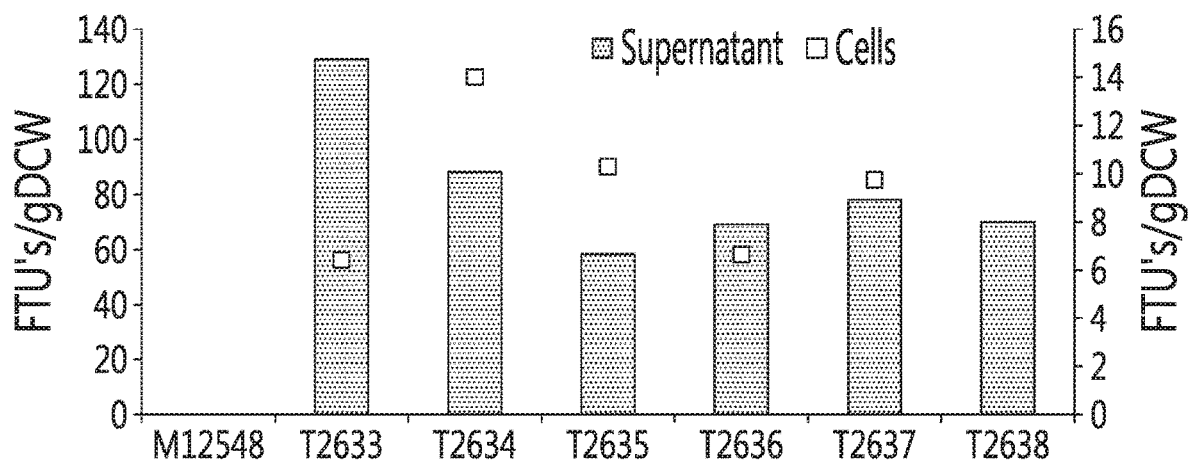

Various preparations of yeast strains expressing the phytase from C. braakii were made and their FTU activity was determined. Some strains expressed the phytase in a secreted form (T2633), other strains expressed the phytase in a tethered form (T2634, T2635, T2636, T2637 and T2638) using different tethers. The results are shown in FIGS. 7A and 7B for both the supernatant and the cells themselves.

Figure 9:
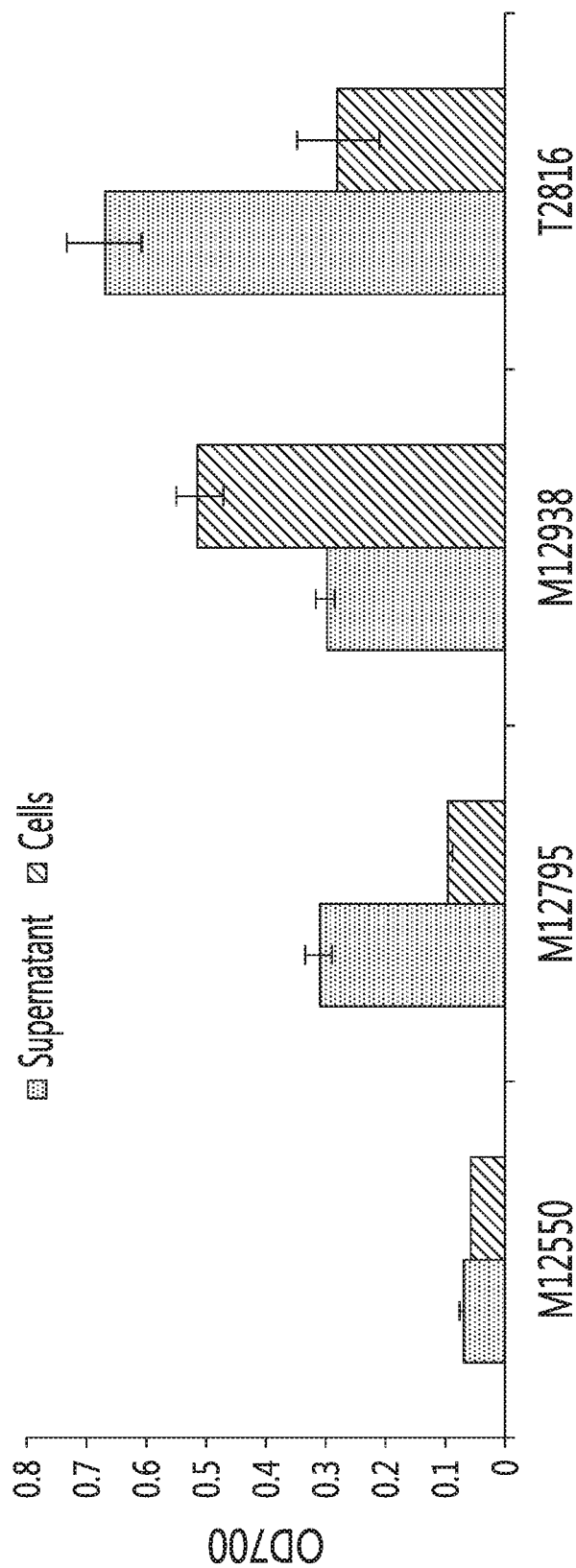
FIG. 9 provides the phytase activity in culture supernatant (grey bars) or associated with cells (diagonally hatched bars) for strains expressing *E. coli* phytase fused with either an N-terminal tether with or without overexpression of AGA1 compared to *E. coli* phytase fused with a C-terminal Sed1 tether. Supernatant was incubated with 5 mM sodium phytate solution pH 5.5 for 30 minutes and cells were incubated in the same solution for 2 hours. Results are shown as the optical density at 700 nm in function of each strain (M12550, M12795, M12983 and T2816).

Various preparations of yeast strains expressing the phytase from E. coli were made and their FTU activity was determined. Some strains expressed the phytase in a secreted form (M11312), other strains expressed the phytase in a tethered form (T2705, T2706, M12795, M12938, T2816) using the different configurations of tethers. The results are shown in FIGS. 8 and 9 for both the supernatant and the cells themselves.

Heterologous chimeric thermo-tolerant P. furiosus alpha-amylase-SPI1 constructs and T. hydrothermalis alpha-amylase-CCW12 constructs were made using various truncations of the tethering moieties. The alpha-amylase activity associated with the washed cells of the strains expressing the chimeric polypeptides with the truncated GPI anchoring portions were compared to the non-truncated GPI anchoring portion is shown in FIGS. 13 and 14.

Figure 13:
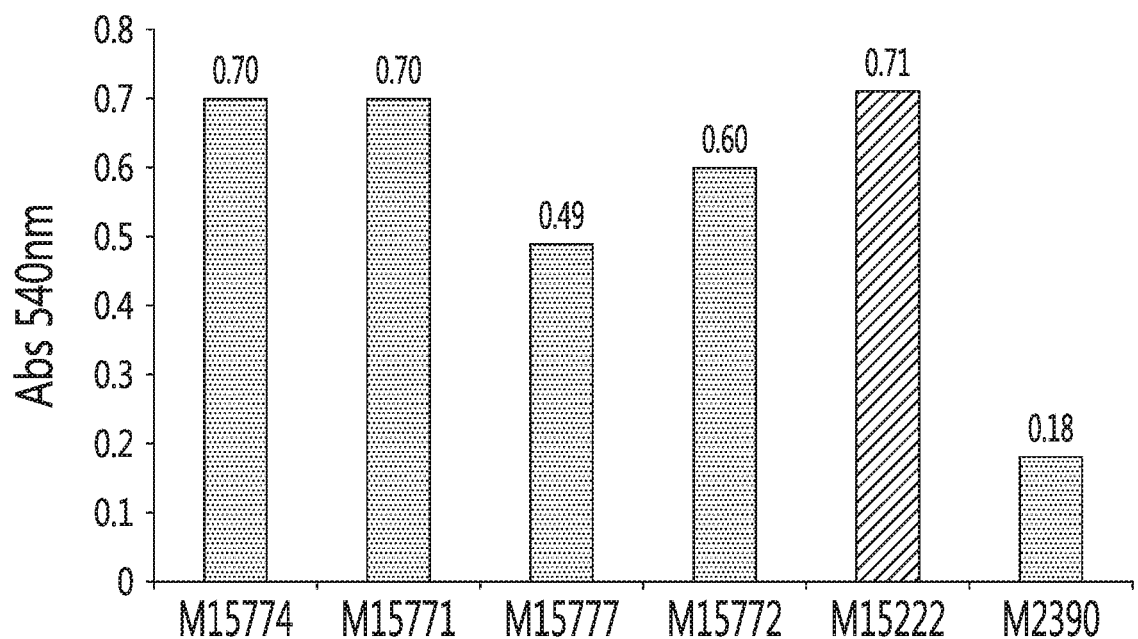
FIG. 13 shows the alpha-amylase activity associated with the cells of yeast strains expressing various chimeric proteins comprising a thermo-tolerant alpha-amylase derived from *Pyrococcus furiosus* (SEQ ID NO: 71) in combination with different tethering moieties derived from the SPI1 protein or associated truncations (M15774, M15771, M15777, M15772 and M15222) compared to a control strain (M2390). Results are shown as the absorbance at 540 nm in function of the yeast strain used.

As seen from FIG. 13, the chimeric polypeptide with the full length tethering moiety (expressed from strain M15222) showed the same or higher alpha-amylase activity than the polypeptides with truncated tethering moieties (expressed from strains M15774 (21 aa-long truncation), M15771 (51 aa-long truncation), M1577 (81 aa-long truncation) or M15772 (130 aa-long truncation)).

Figure 14:
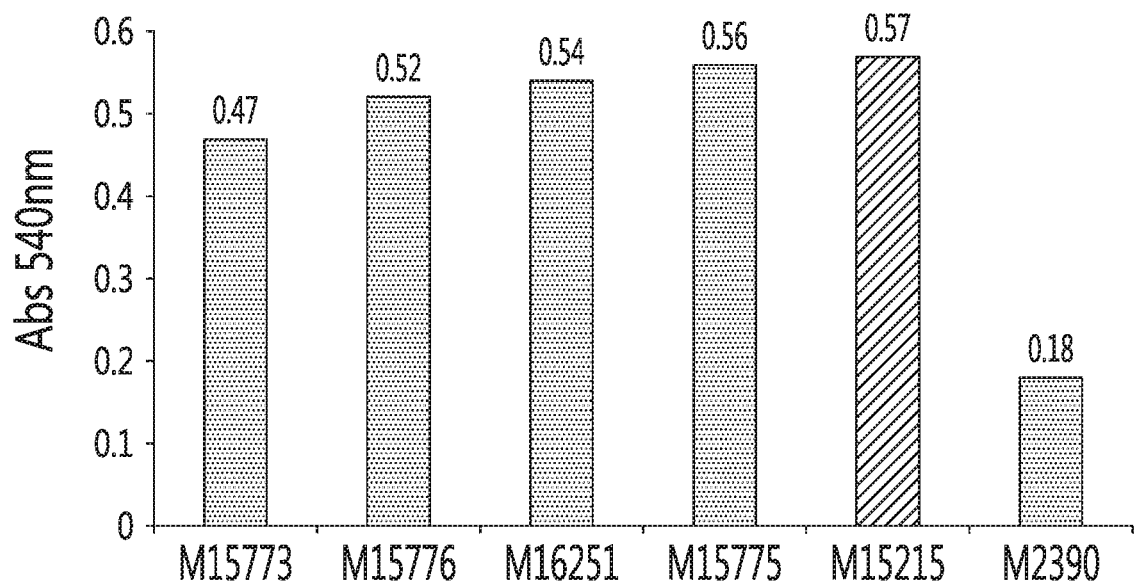
FIG. 14 shows the alpha-amylase activity associated with cells of yeast strains expressing various chimeric proteins comprising an alpha-amylases derived from *Thermococcus hydrothermalis* (SEQ ID NO: 72) in combination with different tethering moieties derived from the CCW12 protein or associated truncations (M15773, M15776, M16251 and M15215) compared to a control strain (M2390). Results are shown as the absorbance at 540 nm in function of the yeast strain used.

As seen from FIG. 14, the chimeric polypeptides with the full length tethering moiety (expression from strain M15215) exhibited similar or higher alpha-amylase activity when compared to chimeric polypeptides having a truncated tethering moiety (expressed from strains M15773 (24 aa-long truncation), M15776 (49 aa-long truncation), M16251 (74 aa-long truncation) or M15775 (99 aa-long truncation)).

Heterologous chimeric thermo-tolerant P. furiosus alpha-amylase-SPI1 constructs and T. hydrothermalis alpha-amylase-CCW12 constructs were made using various linkers and the same tethering moiety. The alpha-amylase activity associated with the washed cells of the strains expressing the chimeric polypeptides with the different linkers is shown in FIGS. 15 and 16.

Figure 15:
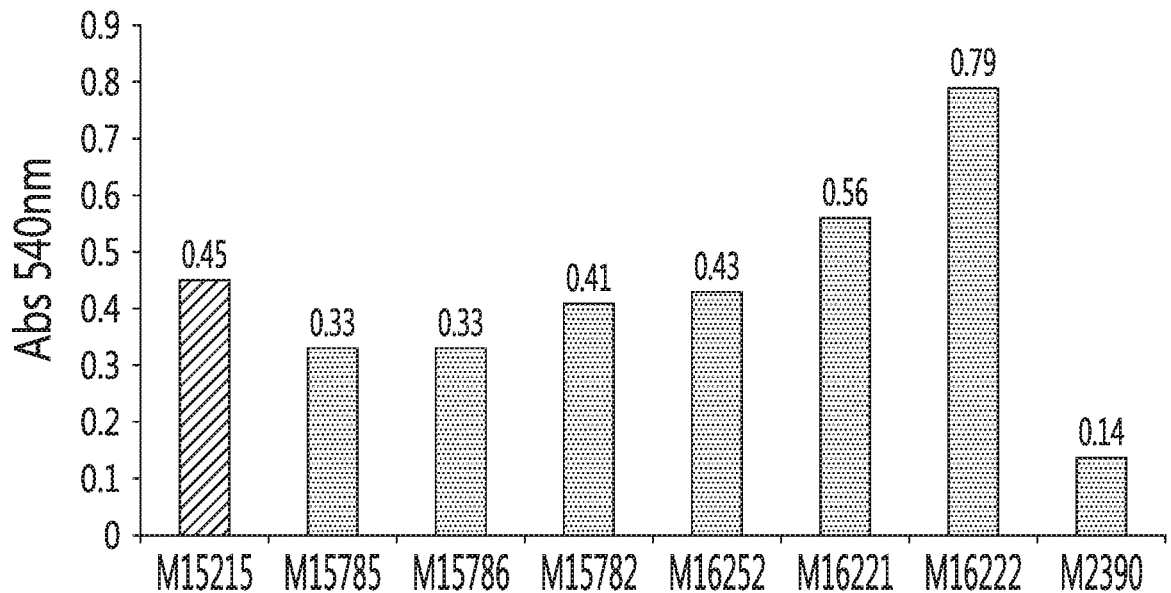
FIG. 15 shows the alpha-amylase activity associated with the cells of yeast strains expressing various chimeric proteins comprising an alpha-amylase derived from T. hydrothermalis (SEQ ID NO: 72) in combination with a tethering moiety derived from the CCW12 protein and different linkers (M15785, M15786, M15782, M16252, M16221 and M16222) compared to a control strain (M2390). Results are shown as the absorbance at 540 nm in function of the yeast strain.

As seen from FIG. 15, the alpha-amylase activity of all the strains was higher than the control strain (M2390), irrespective of type of linker used. The alpha-amylase activity was the highest when linker 7 (SEQ ID NO: 99) was used (strain M16222).

Figure 16:
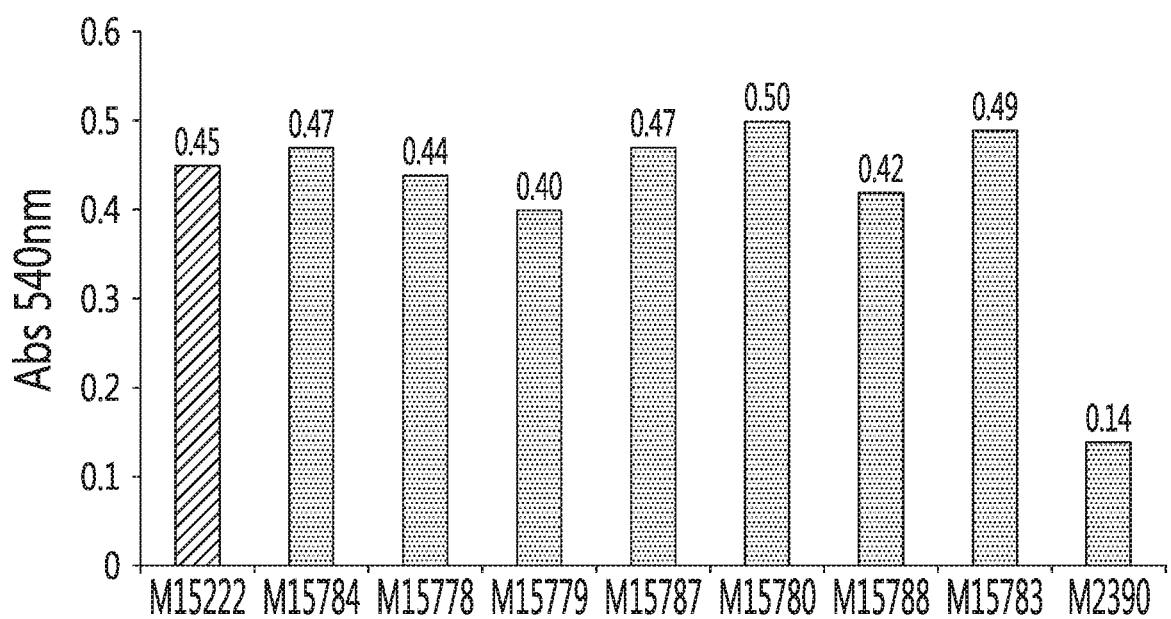
FIG. 16 shows the alpha-amylase activity associated with the cells of yeast strains expressing various chimeric proteins comprising an alpha-amylase derived from P. furiosus (SEQ ID NO: 71), a tethering moiety derived from the SPI1 protein and different linkers (M15784, M15778, M15779, M15787, M15780, M15788 and M15783) compared to a control strain (M2390). Results are shown as the absorbance at 540 nm in function of the yeast strain.

As seen from FIG. 16, the alpha-amylase activity of all the strains was higher than the control strain (M2390), irrespective of type of linker used. The alpha-amylase activity was the highest when linker 5 (SEQ ID NO: 97) was used (strain M15780).

Figure 17:
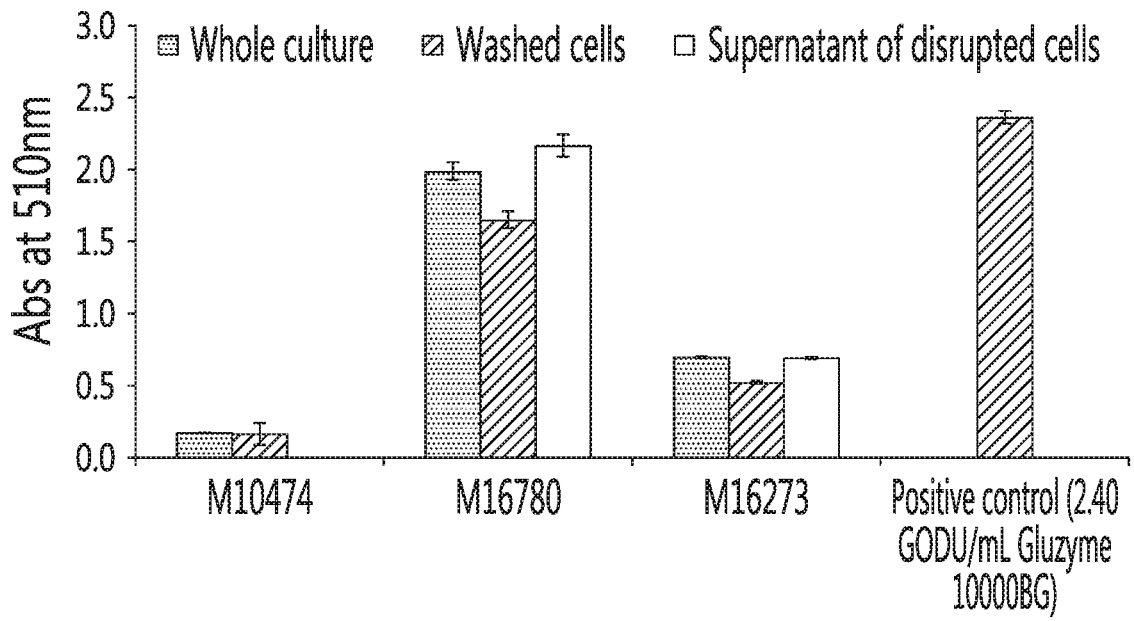
FIG. 17 shows the glucose oxidase (GO) activity associated with the whole culture (grey bars), washed cells (diagonal hatch bars) or the supernatant of disrupted washed cells (white bars) of yeast strains expressing a glucose oxidase derived from Aspergillus niger, expressed in a secreted form (M16780) or intracellularly (M16273) compared to a negative control strain (M10474) and a positive control amount of a commercially available purified glucose oxidase (positive control, Gluzyme Mono®). Results are shown as absorbance at 510 nm in function of the yeast strain/control used.
Figure 18:
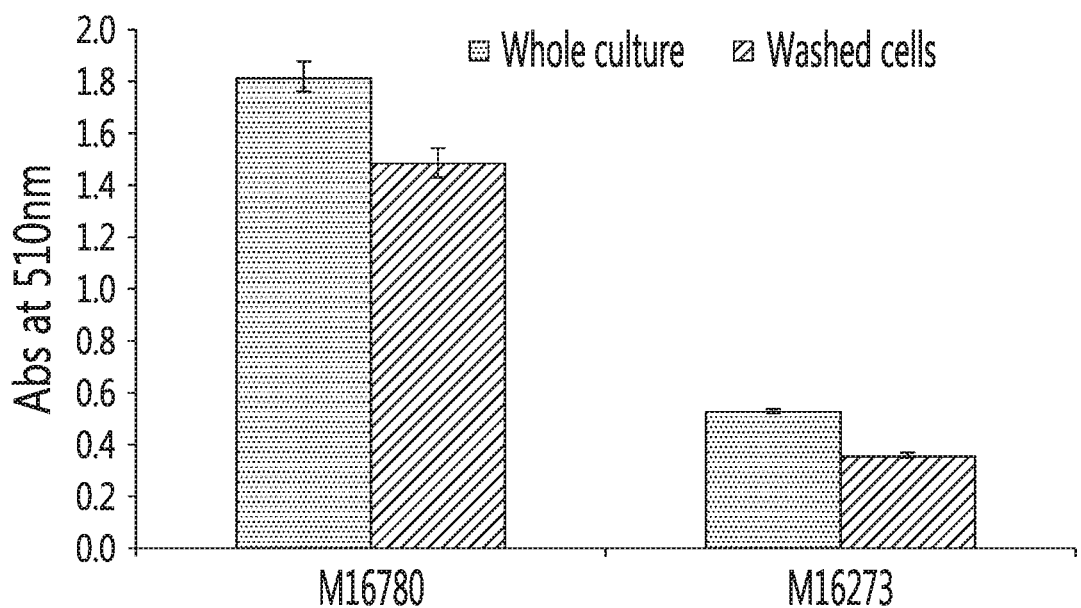
FIG. 18 shows the glucose oxidase (GO) activity associated with the whole culture (grey bars), washed cells (diagonal hatch bars) of yeast strains expressing a glucose oxidase derived from Aspergillus niger, expressed in a secreted form (M16780) or intracellularly (M16273). Results are shown as absorbance at 510 nm (corrected to remove the absorbance associated with control strain M10474) in function of the yeast strain used.

Heterologous chimeric glucose oxidase (GO) constructs were expressed intracellularly or in a secreted form. The GO activity obtained from various cellular fractions was compared to a control strain (M10474) or a positive control enzymatic preparation Gluzyme Mono® (FIG. 17). The GO activity associated with strains M16780 and M16273 was higher than the control GO activity associated with the parental strain M10474 (FIG. 18).

Strain M16780 was also used to supplement the dough of bread loaves which were compared to negative control (non-supplemented dough) loaves and positive control (Gluzyme Mono® supplemented dough) loaves. As shown in FIG. 21, higher oven spring and finer crumb structure (which is observed for M16780 cell pellet doughs) are indicators of glucose oxidase function in the supplemented dough.

Figure 19:
FIG. 19 shows the fungal amylase (FA) activity associated with the whole culture (grey bars), washed cells (diagonal bars) or the supernatant of disrupted washed cells (white bars) of yeast strains expressing a fungal amylase derived from Aspergillus oryzae expressed in a secreted form with a different signal peptides (S. cerevisiae invertase for M16772, A. oryzae native alpha-amylase signal peptide for M16540) compared to a negative control strain (M10474) and a positive control amount of a commercially available purified fungal alpha-amylase (positive control, Fungamyl®). Results are shown as absorbance at 540 nm in function of the yeast strain/control used.
Figure 20:
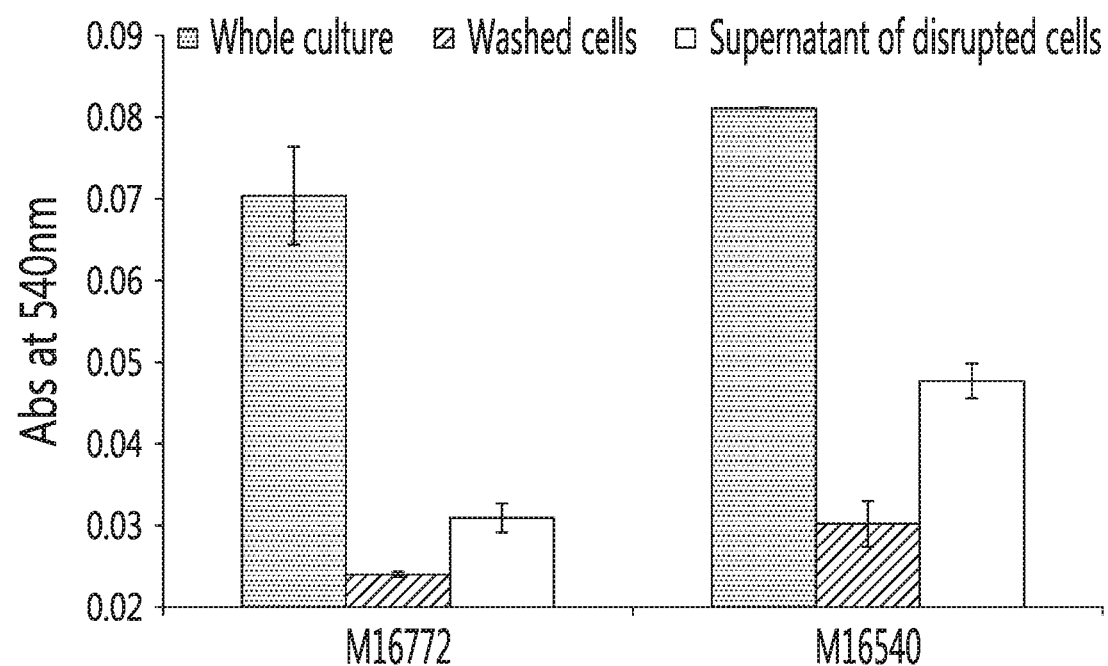
FIG. 20 shows the fungal amylase (FA) activity associated with the whole culture (grey bars), washed cells (diagonal hatch bars) or the supernatant of disrupted washed cells (white bars) of yeast strains expressing a fungal amylase derived from Aspergillus oryzae expressed in a secreted form with a different signal peptides (S. cerevisiae invertase for M16772, A. oryzae native alpha-amylase signal peptide for M16540). Results are shown as absorbance at 540 nm (corrected to remove the absorbance associated with control strain M10474) in function of the yeast strain used.

Heterologous chimeric fungal amylase (FA) constructs were expressed in a secreted form. The FA activity obtained from various cellular fractions was compared to control strain M10474 or a positive control enzymatic preparation Fungamyl® (FIG. 19). The FA activity associated with strains M16772 and M16540 was higher than the control activity associated with the parental strain M10474 (FIG. 20).

While the invention has been described in connection with specific embodiments thereof, it will be understood that the scope of the claims should not be limited by the preferred embodiments set forth in the examples, but should be given the broadest interpretation consistent with the description as a whole.

REFERENCES

Pérez-Torrado R, Bruno-Bárcena J M, Matallana E. Monitoring stress-related genes during the process of biomass propagation of *Saccharomyces cerevisiae* strains used for wine making. Appl Environ Microbiol. 2005 Nov.;71 (11): 6831-7.

Praekelt U M, Meacock P A. MOL1, a *Saccharomyces cerevisiae* gene that is highly expressed in early stationary phase during growth on molasses. Yeast. 1992 Sep.;8 (9): 699-710.

---

What is claimed is:

1. A process for making a food or a feed product, said process comprising including a recombinant yeast host cell or an additive comprising the recombinant yeast host cell in the food or the feed product, wherein the recombinant yeast host cell has a heterologous nucleic acid molecule encoding a cell-associated heterologous maltogenic alpha-amylase, wherein the maltogenic alpha-amylase has at least 80% identity to the amino acid sequence of SEQ ID NO: 1, 51, 65 or 108, wherein the heterologous nucleic acid molecule is operatively associated with a promoter allowing expression of the heterologous nucleic acid molecule during propagation under aerobic conditions.

2. The process of claim 1, wherein the heterologous nucleic acid molecule allows intracellular expression of the heterologous maltogenic alpha-amylase.

3. The process of claim 1, wherein the heterologous nucleic acid molecule allows expression of a membrane-associated heterologous maltogenic alpha-amylase.

4. The process of claim 1, wherein the heterologous nucleic acid molecule allows expression of a tethered heterologous maltogenic alpha-amylase.

5. The process of claim 4, wherein the tethered heterologous maltogenic alpha-amylase is a chimeric protein of formula (I) or (II):

(NH$_2$)FFE-L-TT(COOH)　　(I)

(NH$_2$)TT-L-FFE(COOH)　　(II)

wherein FFE is the maltogenic alpha-amylase;
L is present or absent and is an amino acid linker;
TT is an amino acid tethering moiety for associating the maltogenic alpha-amylase to a cell wall of the recombinant yeast host cell;
(NH2) indicates the amino terminus of the chimeric protein;
(COOH) indicates the carboxyl terminus of the chimeric protein; and
"-" is an amide linkage.

6. The process of claim 1, wherein the promoter is a heterologous promoter.

7. The process of claim 6, wherein the heterologous promoter comprises the promoter from the tdh1 gene, the hor7 gene, the hsp150 gene, the hxt7 gene, the gpm1 gene, the pgk1 gene and/or the stl1 gene.

8. The process of claim 1, wherein the recombinant yeast host cell is from the genus *Saccharomyces* sp.

9. The process of claim 1, wherein the recombinant yeast host cell is from the species *Saccharomyces cerevisiae*.

10. The process of claim 1, wherein the additive is a food additive, a dough conditioner, or a feed additive.

11. The process of claim 1, further comprising fermenting the food or the feed product with the recombinant yeast host cell present, and/or baking the food or the feed product to provide a baked product.

12. The process of claim 11, wherein the baked product is a bread.

13. The process of claim 3, wherein the membrane-associated heterologous maltogenic alpha-amylase has a heterologous signal peptide.

14. The process of claim 4, wherein the tethered heterologous maltogenic alpha-amylase has a heterologous signal peptide.

15. The process of claim 1, wherein the promoter is a native promoter.

* * * * *